US010196649B2

(12) United States Patent
Molina Fernandez et al.

(10) Patent No.: US 10,196,649 B2
(45) Date of Patent: Feb. 5, 2019

(54) METHOD FOR INCREASING PATHOGEN RESISTANCE IN PLANTS

(71) Applicant: UNIVERSIDAD POLITECNICA DE MADRID, Madrid (ES)

(72) Inventors: Antonio Molina Fernandez, Pozuelo de Alarcon (ES); Lucia Jorda Miro, Pozuelo de Alarcon (ES); Clara Sanchez Rodriguez, Pozuelo de Alarcon (ES); Sara Sopena Torres, Pozuelo de Alarcon (ES); Gemma Lopez Garcia, Pozuelo de Alarcon (ES); Eva Miedes Vicente, Pozuelo de Alarcon (ES); Andrea Sanchez Vallet, Pozuelo de Alarcon (ES); Viviana Pamela Escudero Welsch, Pozuelo de Alarcon (ES)

(73) Assignee: UNIVERSIDAD POLITECNICA DE MADRID, Madrid (ES)

( * ) Notice: Subject to any disclaimer, the term of this patent is extended or adjusted under 35 U.S.C. 154(b) by 0 days.

(21) Appl. No.: 14/652,285

(22) PCT Filed: Dec. 18, 2013

(86) PCT No.: PCT/EP2013/077076
§ 371 (c)(1),
(2) Date: Jun. 15, 2015

(87) PCT Pub. No.: WO2014/095990
PCT Pub. Date: Jun. 26, 2014

(65) Prior Publication Data
US 2016/0108424 A1 Apr. 21, 2016

(30) Foreign Application Priority Data
Dec. 18, 2012 (EP) .................................... 12197751

(51) Int. Cl.
*C12N 15/82* (2006.01)
*C12N 9/12* (2006.01)
(52) U.S. Cl.
CPC ........... *C12N 15/8281* (2013.01); *C12N 9/12* (2013.01); *C12N 9/1205* (2013.01); *C12N 15/8216* (2013.01); *C12N 15/8282* (2013.01); *C12Y 207/12002* (2013.01)

(58) Field of Classification Search
None
See application file for complete search history.

(56) References Cited

U.S. PATENT DOCUMENTS 7,320,892 B2 * 1/2008 Gabriels ............ C12N 15/8279
435/419

FOREIGN PATENT DOCUMENTS

WO  WO 2009009142  *  1/2009

OTHER PUBLICATIONS

Fourgoux-Nicol et al. (1999) Plant Molecular Biology 40: 857-872.*
International Search Report dated Feb. 26, 2014 for PCT/EP2013/077076.
D.C. Bergmann; Stomatal development and pattern controlled by a MAPKK kinase; Science; vol. 304; No. 5676; Jun. 2004; XP055062099; pp. 1494-1497.
F. Llorente, et al; Erecta receptor-like kinase and heterotrimeric G protein from arabidopsis . . . ; The Plant Journal; vol. 43; No. 2; Jul. 2005; XP055062159; pp. 165-180.
K.A. Lease, et al; A mutant *Arabidopsis* heterotrimeric G-protein [beta] subunit affects leaf . . . ; The Plant Cell; vol. 13; No. 12; Dec. 2001; XP055062163; pp. 2631-2641.
A. Molina; Plant innate immunity and resistance to necrotic fungi; www.cbgp.upm.es/plant_innate.php; Jun. 2012; XP002696638.
C. Sanchez-Rodriguez, et al; The erecta receptor-like kinase regulates cell wall-mediated resistance . . . ; Molecular Plant-Microbe Interactions; vol. 22; No. 8; Aug. 2009; XP055062169; pp. 953-963.

* cited by examiner

*Primary Examiner* — Medina A Ibrahim
(74) *Attorney, Agent, or Firm* — Myers Bigel, P.A.

(57) ABSTRACT

The invention relates to a method of increasing the resistance to one or more pathogens, preferably fungal or bacterial pathogens, in a monocotyledonous or dicotyledonous plant or a part of a plant, for example in an organ, tissue, a cell or a part of a plant cell, for example in an organelle, wherein a DNA sequence which codes for YODA protein or wherein an endogenous DNA sequence which codes for a YODA protein is increased in the plant or plant cell in comparison with the original, or wild-type, plant. The invention also relates to plants, to parts of a plant, for example an organ, tissue, a cell or a part of a plant cell, for example an organelle, which are obtained by the above methods, and to the corresponding propagation material.

23 Claims, 14 Drawing Sheets
Specification includes a Sequence Listing.

SEQUENCE LISTING

```
<160> NUMBER OF SEQ ID NOS: 76

<210> SEQ ID NO 1
<211> LENGTH: 3287
<212> TYPE: DNA
<213> ORGANISM: Arabidopsis thaliana
<220> FEATURE:
<221> NAME/KEY: source
<222> LOCATION: 1..3287
<223> OTHER INFORMATION: /mol_type="unassigned DNA"
      /organism="Arabidopsis thaliana"

<400> SEQUENCE: 1
ttactttgta atgttgaaca agagctttta aaagagtgat agtgtgagtg agtgtgcctc      60
ttggtttgtg ggaagaagat catgccttgg tggagtaaat caaaagatga aaaaaagaaa    120
actaataagg agagtatcat tgatgcgttt aatcggaaac tgggattcgc atctgaggat    180
aggtctagtg gaagatcaag aaaatcaaga cgacgacgtg atgagattgt gtctgaaaga    240
ggagctatat ctcgattacc atcaagatct ccctctcctt ctactcgggt ttcacgctgt    300
cagagttttg cagaaagatc tcctgctgta cctcttcctc gtcctattgt ccgtcctcat    360
gtaaccagta ctgattcagg aatgaatgga tcacagagac caggtttaga tgcaaatttg    420
aagccgtcat ggttgccact tccaaagccc catggtgcta caagcatacc tgataatacc    480
ggtgctgagc ctgattttgc cactgcttct gtgtctagtg gaagttctgt gggtgacatt    540
ccatctgatt ctcttctcag tccattggcg tctgattgtg aaaatgggaa ccgaacacca    600
gtaaacatat cttcgaggga tcagtcaatg catagtaaca aaaactcagc tgagatgttt    660
aagccagtcc ctaataaaaa taggattctg tctgcatctc ctaggcggag acctctggga    720
actcatgtga agaatctaca aatcccccaa cgagatttag tgctatgcag tgctccagat    780
agtttgttgt ctagtccttc caggagtcca atgagatcct ttattccaga tcaagtctca    840
aaccatgggt tgttgattag taaaccatat tcagatgttt ccttgcttgg atctggacag    900
tgctcaagcc ccggttcagg ttacaactca ggtaacaatt ccattggtgg agatatggct    960
actcagctgt tttggcctca aagcaggtgt agccctgaat gttccctgt gcctagtcca   1020 agaatgacaa gccctggtcc tagctctaga atacagagtg gtgctgttac acctcttcat   1080
cctcgagctg gagggtcaac tactgggtct cctactagaa gacttgatga taacagacag   1140
caaagccatc gtctgcctct cccgccgtta ttaatctcta atacttgtcc gttttcaccc   1200
acatattcag cagcgacatc tccgtctgtc ccccgaagtc cggcaagggc agaggctacg   1260
gttagccctg gatcgcgatg gaaaaaaggg agattgctgg ggatgggaag ttttggacat   1320
gtgtatcttg gctttaacag tgaaagtggg gagatgtgtg ccatgaaaga ggttactcta   1380
tgctcagatg atcctaagtc aagggagagt gcacaacaat gggggcaaga aatttcagtt   1440
ctaagccgtt tacgacacca aaatatagtg cagtattatg gctctgaaac cgtcgatgac   1500
aagctgtata tatatctgga gtatgtctcc ggtggttcga tctataaact tcttcaagag   1560
```

```
tatggacaat ttggtgagaa tgccattcgt aactatacac aacaaatttt atcagggctc    1620
gcatatttgc acgccaaaaa tactgttcat agggacatca aaggagcaaa tatattggtg    1680
gatcctcatg gacgagtaaa agttgctgat tttgggatgg caaaacatat tactgctcaa    1740
tctggtcctt tatcattcaa ggggagccca tattggatgg cacctgaggt gataaagaat    1800
tcaaatggca gtaaccttgc ggtcgacata tggagtcttg gatgtactgt tttagaaatg    1860
gctacaacga aacctccatg gagccagtat gaaggggttc ctgctatgtt caagattgga    1920
aacagcaagg agcttccaga tatccctgat catttatctg aagagggaa ggattttgta    1980
agaaaatgcc tacaaagaaa ccccgcaaat cgtcctacag ctgctcagct tttggatcat    2040
gcttttgtaa gaaatgtgat gccgatggaa aggcctattg tgagtggcga gcctgcagaa    2100
gccatgaatg tagcttcgag caccatgaga tcactggaca ttggacatgc aaggagtctt    2160
ccgtgcttag actcggaaga tgcaaccaat taccagcaga aaggattaaa acatggctcg    2220
ggattcagta tatcccaatc tcctaggaac atgtcatgcc cgatttcacc agtcggtagt    2280
ccaatctttc actcgcattc accacacatt agcggaagaa gatctccatc cccaatatct    2340
agtccccacg ctctctctgg ttcatcaaca ccttttaactg ggtgtggtgg agccatcccg    2400
ttccatcacc aaagacaaac tacagttaac ttcttgcatg aaggcatagg atcaagcaga    2460
agcccgggaa gtggcggaaa tttctacacc aacagtttct ttcaggagcc tagtaggcag    2520
caagatcggt cgcggagtag tccaaggact cctcctcatg tattttggga caacaacgga    2580
tcgatccagc caggctataa ttggaacaag gacaaccagc cagtcctatc tgatcatgtg    2640
tcccaacagc tcttaagtga gcatctgaaa ctgaagtccc tcgacctgag acccggtttt    2700
tcaactcccg gatcaacaaa cagaggaccc taacccgttc gagtcaaatg attcgacacc    2760
aatgacagaa ccataaaacc cagtggaaaa aaacatcaaa acaagtagct gcagaaactc    2820
ctccaggatc tcggaattgc aacacagcct gaagggtcag gatcttgagg tttaggatcg    2880
gggttagggt tactgagccg cgtctcaaaa ccctgaacca ttggctaata tcatgaatga    2940
ggattcgttt ttttcgtctt tggaaaatct gaagagctct ttgtcttgtc tctctctctt    3000
tctctgagga tatatgggag tgtgagatag agagatcaac aaaaattgat tttgtgtata    3060
ggaacttgtg gtggtagaac agatcatcac ctaatttgtc tatttccctc ttcttccgtc    3120
tctgtctggt ctggttcgtt gctgatgaag aagaagaaaa aaaagagggc aaaagcttaa    3180
atctcttaaa acctaaactc tttgatgtaa tctatcttta ttgtaagaga atctcaaatt    3240
agattattaa tccactctct tctttgatta aaaaaaaaaa aaaaaaa               3287
```

<210> SEQ ID NO 2
<211> LENGTH: 882
<212> TYPE: PRT
<213> ORGANISM: Arabidopsis thaliana

<400> SEQUENCE: 2

```
Met Pro Trp Trp Lys Ser Lys Asp Glu Lys Lys Thr Asn Lys Glu
1               5                   10                  15

Ser Ile Ile Asp Ala Phe Asn Arg Lys Leu Gly Phe Ala Ser Glu Asp
                20                  25                  30

Arg Ser Ser Gly Arg Ser Arg Lys Ser Arg Arg Arg Asp Glu Ile
            35                  40                  45

Val Ser Glu Arg Gly Ala Ile Ser Arg Leu Pro Ser Arg Ser Pro Ser
        50                  55                  60

Pro Ser Thr Arg Val Ser Arg Cys Gln Ser Phe Ala Glu Arg Ser Pro
```

```
                65                  70                  75                  80
Ala Val Pro Leu Pro Arg Pro Ile Val Arg Pro His Val Thr Ser Thr
                        85                  90                  95
Asp Ser Gly Met Asn Gly Ser Gln Arg Pro Gly Leu Asp Ala Asn Leu
                    100                 105                 110
Lys Pro Ser Trp Leu Pro Leu Pro Lys Pro His Gly Ala Thr Ser Ile
                    115                 120                 125
Pro Asp Asn Thr Gly Ala Glu Pro Asp Phe Ala Thr Ala Ser Val Ser
                130                 135                 140
Ser Gly Ser Ser Val Gly Asp Ile Pro Ser Asp Ser Leu Leu Ser Pro
145                 150                 155                 160
Leu Ala Ser Asp Cys Glu Asn Gly Asn Arg Thr Pro Val Asn Ile Ser
                    165                 170                 175
Ser Arg Asp Gln Ser Met His Ser Asn Lys Asn Ser Ala Glu Met Phe
                180                 185                 190
Lys Pro Val Pro Asn Lys Asn Arg Ile Leu Ser Ala Ser Pro Arg Arg
                    195                 200                 205
Arg Pro Leu Gly Thr His Val Lys Asn Leu Gln Ile Pro Gln Arg Asp
                210                 215                 220
Leu Val Leu Cys Ser Ala Pro Asp Ser Leu Leu Ser Ser Pro Ser Arg
225                 230                 235                 240
Ser Pro Met Arg Ser Phe Ile Pro Asp Gln Val Ser Asn His Gly Leu
                    245                 250                 255
Leu Ile Ser Lys Pro Tyr Ser Asp Val Ser Leu Leu Gly Ser Gly Gln
                260                 265                 270
Cys Ser Ser Pro Gly Ser Gly Tyr Asn Ser Gly Asn Asn Ser Ile Gly
                275                 280                 285
Gly Asp Met Ala Thr Gln Leu Phe Trp Pro Gln Ser Arg Cys Ser Pro
                290                 295                 300
Glu Cys Ser Pro Val Pro Ser Pro Arg Met Thr Ser Pro Gly Pro Ser
305                 310                 315                 320
Ser Arg Ile Gln Ser Gly Ala Val Thr Pro Leu His Pro Arg Ala Gly
                    325                 330                 335
Gly Ser Thr Thr Gly Ser Pro Thr Arg Arg Leu Asp Asp Asn Arg Gln
                340                 345                 350
Gln Ser His Arg Leu Pro Leu Pro Pro Leu Leu Ile Ser Asn Thr Cys
                355                 360                 365
Pro Phe Ser Pro Thr Tyr Ser Ala Ala Thr Ser Pro Ser Val Pro Arg
            370                 375                 380
Ser Pro Ala Arg Ala Glu Ala Thr Val Ser Pro Gly Ser Arg Trp Lys
385                 390                 395                 400
Lys Gly Arg Leu Leu Gly Met Gly Ser Phe Gly His Val Tyr Leu Gly
                    405                 410                 415
Phe Asn Ser Glu Ser Gly Glu Met Cys Ala Met Lys Glu Val Thr Leu
                420                 425                 430
Cys Ser Asp Asp Pro Lys Ser Arg Glu Ser Ala Gln Gln Leu Gly Gln
                435                 440                 445
Glu Ile Ser Val Leu Ser Arg Leu Arg His Gln Asn Ile Val Gln Tyr
            450                 455                 460
Tyr Gly Ser Glu Thr Val Asp Asp Lys Leu Tyr Ile Tyr Leu Glu Tyr
465                 470                 475                 480
Val Ser Gly Gly Ser Ile Tyr Lys Leu Leu Gln Glu Tyr Gly Gln Phe
                    485                 490                 495
```

```
Gly Glu Asn Ala Ile Arg Asn Tyr Thr Gln Gln Ile Leu Ser Gly Leu
            500                 505                 510

Ala Tyr Leu His Ala Lys Asn Thr Val His Arg Asp Ile Lys Gly Ala
        515                 520                 525

Asn Ile Leu Val Asp Pro His Gly Arg Val Lys Val Ala Asp Phe Gly
    530                 535                 540

Met Ala Lys His Ile Thr Ala Gln Ser Gly Pro Leu Ser Phe Lys Gly
545                 550                 555                 560

Ser Pro Tyr Trp Met Ala Pro Glu Val Ile Lys Asn Ser Asn Gly Ser
                565                 570                 575

Asn Leu Ala Val Asp Ile Trp Ser Leu Gly Cys Thr Val Leu Glu Met
            580                 585                 590

Ala Thr Thr Lys Pro Pro Trp Ser Gln Tyr Glu Gly Val Pro Ala Met
        595                 600                 605

Phe Lys Ile Gly Asn Ser Lys Glu Leu Pro Asp Ile Pro Asp His Leu
    610                 615                 620

Ser Glu Glu Gly Lys Asp Phe Val Arg Lys Cys Leu Gln Arg Asn Pro
625                 630                 635                 640

Ala Asn Arg Pro Thr Ala Ala Gln Leu Leu Asp His Ala Phe Val Arg
                645                 650                 655

Asn Val Met Pro Met Glu Arg Pro Ile Val Ser Gly Glu Pro Ala Glu
            660                 665                 670

Ala Met Asn Val Ala Ser Ser Thr Met Arg Ser Leu Asp Ile Gly His
        675                 680                 685

Ala Arg Ser Leu Pro Cys Leu Asp Ser Glu Asp Ala Thr Asn Tyr Gln
    690                 695                 700

Gln Lys Gly Leu Lys His Gly Ser Gly Phe Ser Ile Ser Gln Ser Pro
705                 710                 715                 720

Arg Asn Met Ser Cys Pro Ile Ser Pro Val Gly Ser Pro Ile Phe His
                725                 730                 735

Ser His Ser Pro His Ile Ser Gly Arg Arg Ser Pro Ser Pro Ile Ser
            740                 745                 750

Ser Pro His Ala Leu Ser Gly Ser Ser Thr Pro Leu Thr Gly Cys Gly
        755                 760                 765

Gly Ala Ile Pro Phe His His Gln Arg Gln Thr Thr Val Asn Phe Leu
    770                 775                 780

His Glu Gly Ile Gly Ser Ser Arg Ser Pro Gly Ser Gly Asn Phe
785                 790                 795                 800

Tyr Thr Asn Ser Phe Phe Gln Glu Pro Ser Arg Gln Gln Asp Arg Ser
                805                 810                 815

Arg Ser Ser Pro Arg Thr Pro His Val Phe Trp Asp Asn Gly
            820                 825                 830

Ser Ile Gln Pro Gly Tyr Asn Trp Asn Lys Asp Asn Gln Pro Val Leu
        835                 840                 845

Ser Asp His Val Ser Gln Gln Leu Leu Ser Glu His Leu Lys Leu Lys
    850                 855                 860

Ser Leu Asp Leu Arg Pro Gly Phe Ser Thr Pro Gly Ser Thr Asn Arg
865                 870                 875                 880

Gly Pro

<210> SEQ ID NO 3
<211> LENGTH: 3293
<212> TYPE: DNA
```

<213> ORGANISM: Vitis vinifera
<220> FEATURE:
<221> NAME/KEY: source
<222> LOCATION: 1..3293
<223> OTHER INFORMATION: /mol_type="unassigned DNA"
      /organism="Vitis vinifera"

<400> SEQUENCE: 3

| | | | | | |
|---|---|---|---|---|---|
| atgccttcat | ggtgggggaa | atcttcatcc | aaagaagtaa | agaagaagga | aaaccgggaa | 60 |
| agtttcattg | attcaataca | ccggaaattc | aggactgtat | ctgaagagaa | gtgcaacaat | 120 |
| agatcaggag | cttcccaaag | acactgtggt | gacactgtct | cagagaagga | atctcgatcc | 180 |
| agagcacaat | caagatcacc | atctccctcc | acaaaagtat | cacgctgtca | agttttgca | 240 |
| gaaaggcctc | atgcccaacc | acttccactc | cctggaccgc | accttacgag | tgtagtgcgt | 300 |
| actgactctg | gaatcaatgc | atcaaagaaa | caaggattgg | ttgaaggctc | caagacacag | 360 |
| atggttttgc | ccctgccaag | acctggatat | gttgcaaaca | ggctagatcc | tacagatgct | 420 |
| gagggggatc | tagccactgc | ttctgtgttt | agttatagtt | ccattgatag | tgaagatcca | 480 |
| tctgagtcac | gccttctcag | cccccaggca | tctgattatg | agaatggaaa | cagaaccact | 540 |
| atgaacagcc | cttccagcgt | aatgcacaag | gatcagtctc | ctgttctcac | ccaaggaag | 600 |
| ccaagagaag | cattgaggcc | agctaatctt | ttgttaaaca | atcagattca | ctctacatca | 660 |
| cctaaatggg | tacctttaag | cactcatgtg | ccaaattttc | cagttcctca | gaatggcgct | 720 |
| ttctgtagtg | ctccagacag | ctcgatgtca | agtccttcta | gaagtccaat | gagattattt | 780 |
| agccctgagc | aagtcatgaa | ttctagtttc | tggacgggaa | agccttatgc | tgatatagct | 840 |
| ttgcttggat | ctggacactg | ttctagtcca | ggttcaggtc | acaattctgg | acataattca | 900 |
| ataggaggag | atatgtcagg | acagctgttt | tggccgcaca | gcaggtgtag | ccctgagtgt | 960 |
| tctccaatac | caagtcccag | aatgacaagc | cctggtccca | gctccagaat | acagagtggt | 1020 |
| gctgtcaccc | ctctgcatcc | acgagctgga | gcagctgctg | cagagtctcc | taccaaccga | 1080 |
| cctgatgatg | gaaagcaaca | aagccaccga | ttgccccttc | caccgataac | aatttctaat | 1140 |
| tcttgtcctt | tttctcctac | atattctaca | tcaacaactc | cctcagtacc | acgaagtcct | 1200 |
| ggtagggcgg | aaaacccaat | cagccctgga | tcacgctgga | agaagggtcg | gctcttaggg | 1260 |
| agaggcacat | ttgggcatgt | atatcttggg | tttaatagtg | aaagtgggga | gatgtgtgca | 1320 |
| atgaaggagg | ttacattatt | ttcagatgat | gcgaagtcaa | aggaaagtgc | acagcagctg | 1380 |
| ggccaagaaa | tttcgctcct | cagtcgctta | cgtcatccaa | atatagtgca | atactatgga | 1440 |
| tctgagacag | tggatgacaa | actctacata | tatttggaat | atgtatctgg | tggttccata | 1500 |
| tataaacttc | ttcaagagta | tggccagctt | ggtgaaatag | ctattcgtag | ctatactcaa | 1560 |
| caaattctgt | cagggcttgc | atatttgcat | gctaaaaaca | ctgtccatag | ggacatcaaa | 1620 |
| ggagcaaata | tactggtgga | tcccaatggc | cgtgtgaaat | tggcagattt | tggaatggca | 1680 |
| aagcatatta | ctggacaatc | ttgtccgtta | tccttaaagg | ggagccctta | ctggatggca | 1740 |
| cctgaggtca | taaagaactc | aaatggctgt | aatcttgcag | tcgatttatg | gagtcttggg | 1800 |
| tgcacagttt | tggagatggc | tacaacaaaa | ccaccttgga | gccagtatga | aggggttgct | 1860 |
| gctatgttta | agattggtaa | cagtaaagaa | cttcccacaa | tacctgatca | tctctcagag | 1920 |
| gagggcaagg | actttgtaag | gcagtgcttg | caacgcaacc | cattgcatcg | tcccacagct | 1980 |
| gcttggctat | ggagcacccc | ttttgttaga | aatgctgcgc | tctggaaag | acctagtctt | 2040 |
| agttctgagc | ttgaaccacc | acctgcagtt | acaaatgctg | tcagatccat | ggccattgga | 2100 |

```
cacacaagaa atgttttaga gtctgaagga gtggctatcc atcagtctag atgttcaaaa    2160
actggttcag gatccagtga tacccatacc ccaaggaact tatcaagccc tgtttctcct    2220
attgggagcc ctcttctgca ttcaagatca ccacaacata tgagtgggag gatgtctccc    2280
tctcccatat ccagtcctcg caccacatct ggttcatcca cgcctctcag tgggggtagt    2340
ggtgccatac cttttcatca tccaaagcca ataaactaca tgcatgaagg catcggaatc    2400
atcccaagat cccagagcag tctctatgct aatggcagca gctcctacca agatccccag    2460
cctgatcttt ttcgagggat gccacaagta tctcatgttt ccgggagat gatttcatct     2520 gaaagtggca gttttggaaa tcagtttgga cgacctgtcc atggagaccc cagggacctg    2580
tgtgatgcac aatcagtctt gtctgatcgc gtagctcagc agcttttgag ggaccataca    2640
aacttgcacc tttctctgga cctaaatcct ggttctccta tgctcacgcg cactaatgga    2700
atttaattca cattggttcc ctgagcagag caagttttg ggcaaagatc agatacctct     2760
caaaaagtgt cgaagtttgt tttgtcatca tatttatggc aaaggaacac caattgtacg    2820
ataggaatcc aaagctgaga atctgtcgaa taaatttgga tctttttgga gctgaagtggc   2880 agaaaagaga ttcggatgca gttcccttga taagatagat ggctttggat atccagcatt    2940
gagcagagtt gcagtaaaac gttttcacca gtgtaaagaa ctgtaaattc tatcacactt    3000
gcaaaacaga gaaattggaa agcacatatg gctattggac tcgggttatt ttatctatt     3060 ttacttttgg aggggttgca aaactactgt acagaagaag ggtcgggaac taaattagat    3120
tccagatttt gttgaggcgg caactgtaac ttgtaagttt gctaagcttg gtatgtttat    3180
tttgcatcag ttcttagcag tttgatttta accctcctca tcaactgccc acctgatatt    3240
gttgtaccta cattaatcga gaaatcgat aatttcaagt aatatttctg gat            3293

<210> SEQ ID NO 4
<211> LENGTH: 901
<212> TYPE: PRT
<213> ORGANISM: Vitis vinifera

<400> SEQUENCE: 4

Met Pro Ser Trp Trp Gly Lys Ser Ser Lys Glu Val Lys Lys
1               5                   10                  15

Glu Asn Arg Glu Ser Phe Ile Asp Ser Ile His Arg Lys Phe Arg Thr
                20                  25                  30

Val Ser Glu Glu Lys Cys Asn Asn Arg Ser Gly Ala Ser Gln Arg His
            35                  40                  45

Cys Gly Asp Thr Val Ser Glu Lys Glu Ser Arg Ser Arg Ala Gln Ser
        50                  55                  60

Arg Ser Pro Ser Pro Ser Thr Lys Val Ser Arg Cys Gln Ser Phe Ala
65                  70                  75                  80

Glu Arg Pro His Ala Gln Pro Leu Pro Leu Pro Gly Pro His Leu Thr
                85                  90                  95

Ser Val Val Arg Thr Asp Ser Gly Ile Asn Ala Ser Lys Lys Gln Gly
            100                 105                 110

Leu Val Glu Gly Ser Lys Thr Gln Met Val Leu Pro Leu Pro Arg Pro
        115                 120                 125

Gly Tyr Val Ala Asn Arg Leu Asp Pro Thr Ala Glu Gly Asp Leu
    130                 135                 140

Ala Thr Ala Ser Val Phe Ser Tyr Ser Ser Ile Asp Ser Glu Asp Pro
145                 150                 155                 160

Ser Glu Ser Arg Leu Leu Ser Pro Gln Ala Ser Asp Tyr Glu Asn Gly
```

```
            165                 170                 175
Asn Arg Thr Thr Met Asn Ser Pro Ser Ser Val Met His Lys Asp Gln
            180                 185                 190
Ser Pro Val Leu Thr Pro Arg Lys Pro Arg Glu Ala Leu Arg Pro Ala
            195                 200                 205
Asn Leu Leu Leu Asn Asn Gln Ile His Ser Thr Ser Pro Lys Trp Val
            210                 215                 220
Pro Leu Ser Thr His Val Pro Asn Phe Pro Val Pro Gln Asn Gly Ala
225                 230                 235                 240
Phe Cys Ser Ala Pro Asp Ser Ser Met Ser Ser Pro Ser Arg Ser Pro
                    245                 250                 255
Met Arg Leu Phe Ser Pro Glu Gln Val Met Asn Ser Ser Phe Trp Thr
                260                 265                 270
Gly Lys Pro Tyr Ala Asp Ile Ala Leu Leu Gly Ser Gly His Cys Ser
                275                 280                 285
Ser Pro Gly Ser Gly His Asn Ser Gly His Asn Ser Ile Gly Gly Asp
            290                 295                 300
Met Ser Gly Gln Leu Phe Trp Pro His Ser Arg Cys Ser Pro Glu Cys
305                 310                 315                 320
Ser Pro Ile Pro Ser Pro Arg Met Thr Ser Pro Gly Pro Ser Ser Arg
                    325                 330                 335
Ile Gln Ser Gly Ala Val Thr Pro Leu His Pro Arg Ala Gly Ala Ala
                340                 345                 350
Ala Ala Glu Ser Pro Thr Asn Arg Pro Asp Asp Gly Lys Gln Gln Ser
            355                 360                 365
His Arg Leu Pro Leu Pro Pro Ile Thr Ile Ser Asn Ser Cys Pro Phe
        370                 375                 380
Ser Pro Thr Tyr Ser Thr Ser Thr Thr Pro Ser Val Pro Arg Ser Pro
385                 390                 395                 400
Gly Arg Ala Glu Asn Pro Ile Ser Pro Gly Ser Arg Trp Lys Lys Gly
                    405                 410                 415
Arg Leu Leu Gly Arg Gly Thr Phe Gly His Val Tyr Leu Gly Phe Asn
                420                 425                 430
Ser Glu Ser Gly Glu Met Cys Ala Met Lys Glu Val Thr Leu Phe Ser
            435                 440                 445
Asp Asp Ala Lys Ser Lys Glu Ser Ala Gln Gln Leu Gly Gln Glu Ile
        450                 455                 460
Ser Leu Leu Ser Arg Leu Arg His Pro Asn Ile Val Gln Tyr Tyr Gly
465                 470                 475                 480
Ser Glu Thr Val Asp Asp Lys Leu Tyr Ile Tyr Leu Glu Tyr Val Ser
                    485                 490                 495
Gly Gly Ser Ile Tyr Lys Leu Leu Gln Glu Tyr Gly Leu Gly Leu Glu
                500                 505                 510
Ile Ala Ile Arg Ser Tyr Thr Gln Gln Ile Leu Ser Gly Leu Ala Tyr
            515                 520                 525
Leu His Ala Lys Asn Thr Val His Arg Asp Ile Lys Gly Ala Asn Ile
        530                 535                 540
Leu Val Asp Pro Asn Gly Arg Val Lys Leu Ala Asp Phe Gly Met Ala
545                 550                 555                 560
Lys His Ile Thr Gly Gln Ser Cys Pro Leu Ser Leu Lys Gly Ser Pro
                    565                 570                 575
Tyr Trp Met Ala Pro Glu Val Ile Lys Asn Ser Asn Gly Cys Asn Leu
                580                 585                 590
```

Ala Val Asp Leu Trp Ser Leu Gly Cys Thr Val Leu Glu Met Ala Thr
            595                 600                 605

Thr Lys Pro Pro Trp Ser Gln Tyr Glu Gly Val Ala Ala Met Phe Lys
    610                 615                 620

Ile Gly Asn Ser Lys Glu Leu Pro Thr Ile Pro Asp His Leu Ser Glu
625                 630                 635                 640

Glu Gly Lys Asp Phe Val Arg Gln Cys Leu Gln Arg Asn Pro Leu His
            645                 650                 655

Arg Pro Thr Ala Ala Trp Leu Leu Glu His Pro Phe Val Arg Asn Ala
        660                 665                 670

Ala Pro Leu Glu Arg Pro Ser Leu Ser Ser Glu Leu Glu Pro Pro
            675                 680                 685

Ala Val Thr Asn Ala Val Arg Ser Met Ala Ile Gly His Thr Arg Asn
    690                 695                 700

Val Leu Glu Ser Glu Gly Val Ala Ile His Gln Ser Arg Cys Ser Lys
705                 710                 715                 720

Thr Gly Ser Gly Ser Ser Asp Thr His Thr Pro Arg Asn Leu Ser Ser
            725                 730                 735

Pro Val Ser Pro Ile Gly Ser Pro Leu Leu His Ser Arg Ser Pro Gln
        740                 745                 750

His Met Ser Gly Arg Met Ser Pro Ser Pro Ile Ser Ser Pro Arg Thr
    755                 760                 765

Thr Ser Gly Ser Ser Thr Pro Leu Ser Gly Gly Ser Gly Ala Ile Pro
770                 775                 780

Phe His His Pro Lys Pro Ile Asn Tyr Met His Glu Gly Ile Gly Ile
785                 790                 795                 800

Ile Pro Arg Ser Gln Ser Ser Leu Tyr Ala Asn Gly Ser Ser Ser Tyr
            805                 810                 815

Gln Asp Pro Gln Pro Asp Leu Phe Arg Gly Met Pro Gln Val Ser His
        820                 825                 830

Val Phe Arg Glu Met Ile Ser Ser Glu Ser Gly Ser Phe Gly Asn Gln
    835                 840                 845

Phe Gly Arg Pro Val His Gly Asp Pro Arg Asp Leu Cys Asp Ala Gln
850                 855                 860

Ser Val Leu Ser Asp Arg Val Ala Gln Gln Leu Leu Arg Asp His Thr
865                 870                 875                 880

Asn Leu His Leu Ser Leu Asp Leu Asn Pro Gly Ser Pro Met Leu Thr
            885                 890                 895

Arg Thr Asn Gly Ile
            900

```
<210> SEQ ID NO 5
<211> LENGTH: 2679
<212> TYPE: DNA
<213> ORGANISM: Vitis vinifera
<220> FEATURE:
<221> NAME/KEY: source
<222> LOCATION: 1..2679
<223> OTHER INFORMATION: /mol_type="unassigned DNA"
      /organism="Vitis vinifera"

<400> SEQUENCE: 5
atgccttcat ggtggggaaa atcatcatcc aaagaagcaa agaagaaaac aaacaaggaa      60
agtttcatcg acacattaca tcgaaaattt aagattccat ctgaaggtaa ggtgagcaat     120
agatcaggag ggtctcatag acggtgcagt gatacaatat cagagaaggg atctcaatcc     180
```

```
cgagcagaat caagatcacc atcaccttcc aaactagtgt caagatgtca aagttttgtt    240
gaaaggccta atgcccaacc acttccactt cctggtcggc accctgcaag tgtgggtcgt    300
actgattctg gaatcagtat atcaacaaaa caaagactgg aaaaaggctc caagtcatcc    360
tttcttcctc tcccaagacc cagatgcatt gggggcagac ccgatcctac agatttagat    420
ggtgattttg ttgcttcagt ttatagcgaa ggttccactg atagtgaaga tgcagctgac    480
tcacatcatc gtagtcccca ggcaactgac tatgataatg ggactagaac tgctgcaagc    540
atattttcta gtgtaatgct caaggatcag tcacctgttg ctcatgtaaa cgcaagggag    600
gcacaaaaac cagctaatct tttgtttagt aatcatattt ccctacatc acctaaacgg     660 aggcctttaa gcagccatgt accaaattta caggtccctt atcatggtgc tttcggcagt    720
gctccagaca gctcaatgtc aagtccttca agaagtccat tgagagcatt tggcactgac    780
caaggtttga actctgcttt ctgggctggg aaaccttatt cagatgttac tttacttgga    840
tctggccaat gctccagtcc aggttcaggt cagaattctg ggcacaattc aatgggagga    900
gatatgtcag acagttgtt ttggcaaccc agcagggca gcccggagta ttctcctata      960
cctagtccca gaatgacaag ccctggtccc agctccagaa ttcatagtgg tgcagtcaca   1020
cctcttcatc ccagagctgg aggagcagcc tctgaatccc agacaagctg ccagatgag    1080 gggaaacaac aaagccaccg gttgcccctt cctcctgtag cagtttcttc ttcttcacct   1140
ttctctcatt caaattcacc agcagcatct ccctctgtcc cacgcagtcc aggaagagca   1200
gaggctccaa caagcccagg ctctcgctgg aaaaagggaa agttgctggg aagaggcaca   1260
tttggacatg tttatgttgg cttttaacagt gaaagtggtg aaatgtgtgc aatgaaggag   1320 gtgcacactat tttcagatga tgcaaagtca aggaaagtg caaaacagtt ggggcaagaa    1380
attgttctgc ttagccgctt atgccatcca aacattgtgc agtattatgg atctgaaacg   1440
gttggtgaca aactttatat atacttggag tatgtatctg gtggctccat ctataaactt   1500
cttcaagaat atggccaact tggtgaacta gcaattcgta gctataccca acaaatcttg   1560
tcagggctcg cctatttgca tgctaaaaat actgtccata gggatattaa aggggcaaat   1620
atacttgtag acccaagtgg tcgagtcaag ttagcagatt ttggaatggc aaagcatatc   1680
actgggcagt catgtccttt atcattcaag ggaagcccat actggatggc acctgaggtt   1740
ataaggaatt caaatggttg caaccttgct gtggatattt ggagtctagg gtgcacagtt   1800
ttggaaatgg ccacaacaaa accaccctgg agtcagtttg aaggggttgc tgcaatgttc   1860
aagattggga atagtaagga cctcccagca attcctgatc cctttcaga tgaaggtaag    1920 gattttgtaa ggcagtgctt gcaacgaaat ccactacatc gtccaacagc tgctcagctc   1980
ttggagcatc ctttcgtgaa aaatgctgca cctctggaaa gacctatttt gtcccctgaa   2040
acttcagatc cacctcctgg agttaccaat ggagtgaaat ctctgggaat cggacatgct   2100
aaaaatcttt catccttgga ttcagaaaga cttgcagttc attcgtttag agttttaaaa   2160
actggttccc attcaagtga tcctcatatt gcgaggaata tatcatgtcc tgtctctcct   2220
attgggagcc ctcttttgca ttcaaggtca cctcaacacc tgaatggaag aatgtctcct   2280
tctcctatat ccagtcctcg taccacttct ggcccatcca cgcctttgac aggtggcagt   2340
ggtgccattc catttcctca tctaaaacca tcagtttacc tgcaagaggg atttggaaac   2400
gtttctaagc ccctaaacaa tccctattcc aacggcccct cctatcatga tccaaatgcc   2460
gacatctttc gagggatgca gctagggtct cacatattcc cagaaagtga tgctcttgga   2520
```

```
aagcagtttg ggaggactgc tcatgtagaa ttgtatgatg ggcagtcagt cttagctgat    2580
cgcgtctctc ggcagctctt aagggatcaa gtgaagatga atccatctct ggatcttagt    2640
ccctcctcta tgttgcccag ccggaacact ggaatctaa                           2679

<210> SEQ ID NO 6
<211> LENGTH: 892
<212> TYPE: PRT
<213> ORGANISM: Vitis vinifera

<400> SEQUENCE: 6

Met Pro Ser Trp Trp Gly Lys Ser Ser Lys Glu Ala Lys Lys
1               5                   10                  15

Thr Asn Lys Glu Ser Phe Ile Asp Thr Leu His Arg Lys Phe Lys Ile
            20                  25                  30

Pro Ser Glu Gly Lys Val Ser Asn Arg Ser Gly Gly Ser His Arg Arg
        35                  40                  45

Cys Ser Asp Thr Ile Ser Glu Lys Gly Ser Gln Ser Arg Ala Glu Ser
    50                  55                  60

Arg Ser Pro Ser Pro Ser Lys Leu Val Ser Arg Cys Gln Ser Phe Val
65                  70                  75                  80

Glu Arg Pro Asn Ala Gln Pro Leu Pro Leu Pro Gly Arg His Pro Ala
                85                  90                  95

Ser Val Gly Arg Thr Asp Ser Gly Ile Ser Ile Ser Thr Lys Gln Arg
            100                 105                 110

Leu Glu Lys Gly Ser Lys Ser Ser Phe Leu Pro Leu Pro Arg Pro Arg
        115                 120                 125

Cys Ile Gly Gly Arg Pro Asp Pro Thr Asp Leu Asp Gly Asp Phe Val
    130                 135                 140

Ala Ser Val Tyr Ser Glu Gly Ser Thr Asp Ser Glu Asp Ala Ala Asp
145                 150                 155                 160

Ser His His Arg Ser Pro Gln Ala Thr Asp Tyr Asp Asn Gly Thr Arg
                165                 170                 175

Thr Ala Ala Ser Ile Phe Ser Ser Val Met Leu Lys Asp Gln Ser Pro
            180                 185                 190

Val Ala His Val Asn Ala Arg Glu Ala Gln Lys Pro Ala Asn Leu Leu
        195                 200                 205

Phe Ser Asn His Ile Ser Pro Thr Ser Pro Lys Arg Arg Pro Leu Ser
    210                 215                 220

Ser His Val Pro Asn Leu Gln Val Pro Tyr His Gly Ala Phe Gly Ser
225                 230                 235                 240

Ala Pro Asp Ser Ser Met Ser Ser Pro Ser Arg Ser Pro Leu Arg Ala
                245                 250                 255

Phe Gly Thr Asp Gln Gly Leu Asn Ser Ala Phe Trp Ala Gly Lys Pro
            260                 265                 270

Tyr Ser Asp Val Thr Leu Leu Gly Ser Gly Gln Cys Ser Ser Pro Gly
        275                 280                 285

Ser Gly Gln Asn Ser Gly His Asn Ser Met Gly Gly Asp Met Ser Gly
    290                 295                 300

Gln Leu Phe Trp Gln Pro Ser Arg Gly Ser Pro Glu Tyr Ser Pro Ile
305                 310                 315                 320

Pro Ser Pro Arg Met Thr Ser Pro Gly Pro Ser Ser Arg Ile His Ser
                325                 330                 335

Gly Ala Val Thr Pro Leu His Pro Arg Ala Gly Gly Ala Ala Ser Glu
            340                 345                 350
```

-continued

Ser Gln Thr Ser Trp Pro Asp Glu Gly Lys Gln Gln Ser His Arg Leu
    355                 360                 365

Pro Leu Pro Pro Val Ala Val Ser Ser Ser Pro Phe Ser His Ser
370             375                 380

Asn Ser Pro Ala Ala Ser Pro Ser Val Pro Arg Ser Pro Gly Arg Ala
385                 390                 395                 400

Glu Ala Pro Thr Ser Pro Gly Ser Arg Trp Lys Lys Gly Lys Leu Leu
            405                 410                 415

Gly Arg Gly Thr Phe Gly His Val Tyr Val Gly Phe Asn Ser Glu Ser
            420                 425                 430

Gly Glu Met Cys Ala Met Lys Glu Val Thr Leu Phe Ser Asp Asp Ala
        435                 440                 445

Lys Ser Lys Glu Ser Ala Lys Gln Leu Gly Gln Glu Ile Val Leu Leu
450                 455                 460

Ser Arg Leu Cys His Pro Asn Ile Val Gln Tyr Tyr Gly Ser Glu Thr
465                 470                 475                 480

Val Gly Asp Lys Leu Tyr Ile Tyr Leu Glu Tyr Val Ser Gly Gly Ser
                485                 490                 495

Ile Tyr Lys Leu Leu Gln Glu Tyr Gly Gln Leu Gly Glu Leu Ala Ile
            500                 505                 510

Arg Ser Tyr Thr Gln Gln Ile Leu Ser Gly Leu Ala Tyr Leu His Ala
            515                 520                 525

Lys Asn Thr Val His Arg Asp Ile Lys Gly Ala Asn Ile Leu Val Asp
    530                 535                 540

Pro Ser Gly Arg Val Lys Leu Ala Asp Phe Gly Met Ala Lys His Ile
545                 550                 555                 560

Thr Gly Gln Ser Cys Pro Leu Ser Phe Lys Gly Ser Pro Tyr Trp Met
                565                 570                 575

Ala Pro Glu Val Ile Arg Asn Ser Asn Gly Cys Asn Leu Ala Val Asp
            580                 585                 590

Ile Trp Ser Leu Gly Cys Thr Val Leu Glu Met Ala Thr Thr Lys Pro
    595                 600                 605

Pro Trp Ser Gln Phe Glu Gly Val Ala Ala Met Phe Lys Ile Gly Asn
    610                 615                 620

Ser Lys Asp Leu Pro Ala Ile Pro Asp His Leu Ser Asp Glu Gly Lys
625                 630                 635                 640

Asp Phe Val Arg Gln Cys Leu Gln Arg Asn Pro Leu His Arg Pro Thr
                645                 650                 655

Ala Ala Gln Leu Leu Glu His Pro Phe Val Lys Asn Ala Ala Pro Leu
            660                 665                 670

Glu Arg Pro Ile Leu Ser Pro Glu Thr Ser Asp Pro Pro Gly Val
            675                 680                 685

Thr Asn Gly Val Lys Ser Leu Gly Ile Gly His Ala Lys Asn Leu Ser
    690                 695                 700

Ser Leu Asp Ser Glu Arg Leu Ala Val His Ser Phe Arg Val Leu Lys
705                 710                 715                 720

Thr Gly Ser His Ser Ser Asp Pro His Ile Ala Arg Asn Ile Ser Cys
                725                 730                 735

Pro Val Ser Pro Ile Gly Ser Pro Leu Leu His Ser Arg Ser Pro Gln
            740                 745                 750

His Leu Asn Gly Arg Met Ser Pro Ser Pro Ile Ser Ser Pro Arg Thr
    755                 760                 765

```
Thr Ser Gly Pro Ser Thr Pro Leu Thr Gly Gly Ser Gly Ala Ile Pro
        770                 775                 780

Phe Pro His Leu Lys Pro Ser Val Tyr Leu Gln Glu Gly Phe Gly Asn
785                 790                 795                 800

Val Ser Lys Pro Leu Asn Asn Pro Tyr Ser Asn Gly Pro Ser Tyr His
                805                 810                 815

Asp Pro Asn Ala Asp Ile Phe Arg Gly Met Gln Leu Gly Ser His Ile
                820                 825                 830

Phe Pro Glu Ser Asp Ala Leu Gly Lys Gln Phe Gly Arg Thr Ala His
                835                 840                 845

Val Glu Leu Tyr Asp Gly Gln Ser Val Leu Ala Asp Arg Val Ser Arg
850                 855                 860

Gln Leu Leu Arg Asp Gln Val Lys Met Asn Pro Ser Leu Asp Leu Ser
865                 870                 875                 880

Pro Ser Ser Met Leu Pro Ser Arg Asn Thr Gly Ile
                885                 890
```

<210> SEQ ID NO 7
<211> LENGTH: 1000
<212> TYPE: DNA
<213> ORGANISM: Vitis vinifera
<220> FEATURE:
<221> NAME/KEY: source
<222> LOCATION: 1..1000
<223> OTHER INFORMATION: /mol_type="unassigned DNA"
      /organism="Vitis vinifera"

<400> SEQUENCE: 7

```
atgccttcat ggtggggaaa atcatcatcc aaagaagcaa agaagaaaac aaacaaggaa      60
agtttcatcg acacattaca tcgaaaattt aagattccat ctgaaggtaa ggtgagcaat     120
agatcaggag ggtctcatag acggtgcagt gatacaatat cagagaaggg atctcaatcc     180
cgagcagaat caagatcacc atcaccttcc aaactagtgt caagatgtca agttttgtt      240
gaaaggccta atgcccaacc acttccactt cctggtcggc accctgcaag tgtgggtcgt     300
actgattctg gaatcagtat atcaacaaaa caaagactgg aaaaaggctc caagtcatcc     360
tttcttcctc tcccaagacc cagatgcatt gggggcagac ccgatcctac agatttagat     420
ggtgattttg ttgcttcagt ttatagcgaa ggttccactg atagtgaaga tgcagctgac     480
tcacatcatc gtagtcccca ggcaactgac tatgataatg ggactagaac tgctgcaagc     540
atattttcta gtgtaatgct caaggatcag tcacctgttg ctcatgtaaa cgcaagggag     600
gcacaaaaac cagctaatct tttgtttagt aatcatattt ccccctacatc acctaaacgg     660
aggcctttaa gcagccatgt accaaattta caggtccctt atcatggtgc tttcggcagt     720
gctccagaca gctcaatgtc aagtccttca agaagtccat tgagagcatt tggcactgac     780
caaggtttga actctgcttt ctgggctggg aaaccttatt cagatgttac tttacttgga     840
tctggccaat gctccagtcc aggttcaggt cagaattctg ggcacaattc aatggagga      900
gatatgtcag acagttgtt ttggcaaccc agcagggggca gcccggagta ttctcctata     960
cctagtccca gaatgacaag ccctggtccc agctccagaa                           1000
```

<210> SEQ ID NO 8
<211> LENGTH: 919
<212> TYPE: PRT
<213> ORGANISM: Vitis vinifera

<400> SEQUENCE: 8

```
Met Pro Ser Trp Trp Gly Lys Ser Ser Lys Glu Ala Lys Lys Lys
1               5                   10                  15

Thr Asn Lys Glu Ser Phe Ile Asp Thr Leu His Arg Lys Phe Lys Ile
            20                  25                  30

Pro Ser Glu Gly Lys Val Ser Asn Arg Ser Gly Gly Ser His Arg Arg
            35                  40                  45

Cys Ser Asp Thr Ile Ser Glu Lys Gly Ser Gln Ser Arg Ala Glu Ser
50                  55                  60

Arg Ser Pro Ser Pro Ser Lys Leu Val Ser Arg Cys Gln Ser Phe Val
65                  70                  75                  80

Glu Arg Pro Asn Ala Gln Pro Leu Pro Leu Pro Gly Arg His Pro Ala
                85                  90                  95

Ser Val Gly Arg Thr Asp Ser Gly Ile Ser Ile Ser Thr Lys Gln Arg
                100                 105                 110

Leu Glu Lys Gly Ser Lys Ser Ser Phe Leu Pro Leu Pro Arg Pro Arg
            115                 120                 125

Cys Ile Gly Gly Arg Pro Asp Pro Thr Asp Leu Asp Gly Asp Phe Val
            130                 135                 140

Ala Ser Val Tyr Ser Glu Gly Ser Thr Asp Ser Glu Asp Ala Ala Asp
145                 150                 155                 160

Ser His His Arg Ser Pro Gln Ala Thr Asp Tyr Asp Asn Gly Thr Arg
                165                 170                 175

Thr Ala Ala Ser Ile Phe Ser Ser Val Met Leu Lys Asp Gln Ser Pro
                180                 185                 190

Val Ala His Val Asn Ala Arg Glu Ala Gln Lys Pro Ala Asn Leu Leu
                195                 200                 205

Phe Ser Asn His Ile Ser Pro Thr Ser Pro Lys Arg Arg Pro Leu Ser
210                 215                 220

Ser His Val Pro Asn Leu Gln Val Pro Tyr His Gly Ala Phe Gly Ser
225                 230                 235                 240

Ala Pro Asp Ser Ser Met Ser Ser Pro Ser Arg Ser Pro Leu Arg Ala
                245                 250                 255

Phe Gly Thr Asp Gln Gly Leu Asn Ser Ala Phe Trp Ala Gly Lys Pro
                260                 265                 270

Tyr Ser Asp Val Thr Leu Leu Gly Ser Gly Gln Cys Ser Ser Pro Gly
                275                 280                 285

Ser Gly Gln Asn Ser Gly His Asn Ser Met Gly Gly Asp Met Ser Gly
                290                 295                 300

Gln Leu Phe Trp Gln Pro Ser Arg Gly Ser Pro Glu Tyr Ser Pro Ile
305                 310                 315                 320

Pro Ser Pro Arg Met Thr Ser Pro Gly Pro Ser Ser Arg Ile His Ser
                325                 330                 335

Gly Ala Val Thr Pro Leu His Pro Arg Ala Gly Gly Ala Ala Ser Glu
                340                 345                 350

Ser Gln Thr Ser Trp Pro Asp Glu Gly Lys Gln Ser His Arg Leu
                355                 360                 365

Pro Leu Pro Pro Val Ala Val Ser Ser Ser Pro Phe Ser His Ser
370                 375                 380

Asn Ser Pro Ala Ala Ser Pro Ser Val Pro Arg Ser Pro Gly Arg Ala
385                 390                 395                 400

Glu Ala Pro Thr Ser Pro Gly Ser Arg Trp Lys Lys Gly Lys Leu Leu
                405                 410                 415

Gly Arg Gly Thr Phe Gly His Val Tyr Val Gly Phe Asn Ser Glu Ser
```

-continued

```
                420              425              430
Gly Glu Met Cys Ala Met Lys Glu Val Thr Leu Phe Ser Asp Ala
            435              440              445
Lys Ser Lys Glu Ser Ala Lys Gln Leu Gly Gln Glu Ile Val Leu Leu
        450              455              460
Ser Arg Leu Cys His Pro Asn Ile Val Gln Tyr Tyr Gly Ser Glu Thr
465              470              475              480
Val Gly Asp Lys Leu Tyr Ile Tyr Leu Glu Tyr Val Ser Gly Gly Ser
                485              490              495
Ile Tyr Lys Leu Leu Gln Glu Tyr Gly Gln Leu Gly Glu Leu Ala Ile
            500              505              510
Arg Ser Tyr Thr Gln Gln Ile Leu Ser Gly Leu Ala Tyr Leu His Ala
        515              520              525
Lys Asn Thr Val His Arg Asp Ile Lys Gly Ala Asn Ile Leu Val Asp
530              535              540
Pro Ser Gly Arg Val Lys Leu Ala Asp Phe Gly Met Ala Lys His Ile
545              550              555              560
Thr Gly Gln Ser Cys Pro Leu Ser Phe Lys Gly Ser Pro Tyr Trp Met
                565              570              575
Ala Pro Glu Leu Phe Ala Gln Val Ile Arg Asn Ser Asn Gly Cys Asn
            580              585              590
Leu Ala Val Asp Ile Trp Ser Leu Gly Cys Thr Val Leu Glu Met Ala
        595              600              605
Thr Thr Lys Pro Pro Trp Ser Gln Phe Glu Gly Val Ala Ala Met Phe
    610              615              620
Lys Ile Gly Asn Ser Lys Asp Leu Pro Ala Ile Pro Asp His Leu Ser
625              630              635              640
Asp Glu Gly Lys Asp Phe Val Arg Gln Cys Leu Gln Arg Asn Pro Leu
                645              650              655
His Arg Pro Thr Ala Ala Gln Leu Leu Glu His Pro Phe Val Lys Asn
            660              665              670
Ala Ala Pro Leu Glu Arg Pro Ile Leu Ser Pro Glu Thr Ser Asp Pro
        675              680              685
Pro Pro Gly Val Thr Asn Gly Val Lys Ser Leu Gly Ile Gly His Ala
    690              695              700
Lys Asn Leu Ser Ser Leu Asp Ser Glu Arg Leu Ala Val His Ser Phe
705              710              715              720
Arg Val Leu Lys Thr Gly Ser His Ser Ser Asp Pro His Ile Ala Arg
                725              730              735
Asn Ile Ser Cys Pro Val Ser Pro Ile Gly Ser Pro Leu Leu His Ser
            740              745              750
Arg Ser Pro Gln His Leu Asn Gly Arg Met Ser Pro Ser Pro Ile Ser
        755              760              765
Ser Pro Arg Thr Thr Ser Gly Pro Ser Thr Pro Leu Thr Gly Gly Ser
    770              775              780
Gly Ala Ile Pro Phe Pro His Leu Lys Pro Ser Val Tyr Leu Gln Glu
785              790              795              800
Gly Phe Gly Asn Val Ser Lys Pro Leu Asn Asn Pro Tyr Ser Asn Gly
                805              810              815
Pro Ser Tyr His Asp Pro Asn Ala Asp Ile Phe Arg Gly Met Gln Leu
            820              825              830
Gly Ser His Ile Phe Pro Glu Ser Asp Ala Leu Gly Lys Gln Phe Gly
        835              840              845
```

```
Arg Thr Ala His Val Glu Leu Tyr Asp Gly Gln Ser Val Leu Ala Asp
        850                 855                 860

Arg Val Ser Arg Gln Leu Leu Arg Asp Gln Asp Gln Phe Ile Arg Gln
865                 870                 875                 880

Ile Val Cys Asn Lys Asp Pro Lys Leu Lys Leu Trp Asn Lys Leu Asp
                885                 890                 895

Phe Trp Lys Lys Met Trp Trp Lys Thr Tyr Arg Arg Ser Trp Ile Leu
            900                 905                 910

Val Ser Met Val Met Val Phe
        915

<210> SEQ ID NO 9
<211> LENGTH: 2703
<212> TYPE: DNA
<213> ORGANISM: Populus trichocarpa
<220> FEATURE:
<221> NAME/KEY: source
<222> LOCATION: 1..2703
<223> OTHER INFORMATION: /mol_type="unassigned DNA"
      /organism="Populus trichocarpa"

<400> SEQUENCE: 9
atgcggtcat ggtggggaa gtcttcatcc aaagaggaaa agaagaaagc aaacaaggaa      60
agtttcattg atacaataaa taggaaattt aagattacat caaggaaaaa gagcaacaat    120
agatcaggag gatctcggag atgttgtaaa gatactcttt cagaaagggt ttctttgtcc    180
cgcgttccat caagatcacc atctccctcc acacacgtat cacgttgtca agttttttgct   240 gaaaggcctc aggctcaacc acttccactt ccacttccag gggtgcctca tactaaaatt    300
gggcgctgtg attctggaat tagtgcttca gtgaaaccag gattggatgg aggggggcaaa  360 ccattgcatc ttttgccccct accgagacca ggacatgtcc ttaatagact ggaccaagca   420
gatacagcag gggatttagc cactgcctct gtgtccagtg atagctccat agatagtgat    480
gatctgcctg actcgcgtgt ccttagccct ctcacgtcgg actatgaaaa tgggaacaga   540
actgctgtga acagccctcc aagcgtgatg cgacaggatc aatcccctat cataaataga   600
aagaactcaa gagaaactct gaaacatgct aatttacctg caataatca gaccttgtct    660 acaccaccaa acgggcaat ttttagctct caagtgcaaa atttacagat tcctcatcga     720
gtagcattct ttagtgctcc agacagctca atgtcaagtc cttctagaag cccaatgaga   780
gcatttggca ctgagcaagt tatcaacaat ggtttctggg caggaaaaaac ttactcagat   840 attggtttac taggatctgg acagtgctca agtccaggtt caggctataa ttctgggcag    900
aactcaatag gtggagatat gtcaggacag cttctttggc caaacagtag atgcagccct    960
gagtgttctc cattacctag ccccagagtg attagcccag gtcccagctc cagaatacac    1020
agtggtgctg tcactcctct gcacccacga gctgctgggg ttaccataga gtcgcctaca   1080
agccggccag atgatggaaa gcaacaaagt caccgcttgc cccttccacc gataacaatc   1140
tccaacaccc atcccttttc tcctacctat tctgcctcaa catctccttc agtgcctcga    1200
agtcctagta ggatggagaa cccaacaagt tctggtacac gctggcagaa gggtcgtatg   1260
cttgggagag gcagttttgg agatgtatat ctcgggttta acagaaaag aggtgagatg    1320 tgtgcaatga aggaggtaac tctatttttca gatgatgcaa aatcaaagga agcgcacag   1380 cagctgggac aggaaattgg gcttctgagt cgcttacgtc atcctaatat agtgcagtac    1440
tatggatctg aaacggtgga tgacaaatta tatatatact tggagtatgt gtctggtggc   1500
```

-continued

| | |
|---|---|
| tccatctata aactgcttca agaatatggc caatttggtg aaatagctat tcgtagctat | 1560 |
| actcaacaaa tcctgcgtgg gcttgcttat ttgcatgcta aaaaaactgt ccacagagac | 1620 |
| attaaagggg ctaatattct ggtggatccc acgggtcgtg ttaaactggc agattttggg | 1680 |
| atggcaaagc atatctctgg gcagtcttgt ccattatcat tcaaaggaag cccttactgg | 1740 |
| atggcacctg aggtgataaa aaattcaaat ggttgtaatc ttgctgttga tatatggagc | 1800 |
| cttgggtgca ctgttttgga gatggcaaca acaaaaccac cttggagcca atatgaaggg | 1860 |
| gttcctgcta tgtttaagat tggaaatagc aaggaacttc agagattcc tgataatctg | 1920 |
| tcagatgatg aaaggactt tgtgaggcag tgtttgcaac ggaacctatc acatcgccct | 1980 |
| acagctgctc aacttttgga gcacccttt gtgaaaaatg ttgctccgat ggagaggccg | 2040 |
| ttttgtccc cagagctttc agaagaactg cctgcaatta tgaattcagg aagatcaatg | 2100 |
| ggaattggac ctgcaagaaa tgtttcaggc tttgactcag aagggatttc tatgcatcaa | 2160 |
| tctagagcca caaaattgg ttcaggatc agtgatgccc atatgaagaa ctcatcatgc | 2220 |
| ccagtgtctc ctatcgggag ccctcatcta tattcaagat ccccgctgaa tttgagtgga | 2280 |
| aggatgtctc catctcctat atctagccct catactgcat ctggttcatc cacgcctctc | 2340 |
| actggtggtt gtggtgccat cccatttcat catgcaaagc agcacataat gtacttgcaa | 2400 |
| gaaagcaagg gaatggtccc tgggtcccaa agtagtttct atcccaataa caacaacctt | 2460 |
| tatcaggaac caaagcctga cctatttcga ggtatgtcac aagcctcttg tgttttccgg | 2520 |
| gaaataattt catcagaaaa cagcaatcct ggaaatcagt gggatggcc tgaactctat | 2580 |
| gatgggcacc ctgttttagc tgatcgtgtg tcccagcagc tcttaaggga tcatatgaaa | 2640 |
| ttgaagccat ccctggacct gaatccaaac tcgtcaattc gtggccgtac caatggaatc | 2700 |
| taa | 2703 |

<210> SEQ ID NO 10
<211> LENGTH: 900
<212> TYPE: PRT
<213> ORGANISM: Populus trichocarpa

<400> SEQUENCE: 10

Met Arg Ser Trp Trp Gly Lys Ser Ser Lys Glu Glu Lys Lys Lys
1               5                   10                  15

Ala Asn Lys Glu Ser Phe Ile Asp Thr Ile Asn Arg Lys Phe Lys Ile
            20                  25                  30

Thr Ser Lys Glu Lys Ser Asn Asn Arg Ser Gly Gly Ser Arg Arg Cys
        35                  40                  45

Cys Lys Asp Thr Leu Ser Glu Arg Val Ser Leu Ser Arg Val Pro Ser
    50                  55                  60

Arg Ser Pro Ser Pro Ser Thr His Val Ser Arg Cys Gln Ser Phe Ala
65                  70                  75                  80

Glu Arg Pro Gln Ala Gln Pro Leu Pro Leu Pro Leu Pro Gly Val Pro
                85                  90                  95

His Thr Lys Ile Gly Arg Cys Asp Ser Gly Ile Ser Ala Ser Val Lys
            100                 105                 110

Pro Gly Leu Asp Gly Gly Gly Lys Pro Leu His Leu Leu Pro Leu Pro
        115                 120                 125

Arg Pro Gly His Val Leu Asn Arg Leu Asp Gln Ala Asp Thr Ala Gly
    130                 135                 140

Asp Leu Ala Thr Ala Ser Val Ser Ser Asp Ser Ser Ile Asp Ser Asp
145                 150                 155                 160

-continued

Asp Leu Pro Asp Ser Arg Val Leu Ser Pro Leu Thr Ser Asp Tyr Glu
                165                 170                 175

Asn Gly Asn Arg Thr Ala Val Asn Ser Pro Pro Ser Val Met Arg Gln
            180                 185                 190

Asp Gln Ser Pro Ile Ile Asn Arg Lys Asn Ser Arg Glu Thr Leu Lys
            195                 200                 205

His Ala Asn Leu Pro Ala Asn Asn Gln Thr Leu Ser Thr Pro Pro Lys
    210                 215                 220

Arg Ala Ile Phe Ser Ser Gln Val Gln Asn Leu Gln Ile Pro His Arg
225                 230                 235                 240

Val Ala Phe Phe Ser Ala Pro Asp Ser Ser Met Ser Ser Pro Ser Arg
                245                 250                 255

Ser Pro Met Arg Ala Phe Gly Thr Glu Gln Val Ile Asn Asn Gly Phe
                260                 265                 270

Trp Ala Gly Lys Thr Tyr Ser Asp Ile Gly Leu Leu Gly Ser Gly Gln
                275                 280                 285

Cys Ser Ser Pro Gly Ser Gly Tyr Asn Ser Gly Gln Asn Ser Ile Gly
            290                 295                 300

Gly Asp Met Ser Gly Gln Leu Leu Trp Pro Asn Ser Arg Cys Ser Pro
305                 310                 315                 320

Glu Cys Ser Pro Leu Pro Ser Pro Arg Val Ile Ser Pro Gly Pro Ser
                325                 330                 335

Ser Arg Ile His Ser Gly Ala Val Thr Pro Leu His Pro Arg Ala Ala
            340                 345                 350

Gly Val Thr Ile Glu Ser Pro Thr Ser Arg Pro Asp Asp Gly Lys Gln
            355                 360                 365

Gln Ser His Arg Leu Pro Leu Pro Pro Ile Thr Ile Ser Asn Thr His
    370                 375                 380

Pro Phe Ser Pro Thr Tyr Ser Ala Ser Thr Ser Pro Ser Val Pro Arg
385                 390                 395                 400

Ser Pro Ser Arg Met Glu Asn Pro Thr Ser Ser Gly Thr Arg Trp Gln
                405                 410                 415

Lys Gly Arg Met Leu Gly Arg Gly Ser Phe Gly Asp Val Tyr Leu Gly
            420                 425                 430

Phe Asn Arg Glu Arg Gly Glu Met Cys Ala Met Lys Glu Val Thr Leu
    435                 440                 445

Phe Ser Asp Asp Ala Lys Ser Lys Glu Ser Ala Gln Gln Leu Gly Gln
450                 455                 460

Glu Ile Gly Leu Leu Ser Arg Leu Arg His Pro Asn Ile Val Gln Tyr
465                 470                 475                 480

Tyr Gly Ser Glu Thr Val Asp Asp Lys Leu Tyr Ile Tyr Leu Glu Tyr
                485                 490                 495

Val Ser Gly Gly Ser Ile Tyr Lys Leu Leu Gln Glu Tyr Gly Gln Phe
            500                 505                 510

Gly Glu Ile Ala Ile Arg Ser Tyr Thr Gln Gln Ile Leu Arg Gly Leu
    515                 520                 525

Ala Tyr Leu His Ala Lys Lys Thr Val His Arg Asp Ile Lys Gly Ala
    530                 535                 540

Asn Ile Leu Val Asp Pro Thr Gly Arg Val Lys Leu Ala Asp Phe Gly
545                 550                 555                 560

Met Ala Lys His Ile Ser Gly Gln Ser Cys Pro Leu Ser Phe Lys Gly
                565                 570                 575

Ser Pro Tyr Trp Met Ala Pro Glu Val Ile Lys Asn Ser Asn Gly Cys
        580                 585                 590

Asn Leu Ala Val Asp Ile Trp Ser Leu Gly Cys Thr Val Leu Glu Met
    595                 600                 605

Ala Thr Thr Lys Pro Pro Trp Ser Gln Tyr Glu Gly Val Pro Ala Met
610                 615                 620

Phe Lys Ile Gly Asn Ser Lys Glu Leu Pro Glu Ile Pro Asp Asn Leu
625                 630                 635                 640

Ser Asp Asp Gly Lys Asp Phe Val Arg Gln Cys Leu Gln Arg Asn Leu
                645                 650                 655

Ser His Arg Pro Thr Ala Ala Gln Leu Leu Glu His Pro Phe Val Lys
            660                 665                 670

Asn Val Ala Pro Met Glu Arg Pro Phe Leu Ser Pro Glu Leu Ser Glu
        675                 680                 685

Glu Leu Pro Ala Ile Met Asn Ser Gly Arg Ser Met Gly Ile Gly Pro
    690                 695                 700

Ala Arg Asn Val Ser Gly Phe Asp Ser Glu Gly Ile Ser Met His Gln
705                 710                 715                 720

Ser Arg Ala Thr Lys Ile Gly Ser Gly Ile Ser Asp Ala His Met Lys
                725                 730                 735

Asn Ser Ser Cys Pro Val Ser Pro Ile Gly Ser Pro His Leu Tyr Ser
            740                 745                 750

Arg Ser Pro Leu Asn Leu Ser Gly Arg Met Ser Pro Ser Pro Ile Ser
        755                 760                 765

Ser Pro His Thr Ala Ser Gly Ser Ser Thr Pro Leu Thr Gly Gly Cys
    770                 775                 780

Gly Ala Ile Pro Phe His His Ala Lys Gln His Ile Met Tyr Leu Gln
785                 790                 795                 800

Glu Ser Lys Gly Met Val Pro Gly Ser Gln Ser Ser Phe Tyr Pro Asn
                805                 810                 815

Asn Asn Asn Leu Tyr Gln Glu Pro Lys Pro Asp Leu Phe Arg Gly Met
            820                 825                 830

Ser Gln Ala Ser Cys Val Phe Arg Glu Ile Ile Ser Ser Glu Asn Ser
        835                 840                 845

Asn Pro Gly Asn Gln Leu Gly Trp Pro Glu Leu Tyr Asp Gly His Pro
    850                 855                 860

Val Leu Ala Asp Arg Val Ser Gln Gln Leu Leu Arg Asp His Met Lys
865                 870                 875                 880

Leu Lys Pro Ser Leu Asp Leu Asn Pro Asn Ser Ser Ile Arg Gly Arg
                885                 890                 895

Thr Asn Gly Ile
        900

<210> SEQ ID NO 11
<211> LENGTH: 2709
<212> TYPE: DNA
<213> ORGANISM: Populus trichocarpa
<220> FEATURE:
<221> NAME/KEY: source
<222> LOCATION: 1..2709
<223> OTHER INFORMATION: /mol_type="unassigned DNA"
      /organism="Populus trichocarpa"

<400> SEQUENCE: 11
atgccttcat ggtgggaaa gtcatcatct aaagaagtga agaagaaagc aaacaaggaa      60
agttttattg atacattaca cagaagattt aagagtccat ctgatggtaa gctaaatggt     120

```
agacctggag gttctcgaag acgctgcagt gacactatct cagagagggg atctcaatct      180
cgagcagaat caagatcacc atcaccatca ccttcatcaa acatgtttc taggtgtcaa       240 agttttgctg agaggcccca tgcccaacca cttccccttc ctggtgtgca ccctgcaagt      300
gtggggcgta cagactctgg aattggtata tcaacaaaac caagattgca aaagggtgca     360
aagtcatcat tgttttgcc tctcccaaga cctggatgca tgcgcaataa gtcgaatcca     420
acagatttag atggggattt ggccactact tcagttttca gtgagagctc cactgatagt      480
gaagatcctg ctgactcaag tcatcgtagt cctctggcaa ctgactatga ccttgggacc     540
agaactattg ctagcagccc ttccagtgca atggtcaagg atcactgtgc taccgtcagc     600
caagtgaact caagagaggc aaagaaacca gctaaccttt cttttggtaa tcatacctcc     660
ccaacatcac ctaaacggag acctataagc agtcatgtgc cgaatctaca ggttccaaaa    720
catggttctt tctgcagtgc tccagacagc tacatgtcaa gtccttccag aagtcctatg    780
agagcatttg gcgctgagca agtcataaac tccgctttct gggctgggaa gccatacccca   840 gacgtcaatt tactaggatc tggccactgc tccagccctg gttcaggtta caattctgga    900
cataattcaa tgggagggga tatgtcagga caattattct ggcaacaaag caggggtagc    960
cctgaatgtt ctccaatacc tagtcctaga atgaccagtc ctggcccag ctccagagtc    1020 cagagcggtg ctgttactcc aattcatcct agagcaggag ggacaatcga gtcccagaca    1080
agctggccag atgatgggaa acaacaaagt caccggctac ccctcccctcc tgtaacagtt    1140 tccagcccct ctcccttttc tcattcaaac tcggcagcag catctccttc tgtgccacga    1200
agtccaggaa gggcagagaa cccaacaagc cctggatctc gctggaaaaa aggaaagctg    1260
ctaggtagag gcacatttgg acatgtctat cttggattta acagtgaaag tggtgaaatg    1320
tgtgcaatga aggaggtgac attgttttca gatgatgcca agtcaaaaga aagtgctaag    1380
cagttgatgc aggaaattc tcttttaagc cgctttcagc acccaaacat tgtgcagtac    1440 tatgatctg agacggttgg tgaccgactt tatatatact tggagtatgt atctggcggg    1500
tccatatata aacttctcca ggagtatggc cagttgggcg agctagttat tcgcagttat    1560
acccagcaaa tcttgtcagg acttgcattt ttgcattcta aaagcactgt ccatagagat    1620
atcaaaggag caaacatact tgtagatccg aatggtcgtg ttaaattagc tgattttggc    1680
atggcaaaac atatcaccgg acagtcatgt ccactatcat tcaagggaag cccttattgg    1740 atggccctg aggttataaa gaactcaaat ggctgtaatc ttgctgtgga tatatggagt    1800 cttgatgca ctgttttgga gatggctact acaaaaccac cttggagcca gtttgaaggg    1860
gttgctgcca tgtttaaaat tggaaatagc aaggatctcc cagaaattcc agaggacctc    1920
tcggatgaag ggaaggactt tgttaggcaa tgtttgcaac gcaatccagt acatcgtcct    1980
acagcttccc agcttttaga gcatccttttt gtaaaattag ctgcgccttt ggaaagacct    2040
attctgtgcc ttgatcctac agatccaccc cctggggttt caaatggagt taaaattctg    2100
ggcattaatc atgcaagaaa tttccccacc ttggattcag agaggcttgc agttcattca    2160
tctagagttt caaaaactgg tctacatacc agtgatttac acattccaag gaacatatca    2220
tgccctgttt ctcccattgg aagccctctt ttgcattcaa ggtcgccaca acatctgaat    2280
ggaagaatgt ctccttcacc catagctagc ccacggacca cttctggctc atccacacct    2340
ctgacaggtt gcactggtgc tataccttttt aatcacttga agcattcagt tcacttccaa    2400
gagggttttg gaaacatgca aaatcactca aatggtatat atgtcaatgg cttggcttat    2460
```

```
catgattcca gtcctgatct ttttcgagga atgcagccag gttctcccat cttctcagag   2520
ctggttccat gtgaaaatga tctcatagga aagcagcttg gaaggcctac tcaagggaa    2580 ccttatgatg gacaatcagt gttggctgat cgagtgtctc ggcagctttt gagggatcat   2640
gtgaaaatga aaccatccct ggatctaagt cccaactctc ctttacccag tcgaactgga   2700
ggtatataa                                                           2709
```

<210> SEQ ID NO 12
<211> LENGTH: 902
<212> TYPE: PRT
<213> ORGANISM: Populus trichocarpa

<400> SEQUENCE: 12

```
Met Pro Ser Trp Trp Gly Lys Ser Ser Lys Glu Val Lys Lys
1               5                   10                  15

Ala Asn Lys Glu Ser Phe Ile Asp Thr Leu His Arg Arg Phe Lys Ser
            20                  25                  30

Pro Ser Asp Gly Lys Leu Asn Gly Arg Pro Gly Gly Ser Arg Arg
        35                  40                  45

Cys Ser Asp Thr Ile Ser Glu Arg Gly Ser Gln Ser Arg Ala Glu Ser
    50                  55                  60

Arg Ser Pro Ser Pro Ser Ser Lys His Val Ser Arg Cys Gln
65                  70                  75                  80

Ser Phe Ala Glu Arg Pro His Ala Gln Pro Leu Pro Leu Pro Gly Val
                85                  90                  95

His Pro Ala Ser Val Gly Arg Thr Asp Ser Gly Ile Gly Ile Ser Thr
            100                 105                 110

Lys Pro Arg Leu Gln Lys Gly Ala Lys Ser Ser Leu Phe Leu Pro Leu
        115                 120                 125

Pro Arg Pro Gly Cys Met Arg Asn Lys Ser Asn Pro Thr Asp Leu Asp
    130                 135                 140

Gly Asp Leu Ala Thr Thr Ser Val Phe Ser Glu Ser Thr Asp Ser
145                 150                 155                 160

Glu Asp Pro Ala Asp Ser Ser His Arg Ser Pro Leu Ala Thr Asp Tyr
                165                 170                 175

Asp Leu Gly Thr Arg Thr Ile Ala Ser Ser Pro Ser Ser Ala Met Val
            180                 185                 190

Lys Asp His Cys Ala Thr Val Ser Gln Val Asn Ser Arg Glu Ala Lys
        195                 200                 205

Lys Pro Ala Asn Leu Ser Phe Gly Asn His Thr Ser Pro Thr Ser Pro
    210                 215                 220

Lys Arg Arg Pro Ile Ser Ser His Val Pro Asn Leu Gln Val Pro Lys
225                 230                 235                 240

His Gly Ser Phe Cys Ser Ala Pro Asp Ser Tyr Met Ser Ser Pro Ser
                245                 250                 255

Arg Ser Pro Met Arg Ala Phe Gly Ala Glu Gln Val Ile Asn Ser Ala
            260                 265                 270

Phe Trp Ala Gly Lys Pro Tyr Pro Asp Val Asn Leu Leu Gly Ser Gly
        275                 280                 285

His Cys Ser Ser Pro Gly Ser Gly Tyr Asn Ser Gly His Asn Ser Met
    290                 295                 300

Gly Gly Asp Met Ser Gly Gln Leu Phe Trp Gln Gln Ser Arg Gly Ser
305                 310                 315                 320

Pro Glu Cys Ser Pro Ile Pro Ser Pro Arg Met Thr Ser Pro Gly Pro
```

```
                    325                 330                 335
Ser Ser Arg Val Gln Ser Gly Ala Val Thr Pro Ile His Pro Arg Ala
                340                 345                 350
Gly Gly Thr Ile Glu Ser Gln Thr Ser Trp Pro Asp Gly Lys Gln
            355                 360                 365
Gln Ser His Arg Leu Pro Leu Pro Pro Val Thr Val Ser Ser Pro Ser
        370                 375                 380
Pro Phe Ser His Ser Asn Ser Ala Ala Ala Ser Pro Ser Val Pro Arg
385                 390                 395                 400
Ser Pro Gly Arg Ala Glu Asn Pro Thr Ser Pro Gly Ser Arg Trp Lys
                405                 410                 415
Lys Gly Lys Leu Leu Gly Arg Gly Thr Phe Gly His Val Tyr Leu Gly
                420                 425                 430
Phe Asn Ser Glu Ser Gly Glu Met Cys Ala Met Lys Glu Val Thr Leu
            435                 440                 445
Phe Ser Asp Asp Ala Lys Ser Lys Glu Ser Ala Lys Gln Leu Met Gln
        450                 455                 460
Glu Ile Ser Leu Leu Ser Arg Phe Gln His Pro Asn Ile Val Gln Tyr
465                 470                 475                 480
Tyr Gly Ser Glu Thr Val Gly Asp Arg Leu Tyr Ile Tyr Leu Glu Tyr
                485                 490                 495
Val Ser Gly Gly Ser Ile Tyr Lys Leu Leu Gln Glu Tyr Gly Gln Leu
            500                 505                 510
Gly Glu Leu Val Ile Arg Ser Tyr Thr Gln Gln Ile Leu Ser Gly Leu
        515                 520                 525
Ala Phe Leu His Ser Lys Ser Thr Val His Arg Asp Ile Lys Gly Ala
530                 535                 540
Asn Ile Leu Val Asp Pro Asn Gly Arg Val Lys Leu Ala Asp Phe Gly
545                 550                 555                 560
Met Ala Lys His Ile Thr Gly Gln Ser Cys Pro Leu Ser Phe Lys Gly
                565                 570                 575
Ser Pro Tyr Trp Met Ala Pro Glu Val Ile Lys Asn Ser Asn Gly Cys
            580                 585                 590
Asn Leu Ala Val Asp Ile Trp Ser Leu Gly Cys Thr Val Leu Glu Met
        595                 600                 605
Ala Thr Thr Lys Pro Pro Trp Ser Gln Phe Glu Gly Val Ala Ala Met
        610                 615                 620
Phe Lys Ile Gly Asn Ser Lys Asp Leu Pro Glu Ile Pro Glu Asp Leu
625                 630                 635                 640
Ser Asp Glu Gly Lys Asp Phe Val Arg Gln Cys Leu Gln Arg Asn Pro
                645                 650                 655
Val His Arg Pro Thr Ala Ser Gln Leu Leu Glu His Pro Phe Val Lys
                660                 665                 670
Leu Ala Ala Pro Leu Glu Arg Pro Ile Leu Cys Leu Asp Pro Thr Asp
            675                 680                 685
Pro Pro Pro Gly Val Ser Asn Gly Val Lys Ile Leu Gly Ile Asn His
        690                 695                 700
Ala Arg Asn Phe Pro Thr Leu Asp Ser Glu Arg Leu Ala Val His Ser
705                 710                 715                 720
Ser Arg Val Ser Lys Thr Gly Leu His Thr Ser Asp Leu His Ile Pro
                725                 730                 735
Arg Asn Ile Ser Cys Pro Val Ser Pro Ile Gly Ser Pro Leu Leu His
                740                 745                 750
```

Ser Arg Ser Pro Gln His Leu Asn Gly Arg Met Ser Pro Ser Pro Ile
        755                 760                 765

Ala Ser Pro Arg Thr Thr Ser Gly Ser Ser Thr Pro Leu Thr Gly Cys
        770                 775                 780

Thr Gly Ala Ile Pro Phe Asn His Leu Lys His Ser Val His Phe Gln
785                 790                 795                 800

Glu Gly Phe Gly Asn Met Gln Asn His Ser Asn Gly Ile Tyr Val Asn
                805                 810                 815

Gly Leu Ala Tyr His Asp Ser Ser Pro Asp Leu Phe Arg Gly Met Gln
                820                 825                 830

Pro Gly Ser Pro Ile Phe Ser Glu Leu Val Pro Cys Glu Asn Asp Leu
        835                 840                 845

Ile Gly Lys Gln Leu Gly Arg Pro Thr Gln Gly Glu Pro Tyr Asp Gly
        850                 855                 860

Gln Ser Val Leu Ala Asp Arg Val Ser Arg Gln Leu Leu Arg Asp His
865                 870                 875                 880

Val Lys Met Lys Pro Ser Leu Asp Leu Ser Pro Asn Ser Pro Leu Pro
                885                 890                 895

Ser Arg Thr Gly Gly Ile
                900

<210> SEQ ID NO 13
<211> LENGTH: 2706
<212> TYPE: DNA
<213> ORGANISM: Populus trichocarpa
<220> FEATURE:
<221> NAME/KEY: source
<222> LOCATION: 1..2706
<223> OTHER INFORMATION: /mol_type="unassigned DNA"
      /organism="Populus trichocarpa"

<400> SEQUENCE: 13
atgccttcgt ggtggggaaa gtcatcatct aaagaattga agaagaaagc aaacaaggaa      60
agtttcattg atacattaca cagaagattt aagagtccat ctgatggcaa ccttaatggt     120
agatctggag gttctcgaag acattgcagt gacacaattt cagagagggg atctcaatct     180
cgagcagtat caagatcacc ttcaccttca tcaaaacatg tttctaggtg tcagagtttt     240
gccgagagac cccatgccca accacttccc cttcctggtg tgcaccttgc aaatggggga     300
cgcacagact ctggaattgg tatattgact aaacctagat cggaaaaggg tgcaaattcg     360
tcattgtttt tgccccctacc aagaccagga tgcattcgta ataggccaaa tccaccagat     420
ttagatgggg atttggccac tgcttcagtt ccagtgaga gcgccactga tagtgacgat     480
cccgctgact caagtcatcg tagtcctgca gcaactgact atgaccttgg accagaacc      540 accactagca gcccttccag tgcaatgctc aaggatcagt gcgctattgt gagccattca     600
aactcgaaag aggcaaagaa accagctagt ctttcttttg gtaatcacac ctcctctaca     660
tcacctaaac ggagacctgt aagcagtcat gtgctgaatc tacaggttcc acaacatgtt     720
gcttccggca gtgctccaga cagctccatg tcaagtcctt ccagaagtcc catgagagca     780
tctagcaccg agcaagtcat aaactctgct ttctgggcag gcaagccata cccagatgcc     840 aatttttttag gatctggcca ctgctccagt cctggttcag gctacaactc tggacataac     900
tcaatgggag gggatatgtc aggacagtta ttctggcaac aaagcagggg tagccctgaa     960
tgttctccga tccctagtcc tagaatgacc agccctggcc ccagctccag agtccagagt    1020
ggtgctgtta caccaattca tcccagagca ggagggacga tcattgagtc ccagacaagc    1080

```
tggacagatg atgggaaaca acaaagccac cggttgcccc tccctcctgt aataatttcc    1140
agcccctctc cctttctca ttcaaactca gcagcagcat ctccttctgt gccacgaagt    1200
ccaggaaggg cagagaatcc aacaagccca ggatctcgct ggaaaaaagg aaagcttctg    1260
ggtagaggca catttggaca tgtctatgtt ggatttaaca gtgaacgtgg tgaattgtgt    1320
gcaatgaagg aggtgacatt attttcagat gatgccaagt ccaaagaaag tgctaagcag    1380
ttgatgcagg agatttctct tttaagccgt ttacaacacc caaacattgt gcagtaccat    1440
ggatctgaga cggttggtga ccggctttat atatacttgg agtatgtatc tggtgggtcc    1500
atatataaac ttctccagga atatggccaa ttgggcgagc tagttattcg tagttatacc    1560
cagcaaatct tgtcaggact tgcatttttg cattctaaaa gcactgttca tagagatatc    1620
aaaggagcaa acattcttgt agatccaaat ggtcgtgtta aattagctga ttttggcatg    1680
gcaaaacaca tcactgggca gtcatgtcca ctatcattca agggaagtcc ttattggatg    1740
gcacctgagg ttataaagaa ctcaaatggt tgcaatcttg ctgtggatat atggagtctt    1800
ggatgcactg ttttggagat ggctaccaca aaaccacctt ggagccagtt tgaaggagtt    1860
gctgccatgt ttaaaattgg aaatagtaag gatctcccaa caattccaga tcacctctca    1920
gatgaaggaa aagattttgt aaggcaatgt ttgcaacgta atccactaca tcgacctaca    1980
gctgcccagc ttttagagca tccttttgta aaatcagcag cgcctttaga agacctatt    2040
ccgagccctg aacctactga tccacccct ggagttacaa atggagttaa agctatgggc    2100
attaatcaag ctagaaactt tcccaccttg gattcagaga gacttgcagt tcattcatct    2160
agagtttcga aaactggtct acttgccagt gatttacata ttccaaggaa catatcatgc    2220
cctgtttctc ccattggaag ccctctcttt cattcgaggt cgccacaaca cctaaatgga    2280
agaatgtctc cttcacctat agctagcccg cgcaccactt caggctcatc cacacctctg    2340
actggtggaa ctggtgctat acctttaaat cacttgaaac agtcagttta cttgcaagag    2400
ggttttggaa acatgccata tcacacaaat ggtatatatg ccaatggctt ggcttaccat    2460
gattccattc ctgatctttt tcaaggaatg cagcctggct ctcccatctt ctcagagctg    2520
gttccttgtg aaaatgatct catgggaaag cagtttggaa ggcctactca agggaacct    2580
tatgatgggc agtcagtctt ggctgttcga gtgtctcggc agcttttgag ggatcatgtg    2640
aaaatgaaac catccctgga tctaagtccc aactctcctt tacccagtag aaccggaggt    2700
atataa                                                               2706
```

<210> SEQ ID NO 14
<211> LENGTH: 901
<212> TYPE: PRT
<213> ORGANISM: Populus trichocarpa

<400> SEQUENCE: 14

Met Pro Ser Trp Trp Gly Lys Ser Ser Lys Glu Leu Lys Lys
1               5                   10                  15

Ala Asn Lys Glu Ser Phe Ile Asp Thr Leu His Arg Arg Phe Lys Ser
            20                  25                  30

Pro Ser Asp Gly Asn Leu Asn Gly Arg Ser Gly Gly Ser Arg Arg His
        35                  40                  45

Cys Ser Asp Thr Ile Ser Glu Arg Gly Ser Gln Ser Arg Ala Val Ser
    50                  55                  60

Arg Ser Pro Ser Pro Ser Ser Lys His Val Ser Arg Cys Gln Ser Phe
65                  70                  75                  80

```
Ala Glu Arg Pro His Ala Gln Pro Leu Pro Leu Pro Gly Val His Leu
                 85                  90                  95

Ala Asn Gly Gly Arg Thr Asp Ser Gly Ile Gly Ile Leu Thr Lys Pro
            100                 105                 110

Arg Ser Glu Lys Gly Ala Asn Ser Ser Leu Phe Leu Pro Leu Pro Arg
        115                 120                 125

Pro Gly Cys Ile Arg Asn Arg Pro Asn Pro Pro Asp Leu Asp Gly Asp
    130                 135                 140

Leu Ala Thr Ala Ser Val Ser Ser Glu Ser Ala Thr Asp Ser Asp Asp
145                 150                 155                 160

Pro Ala Asp Ser Ser His Arg Ser Pro Ala Ala Thr Asp Tyr Asp Leu
                165                 170                 175

Gly Thr Arg Thr Thr Thr Ser Ser Pro Ser Ser Ala Met Leu Lys Asp
            180                 185                 190

Gln Cys Ala Ile Val Ser His Ser Asn Ser Lys Glu Ala Lys Lys Pro
        195                 200                 205

Ala Ser Leu Ser Phe Gly Asn His Thr Ser Ser Thr Ser Pro Lys Arg
    210                 215                 220

Arg Pro Val Ser Ser His Val Leu Asn Leu Gln Val Pro Gln His Val
225                 230                 235                 240

Ala Ser Gly Ser Ala Pro Asp Ser Ser Met Ser Ser Pro Ser Arg Ser
                245                 250                 255

Pro Met Arg Ala Ser Ser Thr Glu Gln Val Ile Asn Ser Ala Phe Trp
            260                 265                 270

Ala Gly Lys Pro Tyr Pro Asp Ala Asn Phe Leu Gly Ser Gly His Cys
        275                 280                 285

Ser Ser Pro Gly Ser Gly Tyr Asn Ser Gly His Asn Ser Met Gly Gly
    290                 295                 300

Asp Met Ser Gly Gln Leu Phe Trp Gln Gln Ser Arg Gly Ser Pro Glu
305                 310                 315                 320

Cys Ser Pro Ile Pro Ser Pro Arg Met Thr Ser Pro Gly Pro Ser Ser
                325                 330                 335

Arg Val Gln Ser Gly Ala Val Thr Pro Ile His Pro Arg Ala Gly Gly
            340                 345                 350

Thr Ile Ile Glu Ser Gln Thr Ser Trp Thr Asp Asp Gly Lys Gln Gln
        355                 360                 365

Ser His Arg Leu Pro Leu Pro Pro Val Ile Ile Ser Ser Pro Ser Pro
    370                 375                 380

Phe Ser His Ser Asn Ser Ala Ala Ala Ser Pro Ser Val Pro Arg Ser
385                 390                 395                 400

Pro Gly Arg Ala Glu Asn Pro Thr Ser Pro Gly Ser Arg Trp Lys Lys
                405                 410                 415

Gly Lys Leu Leu Gly Arg Gly Thr Phe Gly His Val Tyr Val Gly Phe
            420                 425                 430

Asn Ser Glu Arg Gly Glu Leu Cys Ala Met Lys Glu Val Thr Leu Phe
        435                 440                 445

Ser Asp Asp Ala Lys Ser Lys Glu Ser Ala Lys Gln Leu Met Gln Glu
    450                 455                 460

Ile Ser Leu Leu Ser Arg Leu Gln His Pro Asn Ile Val Gln Tyr His
465                 470                 475                 480

Gly Ser Glu Thr Val Gly Asp Arg Leu Tyr Ile Tyr Leu Glu Tyr Val
                485                 490                 495
```

```
Ser Gly Gly Ser Ile Tyr Lys Leu Leu Gln Glu Tyr Gly Gln Leu Gly
            500                 505                 510

Glu Leu Val Ile Arg Ser Tyr Thr Gln Gln Ile Leu Ser Gly Leu Ala
            515                 520                 525

Phe Leu His Ser Lys Ser Thr Val His Arg Asp Ile Lys Gly Ala Asn
            530                 535                 540

Ile Leu Val Asp Pro Asn Gly Arg Val Lys Leu Ala Asp Phe Gly Met
545                 550                 555                 560

Ala Lys His Ile Thr Gly Gln Ser Cys Pro Leu Ser Phe Lys Gly Ser
            565                 570                 575

Pro Tyr Trp Met Ala Pro Glu Val Ile Lys Asn Ser Asn Gly Cys Asn
            580                 585                 590

Leu Ala Val Asp Ile Trp Ser Leu Gly Cys Thr Val Leu Glu Met Ala
            595                 600                 605

Thr Thr Lys Pro Pro Trp Ser Gln Phe Glu Gly Val Ala Ala Met Phe
            610                 615                 620

Lys Ile Gly Asn Ser Lys Asp Leu Pro Thr Ile Pro Asp His Leu Ser
625                 630                 635                 640

Asp Glu Gly Lys Asp Phe Val Arg Gln Cys Leu Gln Arg Asn Pro Leu
            645                 650                 655

His Arg Pro Thr Ala Ala Gln Leu Leu Glu His Pro Phe Val Lys Ser
            660                 665                 670

Ala Ala Pro Leu Glu Arg Pro Ile Pro Ser Pro Glu Pro Thr Asp Pro
            675                 680                 685

Pro Pro Gly Val Thr Asn Gly Val Lys Ala Met Gly Ile Asn Gln Ala
690                 695                 700

Arg Asn Phe Pro Thr Leu Asp Ser Glu Arg Leu Ala Val His Ser Ser
705                 710                 715                 720

Arg Val Ser Lys Thr Gly Leu Leu Ala Ser Asp Leu His Ile Pro Arg
            725                 730                 735

Asn Ile Ser Cys Pro Val Ser Pro Ile Gly Ser Pro Leu Phe His Ser
            740                 745                 750

Arg Ser Pro Gln His Leu Asn Gly Arg Met Ser Pro Ser Pro Ile Ala
            755                 760                 765

Ser Pro Arg Thr Thr Ser Gly Ser Ser Thr Pro Leu Thr Gly Gly Thr
770                 775                 780

Gly Ala Ile Pro Phe Asn His Leu Lys Gln Ser Val Tyr Leu Gln Glu
785                 790                 795                 800

Gly Phe Gly Asn Met Pro Tyr His Thr Asn Gly Ile Tyr Ala Asn Gly
            805                 810                 815

Leu Ala Tyr His Asp Ser Ile Pro Asp Leu Phe Gln Gly Met Gln Pro
            820                 825                 830

Gly Ser Pro Ile Phe Ser Glu Leu Val Pro Cys Glu Asn Asp Leu Met
            835                 840                 845

Gly Lys Gln Phe Gly Arg Pro Thr Gln Gly Glu Pro Tyr Asp Gly Gln
            850                 855                 860

Ser Val Leu Ala Val Arg Val Ser Arg Gln Leu Leu Arg Asp His Val
865                 870                 875                 880

Lys Met Lys Pro Ser Leu Asp Leu Ser Pro Asn Ser Pro Leu Pro Ser
            885                 890                 895

Arg Thr Gly Gly Ile
            900
```

<210> SEQ ID NO 15
<211> LENGTH: 3798
<212> TYPE: DNA
<213> ORGANISM: Oryza sativa
<220> FEATURE:
<221> NAME/KEY: source
<222> LOCATION: 1..3798
<223> OTHER INFORMATION: /mol_type="unassigned DNA"
      /organism="Oryza sativa"

<400> SEQUENCE: 15

```
ggcctgggcc tttttccgtt gctaccctcc tctcccccct cccctttccg attccccac      60
tttccgcgag ctcctcctct ccttttgccc gcaccatcac caccaccacc gcctccagat     120
tcccctccgg ctttccctcc gcctgtcgga tctccccccc gccggcgagc tcgcctcgcc     180
gtggtggcgc gccggtaagc cttttggggg taaagaaggt gcctgacacc accttgtggt     240
catcaatttg tctgcttcta gctccattgc cagtgcattg cggaagctgg gggttctata     300
tgggttgtta agaaaatcgt gcgctacaca tgttaatctg attggcagaa tatggtaatt     360
atcagcttga ataacaccgt gattagtacc tagccaatta gacataccac aaattatttc     420
atattcaata tgccaccatg gtggggaag tctttctcaa agatgctaa gaaaaccaca      480
aaagaaaacc tcatcgatac atttcatcgg ttgataagtc caaatgatca aaagggaagc     540
acgaagtcga aacggagttg tagacgtggc aatgattcat ctgttgaaaa aagctgccga     600
tctaccacag tgtcacgtcc tacttcaccg tcaaaagaag tttctcgctg ccaaagcttt     660
tcagctgata gaccacatgc ccatcccctc cctattcctg gagtacgtcc tccagtgact     720
cggactgttt ctgatatcac tgaatcaaag cccatattgg aaaaacgtgg caagccacca     780
ctgcttctac cactccctaa acccaaccgg cctccgagga ggcatggaaa tagtgaggtt     840
gtttcagaaa tagtggttgc ttctccctct agtaactgtt ctgatagtga tgatcatggg     900
gattctcagc ttcagagtcc tgttggaaat gatgccgaaa atgcaacact tgttactta      960
aagaacaagt caagtaatgc gcgcaaagaa tgtcctggac ctattacggc aaagaatatg    1020
aaggagatac acagaccagc taatcaagta catggtagcc atatattatc cacatcacca    1080
agggtgtcg cagctgacag ttaccaatcc aatttacaaa atccccgccc attagttctg     1140
gatagtgctc ccaatagttt gatgtcaagt ccttctagaa gtccaagaag aatatgtcct    1200
gatcatattc caacttcggc cttttgggca gtgaaacctc acacagatgt aacttttgtt    1260
ggatctggtc aatgttccag tccaggttca gggcaaacat ctgggcataa ttctgtgggt    1320
ggtgatatgc tagcccagct cttttggcag cccagcagaa gtagcccaga gtgttcacca    1380
attccaagtc caagaatgac aagtcctggc cctagttcga gggtgcatag tggaagtgtt    1440
tcaccattgc atccaaggtc tggagggatg gcccctgaat ctccaacaaa ccgtcatgat    1500
gatgggaaga agaagcaaac tcacaaactt cccctaccac cactgagcat ctctcacagt    1560
tcatttcatc caaataactc cactccaact agtcctattt cagtacctcg cagccctggt    1620
agaactgaga atccaccaag tcctgggtca cgatggaaga agggaagct aattggccgt     1680
ggaacatttg gtcatgtata tgttggctt aacagtgata gtggtgaaat gtgtgcgatg    1740
aaagaagtta ccctattctt ggatgatcct aaatcaaagg aaagtgcaaa gcagttgggg    1800
caggaaatat cactattgag ccgcctacag catccaaata tcgtacaata ctatggatca    1860
gaaacggttg atgataagct ttatatatac ttggagtatg tatctggtgg atctatccat    1920
aaacttctac aagagtatgg acagcttggt gaacaagcaa tacgcagcta cacacagcag    1980
atactttcag ggttggctta tttgcatgcg aagaatacag tccatagga tattaaaggt    2040
```

-continued

```
gcaaatatac tagtagatcc tagtggtcgt gttaagcttg cagattttgg aatggcaaaa    2100
catatcaatg ggcagcagtg tcctttctcc tttaagggta gtccatattg gatggctcca    2160
gaggttataa aaaactcaaa tgggtgcaac ctagctgttg acatatggag tttgggatgc    2220
actgtcctgg agatggctac atcgaaaccg ccatggagcc agtatgaagg gattgctgca    2280
atgttcaaga tcggaaatag caaggaactt ccaccaatac cagatcacct ttcagagcca    2340
ggcaaggact tcatcagaaa gtgcctgcaa cgtgatcctt ctcaacgtcc cactgcaatg    2400
gagcttttgc agcacccatt tgttcaaaaa gcagtatcac tagagaaatc tgttctttct    2460
gaaccattgg aacatttggc tgttatatct tgtagatcga cgccaagat ggctgcgcat     2520 acaagaaata tttcctcatt gggattggag ggtcagacaa tttaccagag aagaggtgca    2580 aaatttctt caaacacag tgatatccgt atacgaagca atatatcttg tccagtttct      2640
ccatgtggaa gtcctttgct aaaatcaagg tccccacaac attccaatgg cagaatgtca    2700
ccttctccta tttcaagccc cagaactact tcaggcacct ccacgcctct gtctggtggt    2760
aatggtgcta ttccttttaa ccatctgaag caatcaacct acagcaacga gggatttgca    2820
atcccatcaa gaagcccgga tgatctcttt gccagccggc ctacagatcc tgatcttggg    2880
caatttattc gagtgcatca agtctctcag gggcttcagg agagggtggt atctgaagct    2940
gacattctaa gccctcagtt tggaaagaga cttggaaatg ttttgatttt gcgtgataag    3000
ctgtcaccat ctgaacgttt cacacatcat gcctttgtgg atcatgtgaa actaaatcct    3060
tcattagact tgacgtctgg atctccacac cttggactca agcatggtaa ctaatatcaa    3120
gaatcagtat tcagatggca ttttttggag cttcgaaagg taactggtgg tttggctgct    3180
ttttagccat ccgatggctt gaagtgtatc atagtatgag gaaagaaaaa tcactaatgt    3240
ctgtagaagc taaagttggc aatggatgga atctttgttg tcatcaacac aattcaagtt    3300
ggcaaagata tcgtccattc ctgttaggca gaactcccgg aagcatacta caattggcgt    3360
actaacatct gtcaaatgac aagactgtat attggtaccc tacagattga aggacctccg    3420
aagtagtagt tcgccgcatg tatactcctc ttgcctttat atgtaactta attttctatt    3480
ttcttcttgg cgtcctgatg ccattgtaca gaggaacctc aactaagagc caagattttg    3540
cacaggagaa acagtccagc cattcagtat cctctctcac acaatatctc acctgaggtt    3600
gaaactactg ctgcaagtca aactgcatac tgaaagtatt ttgtagcaga actcagccaa    3660
tgagccaact tattcactgt accagttact ctggaaattt atacaaagaa tcagatcctt    3720
ggttaaacta gcttctcccg catgtacatg ttcttcagat ctgcaccgtg agctatctat    3780
aagactataa ccattacc                                                  3798
```

<210> SEQ ID NO 16
<211> LENGTH: 894
<212> TYPE: PRT
<213> ORGANISM: Oryza sativa

<400> SEQUENCE: 16

```
Met Pro Pro Trp Trp Gly Lys Ser Phe Ser Lys Asp Ala Lys Lys Thr
1               5                   10                  15

Thr Lys Glu Asn Leu Ile Asp Thr Phe His Arg Leu Ile Ser Pro Asn
                20                  25                  30

Asp Gln Lys Gly Ser Thr Lys Ser Lys Arg Ser Cys Arg Arg Gly Asn
            35                  40                  45

Asp Ser Ser Val Glu Lys Ser Cys Arg Ser Thr Thr Val Ser Arg Pro
```

```
            50                  55                  60
Thr Ser Pro Ser Lys Glu Val Ser Arg Cys Gln Ser Phe Ser Ala Asp
 65                  70                  75                  80

Arg Pro His Ala His Pro Leu Pro Ile Pro Gly Val Arg Pro Pro Val
                 85                  90                  95

Thr Arg Thr Val Ser Asp Ile Thr Glu Ser Lys Pro Ile Leu Glu Lys
                100                 105                 110

Arg Gly Lys Pro Pro Leu Leu Leu Pro Leu Pro Lys Pro Asn Arg Pro
            115                 120                 125

Pro Arg Arg His Gly Asn Ser Glu Val Val Ser Glu Ile Val Val Ala
            130                 135                 140

Ser Pro Ser Ser Asn Cys Ser Asp Ser Asp His Gly Asp Ser Gln
145                 150                 155                 160

Leu Gln Ser Pro Val Gly Asn Asp Ala Glu Asn Ala Thr Leu Val Thr
                165                 170                 175

Leu Lys Asn Lys Ser Ser Asn Ala Arg Lys Glu Cys Pro Gly Pro Ile
            180                 185                 190

Thr Ala Lys Asn Met Lys Glu Ile His Arg Pro Ala Asn Gln Val His
            195                 200                 205

Gly Ser His Ile Leu Ser Thr Ser Pro Arg Gly Val Ala Ala Asp Ser
            210                 215                 220

Tyr Gln Ser Asn Leu Gln Asn Pro Arg Pro Leu Val Leu Asp Ser Ala
225                 230                 235                 240

Pro Asn Ser Leu Met Ser Ser Pro Ser Arg Ser Pro Arg Arg Ile Cys
                245                 250                 255

Pro Asp His Ile Pro Thr Ser Ala Phe Trp Ala Val Lys Pro His Thr
                260                 265                 270

Asp Val Thr Phe Val Gly Ser Gly Gln Cys Ser Ser Pro Gly Ser Gly
            275                 280                 285

Gln Thr Ser Gly His Asn Ser Val Gly Gly Asp Met Leu Ala Gln Leu
            290                 295                 300

Phe Trp Gln Pro Ser Arg Ser Ser Pro Glu Cys Ser Pro Ile Pro Ser
305                 310                 315                 320

Pro Arg Met Thr Ser Pro Gly Pro Ser Ser Arg Val His Ser Gly Ser
                325                 330                 335

Val Ser Pro Leu His Pro Arg Ser Gly Gly Met Ala Pro Glu Ser Pro
            340                 345                 350

Thr Asn Arg His Asp Asp Gly Lys Lys Lys Gln Thr His Lys Leu Pro
            355                 360                 365

Leu Pro Pro Leu Ser Ile Ser His Ser Ser Phe His Pro Asn Asn Ser
            370                 375                 380

Thr Pro Thr Ser Pro Ile Ser Val Pro Arg Ser Pro Gly Arg Thr Glu
385                 390                 395                 400

Asn Pro Pro Ser Pro Gly Ser Arg Trp Lys Lys Gly Lys Leu Ile Gly
                405                 410                 415

Arg Gly Thr Phe Gly His Val Tyr Val Gly Phe Asn Ser Asp Ser Gly
            420                 425                 430

Glu Met Cys Ala Met Lys Glu Val Thr Leu Phe Leu Asp Asp Pro Lys
            435                 440                 445

Ser Lys Glu Ser Ala Lys Gln Leu Gly Gln Glu Ile Ser Leu Leu Ser
            450                 455                 460

Arg Leu Gln His Pro Asn Ile Val Gln Tyr Tyr Gly Ser Glu Thr Val
465                 470                 475                 480
```

```
Asp Asp Lys Leu Tyr Ile Tyr Leu Glu Tyr Val Ser Gly Gly Ser Ile
            485                 490                 495

His Lys Leu Leu Gln Glu Tyr Gly Gln Leu Gly Glu Gln Ala Ile Arg
        500                 505                 510

Ser Tyr Thr Gln Gln Ile Leu Ser Gly Leu Ala Tyr Leu His Ala Lys
        515                 520                 525

Asn Thr Val His Arg Asp Ile Lys Gly Ala Asn Ile Leu Val Asp Pro
    530                 535                 540

Ser Gly Arg Val Lys Leu Ala Asp Phe Gly Met Ala Lys His Ile Asn
545                 550                 555                 560

Gly Gln Gln Cys Pro Phe Ser Phe Lys Gly Ser Pro Tyr Trp Met Ala
                565                 570                 575

Pro Glu Val Ile Lys Asn Ser Asn Gly Cys Asn Leu Ala Val Asp Ile
            580                 585                 590

Trp Ser Leu Gly Cys Thr Val Leu Glu Met Ala Thr Ser Lys Pro Pro
        595                 600                 605

Trp Ser Gln Tyr Glu Gly Ile Ala Ala Met Phe Lys Ile Gly Asn Ser
        610                 615                 620

Lys Glu Leu Pro Pro Ile Pro Asp His Leu Ser Glu Pro Gly Lys Asp
625                 630                 635                 640

Phe Ile Arg Lys Cys Leu Gln Arg Asp Pro Ser Gln Arg Pro Thr Ala
                645                 650                 655

Met Glu Leu Leu Gln His Pro Phe Val Gln Lys Ala Val Ser Leu Glu
            660                 665                 670

Lys Ser Val Leu Ser Glu Pro Leu Glu His Leu Ala Val Ile Ser Cys
        675                 680                 685

Arg Ser Ser Ala Lys Met Ala Ala His Thr Arg Asn Ile Ser Ser Leu
        690                 695                 700

Gly Leu Glu Gly Gln Thr Ile Tyr Gln Arg Arg Gly Ala Lys Phe Ser
705                 710                 715                 720

Ser Lys His Ser Asp Ile Arg Ile Arg Ser Asn Ile Ser Cys Pro Val
                725                 730                 735

Ser Pro Cys Gly Ser Pro Leu Leu Lys Ser Arg Ser Pro Gln His Ser
            740                 745                 750

Asn Gly Arg Met Ser Pro Ser Pro Ile Ser Ser Pro Arg Thr Thr Ser
        755                 760                 765

Gly Thr Ser Thr Pro Leu Ser Gly Gly Asn Gly Ala Ile Pro Phe Asn
        770                 775                 780

His Leu Lys Gln Ser Thr Tyr Ser Asn Glu Gly Phe Ala Ile Pro Ser
785                 790                 795                 800

Arg Ser Pro Asp Asp Leu Phe Ala Ser Arg Pro Thr Asp Pro Asp Leu
                805                 810                 815

Gly Gln Phe Ile Arg Val His Gln Val Ser Gln Gly Leu Gln Glu Arg
            820                 825                 830

Val Val Ser Glu Ala Asp Ile Leu Ser Pro Gln Phe Gly Lys Arg Leu
        835                 840                 845

Gly Asn Val Phe Asp Leu Arg Asp Lys Leu Ser Pro Ser Glu Arg Phe
    850                 855                 860

Thr His His Ala Phe Val Asp His Val Lys Leu Asn Pro Ser Leu Asp
865                 870                 875                 880

Leu Thr Ser Gly Ser Pro His Leu Gly Leu Lys His Gly Asn
                885                 890
```

<210> SEQ ID NO 17
<211> LENGTH: 3725
<212> TYPE: DNA
<213> ORGANISM: Oryza sativa
<220> FEATURE:
<221> NAME/KEY: source
<222> LOCATION: 1..3725
<223> OTHER INFORMATION: /mol_type="unassigned DNA"
      /organism="Oryza sativa"

<400> SEQUENCE: 17

| | | | | | |
|---|---|---|---|---|---|
| accgtctctc | tccgttcctc | tcctctgctc | atcttatctg | ttcgtctgaa | aaaaaaaaac | 60 |
| cgtttccggc | ggacgcacgg | gcggaggctc | ggccagcgtt | ctcctcctcc | gcgacaccga | 120 |
| ctcgcctccg | tcgcgcgcgc | ggccggcgag | cagggccgga | ggcgcagtgc | ggacgggctg | 180 |
| ctgctcccct | tccccgaccc | cctaccgcac | tagtattctc | ccctgtgcgg | ccggccggcg | 240 |
| agcatctcgg | ttcgaatcga | agtatcgaat | tgaagccttt | gtggtgaagg | cattaaacag | 300 |
| aaatcaaagt | agcatgagca | agcactaact | gggaatctcc | ataatacagc | attccagtga | 360 |
| gttgaggact | ttttttttgtc | actacagaaa | ctaaggatac | ctgcgtgatt | tcaaaatttc | 420 |
| aatgtgtgat | tagctcagtg | aaatcctgtc | caacttgttt | catattcaat | atgccaccat | 480 |
| ggtgggggaa | gtcttcatca | aaagaagtaa | agaagactgc | caaagaaaac | ctcattgaca | 540 |
| catttcatcg | gttattaagt | ccaaatgagc | aaaaggggag | aacaaaatca | cggggggaatc | 600 |
| gtagacatag | taaagatcca | actgctgaga | aaggttgctg | gtctactgcc | caatcacgct | 660 |
| ctgcatcccc | ttcaaaagag | gtttctcgtt | gtcaaagctt | tgctgcagcc | agagcacatg | 720 |
| cacaaccact | tccccttcct | agatcccgtg | ctatggtggc | acgtactgct | tctgatatta | 780 |
| ccgaatcaaa | ggtcgttttg | gaaaagcgtg | gcaaaggaca | acaactaccg | ctccctacca | 840 |
| caaattgggt | taaagaaaga | cctgaaacta | ccgaacctgt | tgcagaatta | tcaactgctt | 900 |
| ctatctccag | ccatggttct | atagatagcg | atgatcctgg | agatttgcga | cttcagggac | 960 |
| ctgtggcaaa | tgacaccgac | aatgtggcta | agttgctac | aaccggtaat | tcaagtgttg | 1020 |
| tgcataagga | gtgttctagt | gccatcacca | gaaagggcac | taaggaagtg | acgatgccaa | 1080 |
| ccaatgcttt | cttgagtaat | caaattctat | ctacaagtcc | cagaggtact | gttgttgctg | 1140 |
| acagttacca | gtcaaattta | caaaattcac | gaaaggttgt | tctggacagt | gctcccaata | 1200 |
| gtgtgatgtc | aagcccttct | cgaagcccaa | gaatattatg | ccctgatcag | attccaagtt | 1260 |
| cagcattttg | ggcagttaag | cctcatacag | atgtaacttt | tgttgggtct | gctcagtgct | 1320 |
| ccagtcctgg | ttcagggcaa | acatctgggc | ataattcagt | gggaggtgat | atgctagccc | 1380 |
| agctcttttg | gcaacctagc | cgaggtagtc | cagagtgttc | accaattccc | agcccaagaa | 1440 |
| tgacaagccc | tggtccaagt | tcaagggtac | atagtgaag | tgtctctcca | ttgcatccaa | 1500 |
| gggctggtgg | gatggcacct | gaatctccaa | caaggcgact | tgatgaaggg | aagaggaagc | 1560 |
| aaacccacag | attgcccctt | ccaccactaa | gcatatgtaa | caattccacc | tttttgccaa | 1620 |
| acaattccac | cccaactagt | cctatctcac | atagtcctgg | tagagtagaa | atccaacta | 1680 |
| gtcctggatc | acggtggaag | aagggaaagc | ttgtcggccg | tgggacattt | ggccatgtat | 1740 |
| acattggctt | taacagtgat | aaaggtgaaa | tgtgtgcaat | gaaggaggtc | acccttttct | 1800 |
| cagacgatcc | taaatcaaaa | gaaagtgcaa | agcagttgtg | tcaggaaata | ttacttctga | 1860 |
| atcgtctgca | acatccaaat | attgtacgat | actatgtgatc | tgaaatggtt | gatgataaac | 1920 |
| tttatatata | cctggagtat | gtttctggtg | gatccatcca | taaactactc | caggagtatg | 1980 |

```
ggcaatttgg tgaacctgct atccgcagtt ataccaagca atacttttta ggcttggctt    2040
atctgcatgc aaaaaatacg gttcacaggg acattaaagg tgcaaacata ctggtagatc    2100
ctaatggtcg tgtaaagctt gctgacttcg aatggcaaa acatatcaat gggcagcagt     2160
gtgccttttc atttaagggt agcccgtact ggatggctcc tgaggttata aaaaattcta    2220
atggatgtaa tcttgctgtt gacatatgga gcttaggatg cacggtttta gagatggcta    2280
cctcaaaacc accatggagc caatatgaag ggattgctgc agtgtttaag ataggaaaca    2340
gtaaggagct tccaccaata ccagatcacc tctcagaaga gggcagagac tttataagac    2400
agtgcctgca cgcaatcca tccagccgtc aacagcagt ggatcttttg cagcattcat      2460
ttatacgaaa tgcatctcca cttgaaaaat cactgtcgga tccattgcta cagttgtcta    2520
ctacatcctg caaccagat ctgaaggtgg tcgggcatgc cagaaatatg tcttctttgg     2580
gtttggaagg gcaatccatt taccagagaa gagctgctaa attttcttct gtgcacagtg    2640
atattcatgt acgaagctat atatcttgcc ctgtttctcc atgtgggagc cctcatctga    2700
ggtcaagatc tccacaacat caaaatggta taatgtcacc ctctccgatt cgagcccaa    2760 gaactacttc aggtgcttcc actcctctga ctggtggtaa tggagctatt cctttttaacc   2820 atgcaagaca cctagcttac aataatgagg gtttcacaat tacatcgaga tgtcttgatg   2880
agcccttgcc aaaccagcct ccagatccgg tccttggtcg ttttgttaga gtgaaacaac    2940
cctcgctagg ttttcaggag agggcagtcc ctgaagctga cattctgagc cctcaatttg    3000
gaaggatggg acatgtgagc gtgtggaatt tgcatgataa gccactgcct tctgagcatg    3060
cttcacagaa gggctttgag gatcgggtaa aacttaagcc tccactggat ttgagatctg    3120
gtccaccaca ccttgggtgc aaccatggtc attgatttca cccaaaggtg tgctggatag    3180
gcattgagtt ggagcttgat gagagctgct gagccagttt gcccatctat ttactgcaag    3240
cctggcactg tatcatagta cacgaataat ttcattaatt atttcagaag ctgaccgtct    3300
caacaaaggt gagctatgcc cccaccagga acaggcgttg acttccatat taccatgcct    3360
gttatgtgtt aaccagttac acgtcgttga tgcaattgta tattacagag ggtctagata    3420
gccaaggacc caaaacagta gttcttcacc tgtatactct ggtatctaca ttcgttttcc    3480
tttggacaat ctatgggttt cgaggccatt gtacaggagg aaactcaact agaagtccac    3540
attttgcaaa ggtagaggca attgaaccat tcaatacccca ttcttttttct cagtacttcc    3600 ccttgctgcg agcttttgca actagtcagc tgcagcctgc atagtgaaag cgttgttgct    3660
gtactcaggt aatccattca ctgtatctat tactctggaa attatacaga gattctgatc    3720
gttaa                                                                3725
```

<210> SEQ ID NO 18
<211> LENGTH: 894
<212> TYPE: PRT
<213> ORGANISM: Oryza sativa
<400> SEQUENCE: 18

```
Met Pro Pro Trp Trp Gly Lys Ser Ser Lys Glu Val Lys Lys Thr
1               5                   10                  15

Ala Lys Glu Asn Leu Ile Asp Thr Phe His Arg Leu Leu Ser Pro Asn
            20                  25                  30

Glu Gln Lys Gly Arg Thr Lys Ser Arg Gly Asn Arg Arg His Ser Lys
        35                  40                  45

Asp Pro Thr Ala Glu Lys Gly Cys Trp Ser Thr Ala Gln Ser Arg Ser
    50                  55                  60
```

```
Ala Ser Pro Ser Lys Glu Val Ser Arg Cys Gln Ser Phe Ala Ala Ala
 65                  70                  75                  80

Arg Ala His Ala Gln Pro Leu Pro Leu Pro Arg Ser Arg Ala Met Val
                 85                  90                  95

Ala Arg Thr Ala Ser Asp Ile Thr Glu Ser Lys Val Val Leu Glu Lys
            100                 105                 110

Arg Gly Lys Gly Gln Gln Leu Pro Leu Pro Thr Thr Asn Trp Val Lys
            115                 120                 125

Glu Arg Pro Glu Thr Thr Glu Pro Val Ala Glu Leu Ser Thr Ala Ser
            130                 135                 140

Ile Ser Ser His Gly Ser Ile Asp Ser Asp Pro Gly Asp Leu Arg
145                 150                 155                 160

Leu Gln Gly Pro Val Ala Asn Asp Thr Asp Asn Val Ala Lys Val Ala
                165                 170                 175

Thr Thr Gly Asn Ser Ser Val Val His Lys Glu Cys Ser Ser Ala Ile
            180                 185                 190

Thr Arg Lys Gly Thr Lys Glu Val Thr Met Pro Thr Asn Ala Phe Leu
            195                 200                 205

Ser Asn Gln Ile Leu Ser Thr Ser Pro Arg Gly Thr Val Val Ala Asp
210                 215                 220

Ser Tyr Gln Ser Asn Leu Gln Asn Ser Arg Lys Val Val Leu Asp Ser
225                 230                 235                 240

Ala Pro Asn Ser Val Met Ser Ser Pro Ser Arg Ser Pro Arg Ile Leu
                245                 250                 255

Cys Pro Asp Gln Ile Pro Ser Ser Ala Phe Trp Ala Val Lys Pro His
            260                 265                 270

Thr Asp Val Thr Phe Val Gly Ser Ala Gln Cys Ser Ser Pro Gly Ser
            275                 280                 285

Gly Gln Thr Ser Gly His Asn Ser Val Gly Gly Asp Met Leu Ala Gln
            290                 295                 300

Leu Phe Trp Gln Pro Ser Arg Gly Ser Pro Glu Cys Ser Pro Ile Pro
305                 310                 315                 320

Ser Pro Arg Met Thr Ser Pro Gly Pro Ser Ser Arg Val His Ser Gly
                325                 330                 335

Ser Val Ser Pro Leu His Pro Arg Ala Gly Gly Met Ala Pro Glu Ser
            340                 345                 350

Pro Thr Arg Arg Leu Asp Glu Gly Lys Arg Lys Gln Thr His Arg Leu
            355                 360                 365

Pro Leu Pro Pro Leu Ser Ile Cys Asn Asn Ser Thr Phe Leu Pro Asn
            370                 375                 380

Asn Ser Thr Pro Thr Ser Pro Ile Ser His Ser Pro Gly Arg Val Glu
385                 390                 395                 400

Asn Pro Thr Ser Pro Gly Ser Arg Trp Lys Lys Gly Lys Leu Val Gly
                405                 410                 415

Arg Gly Thr Phe Gly His Val Tyr Ile Gly Phe Asn Ser Asp Lys Gly
            420                 425                 430

Glu Met Cys Ala Met Lys Glu Val Thr Leu Phe Ser Asp Asp Pro Lys
            435                 440                 445

Ser Lys Glu Ser Ala Lys Gln Leu Cys Gln Glu Ile Leu Leu Leu Asn
            450                 455                 460

Arg Leu Gln His Pro Asn Ile Val Arg Tyr Tyr Gly Ser Glu Met Val
465                 470                 475                 480
```

Asp Asp Lys Leu Tyr Ile Tyr Leu Glu Tyr Val Ser Gly Gly Ser Ile
            485                 490                 495

His Lys Leu Leu Gln Glu Tyr Gly Gln Phe Gly Glu Pro Ala Ile Arg
        500                 505                 510

Ser Tyr Thr Lys Gln Ile Leu Leu Gly Leu Ala Tyr Leu His Ala Lys
        515                 520                 525

Asn Thr Val His Arg Asp Ile Lys Gly Ala Asn Ile Leu Val Asp Pro
        530                 535                 540

Asn Gly Arg Val Lys Leu Ala Asp Phe Gly Met Ala Lys His Ile Asn
545                 550                 555                 560

Gly Gln Gln Cys Ala Phe Ser Phe Lys Gly Ser Pro Tyr Trp Met Ala
                565                 570                 575

Pro Glu Val Ile Lys Asn Ser Asn Gly Cys Asn Leu Ala Val Asp Ile
                580                 585                 590

Trp Ser Leu Gly Cys Thr Val Leu Glu Met Ala Thr Ser Lys Pro Pro
        595                 600                 605

Trp Ser Gln Tyr Glu Gly Ile Ala Ala Val Phe Lys Ile Gly Asn Ser
        610                 615                 620

Lys Glu Leu Pro Pro Ile Pro Asp His Leu Ser Glu Glu Gly Arg Asp
625                 630                 635                 640

Phe Ile Arg Gln Cys Leu Gln Arg Asn Pro Ser Ser Arg Pro Thr Ala
                645                 650                 655

Val Asp Leu Leu Gln His Ser Phe Ile Arg Asn Ala Ser Pro Leu Glu
            660                 665                 670

Lys Ser Leu Ser Asp Pro Leu Leu Gln Leu Ser Thr Thr Ser Cys Lys
        675                 680                 685

Pro Asp Leu Lys Val Val Gly His Ala Arg Asn Met Ser Ser Leu Gly
        690                 695                 700

Leu Glu Gly Gln Ser Ile Tyr Gln Arg Arg Ala Ala Lys Phe Ser Ser
705                 710                 715                 720

Val His Ser Asp Ile His Val Arg Ser Tyr Ile Ser Cys Pro Val Ser
                725                 730                 735

Pro Cys Gly Ser Pro His Leu Arg Ser Arg Ser Pro Gln His Gln Asn
            740                 745                 750

Gly Ile Met Ser Pro Ser Pro Ile Ser Ser Pro Arg Thr Thr Ser Gly
        755                 760                 765

Ala Ser Thr Pro Leu Thr Gly Gly Asn Gly Ala Ile Pro Phe Asn His
        770                 775                 780

Ala Arg His Leu Ala Tyr Asn Asn Glu Gly Phe Thr Ile Thr Ser Arg
785                 790                 795                 800

Cys Leu Asp Glu Pro Leu Pro Asn Gln Pro Asp Pro Val Leu Gly
                805                 810                 815

Arg Phe Val Arg Val Lys Gln Pro Ser Leu Gly Phe Gln Glu Arg Ala
            820                 825                 830

Val Pro Glu Ala Asp Ile Leu Ser Pro Gln Phe Gly Arg Met Gly His
        835                 840                 845

Val Ser Val Trp Asn Leu His Asp Lys Pro Leu Pro Ser Glu His Ala
        850                 855                 860

Ser Gln Lys Gly Phe Glu Asp Arg Val Lys Leu Lys Pro Pro Leu Asp
865                 870                 875                 880

Leu Arg Ser Gly Pro Pro His Leu Gly Cys Asn His Gly His
                885                 890

```
<210> SEQ ID NO 19
<211> LENGTH: 3479
<212> TYPE: DNA
<213> ORGANISM: Glycine max
<220> FEATURE:
<221> NAME/KEY: source
<222> LOCATION: 1..3479
<223> OTHER INFORMATION: /mol_type="unassigned DNA"
      /organism="Glycine max"

<400> SEQUENCE: 19
```

| | | | | | |
|---|---|---|---|---|---|
| atgccttcat | ggtggggaaa | atcatcatca | accaagaaga | aagcaaataa | ggaaagtttt          60 |
| attgatgcat | ttcaccgaaa | atttaaaatc | ccatccgaag | gtaaaccaag | cggtagatct         120 |
| ggaggatctc | gtagacattg | cgatgattca | atttcagaga | aaggggctca | gtctcctcct         180 |
| gaatcaagat | ctccttctcc | ttccaaggtg | ggaaggtgtc | aaagctttgt | tgaaaggcct         240 |
| catgctcagc | cactaccact | tcctggcttg | cacccatcaa | atataagccg | agcagattcc         300 |
| gaaattagta | taccatcatc | tagaagaaga | catggaaagg | gctccaaatc | atcgttgttt         360 |
| cttccactac | caaaaccagc | gtgcatgcgt | ggtaggttga | accctgctga | gttggatgga         420 |
| gatttggtca | cggcttcagt | ctctagtgag | agctctgctg | atagtgatga | accagtggac         480 |
| tctcacaatc | gtagtcctct | ggcaactgac | tgtgaaactg | gactagaac  | tgctgcaggc         540 |
| agtccctcca | gcttgatgca | gaaggatcaa | tcatctactg | tttcccaaat | aaactcaagg         600 |
| gaagccaaaa | aaccggcaaa | tattctgggt | aatcatatgt | cttctacttc | accaaaacgt         660 |
| aggcccttaa | gcaaccatgt | tacaaatctg | cagattcctc | ctcatggtgc | cttcttcagt         720 |
| gcgcctgaca | gttcaagatc | aagtccatca | agaagtccat | tgagagcatt | tggtaccgaa         780 |
| caggtgttga | actctgcttt | ttgggccggg | aagccatatc | agaggtcaa  | ttttggtgga         840 |
| tctggccact | gctcaagtcc | tggttctggt | cacaattctg | gcataattc  | aatgggaggg         900 |
| gacatgtcag | acagttatt  | ttggcaacct | agcagggta  | gcccagaata | ttccccgta          960 |
| cctagtccca | gaatgactag | ccctggtcca | agctctagaa | ttcagagtgg | agctgttaca        1020 |
| cctattcatc | caagagctgg | gggaacaccc | aatgaatcac | agacaggaag | gattgatgat        1080 |
| gtaaaaccac | agagtcatcg | tttgccccctt | cctcccttag | cagttacaaa | tactttgcct        1140 |
| ttctctcatt | caaattctgc | agcaacttct | ccatctatgc | caagaagtcc | aggaagagca        1200 |
| gataatccaa | ttagccctgg | atcacgttgg | aaaaaaggaa | agctgcttgg | cagaggcaca        1260 |
| tttggacatg | tctatgttgg | ctttaataag | gaaagtggtg | aaatgtgtgc | tatgaaagag        1320 |
| gtaactcttt | tttcagatga | tgccaaatct | aaagagagtg | ctaagcaatt | aatgcaggaa        1380 |
| attaccttgt | tgagccggtt | acgacatcca | aatattgtgc | agtattatgg | ttctgaaaca        1440 |
| gtaggcgaca | gctttacat  | atatctggag | tatgttgctg | gaggctccat | atataaactt        1500 |
| cttcaagaat | atggacaatt | tggtgaacta | gctattcgta | gttatactca | acaaattttg        1560 |
| tcaggacttg | cttatttaca | tgctaaaaat | actgtccaca | gggacatcaa | aggagcaaat        1620 |
| atactggtag | atactaatgg | ccgggttaag | ttggcagact | ttggcatggc | aaagcatata        1680 |
| acagggcaat | catgtccatt | atcattcaag | ggaagccctt | attggatggc | tcctgaggtt        1740 |
| ataaaaaact | ctaatggttg | caacctagct | gttgatatat | ggagcttgg  | atgcacagtt        1800 |
| ttggaaatgg | ctacaactaa | acctccttgg | agtcagtatg | aaggggttgc | tgccatgttt        1860 |
| aagattggta | atagcaagga | actcccaaca | atcccagatc | atctctccag | tgaaggaaag        1920 |
| gattttgtta | ggaaatgcct | acaacgtaat | ccacacaatc | gcccttcagc | cagtgaatta        1980 |
| ttggaccacc | cttttgtaaa | atgtgctgca | cctttagaaa | gacctattct | gggtcctgag        2040 |

```
tctccttcag acccagcacc agcagtatcg gggatcacac aaggagcgac agcttcgggc   2100
attgggcaag gaaggaatcc gtccaagttg gattcagatc gactttctct tcattcttct   2160
aggttttga  aaactaatcc ccatgcaagt gaaatccata ttccaaggaa tatatcttgc   2220
cctgtttcac ccattggaag cccacttttg aggccaagat caccacaaca catgaatggg   2280
cgaatgtctc cctctcctat atctagccct cggactgctt ctggtgcatc cacgcctctt   2340
aatggtggta gcggtgccat tccatttagt aatcacttag tttacattca agagggtctt   2400
ggaaacttgc caaaatcttc aaatggtgtc tacgttagtg gccctgctca tcatgacttg   2460
aatgttgaca ttttcgagg  aatgcaacag acatctcaca ttacatcaga actggttcca   2520
agtgaaagtg atgttctggg gaagcagttt gcacggactc ctcataatga gccgtatgat   2580
gttcaatcag tcttggctga ccgtgtttgc cggcagctgc tggggataa  tgtgaaaatt   2640
aaccaatgcc ttgatctaag tcccaactct ttgctcagcc gggctaatgg tttatgacat   2700
ggagcatttc ccttggccca cttttgagc  aagtctttga tgtttgtcag aatgatccat   2760
ttattgttct atttctgagg aagtaattgt aaaataagga gccaaagcat aggagaatcg   2820
atgaaataaa ttttgatcta agaatagagg agctggggca cttaattccg ttctgcatgg   2880
cttcaggctc aggcattgtg gagttcagaa cctttaagtt gaagtaccaa actaagccat   2940
acgatgaaac ttcctgacat ttgatttgtc tatatcaact gaagcaaatg ctcactggtt   3000
gctaaaagag gagcttatgt ttgtatgtag aattttcaag atgcagcatc agtgcatgct   3060
aagtagggag cttggatttc tctctggtac ctaagatatg agaatgatag gattaatgtt   3120
aatattaact caaggaatga cttcttctaa tcatatgtat gcagttcctt cagttaaaga   3180
atttatgcaa tgacaactgt ttcttttaga acatcatata gatgccaaaa aaaagtgaa   3240
attggtacaa aatttagctt ctagactatt ttttgggagg tgatgttgct gtacagaata   3300
tgggagactg tattgtgatt ctgcatttat tgatgagaag ccaaggattt gtggaaccca   3360
tatctctt   gattgcatgg tcagatgtat tactgtcatt atataccctt ctgctggatt   3420
tattttgtac attattattt gaagtaaaaa attgaagata tatgatttgt gatcctctc    3479
```

<210> SEQ ID NO 20
<211> LENGTH: 898
<212> TYPE: PRT
<213> ORGANISM: Glycine max

<400> SEQUENCE: 20

```
Met Pro Ser Trp Trp Gly Lys Ser Ser Thr Lys Lys Ala Asn
1               5                   10                  15

Lys Glu Ser Phe Ile Asp Ala Phe His Arg Lys Phe Lys Ile Pro Ser
                20                  25                  30

Glu Gly Lys Pro Ser Gly Arg Ser Gly Ser Arg Arg His Cys Asp
            35                  40                  45

Asp Ser Ile Ser Glu Lys Gly Ala Gln Ser Pro Glu Ser Arg Ser
        50                  55                  60

Pro Ser Pro Ser Lys Val Gly Arg Cys Gln Ser Phe Val Glu Arg Pro
65                  70                  75                  80

His Ala Gln Pro Leu Pro Leu Pro Gly Leu His Pro Ser Asn Ile Ser
                85                  90                  95

Arg Ala Asp Ser Glu Ile Ser Ile Pro Ser Ser Arg Arg Arg His Gly
                100                 105                 110

Lys Gly Ser Lys Ser Ser Leu Phe Leu Pro Leu Pro Lys Pro Ala Cys
```

```
                115                 120                 125
Met Arg Gly Arg Leu Asn Pro Ala Glu Leu Asp Gly Asp Leu Val Thr
130                 135                 140
Ala Ser Val Ser Ser Glu Ser Ser Ala Asp Ser Asp Glu Pro Val Asp
145                 150                 155                 160
Ser His Asn Arg Ser Pro Leu Ala Thr Asp Cys Glu Thr Gly Thr Arg
                165                 170                 175
Thr Ala Ala Gly Ser Pro Ser Ser Leu Met Gln Lys Asp Gln Ser Ser
                180                 185                 190
Thr Val Ser Gln Ile Asn Ser Arg Glu Ala Lys Lys Pro Ala Asn Ile
        195                 200                 205
Leu Gly Asn His Met Ser Ser Thr Ser Pro Lys Arg Arg Pro Leu Ser
        210                 215                 220
Asn His Val Thr Asn Leu Gln Ile Pro Pro His Gly Ala Phe Phe Ser
225                 230                 235                 240
Ala Pro Asp Ser Ser Arg Ser Ser Pro Ser Arg Ser Pro Leu Arg Ala
                245                 250                 255
Phe Gly Thr Glu Gln Val Leu Asn Ser Ala Phe Trp Ala Gly Lys Pro
                260                 265                 270
Tyr Pro Glu Val Asn Phe Gly Gly Ser Gly His Cys Ser Ser Pro Gly
                275                 280                 285
Ser Gly His Asn Ser Gly His Asn Ser Met Gly Gly Asp Met Ser Gly
        290                 295                 300
Gln Leu Phe Trp Gln Pro Ser Arg Gly Ser Pro Glu Tyr Ser Pro Val
305                 310                 315                 320
Pro Ser Pro Arg Met Thr Ser Pro Gly Pro Ser Ser Arg Ile Gln Ser
                325                 330                 335
Gly Ala Val Thr Pro Ile His Pro Arg Ala Gly Gly Thr Pro Asn Glu
                340                 345                 350
Ser Gln Thr Gly Arg Ile Asp Asp Val Lys Pro Gln Ser His Arg Leu
                355                 360                 365
Pro Leu Pro Pro Leu Ala Val Thr Asn Thr Leu Pro Phe Ser His Ser
        370                 375                 380
Asn Ser Ala Ala Thr Ser Pro Ser Met Pro Arg Ser Pro Gly Arg Ala
385                 390                 395                 400
Asp Asn Pro Ile Ser Pro Gly Ser Arg Trp Lys Lys Gly Lys Leu Leu
                405                 410                 415
Gly Arg Gly Thr Phe Gly His Val Tyr Val Gly Phe Asn Lys Glu Ser
                420                 425                 430
Gly Glu Met Cys Ala Met Lys Glu Val Thr Leu Phe Ser Asp Asp Ala
                435                 440                 445
Lys Ser Lys Glu Ser Ala Lys Gln Leu Met Gln Glu Ile Thr Leu Leu
        450                 455                 460
Ser Arg Leu Arg His Pro Asn Ile Val Gln Tyr Tyr Gly Ser Glu Thr
465                 470                 475                 480
Val Gly Asp Lys Leu Tyr Ile Tyr Leu Glu Tyr Val Ala Gly Gly Ser
                485                 490                 495
Ile Tyr Lys Leu Leu Gln Glu Tyr Gly Gln Phe Gly Glu Leu Ala Ile
                500                 505                 510
Arg Ser Tyr Thr Gln Gln Ile Leu Ser Gly Leu Ala Tyr Leu His Ala
                515                 520                 525
Lys Asn Thr Val His Arg Asp Ile Lys Gly Ala Asn Ile Leu Val Asp
        530                 535                 540
```

Thr Asn Gly Arg Val Lys Leu Ala Asp Phe Gly Met Ala Lys His Ile
545                 550                 555                 560

Thr Gly Gln Ser Cys Pro Leu Ser Phe Lys Gly Ser Pro Tyr Trp Met
                565                 570                 575

Ala Pro Glu Val Ile Lys Asn Ser Asn Gly Cys Asn Leu Ala Val Asp
            580                 585                 590

Ile Trp Ser Leu Gly Cys Thr Val Leu Glu Met Ala Thr Thr Lys Pro
        595                 600                 605

Pro Trp Ser Gln Tyr Glu Gly Val Ala Ala Met Phe Lys Ile Gly Asn
    610                 615                 620

Ser Lys Glu Leu Pro Thr Ile Pro Asp His Leu Ser Glu Gly Lys
625                 630                 635                 640

Asp Phe Val Arg Lys Cys Leu Gln Arg Asn Pro His Asn Arg Pro Ser
                645                 650                 655

Ala Ser Glu Leu Leu Asp His Pro Phe Val Lys Cys Ala Ala Pro Leu
            660                 665                 670

Glu Arg Pro Ile Leu Gly Pro Glu Ser Pro Ser Asp Pro Ala Pro Ala
        675                 680                 685

Val Ser Gly Ile Thr Gln Gly Ala Thr Ala Ser Gly Ile Gly Gln Gly
    690                 695                 700

Arg Asn Pro Ser Lys Leu Asp Ser Asp Arg Leu Ser Leu His Ser Ser
705                 710                 715                 720

Arg Phe Leu Lys Thr Asn Pro His Ala Ser Glu Ile His Ile Pro Arg
                725                 730                 735

Asn Ile Ser Cys Pro Val Ser Pro Ile Gly Ser Pro Leu Leu Arg Pro
            740                 745                 750

Arg Ser Pro Gln His Met Asn Gly Arg Met Ser Pro Ser Pro Ile Ser
        755                 760                 765

Ser Pro Arg Thr Ala Ser Gly Ala Ser Thr Pro Leu Asn Gly Gly Ser
    770                 775                 780

Gly Ala Ile Pro Phe Ser Asn His Leu Val Tyr Ile Gln Glu Gly Leu
785                 790                 795                 800

Gly Asn Leu Pro Lys Ser Ser Asn Gly Val Tyr Val Ser Gly Pro Ala
                805                 810                 815

His His Asp Leu Asn Val Asp Ile Phe Arg Gly Met Gln Gln Thr Ser
            820                 825                 830

His Ile Thr Ser Glu Leu Val Pro Ser Glu Ser Asp Val Leu Gly Lys
        835                 840                 845

Gln Phe Ala Arg Thr Pro His Asn Glu Pro Tyr Asp Val Gln Ser Val
    850                 855                 860

Leu Ala Asp Arg Val Cys Arg Gln Leu Leu Gly Asp Asn Val Lys Ile
865                 870                 875                 880

Asn Gln Cys Leu Asp Leu Ser Pro Asn Ser Leu Leu Ser Arg Ala Asn
                885                 890                 895

Gly Leu

<210> SEQ ID NO 21
<211> LENGTH: 3250
<212> TYPE: DNA
<213> ORGANISM: Glycine max
<220> FEATURE:
<221> NAME/KEY: source
<222> LOCATION: 1..3250
<223> OTHER INFORMATION: /mol_type="unassigned DNA"
      /organism="Glycine max"

<400> SEQUENCE: 21

```
tttttgcgta ctcagatttg agctgaatat cacagtgtgg ggttgaactc agattcacgg      60
tgtggaacaa ttcgaaggtt ttagcagcca ttttcagtct ctaatttctg tctctgactc     120
tgaagtactg cttttggaat tattggattc ttcatttggt gaggattttg aaggatcat     180
agtgcttata aactccacct actaatgtga aatgatagac atttcgaact attaacggga    240
tttgtttaag caacttgttt gccacattgc aatatataaa atacaaatat gccttcatgg    300
tgggggaaat catcgtcaac caagaagaaa gcaaataagg aaagttttat caatgcattt    360
caccgaaaat ttaaaatccc atccgaaggt aaaccaaaca gtagatccgg aggatctcgt    420
agacatagca atgactcaat ttcggagaaa ggggctcagt ctcctcctga atcaagatct    480
ccttcgcctt ccaaagtggg aaggtgtcaa agctttgttg ataggcctca tgcccagcca    540
ctaccacttc ctggcctgca cccatcaaat ataagccgag cagattctga aattagtata    600
ccatcatcta gagcaagaca tgaaaagggc tccaaaccat cattgtttct tccactacca    660
aaaccggtgt gcatccgtgg taggttgaac cctgctgatt tggatggaga tttggtcact    720
gcttcagtct ctagtgagag ctctgctgat agtgatgaac cagtggactc tcgcaatcgt    780
agtcctttgg caactgactg tgaaactggg actagaactg ctgcaggcag tccctccagc    840
ttgatggtca aggatcaatc aactactgtt cccaaataa actcaaggga agctaaaaaa    900
ccggcaaaca ttcttggtaa tcatacgtct tctacttcac caaaacgtag gcccttaagc    960
aaccatgtta cgaatctgca gattcctcct catggtgcct tctgcagtgc acctgacagt   1020
tcaagatcaa gtccatcaag aagtccattg agatcatttg gcacagaaca ggtgttgaac   1080
tctgctttt gggccggaaa gccatatcca gaggtcaatt ttggtggatc tggccactgc   1140
tcaagtcctg gttctggtca caattctggg cataattcaa tgggagggga catgtcaggg   1200
cagttatttt ggcaacctag cagggtagc ccagagtatt ccccgtacc tagtcccaga     1260
atgactagcc caggtccaag ctctagaatt cagagtggag ctgttacacc tattcatcca    1320
agagctgggg gaacacccaa tgaatcacaa acaggaaggg ttgatgatgt aaaaccacag   1380
agtcatcgtt taccccttcc tcccttagca gttaccaata ctttgccttt ctctcattca   1440
aattctgcag caacttctcc atctatgcca agaagtcctg gaagagcaga taatccaatt   1500
agccctggat cacgttggaa aaaggaaag ctgcttggca gaggcacatt tggacatgtc    1560
tatgttggct ttaataagga aagtggtgaa atgtgtgcta tgaaagaggt aactctgttt   1620
tcagatgatg ccaaatctaa agaaagtgct aagcaattaa tgcaggaaat taccttgttg   1680
agccggttac gacatccaaa tatagtgcag tattatggtt ccgaaacagt aggcgacaag   1740
ctttacatat atctggagta tgttgctgga ggctccatat ataaacttct tcaagaatat   1800
ggacaatttg gtgaactagc tattcgtagt tttactcaac aaattttgtc aggacttgct   1860
tatttacatg ctaaaaatac tgtccacagg gacatcaaag gagcaaatat actggtagat   1920
actaatggcc gggttaagtt ggcagacttt ggcatggcaa gcatataac agggcaatca    1980
tgtccattat cattcaaggg aagccccctat tggatggctc ctgaggttat aaaaaactct   2040
aatggttgca acctagctgt tgatatatgg agccttggat gcagttttt ggaaatggct    2100
acaactaaac ctccttggag tcagtatgaa ggggttgctg ccatgttcaa gattggtaat   2160
agcaaggaac tccaacaat cccagatcat ctctcttgtg aaggaaagga ttttgttagg    2220
aaatgcctac aacgtaatcc acacaatcgc ccttcagcca gtgaattatt ggaccaccct   2280
```

-continued

```
tttgtaaaat atgctgcacc tttagaaaga cctattctgg gtcctgagtc tccttcagac    2340
ccagcagtat cagggatcac acaaggagct acaacttcgg gcattggaca aggaaggaat    2400
ccatctaagt tggattcaga tcgactttct cttcattctt ctaggttttt gaaaactaat    2460
cctcatgcaa gtgaaatcca tattccaagg aatatatctt gccctgtctc acccattgga    2520
agcccacttt tgaggccaag atcgccacaa cacatgaatg ggcgaatgtc tccctcccct    2580
atatctagcc ctcggactgc ttctggtgca tccacacctc tcaatggtgg tagtggtgcc    2640
attccattta gtaatcactt agtttacatt caagagggtc ttggaagctt gccaaagtct    2700
tcaaatggtg tctacgttag tgtccctgct gctcatcatg acttgaatat tgacattttt    2760
cgaggaatgc aacagacatc tcacattaca tcagaactgg ttccaagtga aagtgatgtt    2820
ttggggaagc agtttgcacg gtctcctcat aatgagccgt atgatgttca atcagtcttg    2880
gctgaccgtg tttgccggca gctgctgggg gataatgtga aaattaaccc atcccttgat    2940
ctaagtccca actctttgct cagccgggct aatggtttat gacatggagc attttccttg    3000
gcccactttt tgagcaagtc ttcgatgttc gtcagaatga tccatttatt gttctatttg    3060
ctgaggaagt aattgtaaaa taaggagcca aagcatagga gaatcaatgt aataaatttt    3120
gatctaagaa tataggagct ggggcatata attccatttt gcatggcttc aggctcaggc    3180
tagtggagtt cagaaccttt cattggaagt gccaaactaa gccttaggat gaaacttcct    3240
gacatttgat                                                          3250
```

<210> SEQ ID NO 22
<211> LENGTH: 888
<212> TYPE: PRT
<213> ORGANISM: Glycine max

<400> SEQUENCE: 22

```
Met Leu Thr Trp Trp Gly Lys Ser Ser Lys Glu Thr Lys Lys Lys
1               5                   10                  15

Ala Asn Lys Glu Ser Phe Phe Asp Thr Leu His Arg Lys Leu Arg Ile
            20                  25                  30

Ser Ser Lys Gly Lys Val Ser Ile Arg Ser Gly Gly Ser Arg Arg His
        35                  40                  45

Cys Asn Asp Thr Ile Ser Glu Lys Gly Asp His Ser Pro Cys Gly Ser
    50                  55                  60

Arg Ser Pro Ser Pro Ser Lys Val Ala Arg Cys Gln Ser Phe Ile Asp
65                  70                  75                  80

Arg Pro His Ala Gln Pro Leu Pro Leu Pro Gly Leu His Pro Ser Ser
                85                  90                  95

Val Gly Arg Val Asp Ser Glu Ile Ser Ile Ser Ser Lys Ser Arg Leu
            100                 105                 110

Glu Lys Val Ser Lys Pro Leu Ser Phe Leu Thr Leu Pro Thr Pro Gly
        115                 120                 125

Cys Ile Arg Cys Arg Pro Asn Pro Ala Asp Leu Asp Gly Asp Met Val
    130                 135                 140

Thr Ala Ser Val Phe Ser Asp Cys Ser Ala Asp Ser Asp Glu Pro Ala
145                 150                 155                 160

Asp Ser His Asn Arg Ser Pro Leu Ala Ile Asp Cys Glu Thr Gly Thr
                165                 170                 175

Arg Thr Ala Ala Gly Ser Pro Ser Ser Leu Met Leu Lys Asp Gln Pro
            180                 185                 190

Pro Ala Val Ser Gln Leu Asn Ser Thr Gly Val Lys Lys Pro Gly Asn
```

```
            195                 200                 205
Ile Leu Ser Asn His Met Ser Ser Thr Ser Pro Lys Arg Arg Pro Leu
210                 215                 220

Arg Asn His Val Pro Asn Leu Gln Val Pro Pro His Gly Ala Phe Tyr
225                 230                 235                 240

Ser Ala Pro Asp Ser Ser Leu Ser Ser Pro Ser Arg Ser Pro Leu Arg
                245                 250                 255

Ala Phe Gly Thr Asp Gln Val Leu Asn Ser Ala Phe Leu Ala Gly Lys
                260                 265                 270

Pro Tyr Pro Glu Ile Asn Phe Val Gly Ser Gly His Cys Ser Ser Pro
                275                 280                 285

Gly Ser Gly His Asn Ser Gly His Asn Ser Met Gly Gly Asp Met Ser
                290                 295                 300

Gly Pro Leu Leu Trp Gln Pro Ser Arg Gly Ser Pro Glu Tyr Ser Pro
305                 310                 315                 320

Val Pro Ser Pro Arg Met Thr Ser Pro Gly Pro Ser Ser Arg Ile Gln
                325                 330                 335

Ser Gly Ala Val Thr Pro Ile His Pro Lys Ala Gly Gly Thr Pro Thr
                340                 345                 350

Glu Ser Gln Thr His Arg Leu Pro Leu Pro Pro Leu Ser Val Ser Asn
                355                 360                 365

Ser Ser Leu Phe Ser His Ser Asn Ser Ala Ala Thr Ser Pro Ser Met
                370                 375                 380

Pro Arg Ser Pro Ala Arg Ala Asp Asn Pro Asn Ser Gly Ser Arg Trp
385                 390                 395                 400

Lys Lys Gly Lys Leu Leu Gly Ser Gly Ser Phe Gly His Val Tyr Leu
                405                 410                 415

Gly Phe Asn Ser Glu Arg Gly Glu Met Cys Ala Val Lys Glu Val Thr
                420                 425                 430

Leu Phe Ser Asp Asp Pro Lys Ser Met Glu Ser Ala Lys Gln Phe Met
                435                 440                 445

Gln Glu Ile His Leu Leu Ser Arg Leu Gln His Pro Asn Ile Val Gln
                450                 455                 460

Tyr Tyr Gly Ser Glu Thr Val Asp Asn Lys Leu Tyr Ile Tyr Leu Glu
465                 470                 475                 480

Tyr Val Ser Gly Gly Ser Ile His Lys Leu Leu Arg Glu Tyr Gly Gln
                485                 490                 495

Phe Gly Glu Leu Val Ile Arg Ser Tyr Thr Gln Gln Ile Leu Ser Gly
                500                 505                 510

Leu Ala Tyr Leu His Ala Lys Asn Thr Leu His Arg Asp Ile Lys Gly
                515                 520                 525

Ala Asn Ile Leu Val Asp Pro Thr Gly Arg Val Lys Leu Ala Asp Phe
                530                 535                 540

Gly Met Ala Lys His Ile Thr Gly Gln Ser Cys Pro Leu Ser Phe Lys
545                 550                 555                 560

Gly Thr Pro Tyr Trp Met Ala Pro Glu Val Ile Lys Asn Ser Asn Gly
                565                 570                 575

Cys Asn Leu Ala Val Asp Ile Trp Ser Leu Gly Cys Thr Val Leu Glu
                580                 585                 590

Met Ala Thr Thr Lys Pro Pro Trp Phe Gln Tyr Glu Gly Val Ala Ala
                595                 600                 605

Met Phe Lys Ile Gly Asn Ser Lys Glu Leu Pro Thr Ile Pro Asp His
                610                 615                 620
```

Leu Ser Asn Glu Gly Lys Asp Phe Val Arg Lys Cys Leu Gln Arg Asn
625                 630                 635                 640

Pro His Asp Arg Pro Ser Ala Ser Glu Leu Leu Asp His Pro Phe Val
            645                 650                 655

Lys Asn Ala Ala Pro Leu Glu Arg Pro Ile Pro Ala Pro Glu Ala Leu
        660                 665                 670

Asp Pro Val Ser Gly Ile Thr Gln Gly Ala Lys Ala Leu Ala Ile Gly
    675                 680                 685

Gln Gly Arg Asn Leu Ser Ser Leu Asp Ser Asp Arg Leu Ser Val His
690                 695                 700

Ser Ser Arg Phe Leu Lys Thr Asn Pro His Glu Ser Glu Ile His Ile
705                 710                 715                 720

Pro Arg Asn Ile Ser Cys Pro Val Ser Pro Ile Gly Ser Pro Leu Leu
                725                 730                 735

Arg Ser Arg Ser Pro Gln His Arg Asn Gly Lys Met Ser Pro Ser Pro
            740                 745                 750

Ile Ser Ser Pro Arg Thr Ala Ser Gly Ala Ser Thr Pro Leu Ala Gly
        755                 760                 765

Gly Ser Gly Ala Ile Pro Phe Gly Asn His Ser Lys Gln Ser Ile Tyr
    770                 775                 780

Phe Gln Glu Gly Phe Gly Ser Ile Pro Lys Ser Ser Asn Gly Val Tyr
785                 790                 795                 800

Met Asn Gly His Ser His His Asp Ser Asn Val Asp Ile Phe Arg Gly
                805                 810                 815

Met Gln Met Gly Ser His Ile Ser Pro Glu Leu Val Ser Glu Asn
            820                 825                 830

Asp Val Leu Val Lys Gln Phe Ala Arg His Pro His Ala Glu Pro Tyr
        835                 840                 845

Asp Phe Gln Ser Val Leu Ala Asp Arg Val Gly Arg Gln Leu Leu Gly
    850                 855                 860

Glu His Val Lys Ile Asn Pro Ser Ile Asp Leu Ser Pro Asn Ser Ser
865                 870                 875                 880

Leu Leu Ser Arg Pro Asn Gly Leu
                885

<210> SEQ ID NO 23
<211> LENGTH: 3456
<212> TYPE: DNA
<213> ORGANISM: Glycine max
<220> FEATURE:
<221> NAME/KEY: source
<222> LOCATION: 1..3456
<223> OTHER INFORMATION: /mol_type="unassigned DNA"
      /organism="Glycine max"

<400> SEQUENCE: 23
gcgatctctt tcacttactt ttaattgcga atattttcac cacaaatcac ttcaaaatcc      60
ttctctgctt gtcgcatttt gagtctctgt gggtcttttg gggctctctc tctcgccgag     120
ctccgcactc ttcagggaat ttcctcactc agattccagc tgaaaattgc gcagtgagtt     180
cacttcaaat tcagagatga ttaattgaag ttttttgcaa taatagttca ataactgatt     240
cctgtctcta attctgaagt tattactttt aaaggtttaa tggctgtgtc atgactttttg     300 taactttgcc tactgaagtg aaatgataga ttttttgaac tcttactggg atccttctaa     360
gaaacttgcg tgccacatct caatttataa aatacaaata tgcttacatg gtggggaaaa     420

```
tcatcatcaa aagaaaccaa gaagaaagca aataaggaaa gtttctttga cacactgcac    480
cgaaaactta gaatttcatc caaaggtaaa gtaagcatta gatctggagg atcacgtaga    540
cattgcaatg acacaatttc agagaaggga gatcattctc catgtggatc aagatcgcct    600
tcaccttcca aagtggcaag gtgtcaaagt tttattgata ggcctcatgc tcagccactt    660
ccacttcctg gtctgcatcc ttcaagtgta ggccgagtag attctgaaat tagcatatca    720
tcaaaatcaa gattggaaaa agtctccaag ccattatcgt ttcttacgct tccaacacct    780
ggatgcatac gttgtaggcc aaaccctgca gatttggatg gagatatggt cactgcttca    840
gtctttagtg attgctctgc tgacagtgat gagccggcag actcacacaa tcgtagtcct    900
ctagcaattg actgtgagac tgggactaga actgctgctg gcagtccttc cagcttaatg    960
ctcaaggatc aaccacctgc tgtttcccaa ctgaattcaa cgggagtaaa gaaaccagga   1020
aatattctaa gtaatcatat gtcttctact tcaccaaaac gtaggccttt acgcaaccat   1080
gttccaaatc ttcaggttcc tcctcatggt gccttctata gtgctcctga tagttccttg   1140
tcaagtccat caagaagtcc attgagggca tttggcacag atcaggtgtt gaattctgct   1200
tttttggctg gaaagccata tccagagatc aatttttgttg ggtctgggca ttgctctagt   1260
ccaggttcag gtcacaattc tgggcacaat tcaatgggag gggacatgtc aggaccgtta   1320
ctttggcaac caagcagggg tagccctgag tattctccag tacctagtcc cagaatgact   1380
agccctggtc caagctctag aattcagagt ggagcagtca cacctattca tcccaaagcc   1440
gggggaacac ccacagaatc acagactcat cgattgcctc ttcctccttt gtcagtttct   1500
aattcctcac tgttctctca ttcaaattct gcagcaacat ctccgtctat gccaagaagt   1560
ccagctagag cagataatcc aaactctggc tcacgttgga agaaagggaa gctgcttggc   1620
agcggctcat ttggacatgt ctatcttggc ttcaatagtg aaagaggcga aatgtgtgca   1680
gtgaaggagg ttaccctgtt ttcagatgat cccaagtcta tggaaagtgc gaagcaattt   1740
atgcaggaaa ttcatttatt aagccgctta cagcatccaa atattgtcca gtattatggt   1800
tctgaaacag tcgataacaa gctttacata taccttgagt atgtatctgg aggctccata   1860
cataaacttc ttcgagaata tgggcaattt ggtgaactag ttattcgtag ttatactcaa   1920
caaattttgt cagggcttgc ttatttgcat gctaaaaata ctctccatag ggatatcaaa   1980
ggagcaaata tactggtaga tccaactggt cgggtcaagt tggcagactt tggcatggca   2040
aaacatataa cagggcaatc gtgcccattg tcattcaagg gaacacctta ctggatggct   2100
cctgaggtta taaaaaattc taatggatgc aaccttgcgg tggatatatg gagtcttgga   2160
tgcacagttt tggaaatggc tacaaccaaa cctccttggt ttcagtatga aggggttgct   2220
gccatgttca gattggtaa tagcaaggaa ctcccaacca tccctgatca tctctcaaat   2280
gaaggaaaag attttgttag gaaatgtctt cagcgtaacc cacatgatcg tccttcagcc   2340
agtgaattgt tggaccaccc ctttgtaaaa aatgctgcac ctttggaaag acctattccg   2400
gctcctgaag ctttggaccc tgtttctggg attacacagg gagcaaaagc tctggctatt   2460
ggacaaggaa ggaatctttc tagcttggat tcagatagac tttctgttca ttcttctaga   2520
tttttgaaaa ctaatcctca tgaaagtgaa atccatattc caaggaatat atcttgccct   2580
gtttctccca ttggaagccc acttttgagg tcaagatcac cacagcacag gaatgggaaa   2640
atgtctcctt ctcctatatc tagccctcgg actgcttctg gggcatctac acctcttgct   2700
ggtggcagtg tgccattcc atttggtaat cactctaaac agtccattta ctttcaagag   2760
ggttttggaa gcattcccaa gtcctcaaat ggtgtctaca tgaatggcca ttctcatcac   2820
```

```
gactcgaatg ttgacatttt tcgaggaatg caaatggggt ctcacatttc accagaactg   2880
gtttccagtg aaaatgatgt tttggttaag cagtttgcaa ggcatcctca tgcagagcca   2940
tatgattttc agtcggtctt ggcagatcgt gttggccggc agctgctggg ggaacatgtt   3000
aagattaacc catccattga tctcagtccc aactcgtctt tgcttagccg gccaaacggt   3060 ttatgcatc aagatttttc ctaaagtttc tcataatacc tttggttagc agatctgttc   3120
attgttctat ttgcaagaat ataactatac aataaggagc aaagcacaa gagaatcaat   3180 gtaaataaat ttgtatccaa gataggcta catggggcac aaaagtgcat tttgcatggc   3240
ttcggctcgg gctgatggag ttcattcgtg ccacagcatt aaacattctg acaatttgtc   3300
catatcaagc aatcaactca tacaaatgct cacttgttcg aagaggaact tcttgttgta   3360
tgtaacatat ttaaagcatc aacgcatgag aggtttctct cctgcactta agatactaga   3420
aatgacagtt tatgcaatga caaatgcatc ttctag                             3456
```

<210> SEQ ID NO 24
<211> LENGTH: 888
<212> TYPE: PRT
<213> ORGANISM: Glycine max

<400> SEQUENCE: 24

```
Met Leu Thr Trp Trp Gly Lys Ser Ser Lys Glu Thr Lys Lys
1               5                   10                  15

Ala Asn Lys Glu Ser Phe Phe Asp Thr Leu His Arg Lys Leu Arg Ile
                20                  25                  30

Ser Ser Lys Gly Lys Val Ser Ile Arg Ser Gly Ser Arg Arg His
            35                  40                  45

Cys Asn Asp Thr Ile Ser Glu Lys Gly Asp His Ser Pro Cys Gly Ser
        50                  55                  60

Arg Ser Pro Ser Pro Ser Lys Val Ala Arg Cys Gln Ser Phe Ile Asp
65                  70                  75                  80

Arg Pro His Ala Gln Pro Leu Pro Leu Pro Gly Leu His Pro Ser Ser
                85                  90                  95

Val Gly Arg Val Asp Ser Glu Ile Ser Ile Ser Ser Lys Ser Arg Leu
            100                 105                 110

Glu Lys Val Ser Lys Pro Leu Ser Phe Leu Thr Leu Pro Thr Pro Gly
        115                 120                 125

Cys Ile Arg Cys Arg Pro Asn Pro Ala Asp Leu Asp Gly Asp Met Val
    130                 135                 140

Thr Ala Ser Val Phe Ser Asp Cys Ser Ala Asp Ser Asp Glu Pro Ala
145                 150                 155                 160

Asp Ser His Asn Arg Ser Pro Leu Ala Ile Asp Cys Glu Thr Gly Thr
                165                 170                 175

Arg Thr Ala Ala Gly Ser Pro Ser Ser Leu Met Leu Lys Asp Gln Pro
            180                 185                 190

Pro Ala Val Ser Gln Leu Asn Ser Thr Gly Val Lys Lys Pro Gly Asn
        195                 200                 205

Ile Leu Ser Asn His Met Ser Ser Thr Ser Pro Lys Arg Arg Pro Leu
    210                 215                 220

Arg Asn His Val Pro Asn Leu Gln Val Pro Pro His Gly Ala Phe Tyr
225                 230                 235                 240

Ser Ala Pro Asp Ser Ser Leu Ser Pro Ser Arg Ser Pro Leu Arg
                245                 250                 255
```

```
Ala Phe Gly Thr Asp Gln Val Leu Asn Ser Ala Phe Leu Ala Gly Lys
            260                 265                 270

Pro Tyr Pro Glu Ile Asn Phe Val Gly Ser Gly His Cys Ser Ser Pro
        275                 280                 285

Gly Ser Gly His Asn Ser Gly His Asn Ser Met Gly Gly Asp Met Ser
    290                 295                 300

Gly Pro Leu Leu Trp Gln Pro Ser Arg Gly Ser Pro Glu Tyr Ser Pro
305                 310                 315                 320

Val Pro Ser Pro Arg Met Thr Ser Pro Gly Pro Ser Ser Arg Ile Gln
                325                 330                 335

Ser Gly Ala Val Thr Pro Ile His Pro Lys Ala Gly Gly Thr Pro Thr
                340                 345                 350

Glu Ser Gln Thr His Arg Leu Pro Leu Pro Pro Leu Ser Val Ser Asn
            355                 360                 365

Ser Ser Leu Phe Ser His Ser Asn Ser Ala Ala Thr Ser Pro Ser Met
    370                 375                 380

Pro Arg Ser Pro Ala Arg Ala Asp Asn Pro Asn Ser Gly Ser Arg Trp
385                 390                 395                 400

Lys Lys Gly Lys Leu Leu Gly Ser Gly Ser Phe Gly His Val Tyr Leu
                405                 410                 415

Gly Phe Asn Ser Glu Arg Gly Glu Met Cys Ala Val Lys Glu Val Thr
            420                 425                 430

Leu Phe Ser Asp Asp Pro Lys Ser Met Glu Ser Ala Lys Gln Phe Met
        435                 440                 445

Gln Glu Ile His Leu Leu Ser Arg Leu Gln His Pro Asn Ile Val Gln
    450                 455                 460

Tyr Tyr Gly Ser Glu Thr Val Asp Asn Lys Leu Tyr Ile Tyr Leu Glu
465                 470                 475                 480

Tyr Val Ser Gly Gly Ser Ile His Lys Leu Leu Arg Glu Tyr Gly Gln
                485                 490                 495

Phe Gly Glu Leu Val Ile Arg Ser Tyr Thr Gln Gln Ile Leu Ser Gly
            500                 505                 510

Leu Ala Tyr Leu His Ala Lys Asn Thr Leu His Arg Asp Ile Lys Gly
        515                 520                 525

Ala Asn Ile Leu Val Asp Pro Thr Gly Arg Val Lys Leu Ala Asp Phe
    530                 535                 540

Gly Met Ala Lys His Ile Thr Gly Gln Ser Cys Pro Leu Ser Phe Lys
545                 550                 555                 560

Gly Thr Pro Tyr Trp Met Ala Pro Glu Val Ile Lys Asn Ser Asn Gly
                565                 570                 575

Cys Asn Leu Ala Val Asp Ile Trp Ser Leu Gly Cys Thr Val Leu Glu
            580                 585                 590

Met Ala Thr Thr Lys Pro Pro Trp Phe Gln Tyr Glu Gly Val Ala Ala
        595                 600                 605

Met Phe Lys Ile Gly Asn Ser Lys Glu Leu Pro Thr Ile Pro Asp His
    610                 615                 620

Leu Ser Asn Glu Gly Lys Asp Phe Val Arg Lys Cys Leu Gln Arg Asn
625                 630                 635                 640

Pro His Asp Arg Pro Ser Ala Ser Glu Leu Leu Asp His Pro Phe Val
                645                 650                 655

Lys Asn Ala Ala Pro Leu Glu Arg Pro Ile Pro Ala Pro Glu Ala Leu
            660                 665                 670

Asp Pro Val Ser Gly Ile Thr Gln Gly Ala Lys Ala Leu Ala Ile Gly
```

```
                675                 680                 685
Gln Gly Arg Asn Leu Ser Ser Leu Asp Ser Asp Arg Leu Ser Val His
            690                 695                 700

Ser Ser Arg Phe Leu Lys Thr Asn Pro His Glu Ser Glu Ile His Ile
705                 710                 715                 720

Pro Arg Asn Ile Ser Cys Pro Val Ser Pro Ile Gly Ser Pro Leu Leu
                725                 730                 735

Arg Ser Arg Ser Pro Gln His Arg Asn Gly Lys Met Ser Pro Ser Pro
            740                 745                 750

Ile Ser Ser Pro Arg Thr Ala Ser Gly Ala Ser Thr Pro Leu Ala Gly
                755                 760                 765

Gly Ser Gly Ala Ile Pro Phe Gly Asn His Ser Lys Gln Ser Ile Tyr
            770                 775                 780

Phe Gln Glu Gly Phe Gly Ser Ile Pro Lys Ser Ser Asn Gly Val Tyr
785                 790                 795                 800

Met Asn Gly His Ser His His Asp Ser Asn Val Asp Ile Phe Arg Gly
                805                 810                 815

Met Gln Met Gly Ser His Ile Ser Pro Glu Leu Val Ser Ser Glu Asn
            820                 825                 830

Asp Val Leu Val Lys Gln Phe Ala Arg His Pro His Ala Glu Pro Tyr
                835                 840                 845

Asp Phe Gln Ser Val Leu Ala Asp Arg Val Gly Arg Gln Leu Leu Gly
            850                 855                 860

Glu His Val Lys Ile Asn Pro Ser Ile Asp Leu Ser Pro Asn Ser Ser
865                 870                 875                 880

Leu Leu Ser Arg Pro Asn Gly Leu
                885

<210> SEQ ID NO 25
<211> LENGTH: 3351
<212> TYPE: DNA
<213> ORGANISM: Glycine max
<220> FEATURE:
<221> NAME/KEY: source
<222> LOCATION: 1..3351
<223> OTHER INFORMATION: /mol_type="unassigned DNA"
      /organism="Glycine max"

<400> SEQUENCE: 25
gtaatcatca gttgtgaaca ctgattgaga cggagacccc ttctttcacc ctctctttct      60
ctctctcctt ctctacgcga tctctttcac ttacttttaa ttgcgaatat tttcaccaca     120
aatcacttca aaatccttct ctgtttgttg cattttgagt cacggagtcc tttggggttc     180
tctctctctc gcgccgagct ccgaacgctt cagggaattt cctcactcag atttgagctg     240
aaaattgcgc agtgagttca cttcaaattc agagctgatt aattgaagtt ttttgcaata     300
atagttcaat aactgactcc tgtctctaat tctgaagtta ttgcttttgc aatttgtgat     360
tctcccactt ttaaaggtta atggctgcgt catggctttt gtaattctgt ctactgatgt     420
gaaatgatag attttgtgaa ctattactgg gatcctttta agaaacttgc ttgccacatc     480
ttaatttata aaatacaaat atgcttacat ggtgggggaa atcatcatca aaaaaaacca     540
agaagaaagc aaataaggaa agttttttg acacactgca ccgaaaactc agaatttcat     600
ctgaaggtaa agtaaacatt agatctggag gatctcgtag gcattgcaat gacacaattt     660
cagagaaggg ggatcattct ccatctggat caagatcgcc ttcaccttcc aaagtggcaa     720
ggtgtcaaag ttttattgat aggcctcatg ctcagccact tccacttcct ggtctgcacc     780
```

```
cttcaagtgt aggccgagta gattccgaaa ttagcatatc atcaaaatca agattggaaa    840
aagtctccaa gccatcattg tttcttccac ttccaacacc tggatgcata cgttgtaggc    900
cgaaccctgc agatttggat ggagatatgg tcactccttc agtctttagt gattgctctg    960
ctgacagtga tgagccggca gactcacaca atcgtagtcc tctagcaact gactgtgaga   1020
ctgggactag aactgctgct ggcagtcctt ccagctcgat gctcaaggat caaccaccta   1080
ctgtttccct actgaattca acaggagtaa agaaaccagg aaatattcta agtaatcata   1140
tgtcttctac ttcaccaaaa cataggcctt tacgcaacca tgttccaaat cttcaggttc   1200
ctcctcatgt tgccttctat agtactcctg atagttcctt gtcaagtcca tcaagaagtc   1260
cattgagagc atttggcaca gatcaggtgt tgaattctgc ttttttggct ggaaagccat   1320
atccagaggt caattttgtt gggtctgggc attgctctag tccaggttca ggtcacaatt   1380
ctgggtataa ttcaatggga ggggacatgt caggaccgtt actttggcaa ccaagcaggg   1440
gtagccctga gtattctcca gtacctagtc ccagaatgac tagccctggt ccaagctcta   1500
gaattcagag tggagcagtc acacctattc atcccaaagc cggggaaaca cccacagaat   1560
cacagactca tcgtttgcct cttcctcctt tgtcagtttc taattcctca ccgttctctc   1620
attcaaattc tgcagcaaca tctccatcta tgccaagaag tccagctaga gcagataatc   1680
caagctctgg ctcacgttgg aagaaaggga agctgcttgg cagcggctca tttgacatg    1740
tctatcttgg tttcaatagt gaaagtggcg aaatgtgtgc agtgaaggag gttaccctgt   1800
tttcagatga tcccaagtct atggaaagtg ctaagcaatt tatgcaggaa attcattat    1860
taagccgttt acagcatcca aatatcgtcc agtattatgg ttctgaaaca gttgatgaca   1920
agctttacat ataccttgaa tatgtatctg gaggctccat acataaactt cttcaagaat   1980
atgggcaatt tggtgaacta gttattcgta gttatactca acagattttg tcagggcttg   2040
cttatttgca tgctaaaaat actctccata gggatatcaa aggagcaaat atactggtag   2100
atccaactgg tcgggtcaag ttggcagact ttggcatggc aaaacatata acagggcaat   2160
cgtgtctatt gtcattcaag gaacccctt actggatggc tcctgaggtt ataaagaact   2220
ctaatggatg caaccttgca gtggatatat ggagtcttgg atgcacggtt ttggaaatgg   2280
ctactaccaa acctccttgg tttcagtatg aagcggttgc tgccatgttc aagattggta   2340
atagcaagga actcccaaca atccctgatc atctctcaaa tgaaggaaaa gattttgtta   2400
ggaaatgtct tcagcgtaac ccgtatgatc gcccttcagc ctgtgaattg ttggaccacc   2460
cttttgtaaa aaatgctgca cctttggaaa gacctattct ggctcctgaa gtgttggacc   2520
ctgtttctgg gatcatacag ggagcaaaag ctctggccgc tggacaagga agaatctttt   2580
ctagcttgga ttcagataga cttttctatt attcttctag atttttgaaa actaatcctc   2640
gtgaaagtga atccatatt ccaaggaata tatcttgccc tgtttctccc attggaagcc    2700
cacttttgag gtcaagatca ccacagcaca ggaatgggaa aatgtctcct cctatatcta   2760
gccctcggac tgcttctggg gcgtccaccc ctcttgctgg tggcagtggt gccattccat   2820
ttggtaatca ctctaaacag ccaatttact ttcaagaggg ttttggaagc attcccaagt   2880
cctcaaatgg tgtctacatt aatggccatt ctcatcacga ctcgagtgtt gacatttttc   2940
gaggaatgca aataggatct cacattcaac cagaattggt ttccagtgaa aatgatgttt   3000
tggttaatca gtttgcaagg catcctcatg cagagccata tgattttcag tcagtcttgg   3060
cagatcgtgt tggccggcag ctgctgaggg aacatgttaa gattaaccca tccattgatc   3120
```

-continued

```
tcagtcccaa ctcgtctttg cttagccggc caaacggttt atgacatcaa gattttccct    3180
taagtttctc atagtacctt tggttatgca gatctgttca ttgttctatt tgcaagaata    3240
taactataca ataaggagcc aaagcacaag agaatcgatg taaataaatt tgcatctgag    3300
aataggctac atgggcaca aaagtgcatt ttgcatggct tctgctcggg c              3351
```

<210> SEQ ID NO 26
<211> LENGTH: 887
<212> TYPE: PRT
<213> ORGANISM: Glycine max

<400> SEQUENCE: 26

```
Met Leu Thr Trp Trp Gly Lys Ser Ser Lys Lys Thr Lys Lys Lys
1               5                   10                  15

Ala Asn Lys Glu Ser Phe Phe Asp Thr Leu His Arg Lys Leu Arg Ile
                20                  25                  30

Ser Ser Glu Gly Lys Val Asn Ile Arg Ser Gly Gly Ser Arg Arg His
            35                  40                  45

Cys Asn Asp Thr Ile Ser Glu Lys Gly Asp His Ser Pro Ser Gly Ser
        50                  55                  60

Arg Ser Pro Ser Pro Ser Lys Val Ala Arg Cys Gln Ser Phe Ile Asp
65                  70                  75                  80

Arg Pro His Ala Gln Pro Leu Pro Leu Pro Gly Leu His Pro Ser Ser
                85                  90                  95

Val Gly Arg Val Asp Ser Glu Ile Ser Ile Ser Ser Lys Ser Arg Leu
            100                 105                 110

Glu Lys Val Ser Lys Pro Ser Leu Phe Leu Pro Leu Pro Thr Pro Gly
        115                 120                 125

Cys Ile Arg Cys Arg Pro Asn Pro Ala Asp Leu Asp Gly Asp Met Val
    130                 135                 140

Thr Pro Ser Val Phe Ser Asp Cys Ser Ala Asp Ser Asp Glu Pro Ala
145                 150                 155                 160

Asp Ser His Asn Arg Ser Pro Leu Ala Thr Asp Cys Glu Thr Gly Thr
                165                 170                 175

Arg Thr Ala Ala Gly Ser Pro Ser Ser Met Leu Lys Asp Gln Pro
            180                 185                 190

Pro Thr Val Ser Leu Leu Asn Ser Thr Gly Val Lys Lys Pro Gly Asn
        195                 200                 205

Ile Leu Ser Asn His Met Ser Ser Thr Ser Pro Lys His Arg Pro Leu
    210                 215                 220

Arg Asn His Val Pro Asn Leu Gln Val Pro Pro His Gly Ala Phe Tyr
225                 230                 235                 240

Ser Thr Pro Asp Ser Ser Leu Ser Ser Pro Ser Arg Ser Pro Leu Arg
                245                 250                 255

Ala Phe Gly Thr Asp Gln Val Leu Asn Ser Ala Phe Leu Ala Gly Lys
            260                 265                 270

Pro Tyr Pro Glu Val Asn Phe Val Gly Ser Gly His Cys Ser Ser Pro
        275                 280                 285

Gly Ser Gly His Asn Ser Gly Tyr Asn Ser Met Gly Gly Asp Met Ser
    290                 295                 300

Gly Pro Leu Leu Trp Gln Pro Ser Arg Gly Ser Pro Glu Tyr Ser Pro
305                 310                 315                 320

Val Pro Ser Pro Arg Met Thr Ser Pro Gly Pro Ser Ser Arg Ile Gln
                325                 330                 335
```

```
Ser Gly Ala Val Thr Pro Ile His Pro Lys Ala Gly Thr Pro Thr
            340             345             350
Glu Ser Gln Thr His Arg Leu Pro Leu Pro Pro Leu Ser Val Ser Asn
        355             360             365
Ser Ser Pro Phe Ser His Ser Asn Ser Ala Ala Thr Ser Pro Ser Met
370             375             380
Pro Arg Ser Pro Ala Arg Ala Asp Asn Pro Ser Ser Gly Ser Arg Trp
385             390             395             400
Lys Lys Gly Lys Leu Leu Gly Ser Gly Ser Phe Gly His Val Tyr Leu
                405             410             415
Gly Phe Asn Ser Glu Ser Gly Glu Met Cys Ala Val Lys Glu Val Thr
            420             425             430
Leu Phe Ser Asp Asp Pro Lys Ser Met Glu Ser Ala Lys Gln Phe Met
        435             440             445
Gln Glu Ile His Leu Leu Ser Arg Leu Gln His Pro Asn Ile Val Gln
    450             455             460
Tyr Tyr Gly Ser Glu Thr Val Asp Asp Lys Leu Tyr Ile Tyr Leu Glu
465             470             475             480
Tyr Val Ser Gly Gly Ser Ile His Lys Leu Leu Gln Glu Tyr Gly Gln
                485             490             495
Phe Gly Glu Leu Val Ile Arg Ser Tyr Thr Gln Gln Ile Leu Ser Gly
            500             505             510
Leu Ala Tyr Leu His Ala Lys Asn Thr Leu His Arg Asp Ile Lys Gly
        515             520             525
Ala Asn Ile Leu Val Asp Pro Thr Gly Arg Val Lys Leu Ala Asp Phe
    530             535             540
Gly Met Ala Lys His Ile Thr Gly Gln Ser Cys Leu Leu Ser Phe Lys
545             550             555             560
Gly Thr Pro Tyr Trp Met Ala Pro Glu Val Ile Lys Asn Ser Asn Gly
                565             570             575
Cys Asn Leu Ala Val Asp Ile Trp Ser Leu Gly Cys Thr Val Leu Glu
            580             585             590
Met Ala Thr Thr Lys Pro Pro Trp Phe Gln Tyr Glu Ala Val Ala Ala
        595             600             605
Met Phe Lys Ile Gly Asn Ser Lys Glu Leu Pro Thr Ile Pro Asp His
    610             615             620
Leu Ser Asn Glu Gly Lys Asp Phe Val Arg Lys Cys Leu Gln Arg Asn
625             630             635             640
Pro Tyr Asp Arg Pro Ser Ala Cys Glu Leu Leu Asp His Pro Phe Val
                645             650             655
Lys Asn Ala Ala Pro Leu Glu Arg Pro Ile Leu Ala Pro Glu Val Leu
            660             665             670
Asp Pro Val Ser Gly Ile Ile Gln Gly Ala Lys Ala Leu Ala Ala Gly
        675             680             685
Gln Gly Lys Asn Leu Ser Ser Leu Asp Ser Asp Arg Leu Ser Ile His
    690             695             700
Ser Ser Arg Phe Leu Lys Thr Asn Pro Arg Glu Ser Glu Ile His Ile
705             710             715             720
Pro Arg Asn Ile Ser Cys Pro Val Ser Pro Ile Gly Ser Pro Leu Leu
                725             730             735
Arg Ser Arg Ser Pro Gln His Arg Asn Gly Lys Met Ser Pro Pro Ile
            740             745             750
Ser Ser Pro Arg Thr Ala Ser Gly Ala Ser Thr Pro Leu Ala Gly Gly
```

|     |     |     |     | 755 |     |     |     |     | 760 |     |     |     |     | 765 |
| --- | --- | --- | --- | --- | --- | --- | --- | --- | --- | --- | --- | --- | --- | --- |

Ser Gly Ala Ile Pro Phe Gly Asn His Ser Lys Gln Pro Ile Tyr Phe
        770                 775                 780

Gln Glu Gly Phe Gly Ser Ile Pro Lys Ser Ser Asn Gly Val Tyr Ile
785                 790                 795                 800

Asn Gly His Ser His His Asp Ser Ser Val Asp Ile Phe Arg Gly Met
                805                 810                 815

Gln Ile Gly Ser His Ile Gln Pro Glu Leu Val Ser Ser Glu Asn Asp
                820                 825                 830

Val Leu Val Asn Gln Phe Ala Arg His Pro His Ala Glu Pro Tyr Asp
            835                 840                 845

Phe Gln Ser Val Leu Ala Asp Arg Val Gly Arg Gln Leu Leu Arg Glu
        850                 855                 860

His Val Lys Ile Asn Pro Ser Ile Asp Leu Ser Pro Asn Ser Ser Leu
865                 870                 875                 880

Leu Ser Arg Pro Asn Gly Leu
                885

```
<210> SEQ ID NO 27
<211> LENGTH: 2535
<212> TYPE: DNA
<213> ORGANISM: Glycine max
<220> FEATURE:
<221> NAME/KEY: source
<222> LOCATION: 1..2535
<223> OTHER INFORMATION: /mol_type="unassigned DNA"
      /organism="Glycine max"

<400> SEQUENCE: 27
```

| | | | | |
|---|---|---|---|---|
| atgtcatcat | ggtgggaaaa | gtcttcatcc | aaagatgtaa | agaggaaaga aaaaggaaa | 60 |
| agtattattg | atacaataca | aaggaaatta | aataaatcaa | gagggtctag gagaaatcat | 120 |
| agtcacacta | actcagagaa | gggaaccaca | tcccttgtac | ctacaacatc accatcaccc | 180 |
| tcaacacatg | tttcccgcct | acaaagtttt | gcggaaagac | ctcttgctca gccactccca | 240 |
| ctcccaggga | cgcactgctc | ctccaccaat | cgagcaaatt | ctggaactag tgtaacatca | 300 |
| aaaccacaaa | gcacctgggg | cttgaaatca | tctctatatt | tccccttacc aaaacctggt | 360 |
| tgtgttttta | acggggagaa | acctacagat | gccgaggaag | atattgccac tgcatcaatt | 420 |
| tctagtggca | gctctattga | tagtgatgac | caatgtgact | cacatttcct tagtcctctg | 480 |
| gcatctgatt | ctgaaaatgg | aaaccaagct | accgttcaca | taccgtcag tgtggttcac | 540 |
| aaggatcaac | cacccattac | tatccaaaaa | aactcaagag | tatcctcaaa accagctcct | 600 |
| caactgtgta | atcatcaact | tttatataac | acacccaaag | gggcttcttt gcatctgccg | 660 |
| aatccgcaaa | tagcttcttc | aggtggtttg | tggagtgctc | cagacagttc aatgtcaagt | 720 |
| ccttctagaa | gtccactgag | aatgtttggt | tccgagcaag | ttttgaattc tggattctgt | 780 |
| acaggaaagc | tatatccaga | tttagctact | aggcactgtt | ctagtcctgg ttcaggccat | 840 |
| aattcagttg | gtggggatct | gacagggcat | aattctccga | tacccagtcc tggaatgaaa | 900 |
| agtcctggtt | tcagttccag | gatacacagt | ggtgctgtca | cccctcttca tccacgtgct | 960 |
| ggaagtgctg | cattagaatc | gcccacaaga | cgccctgatg | acgtgaaaca gactcaccga | 1020 |
| ttacctcttc | ctccaataac | aatacctaat | cattgtccat | tttctccaac atattctgca | 1080 |
| actactactc | cttcagcgcc | tcgtagtccc | agcatagcag | aaaatctaac atatcctggc | 1140 |
| tcgcgctgga | aaaaggggca | actgcttgga | aggggacat | ttgggcatgt atatcttggt | 1200 |

```
tttaacagtg aaagtggtga gatgtgtgca atgaaggagg taactctttt ttcagatgat    1260
gctaaatcaa gggaaagtgc tcaacaactt ggccaagaaa ttgcattgct aagtcacctg    1320
cggcatccaa atatagtcca atattatgga tctgagacgg tagatgataa actttatata    1380
tacttggagt atgtctctgg tgggtcaatc tataagttgc ttcaacagta tggccagctt    1440
agtgaaattg ttattcgtaa ttatactcgg caaattctgt taggtcttgc ttatttacat    1500
gctaaaaaca ctgttcatag agacattaaa gccgcaaaca tattggtgga tcctaatggg    1560
agggtaaaat tggcagattt tggcatggca aagcatataa gtgggcaatc ctgtccatta    1620
tctttcaaag gaagtcctta ctggatggca cctgaggtga taagaattc aaatggttgt     1680
aatcttgctg ttgatatatg gagccttggc tccaccgttt tcgagatggc tactacaaaa    1740
cctccttgga gccaatacga aggggttgcg gctatgttta agattggaaa cagcaaggac    1800
cttcctgcaa tgccagatca tctatcagaa gatggaaaag attttatcag gcaatgcttg    1860
caaaggaatc cagtgcatcg tccctctgct gctcaacttc tgctgcatcc atttgttaaa    1920
aaagccacac tgggaagacc tgttctgtct gctgatcctt tagaagcaaa acctgatttt    1980
gtaaatacta tgagatctct ggctattgga cctgcaaaac ataatttagg cttagtttca    2040
gaagcagctg tacatatct gtctagaagc ttgagaactg gctcaggatc aagtgaagcc     2100
catacaccaa ggaacatttc atatcctgtg tctcctactg ggaacccact tttgcctcct    2160
aggttactgc atgtgagtgg aaggctgtct ccatcagtc ctcacactgc atctggctca     2220
tctacaccgc tcactggtgg cattggtgca gtcccttttc atcaaacaaa gcagccaatg    2280
ttctcacatg aaggtatcag tgtaatacaa aggcctcaaa gttatcagga gccaatgcat    2340
gacccacttt gggggattct gaaaagcact cttgcttgcc cggatatagt ttcgtccaat    2400
aatgatgctc ttggaaacca ataggaggg ttggccagg gactcccaag agatttttat       2460
gatgggaagt catatttagc ggatcgtgta tcgcaacagc tgttaaacga tcatgtaaga    2520
aaatttcatt cctag                                                      2535
```

<210> SEQ ID NO 28
<211> LENGTH: 844
<212> TYPE: PRT
<213> ORGANISM: Glycine max

<400> SEQUENCE: 28

Met Ser Ser Trp Trp Glu Lys Ser Ser Lys Asp Val Lys Arg Lys
1               5                   10                  15

Glu Lys Arg Lys Ser Ile Ile Asp Thr Ile Gln Arg Lys Leu Asn Lys
            20                  25                  30

Ser Arg Gly Ser Arg Arg Asn His Ser His Thr Asn Ser Glu Lys Gly
        35                  40                  45

Thr Thr Ser Leu Val Pro Thr Thr Ser Pro Ser Pro Ser Thr His Val
    50                  55                  60

Ser Arg Leu Gln Ser Phe Ala Glu Arg Pro Leu Ala Gln Pro Leu Pro
65                  70                  75                  80

Leu Pro Gly Thr His Cys Ser Ser Thr Asn Arg Ala Asn Ser Gly Thr
                85                  90                  95

Ser Val Thr Ser Lys Pro Gln Ser Thr Trp Gly Leu Lys Ser Ser Leu
            100                 105                 110

Tyr Phe Pro Leu Pro Lys Pro Gly Cys Val Phe Asn Arg Gly Glu Pro
        115                 120                 125

Thr Asp Ala Glu Glu Asp Ile Ala Thr Ala Ser Ile Ser Ser Gly Ser

-continued

```
            130                 135                 140
Ser Ile Asp Ser Asp Asp Gln Cys Asp Ser His Phe Leu Ser Pro Leu
145                 150                 155                 160

Ala Ser Asp Ser Glu Asn Gly Asn Gln Ala Thr Val His Asn Thr Val
                165                 170                 175

Ser Val Val His Lys Asp Gln Pro Pro Ile Thr Ile Gln Lys Asn Ser
                180                 185                 190

Arg Val Ser Ser Lys Pro Ala Pro Gln Leu Cys Asn His Gln Leu Leu
                195                 200                 205

Tyr Asn Thr Pro Lys Gly Ala Ser Leu His Leu Pro Asn Pro Gln Ile
                210                 215                 220

Ala Ser Ser Gly Gly Leu Trp Ser Ala Pro Asp Ser Ser Met Ser Ser
225                 230                 235                 240

Pro Ser Arg Ser Pro Leu Arg Met Phe Gly Ser Glu Gln Val Leu Asn
                245                 250                 255

Ser Gly Phe Cys Thr Gly Lys Leu Tyr Pro Asp Leu Ala Thr Arg His
                260                 265                 270

Cys Ser Ser Pro Gly Ser Gly His Asn Ser Val Gly Gly Asp Leu Thr
                275                 280                 285

Gly His Asn Ser Pro Ile Pro Ser Pro Gly Met Lys Ser Pro Gly Phe
                290                 295                 300

Ser Ser Arg Ile His Ser Gly Ala Val Thr Pro Leu His Pro Arg Ala
305                 310                 315                 320

Gly Ser Ala Ala Leu Glu Ser Pro Thr Arg Arg Pro Asp Asp Val Lys
                325                 330                 335

Gln Thr His Arg Leu Pro Leu Pro Pro Ile Thr Ile Pro Asn His Cys
                340                 345                 350

Pro Phe Ser Pro Thr Tyr Ser Ala Thr Thr Pro Ser Ala Pro Arg
                355                 360                 365

Ser Pro Ser Ile Ala Glu Asn Leu Thr Tyr Pro Gly Ser Arg Trp Lys
                370                 375                 380

Lys Gly Gln Leu Leu Gly Arg Gly Thr Phe Gly His Val Tyr Leu Gly
385                 390                 395                 400

Phe Asn Ser Glu Ser Gly Glu Met Cys Ala Met Lys Glu Val Thr Leu
                405                 410                 415

Phe Ser Asp Asp Ala Lys Ser Arg Glu Ser Ala Gln Gln Leu Gly Gln
                420                 425                 430

Glu Ile Ala Leu Leu Ser His Leu Arg His Pro Asn Ile Val Gln Tyr
                435                 440                 445

Tyr Gly Ser Glu Thr Val Asp Asp Lys Leu Tyr Ile Tyr Leu Glu Tyr
                450                 455                 460

Val Ser Gly Gly Ser Ile Tyr Lys Leu Leu Gln Tyr Gly Gln Leu
465                 470                 475                 480

Ser Glu Ile Val Ile Arg Asn Tyr Thr Arg Gln Ile Leu Leu Gly Leu
                485                 490                 495

Ala Tyr Leu His Ala Lys Asn Thr Val His Arg Asp Ile Lys Ala Ala
                500                 505                 510

Asn Ile Leu Val Asp Pro Asn Gly Arg Val Lys Leu Ala Asp Phe Gly
                515                 520                 525

Met Ala Lys His Ile Ser Gly Gln Ser Cys Pro Leu Ser Phe Lys Gly
                530                 535                 540

Ser Pro Tyr Trp Met Ala Pro Glu Val Ile Lys Asn Ser Asn Gly Cys
545                 550                 555                 560
```

Asn Leu Ala Val Asp Ile Trp Ser Leu Gly Ser Thr Val Phe Glu Met
                565                 570                 575

Ala Thr Thr Lys Pro Pro Trp Ser Gln Tyr Glu Gly Val Ala Ala Met
            580                 585                 590

Phe Lys Ile Gly Asn Ser Lys Asp Leu Pro Ala Met Pro Asp His Leu
        595                 600                 605

Ser Glu Asp Gly Lys Asp Phe Ile Arg Gln Cys Leu Gln Arg Asn Pro
    610                 615                 620

Val His Arg Pro Ser Ala Ala Gln Leu Leu His Pro Phe Val Lys
625                 630                 635                 640

Lys Ala Thr Leu Gly Arg Pro Val Leu Ser Ala Asp Pro Leu Glu Ala
            645                 650                 655

Lys Pro Asp Phe Val Asn Thr Met Arg Ser Leu Ala Ile Gly Pro Ala
        660                 665                 670

Lys His Asn Leu Gly Leu Val Ser Glu Ala Ala Gly Thr Tyr Leu Ser
    675                 680                 685

Arg Ser Leu Arg Thr Gly Ser Gly Ser Ser Glu Ala His Thr Pro Arg
690                 695                 700

Asn Ile Ser Tyr Pro Val Ser Pro Thr Gly Asn Pro Leu Leu Pro Pro
705                 710                 715                 720

Arg Leu Leu His Val Ser Gly Arg Leu Ser Pro Ser Pro His Thr
            725                 730                 735

Ala Ser Gly Ser Ser Thr Pro Leu Thr Gly Gly Ile Gly Ala Val Pro
        740                 745                 750

Phe His Gln Thr Lys Gln Pro Met Phe Ser His Glu Gly Ile Ser Val
    755                 760                 765

Ile Gln Arg Pro Gln Ser Tyr Gln Glu Pro Met His Asp Pro Leu Trp
770                 775                 780

Gly Ile Leu Lys Ser Thr Leu Ala Cys Pro Asp Ile Val Ser Ser Asn
785                 790                 795                 800

Asn Asp Ala Leu Gly Asn His Asn Arg Arg Val Gly Gln Gly Leu Pro
            805                 810                 815

Arg Asp Phe Tyr Asp Gly Lys Ser Tyr Leu Ala Asp Arg Val Ser Gln
        820                 825                 830

Gln Leu Leu Asn Asp His Val Arg Lys Phe His Ser
    835                 840

<210> SEQ ID NO 29
<211> LENGTH: 3117
<212> TYPE: DNA
<213> ORGANISM: Glycine max
<220> FEATURE:
<221> NAME/KEY: source
<222> LOCATION: 1..3117
<223> OTHER INFORMATION: /mol_type="unassigned DNA"
     /organism="Glycine max"

<400> SEQUENCE: 29
atgcggttgt ggtggggaaa gtcttcttcc aaagagtcga agaggaaggc aaacaaggaa     60
actattattg atacaataca gcggaaatta aagaatactt ctgaagagaa gtgcaacaat    120
aaatcaggaa ggtcaaggag acatcatgat gatgccatat ctaagaaggg ttctagatct    180
ctcacaccct tcaacatcag catcccctca acacatgtgt ctcgcgttcc aagttttaca    240
gaaaggcctc tttctcaacc actcccatta ccagggtcac atcttccagc tgccattgat    300
gtaagttctg gagttatttt aacatcaaaa ctggaaagag ccataggctc taagctatct    360

```
ctgaattttc ctcttcaaaa acctggctat gtatcaaaca aggaagatcc tacagatgca    420
gcaggagata tagcctctgc atctgtttct agtgacagct caattgatag tggcaactca    480
tttgattcgc cacatcttgt tagtccactg gcatctgact gtgaaaatgg aaacccagcc    540
accattaata gttctttaag tgtggtgcac aggaatcagt cacttattac tatccaaaga    600
aactcaagag catcctcaaa atcatctcct cagttgtgca ataataaaac ttcatcaacc    660
tcaccaagag gggctccatt acatctgcaa aatctgaaaa tagctcaacc aggtggtttg    720
tgtagtgctc cagatagttc agtgtcaagt ccttctagaa atcaaatggg agcatttgga    780
cctgagcaaa tgttgaactc tgaattacac acaggaaagc cttatccaga tatccttct     840 gggcgctgct ataatccagt ttcgggtcgt gattctggtc ataattcagt tggggggat     900 atttcaggac agatgatttt gccacagaac aagcgtagcc ctgagtgttc ttcaatacct    960
agtcccagaa ttacaagccc tggtcccagt tccaggacac agagtggtac tgtgacccct   1020
ctgcatccta aagctggagg cgctgcagca gaagcaccta caagacgtcc tgatgatgtg   1080
aaacaaaaaa atcatcagtt agcaattcct ccaataacag ccactaaatc ttgtccattt   1140
tctccaacct attctgcatt gacaactcct tcagcccctc gtagtcctgg cagatcagaa   1200
aattcatcaa gcccaggttc acgctggaaa aaggggcagt tgcttggaag gggaacattt   1260
ggacatgtat atcttggttt aacagagaa tgtggtgaga tgtgtgcaat gaaggaggta    1320 acccttttt ctgatgatgc taaatcaagg gaaagtgcgc agcaacttgg ccaagaaatt    1380
gcaatgctta gtcagttgcg gcatccaaat attgttcagt attatggatc tgagacggta   1440
gatgacagac tttatgtata cttggagtat gtctctggtg ggtcaatcta taagctggtt   1500
aaagaatatg ccagttagg tgaaattgct attcgtaatt atactcggca aattctatta    1560
ggacttgcgt atttgcacac caagaacact gttcacaggg acattaaagg agcaaacata   1620
ttggtggacc ctagtgggcg gataaaattg gcagattttg ggatggcaaa gcatataagc   1680
gggtcctctt gtccattttc tttcaaagga agtccttact ggatggcacc tgaggttata   1740
aaaaattcaa atggttgtaa tcttgcggtt gatatatgga gtctaggatg cactgttttg   1800
gagatggcaa caacaaaacc tccttggagc caatatgaag gggttgctgc tttgtttaag   1860
attgggaata gcaaggaact tcctacaatt ccagatcatc tatcagaaga tggaaaagat   1920
tttgtcaggc tttgtttgca aaggaatcct ctaaatcgtc cctcagctgc tcaacttcta   1980
gatcatccat tgttaaaaa tgctatgctg gaaagatcca ttttaactgc cgttccttca    2040
gaagatccaa ctgccataat aaatgcagtg agatctctgg ccgttggacc tgtaaaacat   2100
aatttatgct tagactcaga agtggctggg atctatccac tcagaagctt gagaactggt   2160
tctggatcaa gcaatgctca tacaccaagg aacatctctt gtcccgtttc tcctctcttg   2220
ccttataaat cattgcatag aagtggaaga atgtctcctt ctccaatacc cagccctaat   2280
actgcatctg gctcatcttc accactaacc agtggtggcg tgctattcc atttcatcag    2340 acaaagcaac cactatttc acatgaagtt gtgggtatga tccaaaagtc tcagaatggc   2400
gctattccaa caggtagacc ttgtgctgtg tctggctcat cttcaccacg aaccagtggc   2460
ggtggtgttg tccatttca tcagacaaag aagacactat tatcatatga agttgtggg    2520 atgatccaaa agtctcggaa tggtgctatt ccaatatcta gccctcatac tgcatctggt   2580
tcatcttcgc cactaaccag tggtggtggt gccattccat ttcatcagac aaagcaacca   2640
ctattctcaa atgaagttgt ggctatgatc caaaagtctc aaagtggtgc tattcctata   2700
```

```
tctagccctc gtactgggtc tgggtcatct tcgccactaa ccagtggtgg cggtgctatt    2760
ccatttcatc agacaaatca accactattc tcacatgaag ttgtgggtat gatccaaaag    2820
cctccgaatg ttttttattc aaatggaaat actgcttatc aggggtctaa gcatgagcag    2880
tttgggagaa acttgcaaac tacacatcct tgctgggatg tagtttcatc tgataatgat    2940
gctcttccaa accattccag gagggctgtc cagggagacc caataaaatt tcgtgatgag    3000
aagtcatgct tggctgattg tgtgtcacag caactgttga gggattatgt tcgcctaaat    3060
gcatgccttg ataataagct caataccccca aatcctgatt gcattaatgg cttgtga      3117
```

<210> SEQ ID NO 30
<211> LENGTH: 1038
<212> TYPE: PRT
<213> ORGANISM: Glycine max

<400> SEQUENCE: 30

```
Met Arg Leu Trp Trp Gly Lys Ser Ser Lys Glu Ser Lys Arg Lys
1               5                   10                  15

Ala Asn Lys Glu Thr Ile Ile Asp Thr Ile Gln Arg Lys Leu Lys Asn
            20                  25                  30

Thr Ser Glu Glu Lys Cys Asn Asn Lys Ser Gly Arg Ser Arg Arg His
        35                  40                  45

His Asp Asp Ala Ile Ser Lys Lys Gly Ser Arg Ser Leu Thr Pro Ser
    50                  55                  60

Thr Ser Ala Ser Pro Ser Thr His Val Ser Arg Val Pro Ser Phe Thr
65                  70                  75                  80

Glu Arg Pro Leu Ser Gln Pro Leu Pro Leu Pro Gly Ser His Leu Pro
                85                  90                  95

Ala Ala Ile Asp Val Ser Ser Gly Val Ile Leu Thr Ser Lys Leu Glu
            100                 105                 110

Arg Ala Ile Gly Ser Lys Leu Ser Leu Asn Phe Pro Leu Gln Lys Pro
        115                 120                 125

Gly Tyr Val Ser Asn Lys Glu Asp Pro Thr Asp Ala Ala Gly Asp Ile
    130                 135                 140

Ala Ser Ala Ser Val Ser Ser Asp Ser Ser Ile Asp Ser Gly Asn Ser
145                 150                 155                 160

Phe Asp Ser Pro His Leu Val Ser Pro Leu Ala Ser Asp Cys Glu Asn
                165                 170                 175

Gly Asn Pro Ala Thr Ile Asn Ser Ser Leu Ser Val Val His Arg Asn
            180                 185                 190

Gln Ser Leu Ile Thr Ile Gln Arg Asn Ser Arg Ala Ser Ser Lys Ser
        195                 200                 205

Ser Pro Gln Leu Cys Asn Asn Lys Thr Ser Ser Thr Ser Pro Arg Gly
    210                 215                 220

Ala Pro Leu His Leu Gln Asn Leu Lys Ile Ala Gln Pro Gly Gly Leu
225                 230                 235                 240

Cys Ser Ala Pro Asp Ser Ser Val Ser Ser Pro Ser Arg Asn Gln Met
                245                 250                 255

Gly Ala Phe Gly Pro Glu Gln Met Leu Asn Ser Glu Leu His Thr Gly
            260                 265                 270

Lys Pro Tyr Pro Asp Ile Pro Ser Gly Arg Cys Tyr Asn Pro Val Ser
        275                 280                 285

Gly Arg Asp Ser Gly His Asn Ser Val Gly Gly Asp Ile Ser Gly Gln
    290                 295                 300
```

```
Met Ile Leu Pro Gln Asn Lys Arg Ser Pro Glu Cys Ser Ser Ile Pro
305                 310                 315                 320

Ser Pro Arg Ile Thr Ser Pro Gly Pro Ser Arg Thr Gln Ser Gly
            325                 330                 335

Thr Val Thr Pro Leu His Pro Lys Ala Gly Ala Ala Ala Glu Ala
                340                 345                 350

Pro Thr Arg Arg Pro Asp Asp Val Lys Gln Lys Asn His Gln Leu Ala
            355                 360                 365

Ile Pro Pro Ile Thr Ala Thr Lys Ser Cys Pro Phe Ser Pro Thr Tyr
        370                 375                 380

Ser Ala Leu Thr Thr Pro Ser Ala Pro Arg Ser Pro Gly Arg Ser Glu
385                 390                 395                 400

Asn Ser Ser Ser Pro Gly Ser Arg Trp Lys Lys Gly Gln Leu Leu Gly
                405                 410                 415

Arg Gly Thr Phe Gly His Val Tyr Leu Gly Phe Asn Arg Glu Cys Gly
            420                 425                 430

Glu Met Cys Ala Met Lys Glu Val Thr Leu Phe Ser Asp Asp Ala Lys
            435                 440                 445

Ser Arg Glu Ser Ala Gln Gln Leu Gly Gln Glu Ile Ala Met Leu Ser
    450                 455                 460

Gln Leu Arg His Pro Asn Ile Val Gln Tyr Tyr Gly Ser Glu Thr Val
465                 470                 475                 480

Asp Asp Arg Leu Tyr Val Tyr Leu Glu Tyr Val Ser Gly Gly Ser Ile
                485                 490                 495

Tyr Lys Leu Val Lys Glu Tyr Gly Gln Leu Gly Glu Ile Ala Ile Arg
        500                 505                 510

Asn Tyr Thr Arg Gln Ile Leu Leu Gly Leu Ala Tyr Leu His Thr Lys
        515                 520                 525

Asn Thr Val His Arg Asp Ile Lys Gly Ala Asn Ile Leu Val Asp Pro
    530                 535                 540

Ser Gly Arg Ile Lys Leu Ala Asp Phe Gly Met Ala Lys His Ile Ser
545                 550                 555                 560

Gly Ser Ser Cys Pro Phe Ser Phe Lys Gly Ser Pro Tyr Trp Met Ala
                565                 570                 575

Pro Glu Val Ile Lys Asn Ser Asn Gly Cys Asn Leu Ala Val Asp Ile
            580                 585                 590

Trp Ser Leu Gly Cys Thr Val Leu Glu Met Ala Thr Thr Lys Pro Pro
        595                 600                 605

Trp Ser Gln Tyr Glu Gly Val Ala Ala Leu Phe Lys Ile Gly Asn Ser
    610                 615                 620

Lys Glu Leu Pro Thr Ile Pro Asp His Leu Ser Glu Asp Gly Lys Asp
625                 630                 635                 640

Phe Val Arg Leu Cys Leu Gln Arg Asn Pro Leu Asn Arg Pro Ser Ala
                645                 650                 655

Ala Gln Leu Leu Asp His Pro Phe Val Lys Asn Ala Met Leu Glu Arg
            660                 665                 670

Ser Ile Leu Thr Ala Val Pro Ser Glu Asp Pro Thr Ala Ile Ile Asn
    675                 680                 685

Ala Val Arg Ser Leu Ala Val Gly Pro Val Lys His Asn Leu Cys Leu
    690                 695                 700

Asp Ser Glu Val Ala Gly Ile Tyr Pro Leu Arg Ser Leu Arg Thr Gly
705                 710                 715                 720

Ser Gly Ser Ser Asn Ala His Thr Pro Arg Asn Ile Ser Cys Pro Val
```

```
                    725                 730                 735
Ser Pro Ser Leu Pro Tyr Lys Ser Leu His Arg Ser Gly Arg Met Ser
                740                 745                 750

Pro Ser Pro Ile Pro Ser Pro Asn Thr Ala Ser Gly Ser Ser Ser Pro
            755                 760                 765

Leu Thr Ser Gly Gly Gly Ala Ile Pro Phe His Gln Thr Lys Gln Pro
        770                 775                 780

Leu Phe Ser His Glu Val Val Gly Met Ile Gln Lys Ser Gln Asn Gly
785                 790                 795                 800

Ala Ile Pro Thr Gly Arg Pro Cys Ala Val Ser Gly Ser Ser Ser Pro
                805                 810                 815

Arg Thr Ser Gly Gly Gly Val Val Pro Phe His Gln Thr Lys Lys Thr
                820                 825                 830

Leu Leu Ser Tyr Glu Val Val Gly Met Ile Gln Lys Ser Arg Asn Gly
                835                 840                 845

Ala Ile Pro Ile Ser Ser Pro His Thr Ala Ser Gly Ser Ser Ser Pro
            850                 855                 860

Leu Thr Ser Gly Gly Gly Ala Ile Pro Phe His Gln Thr Lys Gln Pro
865                 870                 875                 880

Leu Phe Ser Asn Glu Val Val Ala Met Ile Gln Lys Ser Gln Ser Gly
                885                 890                 895

Ala Ile Pro Ile Ser Ser Pro Arg Thr Gly Ser Gly Ser Ser Ser Pro
            900                 905                 910

Leu Thr Ser Gly Gly Gly Ala Ile Pro Phe His Gln Thr Asn Gln Pro
                915                 920                 925

Leu Phe Ser His Glu Val Val Gly Met Ile Gln Lys Pro Pro Asn Val
930                 935                 940

Phe Tyr Ser Asn Gly Asn Thr Ala Tyr Gln Gly Ser Lys His Glu Gln
945                 950                 955                 960

Phe Gly Arg Asn Leu Gln Thr Thr His Pro Cys Trp Asp Val Val Ser
                965                 970                 975

Ser Asp Asn Asp Ala Leu Pro Asn His Ser Arg Arg Ala Val Gln Gly
            980                 985                 990

Asp Pro Ile Lys Phe Arg Asp Glu Lys Ser Cys Leu Ala Asp Cys Val
        995                 1000                1005

Ser Gln Gln Leu Leu Arg Asp Tyr Val Arg Leu Asn Ala Cys Leu Asp
        1010                1015                1020

Asn Lys Leu Asn Thr Pro Asn Pro Asp Cys Ile Asn Gly Leu
1025                1030                1035
```

<210> SEQ ID NO 31
<211> LENGTH: 2670
<212> TYPE: DNA
<213> ORGANISM: Cucumis melo
<220> FEATURE:
<221> NAME/KEY: source
<222> LOCATION: 1..2670
<223> OTHER INFORMATION: /mol_type="unassigned DNA"
      /organism="Cucumis melo"

<400> SEQUENCE: 31

```
atgccttcat ggtgggggaa gtcatcatca aaagaagtaa agaaaagcaa ggaaagttta      60
atcgacacat tgcagagaaa acttagaact actgatggta aaacgaacag caaatcagga     120
gagtctccga gaaattgtaa tgacacaatt tctgagcagg gatctcgatc tcctattttt     180
tcaagatcag cttccccttc caaacaagtt ttaagatgtc aaagcttttc cgagaggcca     240
```

```
caagcacaac ctcttccact tcctggtgtc cagccgccaa ttgtaggtcg gacagactct    300
gggattagga tttcaccaaa accaagatct gaaagggget ccaagccatc atcatttcta    360
ccacttccaa gaccagcatg cattcgtggg cagccaaacc atgcagattt agatgcagat    420
gttggtgttg gctcagtgtc cagtgagagc tcaactgata gcacggatct atcggattca    480
cgccatcgta gtcctcaggc aactgactat gatcttggga ctaaaactgc cgcaagcagt    540
ccttccagtg tcattctcaa ggatcagtct tctactctca cccaaccaag ttcgcaaaag    600
gccagaaaac cggctaatat ctcattgagc aaccacattt tctcaacatc acccaagcgg    660
agacctttaa gcagtcatgt tccaaatctg caagttccat atcatgggaa tgtatgcatt    720
gcacctgata gttcaatgtc aagtccttct aggagtccca aagggcatt tagctccgag    780 caagttatta ataatgctgt cagtactgga aagttctata tggatgtcac atttcctggg    840
tcaggccatt gttccagtcc tggttctggt tacaattctg gccataattc tatgggtggg    900
gatttgtcag ggcagttatt tttgcaacaa agccggggta gccctgaata ttctccagta    960
cctagtccca gaatgaccag ccctggccca agctccagag tccatagtgg tgcagtgacc   1020
ccaattcatc ctagggcggg aggtatacca actgagtcac agacaagctg gcctgatgag   1080
aagcaaactc accgcctgcc cctacctccc gttgcaattt ccaatgctcc ttttctcat    1140 tccaattcag ctgcaacttc tccctctgtt ccaagaagtc ctggaagggc tgataatccg   1200
gcaagcccgg gctcccgttg gaaaaagggg aagcttttgg gtaggggtac ttttggacat   1260
gtgtatgttg gttttaacag tgaaagtggt gaaatgtgtg caatgaagga agttacatta   1320
ttttctgacg atgcgaagtc caaggagagt gccaagcaat taatgcaaga aattaccttg   1380
ttgagtcgtt tacgacatcc aaatattgtg cagtattatg gatctgaaac ggttggggac   1440
aggttttaca tttaccttga atatgtatct ggtggctcta tttacaagct tctccaggaa   1500
tatggacagc ttggagattc agcacttcgt agttatactc agcaaatatt gtctgggctt   1560
gcatatttac acgctaaaag cacagttcac agggatatca aaggagcaaa tacttgtt    1620 gatcccactg ggcgtgttaa gttggctgac tttgggatgg caaaacatat cactggccaa   1680
tcgtgcccct tgtcatttaa aggaagcccg tattggatgg cacctgaggt tatcaaaaac   1740
tcaaatggtt gcaaccttgc ggtagatatt tggagtcttg gatgcactgt tttggagatg   1800
gcaacaacaa aacctccttg gagtcaatat gagggagttg ctgcgatgtt caagattggc   1860
aacagcaaag aacttcctga aatcccagat cacctttcac atgatggaaa agatttcgtt   1920
agacaatgtc tgcaacggaa tcctgctcat cgtcctacag ctgctcagct tttgaacat    1980 ccttttgtga acatgctgc acctcttgaa agaccgattt taggttctga acattcagat   2040
ccaactccag gaattacaaa tggagtaaga acattgggta ttgaacaagg aaggaatccc   2100
agcttcttgg attctgatag atctgcagct cattcatcta gactcccaac agctgctttc   2160
cattccagtg aaattcatat tccaaggaac ctatcgtgcc ctgtttcgcc catcggaagc   2220
cctctggtgc actcacgatc gcctcaacat cctagtggaa gaatgtctcc gtcacccata   2280
tctagccctc gtaacatgtc gggtgcatct actcctctca caggaggaag tggtgccatt   2340
ccacatcagc atctcaagca atcactgtac cttcaggagg gatttgggaa cttgccaaaa   2400
ccttcgatgg ctccttatag caatggtcct tcctttcacg atataaaccc tgacatcttt   2460
caggggattc agccaggctc acacatcttt tctgagcttg tacaccatga aaccgatttt   2520
ctgggcaagc agtttggaaa gcctgcctgg gaattgtatg atgggcaggc ggtcttggct   2580
```

-continued

```
gatcgtgttt ccaggcagct gctgagtgat cacataacaa ctccctcct ggatttaagt    2640 ccaagctctc ttttgaccaa ccgcaaatag                                    2670
```

<210> SEQ ID NO 32
<211> LENGTH: 889
<212> TYPE: PRT
<213> ORGANISM: Cucumis melo

<400> SEQUENCE: 32

| | | | | | | | | | | | | | | |
|---|---|---|---|---|---|---|---|---|---|---|---|---|---|---|
| Met | Pro | Ser | Trp | Trp | Gly | Lys | Ser | Ser | Lys | Glu | Val | Lys | Lys | Ser |
| 1 | | | | 5 | | | | | 10 | | | | | 15 |
| Lys | Glu | Ser | Leu | Ile | Asp | Thr | Leu | Gln | Arg | Lys | Leu | Arg | Thr | Thr | Asp |
| | | | 20 | | | | | 25 | | | | | 30 | | |
| Gly | Lys | Thr | Asn | Ser | Lys | Ser | Gly | Glu | Ser | Pro | Arg | Asn | Cys | Asn | Asp |
| | | | 35 | | | | | 40 | | | | | 45 | | |
| Thr | Ile | Ser | Glu | Gln | Gly | Ser | Arg | Ser | Pro | Ile | Phe | Ser | Arg | Ser | Ala |
| | | | 50 | | | | | 55 | | | | | 60 | | |
| Ser | Pro | Ser | Lys | Gln | Val | Leu | Arg | Cys | Gln | Ser | Phe | Ser | Glu | Arg | Pro |
| 65 | | | | | 70 | | | | | 75 | | | | | 80 |
| Gln | Ala | Gln | Pro | Leu | Pro | Leu | Pro | Gly | Val | Gln | Pro | Pro | Ile | Val | Gly |
| | | | | 85 | | | | | 90 | | | | | 95 | |
| Arg | Thr | Asp | Ser | Gly | Ile | Arg | Ile | Ser | Pro | Lys | Pro | Arg | Ser | Glu | Arg |
| | | | 100 | | | | | 105 | | | | | 110 | | |
| Gly | Ser | Lys | Pro | Ser | Ser | Phe | Leu | Pro | Leu | Pro | Arg | Pro | Ala | Cys | Ile |
| | | | 115 | | | | | 120 | | | | | 125 | | |
| Arg | Gly | Gln | Pro | Asn | His | Ala | Asp | Leu | Asp | Ala | Asp | Val | Gly | Val | Gly |
| | | | 130 | | | | | 135 | | | | | 140 | | |
| Ser | Val | Ser | Ser | Glu | Ser | Ser | Thr | Asp | Ser | Thr | Asp | Leu | Ser | Asp | Ser |
| 145 | | | | | 150 | | | | | 155 | | | | | 160 |
| Arg | His | Arg | Ser | Pro | Gln | Ala | Thr | Asp | Tyr | Asp | Leu | Gly | Thr | Lys | Thr |
| | | | | 165 | | | | | 170 | | | | | 175 | |
| Ala | Ala | Ser | Ser | Pro | Ser | Ser | Val | Ile | Leu | Lys | Asp | Gln | Ser | Ser | Thr |
| | | | 180 | | | | | 185 | | | | | 190 | | |
| Leu | Thr | Gln | Pro | Ser | Ser | Gln | Lys | Ala | Arg | Lys | Pro | Ala | Asn | Ile | Ser |
| | | | 195 | | | | | 200 | | | | | 205 | | |
| Leu | Ser | Asn | His | Ile | Phe | Ser | Thr | Ser | Pro | Lys | Arg | Arg | Pro | Leu | Ser |
| | | | 210 | | | | | 215 | | | | | 220 | | |
| Ser | His | Val | Pro | Asn | Leu | Gln | Val | Pro | Tyr | His | Gly | Asn | Val | Cys | Ile |
| 225 | | | | | 230 | | | | | 235 | | | | | 240 |
| Ala | Pro | Asp | Ser | Ser | Met | Ser | Ser | Pro | Ser | Arg | Ser | Pro | Ile | Arg | Ala |
| | | | | 245 | | | | | 250 | | | | | 255 | |
| Phe | Ser | Ser | Glu | Gln | Val | Ile | Asn | Asn | Ala | Val | Ser | Thr | Gly | Lys | Phe |
| | | | | 260 | | | | | 265 | | | | | 270 | |
| Tyr | Met | Asp | Val | Thr | Phe | Pro | Gly | Ser | Gly | His | Cys | Ser | Ser | Pro | Gly |
| | | | 275 | | | | | 280 | | | | | 285 | | |
| Ser | Gly | Tyr | Asn | Ser | Gly | His | Asn | Ser | Met | Gly | Gly | Asp | Leu | Ser | Gly |
| | | | 290 | | | | | 295 | | | | | 300 | | |
| Gln | Leu | Phe | Leu | Gln | Gln | Ser | Arg | Gly | Ser | Pro | Glu | Tyr | Ser | Pro | Val |
| 305 | | | | | 310 | | | | | 315 | | | | | 320 |
| Pro | Ser | Pro | Arg | Met | Thr | Ser | Pro | Gly | Pro | Ser | Ser | Arg | Val | His | Ser |
| | | | | 325 | | | | | 330 | | | | | 335 | |
| Gly | Ala | Val | Thr | Pro | Ile | His | Pro | Arg | Ala | Gly | Gly | Ile | Pro | Thr | Glu |
| | | | 340 | | | | | 345 | | | | | 350 | | |
| Ser | Gln | Thr | Ser | Trp | Pro | Asp | Glu | Lys | Gln | Thr | His | Arg | Leu | Pro | Leu |

```
                355                 360                 365
        Pro Pro Val Ala Ile Ser Asn Ala Pro Phe Ser His Ser Asn Ser Ala
            370                 375                 380

Ala Thr Ser Pro Ser Val Pro Arg Ser Pro Gly Arg Ala Asp Asn Pro
        385                 390                 395                 400

Ala Ser Pro Gly Ser Arg Trp Lys Lys Gly Lys Leu Leu Gly Arg Gly
                        405                 410                 415

Thr Phe Gly His Val Tyr Val Gly Phe Asn Ser Glu Ser Gly Glu Met
                    420                 425                 430

Cys Ala Met Lys Glu Val Thr Leu Phe Ser Asp Asp Ala Lys Ser Lys
                435                 440                 445

Glu Ser Ala Lys Gln Leu Met Gln Glu Ile Thr Leu Leu Ser Arg Leu
            450                 455                 460

Arg His Pro Asn Ile Val Gln Tyr Tyr Gly Ser Glu Thr Val Gly Asp
        465                 470                 475                 480

Arg Phe Tyr Ile Tyr Leu Glu Tyr Val Ser Gly Gly Ser Ile Tyr Lys
                        485                 490                 495

Leu Leu Gln Glu Tyr Gly Gln Leu Gly Asp Ser Ala Leu Arg Ser Tyr
                    500                 505                 510

Thr Gln Gln Ile Leu Ser Gly Leu Ala Tyr Leu His Ala Lys Ser Thr
                515                 520                 525

Val His Arg Asp Ile Lys Gly Ala Asn Ile Leu Val Asp Pro Thr Gly
            530                 535                 540

Arg Val Lys Leu Ala Asp Phe Gly Met Ala Lys His Ile Thr Gly Gln
        545                 550                 555                 560

Ser Cys Pro Leu Ser Phe Lys Gly Ser Pro Tyr Trp Met Ala Pro Glu
                        565                 570                 575

Val Ile Lys Asn Ser Asn Gly Cys Asn Leu Ala Val Asp Ile Trp Ser
                    580                 585                 590

Leu Gly Cys Thr Val Leu Glu Met Ala Thr Thr Lys Pro Pro Trp Ser
                595                 600                 605

Gln Tyr Glu Gly Val Ala Ala Met Phe Lys Ile Gly Asn Ser Lys Glu
            610                 615                 620

Leu Pro Glu Ile Pro Asp His Leu Ser His Asp Gly Lys Asp Phe Val
        625                 630                 635                 640

Arg Gln Cys Leu Gln Arg Asn Pro Ala His Arg Pro Thr Ala Ala Gln
                        645                 650                 655

Leu Leu Glu His Pro Phe Val Lys His Ala Ala Pro Leu Glu Arg Pro
                    660                 665                 670

Ile Leu Gly Ser Glu His Ser Asp Pro Thr Pro Gly Ile Thr Asn Gly
                675                 680                 685

Val Arg Thr Leu Gly Ile Glu Gln Gly Arg Asn Pro Ser Phe Leu Asp
            690                 695                 700

Ser Asp Arg Ser Ala Ala His Ser Ser Arg Leu Pro Thr Ala Ala Phe
        705                 710                 715                 720

His Ser Ser Glu Ile His Ile Pro Arg Asn Leu Ser Cys Pro Val Ser
                        725                 730                 735

Pro Ile Gly Ser Pro Leu Val His Ser Arg Ser Pro Gln His Pro Ser
                    740                 745                 750

Gly Arg Met Ser Pro Ser Pro Ile Ser Ser Pro Arg Asn Met Ser Gly
                755                 760                 765

Ala Ser Thr Pro Leu Thr Gly Gly Ser Gly Ala Ile Pro His Gln His
            770                 775                 780
```

```
Leu Lys Gln Ser Leu Tyr Leu Gln Glu Gly Phe Gly Asn Leu Pro Lys
785                 790                 795                 800

Pro Ser Met Ala Pro Tyr Ser Asn Gly Pro Ser Phe His Asp Ile Asn
            805                 810                 815

Pro Asp Ile Phe Gln Gly Ile Gln Pro Gly Ser His Ile Phe Ser Glu
        820                 825                 830

Leu Val His His Glu Thr Asp Phe Leu Gly Lys Gln Phe Gly Lys Pro
            835                 840                 845

Ala Trp Glu Leu Tyr Asp Gly Gln Ala Val Leu Ala Asp Arg Val Ser
    850                 855                 860

Arg Gln Leu Leu Ser Asp His Ile Thr Thr Pro Ser Leu Asp Leu Ser
865                 870                 875                 880

Pro Ser Ser Leu Leu Thr Asn Arg Lys
                885
```

<210> SEQ ID NO 33
<211> LENGTH: 2993
<212> TYPE: DNA
<213> ORGANISM: Solanum Lycopersicum
<220> FEATURE:
<221> NAME/KEY: source
<222> LOCATION: 1..2993
<223> OTHER INFORMATION: /mol_type="unassigned DNA"
      /organism="Solanum Lycopersicum"

<400> SEQUENCE: 33

```
gccagtttga gcacttctat gcaaaaaatg agcatccaaa gggattcctc acagagtttta      60 actatttagc tggctgtatc cagctaaaag tttggtacat gcaacagctg actgttcttg     120
ctcacgctaa ttttatatag caatgcgttc atggtggggg aagtcttcat ctaaggatgt     180
aaggaggaaa tccactaagg agagtttcat tgacataata aatcggaaac tgaagatttt     240
caccacggaa aaatcaagtg gtaaatctgg atcatctcga agacgacgta aagatacaaa     300
ttcagtgaag ggttctcaat caagggtttc aaggtcacca tcaccatcta ctggatccat     360
aatattagtg accggtgaag tctccgagcc atcattgact ttgcctcttc ccatgcccag     420
gcatcttcca catggaccaa ctgctgcagg agttgacagg gacttaccaa ctgcttctgt     480
ttcttgtgac agctccagtg acagtgatga tcttactgac tcacgatttc taagtcccca     540
aacatctgat tatgaaaacg ggagcagaac tgccttgaat agtccttcca gtttgaagca     600
gaaggttcag tccctattg catccaatgc aagctcagga gagatgctga agtcagctac     660
tcttttgtca gacaatcagg cgatccctac atctcctaga cagaggcttt taagatctca     720
tgtaccacca ggcttacaga ttcctcatca tggcgcttcc tacagtgctc ctgacagctc     780
gatgtcaagt ccttcaagaa gtcccatgag ggtatttggg catgaaacgg tcatgaaccc     840
tggtttctgg ctagggaagc cacatggaga gataaccttc ttaggatcag ggcactgctc     900
cagtccaggt tctggccaaa actctgggca caattcaatt ggaggtgata tgttagcgca     960 gccctttttgg ccacacagca ggtgtagtcc tgagtgttca cctgtaccta gccctagaat    1020
gactagtcct ggtcctggct ctaggataca tagtggtgct gtaactccct tgcatcctcg    1080
agctggagga acgttggctg agtcttccac agcttcactt gataatggaa acaacaaag    1140 tcatcgtctg cctcttcctc ccatatcaat ccctcattct tctacttttt ctttgtcatg    1200
ttcaatgact cctgcaattc cacgaagtcc tggtagaaca ggtaatcctc caagccctgg    1260
gccacgttgg aagaaaggac gtctgattgg tagtggcaca tttggacatg tgtaccttgg    1320
```

|  |  |  |  |  |  |  |  |  |
|---|---|---|---|---|---|---|---|---|
| ttttaacagt | gaaagcggtg | aaatgtgtgc | aatgaaggaa | gtaacacttt | tttcagacga | 1380 |
| cccaaagtca | agagaaagtg | cacagcagct | tggacaagaa | atatctctgc | taagtcggtt | 1440 |
| acgccatcca | aatattgtgc | aatattatgg | ctctgaaacg | gtagatgaca | agctatacat | 1500 |
| ataccttgag | tatgtttcag | gtggttcgat | ctataaaatt | cttcaagaat | acggtcagtt | 1560 |
| gggtgagcta | gcaattcaaa | gttacactca | acaaattctg | tctggacttg | catatttgca | 1620 |
| tgctaaaaac | acagtgcaca | gagatattaa | aggagcaaat | atactggttg | acccaaatgg | 1680 |
| ccgcgttaaa | ttggcagact | ttgggatggc | aaaacatata | actggtcact | actgtccttt | 1740 |
| gtctttcaag | ggaagtcctt | actggatggc | acctgaggtt | attaaaaatt | caaatggttg | 1800 |
| caatcttgcg | gtagatatat | ggagccttgg | atgcacggtt | ttggagatgg | caacaacaaa | 1860 |
| accaccttgg | agtcagtatg | aaggggtcgc | tgctattttt | aagattggaa | acagcaagga | 1920 |
| agttccagca | attccctatc | acctgtcaga | taagggcaag | gattttgtgc | ggcaatgtct | 1980 |
| acaacgcaat | ccactccacc | gtccaacagc | ttctcagctc | ttgaaacatc | cctttgtcaa | 2040 |
| aagtactgct | ccaatggaaa | gattcattgg | cattggacat | taaaagatc | caccatgtgt | 2100 |
| gggctcagaa | gaagttgcag | tgcatcatga | gcctagaagt | tcaatttttt | ttcctggatt | 2160 |
| tagcgacgta | cctgttccaa | gatcttgccc | agtttctcca | gttgggatag | agagccctgt | 2220 |
| ttaccattca | caatcaccta | aacatatgag | tggaagattg | tccccctcta | ccatatcaag | 2280 |
| cccccgtgct | gtatctggtt | catcaacacc | tcttagcggt | ggtggtggtg | ctgttccact | 2340 |
| atctaaccca | attatgccta | caacttcttc | atcagaagac | atgggaacat | caccaaaggc | 2400 |
| ccaaagttgt | ttttaccctg | atgcttacac | tagtcacggt | ctgaagtctg | acatgtctcg | 2460 |
| agaagcacct | ccatatggca | atggttttt | tggagaaaat | tttgggggcc | atgctcaaag | 2520 |
| tggtgttaat | ggacaaccat | atcagggaca | gtcagtatta | gctaataggg | ttgctcagca | 2580 |
| gcttttaagg | gaccaagtaa | aattgagccc | atcgtttgac | ctgaacccag | gctctccagt | 2640 |
| tttagttgg | gataatgggg | tctaactttg | taaaagtcac | ctgaaaaaga | atgatatgtc | 2700 |
| atggaacaac | tgtacagtaa | ccataccaaa | atgactgtag | ttcactgaat | aaaagtattg | 2760 |
| aagctgatga | aaggagaagg | ctctctcagt | atcccaatct | attcgttccc | agttgctatc | 2820 |
| gtaagttact | tctacctgta | acagtttttg | catatggttt | ccacatcacc | ctgatatttt | 2880 |
| tgactagtac | tttatttag | ttctccagca | atcaccatgc | taggagcctc | gtacagcagt | 2940 |
| gctatgaatc | ctcttttctt | ttgggatcct | cattgcatat | aagatctttt | ctt | 2993 |

<210> SEQ ID NO 34
<211> LENGTH: 827
<212> TYPE: PRT
<213> ORGANISM: Solanum Lycopersicum

<400> SEQUENCE: 34

```
Trp Trp Gly Lys Ser Ser Lys Asp Val Arg Arg Lys Ser Thr Lys
1               5                   10                  15

Glu Ser Phe Ile Asp Ile Ile Asn Arg Lys Leu Lys Ile Phe Thr Thr
            20                  25                  30

Glu Lys Ser Ser Gly Lys Ser Gly Ser Ser Arg Arg Arg Arg Lys Asp
        35                  40                  45

Thr Asn Ser Val Lys Gly Ser Gln Ser Arg Val Ser Arg Ser Pro Ser
    50                  55                  60

Pro Ser Thr Gly Ser Ile Ile Leu Val Thr Gly Glu Val Ser Glu Pro
65                  70                  75                  80
```

-continued

```
Ser Leu Thr Leu Pro Leu Pro Met Pro Arg His Leu Pro His Gly Pro
             85                  90                  95

Thr Ala Ala Gly Val Asp Arg Asp Leu Pro Thr Ala Ser Val Ser Cys
        100                 105                 110

Asp Ser Ser Ser Asp Ser Asp Leu Thr Asp Ser Arg Phe Leu Ser
        115                 120                 125

Pro Gln Thr Ser Asp Tyr Glu Asn Gly Ser Arg Thr Ala Leu Asn Ser
        130                 135                 140

Pro Ser Ser Leu Lys Gln Lys Val Gln Ser Pro Ile Ala Ser Asn Ala
145                 150                 155                 160

Ser Ser Gly Glu Met Leu Lys Ser Ala Thr Leu Leu Ser Asp Asn Gln
                165                 170                 175

Ala Ile Pro Thr Ser Pro Arg Gln Arg Leu Leu Arg Ser His Val Pro
            180                 185                 190

Pro Gly Leu Gln Ile Pro His His Gly Ala Ser Tyr Ser Ala Pro Asp
        195                 200                 205

Ser Ser Met Ser Ser Pro Ser Arg Ser Pro Met Arg Val Phe Gly His
        210                 215                 220

Glu Thr Val Met Asn Pro Gly Phe Trp Leu Gly Lys Pro His Gly Glu
225                 230                 235                 240

Ile Thr Phe Leu Gly Ser Gly His Cys Ser Ser Pro Gly Ser Gly Gln
                245                 250                 255

Asn Ser Gly His Asn Ser Ile Gly Gly Asp Met Leu Ala Gln Pro Phe
                260                 265                 270

Trp Pro His Ser Arg Cys Ser Pro Glu Cys Ser Pro Val Pro Ser Pro
            275                 280                 285

Arg Met Thr Ser Pro Gly Pro Gly Ser Arg Ile His Ser Gly Ala Val
        290                 295                 300

Thr Pro Leu His Pro Arg Ala Gly Gly Thr Leu Ala Glu Ser Ser Thr
305                 310                 315                 320

Ala Ser Leu Asp Asn Gly Lys Gln Gln Ser His Arg Leu Pro Leu Pro
                325                 330                 335

Pro Ile Ser Ile Pro His Ser Ser Thr Phe Ser Leu Ser Cys Ser Met
            340                 345                 350

Thr Pro Ala Ile Pro Arg Ser Pro Gly Arg Thr Gly Asn Pro Pro Ser
        355                 360                 365

Pro Gly Pro Arg Trp Lys Lys Gly Arg Leu Ile Gly Ser Gly Thr Phe
        370                 375                 380

Gly His Val Tyr Leu Gly Phe Asn Ser Glu Ser Gly Glu Met Cys Ala
385                 390                 395                 400

Met Lys Glu Val Thr Leu Phe Ser Asp Asp Pro Lys Ser Arg Glu Ser
                405                 410                 415

Ala Gln Gln Leu Gly Gln Glu Ile Ser Leu Leu Ser Arg Leu Arg His
            420                 425                 430

Pro Asn Ile Val Gln Tyr Tyr Gly Ser Glu Thr Val Asp Asp Lys Leu
        435                 440                 445

Tyr Ile Tyr Leu Glu Tyr Val Ser Gly Gly Ser Ile Tyr Lys Ile Leu
    450                 455                 460

Gln Glu Tyr Gly Gln Leu Gly Glu Leu Ala Ile Gln Ser Tyr Thr Gln
465                 470                 475                 480

Gln Ile Leu Ser Gly Leu Ala Tyr Leu His Ala Lys Asn Thr Val His
                485                 490                 495

Arg Asp Ile Lys Gly Ala Asn Ile Leu Val Asp Pro Asn Gly Arg Val
```

```
              500             505             510
Lys Leu Ala Asp Phe Gly Met Ala Lys His Ile Thr Gly His Tyr Cys
            515                 520                 525
Pro Leu Ser Phe Lys Gly Ser Pro Tyr Trp Met Ala Pro Glu Val Ile
            530                 535                 540
Lys Asn Ser Asn Gly Cys Asn Leu Ala Val Asp Ile Trp Ser Leu Gly
545                 550                 555                 560
Cys Thr Val Leu Glu Met Ala Thr Thr Lys Pro Pro Trp Ser Gln Tyr
                565                 570                 575
Glu Gly Val Ala Ala Ile Phe Lys Ile Gly Asn Ser Lys Glu Val Pro
                580                 585                 590
Ala Ile Pro Tyr His Leu Ser Asp Lys Gly Lys Asp Phe Val Arg Gln
            595                 600                 605
Cys Leu Gln Arg Asn Pro Leu His Arg Pro Thr Ala Ser Gln Leu Leu
            610                 615                 620
Lys His Pro Phe Val Lys Ser Thr Ala Pro Met Glu Arg Phe Ile Gly
625                 630                 635                 640
Ile Gly His Leu Lys Asp Pro Pro Cys Val Gly Ser Glu Glu Val Ala
                645                 650                 655
Val His His Glu Pro Arg Ser Ser Ile Phe Phe Pro Gly Phe Ser Asp
                660                 665                 670
Val Pro Val Pro Arg Ser Cys Pro Val Ser Pro Val Gly Ile Glu Ser
                675                 680                 685
Pro Val Tyr His Ser Gln Ser Pro Lys His Met Ser Gly Arg Leu Ser
            690                 695                 700
Pro Ser Thr Ile Ser Ser Pro Arg Ala Val Ser Gly Ser Ser Thr Pro
705                 710                 715                 720
Leu Ser Gly Gly Gly Ala Val Pro Leu Ser Asn Pro Ile Met Pro
                725                 730                 735
Thr Thr Ser Ser Ser Glu Asp Met Gly Thr Ser Pro Lys Ala Gln Ser
                740                 745                 750
Cys Phe Tyr Pro Asp Ala Tyr Thr Ser His Gly Leu Lys Ser Asp Met
            755                 760                 765
Ser Arg Glu Ala Pro Pro Tyr Gly Asn Gly Phe Phe Gly Glu Asn Phe
            770                 775                 780
Gly Gly His Ala Gln Ser Gly Val Asn Gly Gln Pro Tyr Gln Gly Gln
785                 790                 795                 800
Ser Val Leu Ala Asn Arg Val Ala Gln Gln Leu Leu Arg Asp Gln Val
                805                 810                 815
Lys Leu Ser Pro Ser Phe Asp Leu Asn Pro Gly
            820                 825

<210> SEQ ID NO 35
<211> LENGTH: 2917
<212> TYPE: DNA
<213> ORGANISM: Solanum Lycopersicum
<220> FEATURE:
<221> NAME/KEY: source
<222> LOCATION: 1..2917
<223> OTHER INFORMATION: /mol_type="unassigned DNA"
      /organism="Solanum Lycopersicum"

<400> SEQUENCE: 35
atgccttcat ggtggaaatc atcaaaagaa gctaagaaga aaccaacaaa agaaagttt       60 attgatacat tgcatcgcaa gtttaagagt ccagctgaag ttaaatctcc cggtaaatca     120
```

-continued

```
ggaggttcta gaaggcataa cagtgacatt gcttctgaga agggttctct atcccaagca    180
caatcaagag cgtcatcacc ttctaaacat gtatcaagat gtcaaagctt tgctgaaagg    240
cctctggccc aaccactacc acttcccggt gtgcgtccag caaatgtagg taggtcggat    300
tctggaataa gtccatcagc aaagtccaga gtagagaagg cctcaaagcc atccttgttt    360
ctgcctctcc ccaagcctgc atgcatcagg cacagactcg accctacaga taccgatgga    420
gagcttgtct ttgcatctat ttcaagcgag tgctctattg agagtgatga ccctattgat    480
tcacgtcagc gtagtcctct tgcaactgat tatgaaactg ggagcagaac tgctgctggt    540
agtccttcca gtttggttgt taaggatcaa tctgcagttg acaaattag cttgaaagaa    600
atgacaagac cagttagtct ttcaccaagt agaaacgttt cctccgtatc tcctaaaaga    660
aggcctttaa gtagtcatgt gaccactcta caggtgcctc ctcctggagc cttttgcagt    720
gctcccgata gttctatgtc aagtccttct agaagtccta tgagagctgc tgcaagtgag    780
caagttacta gttctactct atgggcagga agagcttatc cagatcttcc ttcacttgga    840
tctggccatt gttcaagccc agggtctggt cagaattctg acataattc aatgggagga    900
gatatgtctg acaactgtt ttggcagcct tgtagaggaa gtccagagta ctctcctatt    960
cctagtccta ggatgacaag tccgggacct agctcaagaa ttcatagtgg cacagtcaca   1020
ccaattcatc ctagggctgt tggtggagcc ggtgaattgc agactagttg gcctgatgat   1080
ggaaaagcac aaagtcaccc tttgcctctt cctcctttga caatttccaa ctcttcgccc   1140
ttttcacatt ctaattcagt tgcaacatct ccctcggtgc ctcgtagtcc aggtagagct   1200
gagaaccttg ctagccctgg ctctcgttgg aaaaaaggaa aattgctggg aagaggcaca   1260
tttggccatg tttatgttgg ttttaatagt gatagcggtg aaatgtgtgc aatgaaggag   1320
gttacattat tttcagatga cgcaaagtca aggaaagtg caaagcagtt ggcacaagag   1380
attgcattgt taagccgatt aaggcatcaa acattgttc ggtactacgg gacagaaacg   1440
gttggcgata aactgtatat ctacttggaa tatgtatcgg gtgggtccat ttataagctt   1500
ttacaagaat atggtgcatt tggagaagca gcgatccgta gttatactca acaaatctta   1560
tcagggcttg cattttttaca tgctaaaaac acagtgcata gagatattaa aggagcaaat   1620
attcttgttg atccaaatgg gcgcataaag ctagcagact ttggaatggc aaaacatatc   1680
acagggcagt catgtccatt atcattcaag ggaagtcctt actggatggc ccctgaggtt   1740
ataaagaatt ctagtggctg caaccttgct gttgatatat ggagtcttgg gtgcaccgtc   1800
ttagaaatgg ctacatcaaa gcctcctttt agccagtatg aaggggttgc tgctatgttt   1860
aagattggga atagtaaaga gctcccaact ataccagaac agctctcaga tgaagctaaa   1920
gattttgtga ggaagtgctt gcagcgtgag ccccgtcttc gtcctactgc tgctcagcta   1980
ttggatcatc cttttgtgaa aaatgtggca actctggaga agccaaatat ttctccacct   2040
gcagatcctc catgtgcagg agcaaatggt gttaaatctc tgggcattgg acaggcaagg   2100
aatatcccta catcagaatc agaaaggctt gcaaccccact catccagagt gtcaaaatct   2160
aattttcact gcagtgacat tagcattaca agaaacatat catgccctgt ctcaccgatt   2220
ggtagccctc ttttacatcc aaggtcacct caacacctaa atgggaggct gtctccctca   2280
cccatatcaa gtcctatcac catgtctggc tcatcaacac cactctctgg agggactggt   2340
gctattccat ttcatcatct taatcagtca gtttacttac aggaggcagc accacttcca   2400
cagagtcctt acatgaatgg cccttcttac tgggatcctg atgttttaag agggccacca   2460
tcaggatctc atgctttccg ggaattggca tcctctcaaa atgatgctct tggaaagcag   2520
```

```
tttggggagga ctacaggagg agagctttat gatggacagt cagtgctggc caatcgggtg   2580
tctcagcaac tcttaaggga tcatgtgaaa ttggttcctt cgctagatct aaacccttgt   2640
cctcctttgg acggtcggac aggtgaagca tgattttttt tttgtcagat acaacattca   2700
tgggagactt tccagtttca tagtttacta tcagtgtatg ttggtaactt tgaaggaagc   2760
tgatttgcac aatatggacc catcgggggg aaatttagga aataaaatag catcttcttg   2820
agcagaactt tatccattgt cgagatcaat cagctgatct tattacctcc gtccgccctt   2880
gggtctagtg ttacaaagat gaagcttact tcccagt                            2917

<210> SEQ ID NO 36
<211> LENGTH: 890
<212> TYPE: PRT
<213> ORGANISM: Solanum Lycopersicum

<400> SEQUENCE: 36
```

Met Pro Ser Trp Trp Lys Ser Ser Lys Glu Ala Lys Lys Pro Thr
1               5                   10                  15

Lys Glu Ser Phe Ile Asp Thr Leu His Arg Lys Phe Lys Ser Pro Ala
            20                  25                  30

Glu Val Lys Ser Pro Gly Lys Ser Gly Ser Arg Arg His Asn Ser
        35                  40                  45

Asp Ile Ala Ser Glu Lys Gly Ser Leu Ser Gln Ala Gln Ser Arg Ala
    50                  55                  60

Ser Ser Pro Ser Lys His Val Ser Arg Cys Gln Ser Phe Ala Glu Arg
65                  70                  75                  80

Pro Leu Ala Gln Pro Leu Pro Leu Pro Gly Val Arg Pro Ala Asn Val
                85                  90                  95

Gly Arg Ser Asp Ser Gly Ile Ser Pro Ala Lys Ser Arg Val Glu
            100                 105                 110

Lys Ala Ser Lys Pro Ser Leu Phe Leu Pro Leu Pro Lys Pro Ala Cys
        115                 120                 125

Ile Arg His Arg Leu Asp Pro Thr Asp Thr Asp Gly Glu Leu Val Phe
    130                 135                 140

Ala Ser Ile Ser Ser Glu Cys Ser Ile Glu Ser Asp Asp Pro Ile Asp
145                 150                 155                 160

Ser Arg Gln Arg Ser Pro Leu Ala Thr Asp Tyr Glu Thr Gly Ser Arg
                165                 170                 175

Thr Ala Ala Gly Ser Pro Ser Ser Leu Val Val Lys Asp Gln Ser Ala
            180                 185                 190

Val Gly Gln Ile Ser Leu Lys Glu Met Thr Arg Pro Val Ser Leu Ser
        195                 200                 205

Pro Ser Arg Asn Val Ser Ser Val Ser Pro Lys Arg Arg Pro Leu Ser
    210                 215                 220

Ser His Val Thr Thr Leu Gln Val Pro Pro Gly Ala Phe Cys Ser
225                 230                 235                 240

Ala Pro Asp Ser Ser Met Ser Ser Pro Ser Arg Ser Pro Met Arg Ala
                245                 250                 255

Ala Ala Ser Glu Gln Val Thr Ser Thr Leu Trp Ala Gly Arg Ala
            260                 265                 270

Tyr Pro Asp Leu Pro Ser Leu Gly Ser Gly His Cys Ser Ser Pro Gly
        275                 280                 285

Ser Gly Gln Asn Ser Gly His Asn Ser Met Gly Gly Asp Met Ser Gly
    290                 295                 300

```
Gln Leu Phe Trp Gln Pro Cys Arg Gly Ser Pro Glu Tyr Ser Pro Ile
305                 310                 315                 320

Pro Ser Pro Arg Met Thr Ser Pro Gly Pro Ser Ser Arg Ile His Ser
            325                 330                 335

Gly Thr Val Thr Pro Ile His Pro Arg Ala Val Gly Ala Gly Glu
            340                 345                 350

Leu Gln Thr Ser Trp Pro Asp Asp Gly Lys Ala Gln Ser His Pro Leu
            355                 360                 365

Pro Leu Pro Pro Leu Thr Ile Ser Asn Ser Ser Pro Phe Ser His Ser
370                 375                 380

Asn Ser Val Ala Thr Ser Pro Ser Val Pro Arg Ser Pro Gly Arg Ala
385                 390                 395                 400

Glu Asn Leu Ala Ser Pro Gly Ser Arg Trp Lys Lys Gly Lys Leu Leu
                405                 410                 415

Gly Arg Gly Thr Phe Gly His Val Tyr Val Gly Phe Asn Ser Asp Ser
            420                 425                 430

Gly Glu Met Cys Ala Met Lys Glu Val Thr Leu Phe Ser Asp Asp Ala
            435                 440                 445

Lys Ser Lys Glu Ser Ala Lys Gln Leu Ala Gln Glu Ile Ala Leu Leu
450                 455                 460

Ser Arg Leu Arg His Gln Asn Ile Val Arg Tyr Tyr Gly Thr Glu Thr
465                 470                 475                 480

Val Gly Asp Lys Leu Tyr Ile Tyr Leu Glu Tyr Val Ser Gly Gly Ser
                485                 490                 495

Ile Tyr Lys Leu Leu Gln Glu Tyr Gly Ala Phe Gly Glu Ala Ala Ile
                500                 505                 510

Arg Ser Tyr Thr Gln Gln Ile Leu Ser Gly Leu Ala Phe Leu His Ala
            515                 520                 525

Lys Asn Thr Val His Arg Asp Ile Lys Gly Ala Asn Ile Leu Val Asp
530                 535                 540

Pro Asn Gly Arg Ile Lys Leu Ala Asp Phe Gly Met Ala Lys His Ile
545                 550                 555                 560

Thr Gly Gln Ser Cys Pro Leu Ser Phe Lys Gly Ser Pro Tyr Trp Met
                565                 570                 575

Ala Pro Glu Val Ile Lys Asn Ser Ser Gly Cys Asn Leu Ala Val Asp
            580                 585                 590

Ile Trp Ser Leu Gly Cys Thr Val Leu Glu Met Ala Thr Ser Lys Pro
            595                 600                 605

Pro Phe Ser Gln Tyr Glu Gly Val Ala Ala Met Phe Lys Ile Gly Asn
610                 615                 620

Ser Lys Glu Leu Pro Thr Ile Pro Glu Gln Leu Ser Asp Glu Ala Lys
625                 630                 635                 640

Asp Phe Val Arg Lys Cys Leu Gln Arg Glu Pro Arg Leu Arg Pro Thr
                645                 650                 655

Ala Ala Gln Leu Leu Asp His Pro Phe Val Lys Asn Val Ala Thr Leu
            660                 665                 670

Glu Lys Pro Asn Ile Ser Pro Pro Ala Asp Pro Pro Cys Ala Gly Ala
            675                 680                 685

Asn Gly Val Lys Ser Leu Gly Ile Gly Gln Ala Arg Asn Ile Pro Thr
            690                 695                 700

Ser Glu Ser Glu Arg Leu Ala Thr His Ser Ser Arg Val Ser Lys Ser
705                 710                 715                 720
```

```
Asn Phe His Cys Ser Asp Ile Ser Ile Thr Arg Asn Ile Ser Cys Pro
            725                 730                 735

Val Ser Pro Ile Gly Ser Pro Leu Leu His Pro Arg Ser Pro Gln His
        740                 745                 750

Leu Asn Gly Arg Leu Ser Pro Ser Pro Ile Ser Ser Pro Ile Thr Met
        755                 760                 765

Ser Gly Ser Ser Thr Pro Leu Ser Gly Gly Thr Gly Ala Ile Pro Phe
    770                 775                 780

His His Leu Asn Gln Ser Val Tyr Leu Gln Glu Ala Ala Pro Leu Pro
785                 790                 795                 800

Gln Ser Pro Tyr Met Asn Gly Pro Ser Tyr Trp Asp Pro Asp Val Leu
            805                 810                 815

Arg Gly Pro Pro Ser Gly Ser His Ala Phe Arg Glu Leu Ala Ser Ser
        820                 825                 830

Gln Asn Asp Ala Leu Gly Lys Gln Phe Gly Arg Thr Thr Gly Gly Glu
        835                 840                 845

Leu Tyr Asp Gly Gln Ser Val Leu Ala Asn Arg Val Ser Gln Gln Leu
    850                 855                 860

Leu Arg Asp His Val Lys Leu Val Pro Ser Leu Asp Leu Asn Pro Cys
865                 870                 875                 880

Pro Pro Leu Asp Gly Arg Thr Gly Glu Ala
            885                 890

<210> SEQ ID NO 37
<211> LENGTH: 3011
<212> TYPE: DNA
<213> ORGANISM: Solanum Lycopersicum
<220> FEATURE:
<221> NAME/KEY: source
<222> LOCATION: 1..3011
<223> OTHER INFORMATION: /mol_type="unassigned DNA"
      /organism="Solanum Lycopersicum"

<400> SEQUENCE: 37
cactttagac tgtactagta aattcatttt accttcaaaa caactccccc atcttcatac      60
ttggcttcct cactaccatt tttatccttc accattctca tgcgatctct tctaagaaac    120
gagctcgttt atgcttgcga tgcaacaagt aatcagttga agcaccaga aaagatgcct     180 tcatggtggg gaaagtcaaa agcaaagaag aaagcgacca agagagtttt tattgattca    240
ttgcatcgta agtttaagag tccagctgaa gctaagtctc cgagtaaatc aggtggatct    300
cgaagacaca acaatgagat tgcttctgag aagggttctc agtcccaagc acagtcaagg    360
tcatcatcac cttccaagaa tgtctccaga tgtcaaagtt ttgctgaaaa ggctctagcc    420
caaccacttc cgcttccagg tttgccacca gcaagtgtag tgcgggcaga ctctgggatc    480
agtcaatctg ccaaacccag aatagggaag ggatcaaagt tgtccctgtt tctgcctctc    540
ccaaagcctg catgcatcag gcacagactg gaccctgcag atgctgatgg agaacttgtc    600
tttgcatcaa tttcaagtga gtgctctgtt gagagtgatg atcctactga ttcacgccaa    660
cgtagtccac taacatttga ttatgaaact ggtaaccgga ctcccttggg tagccctcca    720
agattggctg ttaaggatca atctgctgtt ggacaaacaa gcataaaaga ggcaacagaa    780
ctagttaatc tttctcccag tggacatgtc tcctctcgat ctcctaagcg acgaccacta    840
aatagccact gtccagtat acaaattcct tctcatggta cccctttgcag tgttcctgat    900 agttctatat caagtccttc cagaaatcca atgaaagctg ctggctgtga gcaagttagt    960
agttctactt tttgggcggg aaagacttat ccagatcttc ctttacttgg atctggccat   1020
```

-continued

```
tgttcaagcc caggatctgg tcagaattct gggcataatt ccatgggagg agatatggta    1080
ggacaactgt tttggcagcc tagtcgaggg agccccgagt actctccaat tcctagtcct    1140
agaatgacaa gtcctggacc tagctcaaga attcacagtg gtgctgtcac acctattcat    1200
cccaaggctg gaggcggagc atctgaattg cagactaatt ggccagatga tgcaaaacca    1260
gaaagtcatc ctttgccccg tccccccctta gcaatttcca actcttcacc tttttctcat    1320
tccaattcag ttgcaacatc tccctcagtg ccacgaagtc ctggtagggc agagaatctt    1380
tctagcccgg ttctcgctg aaaaagggg aagttgcttg gtagaggcac attcgggcat      1440
gtttatgttg gtttaatag tgatagtgga gaaatgtgtg caatgaagga ggtgactcta     1500
ttttcagatg atgcaaagtc aaaagaaagt gtaaagcagt tgacacagga gatttcattg    1560
ttgagccgat taagacatcc aaatattgtc cagtattatg gctcagagat ggttcctgat    1620
aaactatata tctacttgga atatgtatct ggtgggtcca tttataagct tttacaagaa    1680
tatggtccgt ttggagaaac aacaatccgt agttacactc aacaaatttt atcggggctt    1740
gcatatttac atgctaaaaa cactgtgcat agagatatta aggggcaaa tatccttgtt     1800
gatccaaatg ggcgtataaa gctggcagac ttcggaatgg ccaagcatat tacagggcaa    1860
tcttgtccat tatccttcaa aggaagccct tactggatgg cccctgaggt aataaagaat    1920
actagtggct gcaaccttgc tgttgatgta tggagccttg gatgcactgt cttagaaatg    1980
gctacgtcaa agcctccttg gagtcagtat gaaggagttg ctgccatgtt taagattggg    2040
aatagtaaag aactcccaac aataccggaa gagctttcag atgagggaaa agattttgtg    2100
aggaagtgtt tgcagcgtga gccgcgaaat cgtcctactg ctgctgagct attggagcat    2160
cctttttgtaa aagatgctgc ccctctggaa aagcaaaata tgtttcctac atctttcgat   2220
cttccatgtg ttgctgcaag tgggataaaa cttctgggca ctggatctgc aagaaattat    2280
cctaccccag attcagaaag gctcgctatc cactcatcca gagcgtcaaa atctaaattt    2340
cactgcagtg atatccacat tccgaagaac atatcttgcc ccgtctcccc aataggtagt    2400
cctcttccaa ggtcgcctca taacctaaat gggaggatgt ctccctcgcc tatatccagc    2460
cctctcaaca catctggctc atctacacca atctctggag ggaatggtgt tatcccattt    2520
cgtcacatta atcagtcagt ttacttgcaa gaggccagaa cagttccaaa tagtccctat    2580
atgaatggct cttcttactg ggatcctgat gttttacgag ggtcaccatc aggatctcat    2640
gctttccgag aattggcgtc tgttgaatat gatgccctgg aaagcagtt tgggaggctt     2700
gcgacaggag aactttgcaa tgggcaatca gccttggcca atcgggtgtc acagcaactt    2760
ttaagggatc atgtgaaatc gatttctcct gtagatctaa accctgtcc tcccttggga    2820
ggtcgcccag gtgaacata agcttcaaaa gtttcatatg taaatctgct ttcagctttt    2880
agcatgtttg gaggaagttg ttatgtgaaa caaggatctc cgaagagaag agactaggaa    2940
atgtagtggc atcttggcag aacttcatta tctattgtca gtttgatcta cctgatttct    3000
aaccccctgt t                                                         3011
```

<210> SEQ ID NO 38
<211> LENGTH: 913
<212> TYPE: PRT
<213> ORGANISM: Solanum Lycopersicum

<400> SEQUENCE: 38

```
Met Arg Ser Leu Leu Arg Asn Glu Leu Val Tyr Ala Cys Asp Ala Thr
1               5                   10                  15
```

-continued

```
Ser Asn Gln Leu Lys Ala Pro Glu Lys Met Pro Ser Trp Trp Gly Lys
            20                  25                  30

Ser Lys Ala Lys Lys Ala Thr Lys Glu Ser Phe Ile Asp Ser Leu
        35                  40                  45

His Arg Lys Phe Lys Ser Pro Ala Glu Ala Lys Ser Pro Ser Lys Ser
 50                  55                  60

Gly Gly Ser Arg Arg His Asn Asn Glu Ile Ala Ser Glu Lys Gly Ser
 65                  70                  75                  80

Gln Ser Gln Ala Gln Ser Arg Ser Ser Pro Ser Lys Asn Val Ser
            85                  90                  95

Arg Cys Gln Ser Phe Ala Glu Lys Ala Leu Ala Gln Pro Leu Pro Leu
            100                 105                 110

Pro Gly Leu Pro Pro Ala Ser Val Val Arg Ala Asp Ser Gly Ile Ser
        115                 120                 125

Gln Ser Ala Lys Pro Arg Ile Gly Lys Gly Ser Lys Leu Ser Leu Phe
130                 135                 140

Leu Pro Leu Pro Lys Pro Ala Cys Ile Arg His Arg Leu Asp Pro Ala
145                 150                 155                 160

Asp Ala Asp Gly Glu Leu Val Phe Ala Ser Ile Ser Ser Glu Cys Ser
            165                 170                 175

Val Glu Ser Asp Asp Pro Thr Asp Ser Arg Gln Arg Ser Pro Leu Thr
            180                 185                 190

Phe Asp Tyr Glu Thr Gly Asn Arg Thr Pro Leu Gly Ser Pro Pro Arg
        195                 200                 205

Leu Ala Val Lys Asp Gln Ser Ala Val Gly Gln Thr Ser Ile Lys Glu
        210                 215                 220

Ala Thr Glu Leu Val Asn Leu Ser Pro Ser Gly His Val Ser Ser Arg
225                 230                 235                 240

Ser Pro Lys Arg Arg Pro Leu Asn Ser His Leu Ser Ser Ile Gln Ile
            245                 250                 255

Pro Ser His Gly Thr Leu Cys Ser Val Pro Asp Ser Ser Ile Ser Ser
            260                 265                 270

Pro Ser Arg Asn Pro Met Lys Ala Ala Gly Cys Glu Gln Val Ser Ser
        275                 280                 285

Ser Thr Phe Trp Ala Gly Lys Thr Tyr Pro Asp Leu Pro Leu Leu Gly
        290                 295                 300

Ser Gly His Cys Ser Ser Pro Gly Ser Gly Gln Asn Ser Gly His Asn
305                 310                 315                 320

Ser Met Gly Gly Asp Met Val Gly Gln Leu Phe Trp Gln Pro Ser Arg
            325                 330                 335

Gly Ser Pro Glu Tyr Ser Pro Ile Pro Ser Pro Arg Met Thr Ser Pro
            340                 345                 350

Gly Pro Ser Ser Arg Ile His Ser Gly Ala Val Thr Pro Ile His Pro
        355                 360                 365

Lys Ala Gly Gly Gly Ala Ser Glu Leu Gln Thr Asn Trp Pro Asp Asp
        370                 375                 380

Ala Lys Pro Glu Ser His Pro Leu Pro Arg Pro Leu Ala Ile Ser
385                 390                 395                 400

Asn Ser Ser Pro Phe Ser His Ser Asn Ser Val Ala Thr Ser Pro Ser
            405                 410                 415

Val Pro Arg Ser Pro Gly Arg Ala Glu Asn Leu Ser Ser Pro Gly Ser
            420                 425                 430
```

-continued

```
Arg Trp Lys Lys Gly Lys Leu Leu Gly Arg Gly Thr Phe Gly His Val
            435                 440                 445
Tyr Val Gly Phe Asn Ser Asp Ser Gly Glu Met Cys Ala Met Lys Glu
450                 455                 460
Val Thr Leu Phe Ser Asp Asp Ala Lys Ser Lys Glu Ser Val Lys Gln
465                 470                 475                 480
Leu Thr Gln Glu Ile Ser Leu Leu Ser Arg Leu Arg His Pro Asn Ile
                485                 490                 495
Val Gln Tyr Tyr Gly Ser Glu Met Val Pro Asp Lys Leu Tyr Ile Tyr
            500                 505                 510
Leu Glu Tyr Val Ser Gly Gly Ser Ile Tyr Lys Leu Leu Gln Glu Tyr
            515                 520                 525
Gly Pro Phe Gly Glu Thr Thr Ile Arg Ser Tyr Thr Gln Gln Ile Leu
530                 535                 540
Ser Gly Leu Ala Tyr Leu His Ala Lys Asn Thr Val His Arg Asp Ile
545                 550                 555                 560
Lys Gly Ala Asn Ile Leu Val Asp Pro Asn Gly Arg Ile Lys Leu Ala
                565                 570                 575
Asp Phe Gly Met Ala Lys His Ile Thr Gly Gln Ser Cys Pro Leu Ser
            580                 585                 590
Phe Lys Gly Ser Pro Tyr Trp Met Ala Pro Glu Val Ile Lys Asn Thr
            595                 600                 605
Ser Gly Cys Asn Leu Ala Val Asp Val Trp Ser Leu Gly Cys Thr Val
            610                 615                 620
Leu Glu Met Ala Thr Ser Lys Pro Pro Trp Ser Gln Tyr Glu Gly Val
625                 630                 635                 640
Ala Ala Met Phe Lys Ile Gly Asn Ser Lys Glu Leu Pro Thr Ile Pro
                645                 650                 655
Glu Glu Leu Ser Asp Glu Gly Lys Asp Phe Val Arg Lys Cys Leu Gln
            660                 665                 670
Arg Glu Pro Arg Asn Arg Pro Thr Ala Ala Glu Leu Leu Glu His Pro
            675                 680                 685
Phe Val Lys Asp Ala Ala Pro Leu Glu Lys Gln Asn Met Phe Pro Thr
690                 695                 700
Ser Phe Asp Leu Pro Cys Val Ala Ala Ser Gly Ile Lys Leu Leu Gly
705                 710                 715                 720
Thr Gly Ser Ala Arg Asn Tyr Pro Thr Pro Asp Ser Glu Arg Leu Ala
                725                 730                 735
Ile His Ser Ser Arg Ala Ser Lys Ser Lys Phe His Cys Ser Asp Ile
            740                 745                 750
His Ile Pro Lys Asn Ile Ser Cys Pro Val Ser Pro Ile Gly Ser Pro
            755                 760                 765
Leu Pro Arg Ser Pro His Asn Leu Asn Gly Arg Met Ser Pro Ser Pro
            770                 775                 780
Ile Ser Ser Pro Leu Asn Thr Ser Gly Ser Thr Pro Ile Ser Gly Gly
785                 790                 795                 800
Gly Asn Gly Val Ile Pro Phe Arg His Ile Asn Gln Ser Val Tyr Leu
                805                 810                 815
Gln Glu Ala Arg Thr Val Pro Asn Ser Pro Tyr Met Asn Gly Ser Ser
            820                 825                 830
Tyr Trp Asp Pro Asp Val Leu Arg Gly Ser Pro Ser Gly Ser His Ala
            835                 840                 845
Phe Arg Glu Leu Ala Ser Val Glu Tyr Asp Ala Leu Gly Lys Gln Phe
```

```
                850           855              860
Gly Arg Leu Ala Thr Gly Glu Leu Cys Asn Gly Gln Ser Ala Leu Ala
865             870              875              880

Asn Arg Val Ser Gln Gln Leu Leu Arg Asp His Val Lys Ser Ile Ser
                885              890              895

Pro Val Asp Leu Asn Pro Cys Pro Pro Leu Gly Arg Pro Gly Gly
                900              905              910

Thr

<210> SEQ ID NO 39
<211> LENGTH: 3140
<212> TYPE: DNA
<213> ORGANISM: Sorghum bicolor
<220> FEATURE:
<221> NAME/KEY: source
<222> LOCATION: 1..3140
<223> OTHER INFORMATION: /mol_type="unassigned DNA"
      /organism="Sorghum bicolor"

<400> SEQUENCE: 39
atgccgacat ggtggggtaa atcatcgtca aaagatgtta agaaaaccac caaggaaaac    60
ctgatcgata catttcatcg cttgataagt ccaaatgagc aaaagggaag cacaaaatca   120
aaacggaatt gtaggcgtgg caatacagct gctgagaaag tttgcaaatc aacaacagtg   180
tcacgtccaa cttctccttc aaaagaagtt tcccgctgcc aaagttttc ggctgatagg    240 ctgcatgctc agccacttcc tattcctgga gtacgccctc gagtaactcg tgcagttgct   300
gatgtcaatg attcaaagcc catattggaa aacgtggca aaccaccact acttctgcca    360
cttcctaaac ccaatccgct tcaacgggga cctggaagca gtgatattcc ttcagaaata   420
gtggttgctt ctgtctctag caattgttct gctgatagtg aggatcgtgc agattctcag    480
cttcagagcc ctgttgggaa tgatagtgac aatgtaacaa aggtttcttc aaagaaaaag   540
tcaagtaatg ttcgcaagga tcaatctggt gctattacta ccaagaccac gaaggaaata   600
ttgaagccag ctgctaatgc attccccagt aaccatacac agtccacgcc accaagaggt   660
atttcagctg acaataatca accagattta caaaatctcc ggccagtagt tttcgagagt   720
gctcccaata gtttgatgtc aagtccttcg agaagtccaa gaccaatatg tcctgatcat   780
attccgactt cagcctttg ggcagtgaag cctcatgctg atgtaacttt ccttggatct    840
ggtcagtgct ccagtccagg ttcagggcaa acatctggac ataattcagt gggtggcgat   900
atgctagccc agctttttg gcaacccacc aggggtagtc cagagtgttc accagttcct    960
agcccaagaa tgacgagtcc tggccctagt tctcgtgtgc atagtggaag tgtttccccg  1020
ttgcatccaa ggtctggagg agtggcacct gaatctccta cgagtcggca tgatgatgga  1080
aagaagaagc aaacccataa attgcccctt ccaccattga gcatctctaa cactaacagt  1140
tcatttcttc caaataactc catgccaagc agtcctattt cagtaccccg cagccctggc  1200
agaacagaga atccatcaag tcctgcatca cgatggaaga agggcaagct gattggtcgt  1260
gggacatttg gtcatgtata tgttggcttc aacaatgata gcggtgaaat gtgcgcaatg  1320
aaagaggtta ccctattctt ggatgatcct aaatcaaagg agagtgcaaa gcaattgcgg  1380
caggaagtat cactcttgag ccgcttaagg catccaaata ttgtacaata ctatggatca  1440
gaaatggttg aagataaact ttacatatat ttgaatatg tttctggtgg atccatacat   1500
aaacttcttc aagagtatgg acagcttggt gaaccagcaa tacgcagcta cacccaacag  1560
atactttcag gcttagctta tttgcatgcc aagaataccg tccatagggga catcaaaggt  1620
```

```
gcaaacatac tagttgatcc aagtggccgt gttaagcttg cagactttgg aatggcaaag    1680
catatcaatg gacagcactg tcctttttca tttaagggta gtccatactg gatggctcca    1740
gaggttataa aaaattctaa tggatgcaac cttgcggttg acatatggag tttaggttgc    1800
actgtcctgg aaatggctac ctcaaagcca ccatggagcc agtatgaagg gattgctgca    1860
gtgttcaaga ttgggaacag caaggaactt ccgccaatac cggatcaccT ctcggagcac    1920
tgcaaggact tcattaggaa gtgtctgcaa cgtgatccat ctcagcgtcc aacgtcagtt    1980
gagcttttgc aacacccatt catacaaaat ggagtttcac ttgagaaatc tgttattcct    2040
aatcatttgg agcatttggc tgccatatca tgcagaacaa acccaaggt ggccgtgcag    2100 acaagaaatg cctccttagg tttcgagggt cagactattt accaagaag gggtgtaaaa    2160 ttatcttcaa aacacagtga tattcatatt cgaagcaata tatcctgtcc agtttctcca    2220
tgtggaagcc ccctgctaaa gtcgaggtcc ccccaacaca caagtggcag aatgtcaccc    2280
tctcctattt cgagcccag aactatgtca ggcacttcca caccctatc tggtggcaat    2340 ggtgctattc cttttaacca cctaaggtat gcaacttaca gcagtgaggg atttgggacc    2400
acatcaagag gcctagacga tcatttcccg aaccggcata agatccgat ccttgggcat    2460 tttgctcagg cacatcaagt ctcacaggga cctcgggaaa gagtagtatc tgaagctgat    2520
attctgagcc ctcaatttgg aaagaaactt ggaaatgttt ttgacttgcg ggaaaggcta    2580
tccccttctg aacattttac tcgtcatgcc ttggtggatc atgtggatct aaatccttca    2640
ctagacctga catctggctc tctacaccct ggactaaagc gtggtaaata actattgaat    2700 gtaaaagca gggtggcatt ttttgagttt tttggctgct atgaccattc aatgactgca    2760
actgtatcat agtatcagaa agattgacaa tttctttaga agctaatggt tggcaatgga    2820
tgggatcttt gttgtcatca atgcaattca agtcaacaaa gattctgcct attcctacat    2880
ggctgagcaa gtctccttag catactaaac tcgcgtgcta acaagtaaca agtgtcgaat    2940
gatgggactg tatattggat tcccagactg aatcactgaa ggacccaaag cagtaactct    3000
ccatttgtat accctactca ccccaatatg taacctattc tttgttccat ttttttttctt    3060 ggcgtcctga tgccagtgta cagaaggatt ctcaactagg agcctggttt ttgcacagga    3120
aaaaaacagt tgaactagtc                                                 3140
```

<210> SEQ ID NO 40
<211> LENGTH: 896
<212> TYPE: PRT
<213> ORGANISM: Sorghum bicolor

<400> SEQUENCE: 40

```
Met Pro Thr Trp Trp Gly Lys Ser Ser Lys Asp Val Lys Thr
1               5                   10                  15

Thr Lys Glu Asn Leu Ile Asp Thr Phe His Arg Leu Ile Ser Pro Asn
            20                  25                  30

Glu Gln Lys Gly Ser Thr Lys Ser Arg Asn Cys Arg Gly Asn
        35                  40                  45

Thr Ala Ala Glu Lys Val Cys Lys Ser Thr Thr Val Ser Arg Pro Thr
    50                  55                  60

Ser Pro Ser Lys Glu Val Ser Arg Cys Gln Ser Phe Ser Ala Asp Arg
65                  70                  75                  80

Leu His Ala Gln Pro Leu Pro Ile Pro Gly Val Arg Pro Arg Val Thr
                85                  90                  95
```

```
Arg Ala Val Ala Asp Val Asn Asp Ser Lys Pro Ile Leu Glu Lys Arg
            100                 105                 110

Gly Lys Pro Pro Leu Leu Leu Pro Leu Pro Lys Pro Asn Pro Leu Gln
        115                 120                 125

Arg Gly Pro Gly Ser Ser Asp Ile Pro Ser Glu Ile Val Val Ala Ser
    130                 135                 140

Val Ser Ser Asn Cys Ser Ala Asp Ser Glu Asp Arg Ala Asp Ser Gln
145                 150                 155                 160

Leu Gln Ser Pro Val Gly Asn Asp Ser Asp Asn Val Thr Lys Val Ser
                165                 170                 175

Ser Lys Lys Lys Ser Ser Asn Val Arg Lys Asp Gln Ser Gly Ala Ile
            180                 185                 190

Thr Thr Lys Thr Thr Lys Glu Ile Leu Lys Pro Ala Ala Asn Ala Phe
        195                 200                 205

Pro Ser Asn His Thr Gln Ser Thr Pro Pro Arg Gly Ile Ser Ala Asp
    210                 215                 220

Asn Asn Gln Pro Asp Leu Gln Asn Leu Arg Pro Val Val Phe Glu Ser
225                 230                 235                 240

Ala Pro Asn Ser Leu Met Ser Ser Pro Ser Arg Ser Pro Arg Pro Ile
                245                 250                 255

Cys Pro Asp His Ile Pro Thr Ser Ala Phe Trp Ala Val Lys Pro His
            260                 265                 270

Ala Asp Val Thr Phe Leu Gly Ser Gly Gln Cys Ser Ser Pro Gly Ser
        275                 280                 285

Gly Gln Thr Ser Gly His Asn Ser Val Gly Gly Asp Met Leu Ala Gln
    290                 295                 300

Leu Phe Trp Gln Pro Thr Arg Gly Ser Pro Glu Cys Ser Pro Val Pro
305                 310                 315                 320

Ser Pro Arg Met Thr Ser Pro Gly Pro Ser Ser Arg Val His Ser Gly
                325                 330                 335

Ser Val Ser Pro Leu His Pro Arg Ser Gly Val Ala Pro Glu Ser
        340                 345                 350

Pro Thr Ser Arg His Asp Asp Gly Lys Lys Lys Gln Thr His Lys Leu
    355                 360                 365

Pro Leu Pro Pro Leu Ser Ile Ser Asn Thr Asn Ser Ser Phe Leu Pro
370                 375                 380

Asn Asn Ser Met Pro Ser Ser Pro Ile Ser Val Pro Arg Ser Pro Gly
385                 390                 395                 400

Arg Thr Glu Asn Pro Ser Ser Pro Ala Ser Arg Trp Lys Lys Gly Lys
                405                 410                 415

Leu Ile Gly Arg Gly Thr Phe Gly His Val Tyr Val Gly Phe Asn Asn
            420                 425                 430

Asp Ser Gly Glu Met Cys Ala Met Lys Glu Val Thr Leu Phe Leu Asp
        435                 440                 445

Asp Pro Lys Ser Lys Glu Ser Ala Lys Gln Leu Arg Gln Glu Val Ser
    450                 455                 460

Leu Leu Ser Arg Leu Arg His Pro Asn Ile Val Gln Tyr Tyr Gly Ser
465                 470                 475                 480

Glu Met Val Glu Asp Lys Leu Tyr Ile Tyr Leu Glu Tyr Val Ser Gly
                485                 490                 495

Gly Ser Ile His Lys Leu Leu Gln Glu Tyr Gly Gln Leu Gly Glu Pro
            500                 505                 510

Ala Ile Arg Ser Tyr Thr Gln Gln Ile Leu Ser Gly Leu Ala Tyr Leu
```

```
              515                 520                 525
His Ala Lys Asn Thr Val His Arg Asp Ile Lys Gly Ala Asn Ile Leu
530                 535                 540

Val Asp Pro Ser Gly Arg Val Lys Leu Ala Asp Phe Gly Met Ala Lys
545                 550                 555                 560

His Ile Asn Gly Gln His Cys Pro Phe Ser Phe Lys Gly Ser Pro Tyr
                565                 570                 575

Trp Met Ala Pro Glu Val Ile Lys Asn Ser Asn Gly Cys Asn Leu Ala
                580                 585                 590

Val Asp Ile Trp Ser Leu Gly Cys Thr Val Leu Glu Met Ala Thr Ser
            595                 600                 605

Lys Pro Pro Trp Ser Gln Tyr Glu Gly Ile Ala Ala Val Phe Lys Ile
610                 615                 620

Gly Asn Ser Lys Glu Leu Pro Pro Ile Pro Asp His Leu Ser Glu His
625                 630                 635                 640

Cys Lys Asp Phe Ile Arg Lys Cys Leu Gln Arg Asp Pro Ser Gln Arg
                645                 650                 655

Pro Thr Ser Val Glu Leu Leu Gln His Pro Phe Ile Gln Asn Gly Val
                660                 665                 670

Ser Leu Glu Lys Ser Val Ile Pro Asn His Leu Glu His Leu Ala Ala
            675                 680                 685

Ile Ser Cys Arg Thr Lys Pro Lys Val Ala Val Gln Thr Arg Asn Ala
690                 695                 700

Ser Leu Gly Phe Glu Gly Gln Thr Ile Tyr Gln Arg Arg Gly Val Lys
705                 710                 715                 720

Leu Ser Ser Lys His Ser Asp Ile His Ile Arg Ser Asn Ile Ser Cys
                725                 730                 735

Pro Val Ser Pro Cys Gly Ser Pro Leu Leu Lys Ser Arg Ser Pro Gln
                740                 745                 750

His Thr Ser Gly Arg Met Ser Pro Ser Pro Ile Ser Ser Pro Arg Thr
            755                 760                 765

Met Ser Gly Thr Ser Thr Pro Leu Ser Gly Gly Asn Gly Ala Ile Pro
770                 775                 780

Phe Asn His Leu Arg Tyr Ala Thr Tyr Ser Ser Glu Gly Phe Gly Thr
785                 790                 795                 800

Thr Ser Arg Gly Leu Asp Asp His Phe Pro Asn Arg His Lys Asp Pro
                805                 810                 815

Ile Leu Gly His Phe Ala Gln Ala His Gln Val Ser Gln Gly Pro Arg
                820                 825                 830

Glu Arg Val Val Ser Glu Ala Asp Ile Leu Ser Pro Gln Phe Gly Lys
            835                 840                 845

Lys Leu Gly Asn Val Phe Asp Leu Arg Glu Arg Leu Ser Pro Ser Glu
850                 855                 860

His Phe Thr Arg His Ala Leu Val Asp His Val Asp Leu Asn Pro Ser
865                 870                 875                 880

Leu Asp Leu Thr Ser Gly Ser Leu His Pro Gly Leu Lys Arg Gly Lys
                885                 890                 895

<210> SEQ ID NO 41
<211> LENGTH: 2688
<212> TYPE: DNA
<213> ORGANISM: Sorghum bicolor
<220> FEATURE:
<221> NAME/KEY: source
<222> LOCATION: 1..2688
```

<223> OTHER INFORMATION: /mol_type="unassigned DNA"
/organism="Sorghum bicolor"

<400> SEQUENCE: 41

```
atgccaccat ggtggggaaa atcttcatcc aaagaagtga aaagacagc caagaaaac      60
ctcattgaca catttcagcg tctcataagt tcaaatgagc aaaagggaag cagaaaatca    120
cgaggtagtc gtaaacatgg taaagacaca gctggtgaca aaggttgctg gtctactgcc    180
caatcccgct caacatcccc ttcaaaagag gtctctcggt gtcagagctt tgcagcagat    240
agaccacctg cgcaaccact tcctcttcct aaatcacgtg ctagggtgac gcgtacttct    300
tctgatatta ccaactcaaa gtccactttg gaaaagcatg gcaaaggaca actgcttcca    360
ctcccccccta ctcagcctag aaaaagacct gaagctactg aacctgttac tgaagtagct    420
actgcttctg tctccagcaa ctgttctatt gatagtgatg atcctggtga ttctcggctt    480
cagagccctg tgggaaatga ggttgaaaat gcgactagaa ttactgcaac aagtagttca    540
agtgttttgc acaaagagcg ttctagtgct atcaccaaaa agagcaccaa ggaagttgca    600
aagccaaaca atgcttttct cagtaaccaa atcttgtcaa catctccaag aggtaccgtt    660
gctgatggtt atcaatccaa tttacaaagc ccccgacaga ttgccctgga gagtgctccg    720
aatagtttga tgtcaagtcc ttctcgaagc ccaaggatta tatgtcctga tcagattcca    780
acttcagctt tttgggcagt aaagcctcat actgatataa cttccttgg gtctggtcag     840
tgctcgagtc caggttctgg tcagacatct gggcataatt cagtgggagg tgatatgcta    900
ggcccaatct tttggcagcc tagccgaggt agtccagagt gttcaccaat tccaagccca    960
agaatgacaa gtcctggtcc aagttctagg gtgcatagtg gaagtgtctc tcctttgcat   1020
ccaagagctg gtggggtcac tcctgaatct ccaacaaatc gacacgctga agggaacaag   1080
aaacaaaccc acagattgcc gcttcctcca ataagcacag ctaatatttc cacctttttg   1140
ccaaacagct ctaccccagc tagtcctata tctcgtagtc ctggtagaac agagaatcca   1200
ccgagtcctg gttcacggtg gaagaaggga aaactgattg gccgtgggac atttggccat   1260
gtatacgttg gttttaacag tgacagaggt gaaatgtgtg cgatgaagga ggttaccctt   1320
ttcgcagatg atcctaaatc aaaagaaagt gcaaacagc tgtgccagga aatatcactt    1380
ctgagccgac tgcagcaccc aaacattgtg cgatactatg gatctgaaac tgttgatgat   1440
aagctttaca tatacctgga gtatgttct ggtggatcta tacataagct tctccaagag    1500
tacggccagt ttggtgaaca ggccattcgc agttatacta agcaaatact tttgggccta    1560
gcttatttgc atgcaaagaa tacagtacac agggacatca aaggtgcaaa catattggta    1620
gaccctaatg gccgtgtaaa gcttgctgac ttcgggatgg caaaacatat caatgggcag    1680
cagtgccctt tctcatttaa gggtagcccg tactggatgg ctcctgaggt tataaaaaat    1740
gctagtggat gtaaccttgc agttgatata tggagtttag gatgcacggt cctagagatg    1800
gctacttcaa aaccaccatg gagccaatat gaagggattg ctgcaatgtt taagatagga    1860
aacagtaagg agcttccgcc aataccagat cacctctcag aagaggggaa agacttcata   1920
agaaagtgct tgcaacgcga tccatccagc cgtccaacag cagtggatct tttgcagcat   1980
gcattcgtac gaaatgcacc accacttgaa aaatcatctg cctctcatcc actggaggtg   2040
gaacagttga cggctatatc atgcagaaca aattcaaagg tggttgagca tgccagaaat   2100
atgtcctcgc ttggtttgga aggccaatca attttgcaga gaagagctgc caaattttct   2160
ttgccaatta gtgatatcca tatacggagt aacatatctt gtcctgtatc tccatgtgga   2220
```

```
agtcctcttc tgagatcaag atccccacaa catcaaaatg gtagaatgtc accttctcca    2280
atttctagcc ccagaacaac ttcgggtgct tcaactcctc tgactggtgg tagtggagct    2340
gttcctttaa accatgtgag gcaaccagct tacagaaatg agggcttcac agtcacatca    2400
agaggttttg atgaccacat acctagccgg cctgttgatc cagtacatgg acgttttatt    2460
cgagtgcagc aatttttctgc gggccgtcag gagagggtag tctccgaagc tgacattctg    2520
agctctcaat ttggaaagat gaggcatgca aatgtgtggg attcgcatga taggccattg    2580
ccttctgagc gttcctctca gcagtgcttt ggggatcatg tgaagctaaa accttcactg    2640
gacttgaggt ctggtcctcg gcaccctggg cgcaaccatg gccattga                 2688
```

<210> SEQ ID NO 42
<211> LENGTH: 895
<212> TYPE: PRT
<213> ORGANISM: Sorghum bicolor

<400> SEQUENCE: 42

```
Met Pro Pro Trp Trp Gly Lys Ser Ser Lys Glu Val Lys Lys Thr
1               5                   10                  15

Ala Lys Glu Asn Leu Ile Asp Thr Phe Gln Arg Leu Ile Ser Ser Asn
            20                  25                  30

Glu Gln Lys Gly Ser Arg Lys Ser Arg Gly Ser Arg Lys His Gly Lys
        35                  40                  45

Asp Thr Ala Gly Asp Lys Gly Cys Trp Ser Thr Ala Gln Ser Arg Ser
    50                  55                  60

Thr Ser Pro Ser Lys Glu Val Ser Arg Cys Gln Ser Phe Ala Ala Asp
65                  70                  75                  80

Arg Pro Pro Ala Gln Pro Leu Pro Leu Pro Lys Ser Arg Ala Arg Val
                85                  90                  95

Thr Arg Thr Ser Ser Asp Ile Thr Asn Ser Lys Ser Thr Leu Glu Lys
            100                 105                 110

His Gly Lys Gly Gln Leu Leu Pro Leu Pro Thr Gln Pro Arg Lys
        115                 120                 125

Arg Pro Glu Ala Thr Glu Pro Val Thr Glu Val Ala Thr Ala Ser Val
    130                 135                 140

Ser Ser Asn Cys Ser Ile Asp Ser Asp Pro Gly Asp Ser Arg Leu
145                 150                 155                 160

Gln Ser Pro Val Gly Asn Glu Val Glu Asn Ala Thr Arg Ile Thr Ala
                165                 170                 175

Thr Ser Ser Ser Val Leu His Lys Glu Arg Ser Ser Ala Ile Thr
            180                 185                 190

Lys Lys Ser Thr Lys Glu Val Ala Lys Pro Asn Asn Ala Phe Leu Ser
        195                 200                 205

Asn Gln Ile Leu Ser Thr Ser Pro Arg Gly Thr Val Ala Asp Gly Tyr
    210                 215                 220

Gln Ser Asn Leu Gln Ser Pro Arg Gln Ile Ala Leu Glu Ser Ala Pro
225                 230                 235                 240

Asn Ser Leu Met Ser Ser Pro Ser Arg Ser Pro Arg Ile Ile Cys Pro
                245                 250                 255

Asp Gln Ile Pro Thr Ser Ala Phe Trp Ala Val Lys Pro His Thr Asp
            260                 265                 270

Ile Thr Phe Leu Gly Ser Gly Gln Cys Ser Ser Pro Gly Ser Gly Gln
        275                 280                 285

Thr Ser Gly His Asn Ser Val Gly Gly Asp Met Leu Gly Pro Ile Phe
```

```
            290                 295                 300
Trp Gln Pro Ser Arg Gly Ser Pro Glu Cys Ser Pro Ile Pro Ser Pro
305                 310                 315                 320

Arg Met Thr Ser Pro Gly Pro Ser Ser Arg Val His Ser Gly Ser Val
                325                 330                 335

Ser Pro Leu His Pro Arg Ala Gly Gly Val Thr Pro Glu Ser Pro Thr
                340                 345                 350

Asn Arg His Ala Glu Gly Asn Lys Lys Gln Thr His Arg Leu Pro Leu
            355                 360                 365

Pro Pro Ile Ser Thr Ala Asn Ile Ser Thr Phe Leu Pro Asn Ser Ser
370                 375                 380

Thr Pro Ala Ser Pro Ile Ser Arg Ser Pro Gly Arg Thr Glu Asn Pro
385                 390                 395                 400

Pro Ser Pro Gly Ser Arg Trp Lys Lys Gly Lys Leu Ile Gly Arg Gly
                405                 410                 415

Thr Phe Gly His Val Tyr Val Gly Phe Asn Ser Asp Arg Gly Glu Met
                420                 425                 430

Cys Ala Met Lys Glu Val Thr Leu Phe Ala Asp Asp Pro Lys Ser Lys
            435                 440                 445

Glu Ser Ala Lys Gln Leu Cys Gln Glu Ile Ser Leu Leu Ser Arg Leu
450                 455                 460

Gln His Pro Asn Ile Val Arg Tyr Tyr Gly Ser Glu Thr Val Asp Asp
465                 470                 475                 480

Lys Leu Tyr Ile Tyr Leu Glu Tyr Val Ser Gly Gly Ser Ile His Lys
                485                 490                 495

Leu Leu Gln Glu Tyr Gly Gln Phe Gly Glu Gln Ala Ile Arg Ser Tyr
                500                 505                 510

Thr Lys Gln Ile Leu Leu Gly Leu Ala Tyr Leu His Ala Lys Asn Thr
            515                 520                 525

Val His Arg Asp Ile Lys Gly Ala Asn Ile Leu Val Asp Pro Asn Gly
530                 535                 540

Arg Val Lys Leu Ala Asp Phe Gly Met Ala Lys His Ile Asn Gly Gln
545                 550                 555                 560

Gln Cys Pro Phe Ser Phe Lys Gly Ser Pro Tyr Trp Met Ala Pro Glu
                565                 570                 575

Val Ile Lys Asn Ala Ser Gly Cys Asn Leu Ala Val Asp Ile Trp Ser
                580                 585                 590

Leu Gly Cys Thr Val Leu Glu Met Ala Thr Ser Lys Pro Pro Trp Ser
            595                 600                 605

Gln Tyr Glu Gly Ile Ala Ala Met Phe Lys Ile Gly Asn Ser Lys Glu
610                 615                 620

Leu Pro Pro Ile Pro Asp His Leu Ser Glu Glu Gly Lys Asp Phe Ile
625                 630                 635                 640

Arg Lys Cys Leu Gln Arg Asp Pro Ser Ser Arg Pro Thr Ala Val Asp
                645                 650                 655

Leu Leu Gln His Ala Phe Val Arg Asn Ala Pro Pro Leu Glu Lys Ser
                660                 665                 670

Ser Ala Ser His Pro Leu Glu Val Glu Gln Leu Thr Ala Ile Ser Cys
            675                 680                 685

Arg Thr Asn Ser Lys Val Val Glu His Ala Arg Asn Met Ser Ser Leu
690                 695                 700

Gly Leu Glu Gly Gln Ser Ile Leu Gln Arg Arg Ala Ala Lys Phe Ser
705                 710                 715                 720
```

```
Leu Pro Ile Ser Asp Ile His Ile Arg Ser Asn Ile Ser Cys Pro Val
            725                 730                 735

Ser Pro Cys Gly Ser Pro Leu Leu Arg Ser Arg Ser Pro Gln His Gln
        740                 745                 750

Asn Gly Arg Met Ser Pro Ser Pro Ile Ser Ser Pro Arg Thr Thr Ser
    755                 760                 765

Gly Ala Ser Thr Pro Leu Thr Gly Gly Ser Gly Ala Val Pro Leu Asn
770                 775                 780

His Val Arg Gln Pro Ala Tyr Arg Asn Glu Gly Phe Thr Val Thr Ser
785                 790                 795                 800

Arg Gly Phe Asp Asp His Ile Pro Ser Arg Pro Val Asp Pro Val His
            805                 810                 815

Gly Arg Phe Ile Arg Val Gln Gln Phe Ser Ala Gly Arg Gln Glu Arg
        820                 825                 830

Val Val Ser Glu Ala Asp Ile Leu Ser Ser Gln Phe Gly Lys Met Arg
    835                 840                 845

His Ala Asn Val Trp Asp Ser His Asp Arg Pro Leu Pro Ser Glu Arg
850                 855                 860

Ser Ser Gln Gln Cys Phe Gly Asp His Val Lys Leu Lys Pro Ser Leu
865                 870                 875                 880

Asp Leu Arg Ser Gly Pro Arg His Pro Gly Arg Asn His Gly His
            885                 890                 895

<210> SEQ ID NO 43
<211> LENGTH: 2682
<212> TYPE: DNA
<213> ORGANISM: Zea mays
<220> FEATURE:
<221> NAME/KEY: source
<222> LOCATION: 1..2682
<223> OTHER INFORMATION: /mol_type="unassigned DNA"
      /organism="Zea mays"

<400> SEQUENCE: 43
atgccaccat ggtggggaaa atcttcatcc aaagaagtga aaaagtctgc caaagaaaac      60
ctcatcgaca catttcagcg tctcataagt tcaaatgagc aaaagggaag cagaaaatca     120
cgaagtagtc gtagacatgg taaagacaca gctggtgaca aaggttgctg gtccactgct     180
caatcccgct caacatcccc ttcaaaagag gtctctcgat gtcagagctt gcagcagat     240 agaccacatg cacagccact tcctcttccc aaatcacgtg ctaaggtgac acgtacttct     300
tctgatatta ccaactcaaa gtccactttg gaaaagcatg gcaaaggaca actgcttcca     360
ctccctccaa ttcagcctaa aaaagacct gaagctactg aacctgttac tgaagtagct     420
actgcttcgg tctccagcaa ctgttctatt gacagtgatg atcctggtga ttctcagctt     480
cagagtcctg tgggaaatga ggctgaaaat gcgactagaa ttactgcaac aagtagttca     540
agtgttgtgc gcaaagaatg ttctagtgct attaccagaa agaacacaaa ggaagttgca     600
aagccaaaca gtgctattct cagtaaccaa attctgtcaa catctccaag aggtaccttt     660
gctgatggtt atcaatccaa tttacaaagc ccccgacaga ttgccctgga gagtgctccg     720
aatagtttga tgtcaagtcc ttctcgaagc caagaaaata tatgtcctgt tcagattcca     780
acttcagctt tttgggcaat aaaacctcat actgatgtaa cttttccttgg gtctggtcag     840 tgctccagtc caggttctgg tcagacatct gggcataatt cagtgggagg tgatatgcta     900
ggcccaatct tttggcagcc tagccgaggt agtccagagt gttcaccaat tccaagccca     960
```

```
agaatgacga gtcctggtcc aagttctcgg gtgcatagtg gaagtgtctc tcctttgcat   1020
ccaagagctg gtggggtcac tcctgaatcc ccaacaaatc gacatgctga agggaacaag   1080
aagcaaaccc atagattgcc gcttccgcca ttaagcattg ctaatagttc tacctttttg   1140
ccaaacagct ctaacccaac tagtcctata tctcgtagtc ctggtagaac agagaatcca   1200
ccgagtcctg gttcacggtg gaagaaggga aaattgattg gccgtgggac atttggccat   1260
gtatatgttg gttttaacag tgacagaggt gaaatgtgtg cgatgaagga ggttacccct   1320
ttctcagatg atcctaaatc aaaagaaagt gcaaacagc tctgccagga aatatcactt   1380
ctgagccgac tgcagcaccc aaacattgtg cgatactatg gatctgaaac tgttgatgat   1440
aagctttaca tatacctgga gtatgtttct ggtggatcta tacataagct tctccaagag   1500
tatggacagt ttggtgaaca ggccatttgc agttatacta agcaaatact ttgggccta   1560 gcttatttgc atgcaaagaa tacagtacac agagacatca aaggcgcaaa catattggta   1620
gaccctaatg gccgcgtgaa gctcgctgac tttgggatgg caaaacatat caatgggcag   1680
cagtgcccct tctcatttaa gggtagcccg tactggatgg ctcctgaggt tataaaaaat   1740
gctagcggat gtaaccttgc agttgatata tggagtttag gatgcacagt cctagagatg   1800
gctacttcaa accaccatg gagccaatat gaagggatt ccgcaatgtt taagatagga    1860
aacagtaagg agcttccacc aataccggat cacctctcag aagaagggaa agacttcata   1920
agacagtgct tgcaacgtga tccatccagc cgtccaacag cagtggatct tctgcagcat   1980
ccattcgtac aaaatgcacc gccacttgaa aaatcatctg cctctcatcc actggaacag   2040
ttgacggcta tatcatgcag aacaaattcg aaggtggttg agcatgccag aaatatgtcc   2100
tcgcttggtt tggaaggcca atcaattttg cagagaagag ctgccaaatt ttctttgcca   2160
aatagtgata tccatatacg gagtaatata tcttgtcctg tatctccatg tggaagtcct   2220
cttctaagat caagatctcc acagcatcaa aatggtagaa tgtcaccttc tccaatttgc   2280
agccccagga ctacttcggg tgcttcaact cctctgactg gtggtagtgg agctgttcct   2340
ttaaaccatg tgaggcaacc agcttacaga aatgagggct tcacggtcac atcaagaggt   2400
tttgatgacc acatgcctag ccggcctgtt gatccagtac atggacgttt tattcgagtg   2460
cagcaaattc ccgtgggtcg gcaggagagg gtagtctctg aagttgacat tctgagctct   2520
caatatggaa agatgagaca tgcaaatgtg tgggatccgc atgataggcc attaccttct   2580
gagcgttcct ctcaacagtg ctttgggaat catgcgaagc taaaaccttc actggacttg   2640
agatctggtc ctcggcaccc tgggcgcaat catggccatt ga                     2682
```

<210> SEQ ID NO 44
<211> LENGTH: 893
<212> TYPE: PRT
<213> ORGANISM: Zea mays

<400> SEQUENCE: 44

Met Pro Pro Trp Trp Gly Lys Ser Ser Lys Glu Val Lys Lys Ser
1               5                   10                  15

Ala Lys Glu Asn Leu Ile Asp Thr Phe Gln Arg Leu Ile Ser Ser Asn
            20                  25                  30

Glu Gln Lys Gly Ser Arg Lys Ser Arg Ser Arg His Gly Lys
        35                  40                  45

Asp Thr Ala Gly Asp Lys Gly Cys Trp Ser Thr Ala Gln Ser Arg Ser
    50                  55                  60

Thr Ser Pro Ser Lys Glu Val Ser Arg Cys Gln Ser Phe Ala Ala Asp

```
               65                  70                  75                  80
Arg Pro His Ala Gln Pro Leu Pro Leu Pro Lys Ser Arg Ala Lys Val
                    85                  90                  95

Thr Arg Thr Ser Ser Asp Ile Thr Asn Ser Lys Ser Thr Leu Glu Lys
                100                 105                 110

His Gly Lys Gly Gln Leu Leu Pro Leu Pro Ile Gln Pro Lys Lys
            115                 120                 125

Arg Pro Glu Ala Thr Glu Pro Val Thr Glu Val Ala Thr Ala Ser Val
130                 135                 140

Ser Ser Asn Cys Ser Ile Asp Ser Asp Pro Gly Asp Ser Gln Leu
145                 150                 155                 160

Gln Ser Pro Val Gly Asn Glu Ala Glu Asn Ala Thr Arg Ile Thr Ala
                165                 170                 175

Thr Ser Ser Ser Val Val Arg Lys Glu Cys Ser Ser Ala Ile Thr
                180                 185                 190

Arg Lys Asn Thr Lys Glu Val Ala Lys Pro Asn Ser Ala Ile Leu Ser
            195                 200                 205

Asn Gln Ile Leu Ser Thr Ser Pro Arg Gly Thr Phe Ala Asp Gly Tyr
            210                 215                 220

Gln Ser Asn Leu Gln Ser Pro Arg Gln Ile Ala Leu Glu Ser Ala Pro
225                 230                 235                 240

Asn Ser Leu Met Ser Ser Pro Ser Arg Ser Pro Arg Asn Ile Cys Pro
                245                 250                 255

Val Gln Ile Pro Thr Ser Ala Phe Trp Ala Ile Lys Pro His Thr Asp
                260                 265                 270

Val Thr Phe Leu Gly Ser Gly Gln Cys Ser Ser Pro Gly Ser Gly Gln
            275                 280                 285

Thr Ser Gly His Asn Ser Val Gly Gly Asp Met Leu Gly Pro Ile Phe
            290                 295                 300

Trp Gln Pro Ser Arg Gly Ser Pro Glu Cys Ser Pro Ile Pro Ser Pro
305                 310                 315                 320

Arg Met Thr Ser Pro Gly Pro Ser Ser Arg Val His Ser Gly Ser Val
                325                 330                 335

Ser Pro Leu His Pro Arg Ala Gly Gly Val Thr Pro Glu Ser Pro Thr
                340                 345                 350

Asn Arg His Ala Glu Gly Asn Lys Lys Gln Thr His Arg Leu Pro Leu
            355                 360                 365

Pro Pro Leu Ser Ile Ala Asn Ser Ser Thr Phe Leu Pro Asn Ser Ser
            370                 375                 380

Asn Pro Thr Ser Pro Ile Ser Arg Ser Pro Gly Arg Thr Glu Asn Pro
385                 390                 395                 400

Pro Ser Pro Gly Ser Arg Trp Lys Lys Gly Lys Leu Ile Gly Arg Gly
                405                 410                 415

Thr Phe Gly His Val Tyr Val Gly Phe Asn Ser Asp Arg Gly Glu Met
            420                 425                 430

Cys Ala Met Lys Glu Val Thr Leu Phe Ser Asp Asp Pro Lys Ser Lys
            435                 440                 445

Glu Ser Ala Lys Gln Leu Cys Gln Glu Ile Ser Leu Leu Ser Arg Leu
            450                 455                 460

Gln His Pro Asn Ile Val Arg Tyr Tyr Gly Ser Glu Thr Val Asp Asp
465                 470                 475                 480

Lys Leu Tyr Ile Tyr Leu Glu Tyr Val Ser Gly Gly Ser Ile His Lys
                485                 490                 495
```

```
Leu Leu Gln Glu Tyr Gly Gln Phe Gly Glu Gln Ala Ile Cys Ser Tyr
            500                 505                 510
Thr Lys Gln Ile Leu Leu Gly Leu Ala Tyr Leu His Ala Lys Asn Thr
            515                 520                 525
Val His Arg Asp Ile Lys Gly Ala Asn Ile Leu Val Asp Pro Asn Gly
530                 535                 540
Arg Val Lys Leu Ala Asp Phe Gly Met Ala Lys His Ile Asn Gly Gln
545                 550                 555                 560
Gln Cys Pro Phe Ser Phe Lys Gly Ser Pro Tyr Trp Met Ala Pro Glu
                565                 570                 575
Val Ile Lys Asn Ala Ser Gly Cys Asn Leu Ala Val Asp Ile Trp Ser
                580                 585                 590
Leu Gly Cys Thr Val Leu Glu Met Ala Thr Ser Lys Pro Pro Trp Ser
            595                 600                 605
Gln Tyr Glu Gly Ile Ala Ala Met Phe Lys Ile Gly Asn Ser Lys Glu
            610                 615                 620
Leu Pro Pro Ile Pro Asp His Leu Ser Glu Glu Gly Lys Asp Phe Ile
625                 630                 635                 640
Arg Gln Cys Leu Gln Arg Asp Pro Ser Ser Arg Pro Thr Ala Val Asp
                645                 650                 655
Leu Leu Gln His Pro Phe Val Gln Asn Ala Pro Pro Leu Glu Lys Ser
                660                 665                 670
Ser Ala Ser His Pro Leu Glu Gln Leu Thr Ala Ile Ser Cys Arg Thr
            675                 680                 685
Asn Ser Lys Val Val Glu His Ala Arg Asn Met Ser Ser Leu Gly Leu
            690                 695                 700
Glu Gly Gln Ser Ile Leu Gln Arg Arg Ala Ala Lys Phe Ser Leu Pro
705                 710                 715                 720
Asn Ser Asp Ile His Ile Arg Ser Asn Ile Ser Cys Pro Val Ser Pro
                725                 730                 735
Cys Gly Ser Pro Leu Leu Arg Ser Arg Ser Pro Gln His Gln Asn Gly
                740                 745                 750
Arg Met Ser Pro Ser Pro Ile Cys Ser Pro Arg Thr Thr Ser Gly Ala
            755                 760                 765
Ser Thr Pro Leu Thr Gly Gly Ser Gly Ala Val Pro Leu Asn His Val
            770                 775                 780
Arg Gln Pro Ala Tyr Arg Asn Glu Gly Phe Thr Val Thr Ser Arg Gly
785                 790                 795                 800
Phe Asp Asp His Met Pro Ser Arg Pro Val Asp Pro Val His Gly Arg
                805                 810                 815
Phe Ile Arg Val Gln Gln Ile Pro Val Gly Arg Gln Glu Arg Val Val
                820                 825                 830
Ser Glu Val Asp Ile Leu Ser Ser Gln Tyr Gly Lys Met Arg His Ala
            835                 840                 845
Asn Val Trp Asp Pro His Asp Arg Pro Leu Pro Ser Glu Arg Ser Ser
            850                 855                 860
Gln Gln Cys Phe Gly Asn His Ala Lys Leu Lys Pro Ser Leu Asp Leu
865                 870                 875                 880
Arg Ser Gly Pro Arg His Pro Gly Arg Asn His Gly His
                885                 890

<210> SEQ ID NO 45
<211> LENGTH: 3634
```

<212> TYPE: DNA
<213> ORGANISM: Triticum aestivum
<220> FEATURE:
<221> NAME/KEY: source
<222> LOCATION: 1..3634
<223> OTHER INFORMATION: /mol_type="unassigned DNA"
      /organism="Triticum aestivum"

<400> SEQUENCE: 45

```
ggccccacgg ccgccgccga cgccccgtc ccgtgccgcc tcctccaagc accccggcc      60
cggcccctca cggcgcgtcc ccgccgtccc cccctttcgc tcgtcggggc gccgcgttcc   120
tgctgcctcc gccccgtcag cggtcccgg ccgccggttt ccgagatatt gttccattgt   180
cggtccgtcg tgaaagccga gggtgttgca tgccataacg agaaaagccc gtgcttatgc   240
tcttctgact ggcagaatat ggtaattgat cagttttggt aacattgtgg tgactgcaca   300
gccggttaga tataccacag atcctttcat attcgatatg ccatcatggt gggggaagtc   360
ttcctcaaaa gatgcaaaga aaaccaccaa agagaacctc atggatacat ttcatcggtt   420
tataagtcca aatgagcaaa aaggaagcac aaaatcaaaa cggaggtaca gacgtggcga   480
tgatacaact gttgaaaagg tctgccagtc taccacagta tcgcgcgcaa cttcaccctc   540
aaaagaagtt tctcgctgtc aaagcttttc agctgatagg gtacattccc aaccgcttcc   600
tgttcctgga tcacgtcctg cagtgacacg cactgcttct gatgtcaccg aatcaaggcc   660
catattagaa aaacgtggca accaccact gcttctgcca cttcctaaac ctaacaggcc   720
tcagagaagg tcagaaatag tgattgcttc actttctagc aactgctctg ttgatagtga   780
tgaccatgga gattctcagc ttccgagccc tgttggaaat gatgctgaaa acacaacaaa   840
tactacttcc aagagcaagt caagtaatgt gcgcaaagag cgtcctggtg ctatcaccac   900
caagaatacg aaggagatgg caaagacagc taatcaattc ctcagtaacc atacattgtc   960
cacatcaccg agaggtattg cagctgacaa tcaccaacct aatccacaaa atcctcggcc  1020
ggtagtcttg gagagtgctc caaatagttt gatgtcaagt ccttctagaa gtccgagaag  1080
aatatgtcca gaccatattc aacttcagc cttttgggca gtgaagcctc atacagatgt  1140
tactttcctt gactctggtc agtgctccag tccaggttca gggcaaacat ctggccataa  1200
ctctgtgggt ggtgatatgc tagcccagct tttctggcag cccagcagag gtagtccaga  1260
gtgttcaccg attcctagcc caagaatgac aagtcctggc cctagttcca gggtgcacag  1320
tggaagtgtt tctccattgc atccgaggtc tggagggatg gcacctgaat ctccgacagg  1380
tcggaatgat ggtgggaaga agaagcaaac ccacagattg cctcttccac cactgagcat  1440
ctctaatagt tcatttttc caaacaagtc cacgccagct agtcctattt cagcgcctcg  1500
tagtcctggc cgaacagaga atccaccaag tcctggatca cgatggaaga aggggaagct  1560
gattggtcgt ggaacatttg gccatgtata tgttggcttt aacagtgata gcggtgaaat  1620
gtgtgctatg aaagaggtga ccctattctc ggatgatcct aaatcaaagg aaagtgcaaa  1680
gcagttgggg caggaaatat cgctcttgag ccgcttacaa cacccaaata tcgtacgata  1740
ctatggcaca gaaacggttg atgacaaact gtatatatac ttggagtttg tgtctggtgg  1800
atctatccat aaaacttctac aagagtatgg acagcttggt gaaccagcaa tacgcagcta  1860
cactcagcag atactctcag gcttagctta tttgcatgcg aagaatacag tccataggga  1920
tatcaaaggt gcaaacatac tagtagatcc tagcggtcgt gttaagcttg cagactttgg  1980
aatggctaaa catatcaatg gcagcaatg tcctttctca tttaagggta gtccatattg  2040
gatggctcca gaggttataa agagttcgaa tggtggttgc aatcttgcgg ttgacatatg  2100
```

-continued

```
gagtttagga tgcactgtcc tggagatggc taccgcaaaa cccccatgga gccagtacga    2160
agggattgct gcaatgttca agattggaaa tagcaaggaa cttccaccaa taccagatca    2220
cctatcagag cagtgcaagg acttcatcag aaagtgtctg cagcgtgatc cttctcaacg    2280
gccgacagca atggagcttt tgcaacaccc gttcatacaa tataaagtcc gacttgagaa    2340
atccgttatg tctgatcctt tggaacattt gcccgtgata tcttgtagac cgaattctaa    2400
ggtggctgga catacaacaa atatctcgtc attgggattg gagggtcaga caatttacca    2460
gaggaggggt gcaaaatatt cttcgaagca tagcgatatc catatacgga gcaatatatc    2520
ctgtccagtt tctccatgtg gaagtcctct gctaaggtca aggtctcccc aacatacaaa    2580
tggccgaatg tcaccatctc caatttcaag ccccagaacc ctttcaggcg cttctactcc    2640
cctgtctggt ggtaatggtg ctattccctt taatcattca aagcaaccaa cctacaacaa    2700
tgaagatttg caatcgcatc aagaggccca gatgatcact tccccaaccg gcctacagat    2760
cgtaaccttg ggcagtttgg tcgagtgcat caagtctcac aggggaatca ggagaggata    2820
gtatctgaag ctaacattct gagccctcaa tttggaaaga ggcttggaaa cgttttttgat   2880
ttgcgtgata gactgtcccc ttctgaacat ttcactcgtc ctgccttggt ggatcatgtg    2940
aagccaaatc cttcactaga cttaacaact ggttctcccc accatggact caagcgtgat    3000
aactaactat caaggatagg ccaagcgaat ttttttggag cttggcaggg taactaagtg    3060
gttttcagct gctttggcca gtcagtggct tgaattgtat cataatataa tatgactatg    3120
ggaaatatca ttgatttatt ttgaagctaa caactgtaga tggatggagt ctttgttgtc    3180
atccccacag atagacaaag gccatccatc catccatcca tccctgttag gcggaacaac    3240
tgggtgtttg catactacta ctactggcgt gctaacaaca tgcgtcgaaa tgacaagact    3300
gtatactagg agactgaaga agccagagca gttggccacc tccctgcctc tacatgttaa    3360
ttgcccttct tggcgtcctg atgccatttg tacagaagta atctcaagta aaagccaacc    3420
aatattttgc acaggagaaa cagttgagcc aaattctttt aacagctacc cgaggttgtg    3480
aagcgacggc tgcaagttac catggaaact cgtacaaaga gcatggtccc taattaaatt    3540
agctctcccg atatgtataa tttctcattt cagatgtacc atgcccgtcc agttgttcat    3600
attgaatcgg tatataaaaa aaaaaaaaaa acga                                3634
```

<210> SEQ ID NO 46
<211> LENGTH: 827
<212> TYPE: PRT
<213> ORGANISM: Triticum aestivum

<400> SEQUENCE: 46

Met Pro Ser Trp Trp Gly Lys Ser Ser Ser Lys Asp Ala Lys Lys Thr
1               5                   10                  15

Thr Lys Glu Asn Leu Met Asp Thr Phe His Arg Phe Ile Ser Pro Asn
            20                  25                  30

Glu Gln Lys Gly Ser Thr Lys Ser Lys Arg Arg Tyr Arg Arg Gly Asp
        35                  40                  45

Asp Thr Thr Val Glu Lys Val Cys Gln Ser Thr Thr Val Ser Arg Ala
    50                  55                  60

Thr Ser Pro Ser Lys Glu Val Ser Arg Cys Gln Ser Phe Ser Ala Asp
65                  70                  75                  80

Arg Val His Ser Gln Pro Leu Pro Val Pro Gly Ser Arg Pro Ala Val
                85                  90                  95

-continued

Thr Arg Thr Ala Ser Asp Val Thr Glu Ser Arg Pro Ile Leu Glu Lys
            100                 105                 110

Arg Gly Lys Pro Pro Leu Leu Leu Pro Leu Pro Lys Pro Asn Arg Pro
        115                 120                 125

Gln Arg Arg Ser Glu Ile Val Ile Ala Ser Leu Ser Ser Asn Cys Ser
    130                 135                 140

Val Asp Ser Asp Asp His Gly Asp Ser Gln Leu Pro Ser Pro Val Gly
145                 150                 155                 160

Asn Asp Ala Glu Asn Thr Thr Asn Thr Thr Ser Lys Ser Lys Ser Ser
                165                 170                 175

Asn Val Arg Lys Glu Arg Pro Gly Ala Ile Thr Thr Lys Asn Thr Lys
            180                 185                 190

Glu Met Ala Lys Thr Ala Asn Gln Phe Leu Ser Asn His Thr Leu Ser
        195                 200                 205

Thr Ser Pro Arg Gly Ile Ala Ala Asp Asn His Gln Pro Asn Pro Gln
    210                 215                 220

Asn Pro Arg Pro Val Val Leu Glu Ser Ala Pro Asn Ser Leu Met Ser
225                 230                 235                 240

Ser Pro Ser Arg Ser Pro Arg Arg Ile Cys Pro Asp His Ile Pro Thr
                245                 250                 255

Ser Ala Phe Trp Ala Val Lys Pro His Thr Asp Val Thr Phe Leu Asp
            260                 265                 270

Ser Gly Gln Cys Ser Ser Pro Gly Ser Gly Gln Thr Ser Gly His Asn
        275                 280                 285

Ser Val Gly Gly Asp Met Leu Ala Gln Leu Phe Trp Gln Pro Ser Arg
    290                 295                 300

Gly Ser Pro Glu Cys Ser Pro Ile Pro Ser Pro Arg Met Thr Ser Pro
305                 310                 315                 320

Gly Pro Ser Ser Arg Val His Ser Gly Ser Val Ser Pro Leu His Pro
                325                 330                 335

Arg Ser Gly Gly Met Ala Pro Glu Ser Pro Thr Gly Arg Asn Asp Gly
            340                 345                 350

Gly Lys Lys Lys Gln Thr His Arg Leu Pro Leu Pro Leu Ser Ile
        355                 360                 365

Ser Asn Ser Ser Phe Phe Pro Asn Lys Ser Thr Pro Ala Ser Pro Ile
370                 375                 380

Ser Ala Pro Arg Ser Pro Gly Arg Thr Glu Asn Pro Pro Ser Pro Gly
385                 390                 395                 400

Ser Arg Trp Lys Lys Gly Lys Leu Ile Gly Arg Gly Thr Phe Gly His
                405                 410                 415

Val Tyr Val Gly Phe Asn Ser Asp Ser Gly Glu Met Cys Ala Met Lys
            420                 425                 430

Glu Val Thr Leu Phe Ser Asp Asp Pro Lys Ser Lys Glu Ser Ala Lys
        435                 440                 445

Gln Leu Gly Gln Glu Ile Ser Leu Leu Ser Arg Leu Gln His Pro Asn
    450                 455                 460

Ile Val Arg Tyr Tyr Gly Thr Glu Thr Val Asp Asp Lys Leu Tyr Ile
465                 470                 475                 480

Tyr Leu Glu Phe Val Ser Gly Gly Ser Ile His Lys Leu Leu Gln Glu
                485                 490                 495

Tyr Gly Gln Leu Gly Glu Pro Ala Ile Arg Ser Tyr Thr Gln Gln Ile
            500                 505                 510

Leu Ser Gly Leu Ala Tyr Leu His Ala Lys Asn Thr Val His Arg Asp

```
            515                 520                 525
Ile Lys Gly Ala Asn Ile Leu Val Asp Pro Ser Gly Arg Val Lys Leu
    530                 535                 540

Ala Asp Phe Gly Met Ala Lys His Ile Asn Gly Gln Gln Cys Pro Phe
545                 550                 555                 560

Ser Phe Lys Gly Ser Pro Tyr Trp Met Ala Pro Glu Val Ile Lys Ser
                565                 570                 575

Ser Asn Gly Gly Cys Asn Leu Ala Val Asp Ile Trp Ser Leu Gly Cys
            580                 585                 590

Thr Val Leu Glu Met Ala Thr Ala Lys Pro Pro Trp Ser Gln Tyr Glu
        595                 600                 605

Gly Ile Ala Ala Met Phe Lys Ile Gly Asn Ser Lys Glu Leu Pro Pro
    610                 615                 620

Ile Pro Asp His Leu Ser Glu Gln Cys Lys Asp Phe Ile Arg Lys Cys
625                 630                 635                 640

Leu Gln Arg Asp Pro Ser Gln Arg Pro Thr Ala Met Glu Leu Leu Gln
                645                 650                 655

His Pro Phe Ile Gln Tyr Lys Val Arg Leu Glu Lys Ser Val Met Ser
            660                 665                 670

Asp Pro Leu Glu His Leu Pro Val Ile Ser Cys Arg Pro Asn Ser Lys
        675                 680                 685

Val Ala Gly His Thr Thr Asn Ile Ser Ser Leu Gly Leu Glu Gly Gln
    690                 695                 700

Thr Ile Tyr Gln Arg Arg Gly Ala Lys Tyr Ser Ser Lys His Ser Asp
705                 710                 715                 720

Ile His Ile Arg Ser Asn Ile Ser Cys Pro Val Ser Pro Cys Gly Ser
                725                 730                 735

Pro Leu Leu Arg Ser Arg Ser Pro Gln His Thr Asn Gly Arg Met Ser
            740                 745                 750

Pro Ser Pro Ile Ser Ser Pro Arg Thr Leu Ser Gly Ala Ser Thr Pro
        755                 760                 765

Leu Ser Gly Gly Asn Gly Ala Ile Pro Phe Asn His Ser Lys Gln Pro
    770                 775                 780

Thr Tyr Asn Asn Glu Asp Leu Gln Ser His Gln Glu Ala Gln Met Ile
785                 790                 795                 800

Thr Ser Pro Thr Gly Leu Gln Ile Val Thr Leu Gly Ser Leu Val Glu
                805                 810                 815

Cys Ile Lys Ser His Arg Gly Ile Arg Arg Gly
            820                 825

<210> SEQ ID NO 47
<211> LENGTH: 3796
<212> TYPE: DNA
<213> ORGANISM: Hordeum vulgare
<220> FEATURE:
<221> NAME/KEY: source
<222> LOCATION: 1..3796
<223> OTHER INFORMATION: /mol_type="unassigned DNA"
      /organism="Hordeum vulgare"

<400> SEQUENCE: 47
gggggcggag ccgagaaaaa taataatcat cagtatcagt agagaagaga gaagcatcgt      60
ccgtcttctt tcccttacct tgttccctc tccctccctc ctcctgctga cccgacccga     120
cctaccaacc cacctccccc accgcagcag ctccaaatct cccctcgccg tccgccgccg     180
cgccgggcct cgccgccgac gcctccgtcc cgggccacct cctccgagca ccgcccgccc     240
```

```
ctcacggcgc ggacccgccg ccatcgcccg cgtccccct  ttcgctcgtc ggggcgtcg    300
ggtccctgcc gcctccaccc cgtccgcagc tcccggccgc cggtttccga gatattcttc    360
catagtcgct ggtccatcgt ggagggtgtt acatgccatc actagaaaag cccgtgttat    420
gctctcatct gattggcaga atatggtaat tgatcagttt tggtaacatt gtggtgcgtg    480
cacagccggt tagatatacc acagatcctt ccatattcga tatgccatca tggtggggga    540
agtcttcctc aaaagatgca aagaaaacca ccaaagagaa cctcatggat acatttcatc    600
gctttataag tccaaatgag caaaaggaa  gcggaaaatc aaaacggagg tatagacgtg    660
gcgatgatac aactgttgaa aaggtctgcc agtctaccac agtatcgcgc gcaacttcgc    720
cctcaaaaga gtttctcgc  tgtcaaagct tttcagctga taggctacat ttccaaccac    780
ttcctgttcc tggatcacgc cctgcagtca cacgcactgc ttctgatgtc actgaatcaa    840
ggcccatatt agaaaaacgc ggcaaaccac cactgcttct gccacttcct aaacctaaca    900
ggcctcagaa aaggtcagaa atagtgattg cttccctctc tagcaactgc tctattgata    960
gtgatgacca tggagattct cagcttccga gccctgttgg aaatgatgct gaaaacacaa   1020
caaatactac ttccaagagc aagtcaagta atgtgcgcaa agagcgtcct ggtgctatca   1080
ccaccaagca taccaaggag atgacaaaga cagctaatca attcctcagt aaccatacat   1140
tgtccacatc cccgagaggt attgcagctg acaatcacca atccaatcca caaaatcctc   1200
ggccggtagt cttggagagt gctccgaata gtttgatgtc aagtccttct agaagtccaa   1260
gaagaatatg tccggatcat attccaactt cagccttttg ggcagtgaag cctcatacag   1320
atgttacttt ccttggctct ggtcagtgct ccagtccagg ttcagggcaa acatctggcc   1380
ataactccgt gggtggtgat atgctagccc agcttttctg gcagcccagc agaggtagtc   1440
cagagtgttc accgattcct agcccaagaa tgacaagtcc tggccctagt tccagggtgc   1500
acagtggaag tgtttctcca ttacatccga ggtctggagg gatggcacct gaatctccga   1560
caggtcggaa tgacggtggg aagaagaagc aaacacacag actgcctctt ccaccattga   1620
gcatctctaa tagttcattt tttccaaaca agtccacgcc agctagtcct atttcagcgc   1680
ctcgtagtcc tggtcgaaca gagaatccac caagtcctgg atcgcgatgg aagaagggga   1740
agctgattgg tcgtgggaca tttggccatg tatatgtcgg ctttaacagt gatagcggtg   1800
aaatgtgtgc tatgaaagag gtgacccctat tctcggatga tcctaaatca aaggaaagtg   1860
caaagcagtt ggggcaggaa atatcgctct tgagccgctt acaacaccca aatatcgtac   1920
gatactatgg cacagaaacg gttgatgaca aactgtatat atacttggag tttgtctctg   1980
gtggatctat ccataaactt ctacaagagt atggacagct tggtgaacca gcaatacgca   2040
gctacactca gcagatactc tcaggcttag cttatttgca tgcgaagaat acagtccata   2100
gggatatcaa aggtgcaaac atactggtag atcctagcgg tcgtgttaag cttgcagact   2160
ttggaatggc taaacatatc aatgggcagc aatgtcccttt ctcatttaag ggtagtccat   2220
attggatggc tccagaggtt ataaagagtt caaatggtgg ttgcaatctt gcggttgaca   2280
tatggagttt aggatgcact gtcttggaga tggcgaccgc aaaaccccca tggagccagt   2340
acgaagggat tgctgcaatg ttcaagattg aaatagcaa  ggaacttcca ccgataccag   2400
atcacctatc agagcagtgc aaggacttca tcagaaagtg tctgcaacgt gatccttctc   2460
aacgtccgac agcaatggag ctttttgcaac actcgttcat acaatataaa gtccgacttg   2520
agaaatccgt tatgtctgat cctttggaac atttgcccgt gatatcttgt agaccgaatt   2580
```

```
ctaaggtggc tggacataca acaaatatct cgtcgttggg attggagggt cagacaattt    2640
accagagaag gggtgcaaaa ttttcttcga agcatagcga tatccatata cggagcaata    2700
tatcctgtcc agtttctcca tgtggaagtc ctctgctaag gtcaaggtct ccgcaacata    2760
caaatggccg aatgtcaccc tctccaattt caagtcccag aacccttca ggcgcttcta     2820 ctcccctgtc tggtggtaat ggtgctattc cctttaatca ttcaaagcaa ccaacctaca    2880
gcaatgaagg atttgcaatc gcatcaagag gcccagatga tcacttcccc aaccggccta    2940
cagatcgcaa ccttgggcaa tttggtcgag tgcatcaagt ctcacagggg attcaggaga    3000
gaatagtatc tgaagctaac attctgagcc ctcaatttgg aaagaggctt gggaacgttt    3060
ttgatttgcg tgatagactg tccccttctg aacatttcac tcgtcctgcc ttggtggatc    3120
atgtgaagcc aagtccttca ctagacttaa caactagttc tccccaccat ggactcaagc    3180
gtgataacta actatcaagg ataggccaag tgattttttt ttggagcttg gcagggtaac    3240
taagtggttt tcagctgctt tggccattca gtggcttgaa ttgtatcata atatgactat    3300
gggaaatatc attgatttat tttgaagcta acaactgtag atggatggag tctttgttgt    3360
catccccaca gatagacaaa gcccatccat ccatggctgt tatgcggaac gactggggtg    3420
tctgcatact actactactg gcgtgctaac aaacatgcgt cgaaatgaca agactgtata    3480
ctaggagact gaagaagcca gagagagtag tcgggcacct ccctgcctct atatgttaat    3540
tgcctttgtt ggcgtcctga tgccatttgt acagaagtaa tctcaagtaa aagccaccaa    3600
tattttgcac aggagaaaca gttgagccag attcttttaa cagctacccg aggttgaagc    3660
agacggctgc aagtcacacc atggaaactc gtacaaagag tatggtcggc ccctgattaa    3720
attagctctc ccgatatgta taattcctcc ttcagatgta ccatgccagt tgttcatatt    3780
gaatcggtat atatgc                                                    3796
```

<210> SEQ ID NO 48
<211> LENGTH: 889
<212> TYPE: PRT
<213> ORGANISM: Hordeum vulgare

<400> SEQUENCE: 48

```
Met Pro Ser Trp Trp Gly Lys Ser Ser Lys Asp Ala Lys Lys Thr
1               5                   10                  15

Thr Lys Glu Asn Leu Met Asp Thr Phe His Arg Phe Ile Ser Pro Asn
            20                  25                  30

Glu Gln Lys Gly Ser Gly Lys Ser Lys Arg Arg Tyr Arg Arg Gly Asp
        35                  40                  45

Asp Thr Thr Val Glu Lys Val Cys Gln Ser Thr Val Ser Arg Ala
    50                  55                  60

Thr Ser Pro Ser Lys Glu Val Ser Arg Cys Gln Ser Phe Ser Ala Asp
65                  70                  75                  80

Arg Leu His Phe Gln Pro Leu Pro Val Pro Gly Ser Arg Pro Ala Val
                85                  90                  95

Thr Arg Thr Ala Ser Asp Val Thr Glu Ser Arg Pro Ile Leu Glu Lys
            100                 105                 110

Arg Gly Lys Pro Pro Leu Leu Leu Pro Leu Pro Lys Pro Asn Arg Pro
        115                 120                 125

Gln Lys Arg Ser Glu Ile Val Ile Ala Ser Leu Ser Ser Asn Cys Ser
    130                 135                 140

Ile Asp Ser Asp Asp His Gly Asp Ser Gln Leu Pro Ser Pro Val Gly
145                 150                 155                 160
```

-continued

Asn Asp Ala Glu Asn Thr Thr Asn Thr Thr Ser Lys Ser Lys Ser Ser
                165                 170                 175

Asn Val Arg Lys Glu Arg Pro Gly Ala Ile Thr Thr Lys His Thr Lys
            180                 185                 190

Glu Met Thr Lys Thr Ala Asn Gln Phe Leu Ser Asn His Thr Leu Ser
        195                 200                 205

Thr Ser Pro Arg Gly Ile Ala Ala Asp Asn His Gln Ser Asn Pro Gln
    210                 215                 220

Asn Pro Arg Pro Val Val Leu Glu Ser Ala Pro Asn Ser Leu Met Ser
225                 230                 235                 240

Ser Pro Ser Arg Ser Pro Arg Arg Ile Cys Pro Asp His Ile Pro Thr
                245                 250                 255

Ser Ala Phe Trp Ala Val Lys Pro His Thr Asp Val Thr Phe Leu Gly
            260                 265                 270

Ser Gly Gln Cys Ser Ser Pro Gly Ser Gly Gln Thr Ser Gly His Asn
        275                 280                 285

Ser Val Gly Gly Asp Met Leu Ala Gln Leu Phe Trp Gln Pro Ser Arg
    290                 295                 300

Gly Ser Pro Glu Cys Ser Pro Ile Pro Ser Pro Arg Met Thr Ser Pro
305                 310                 315                 320

Gly Pro Ser Ser Arg Val His Ser Gly Ser Val Ser Pro Leu His Pro
                325                 330                 335

Arg Ser Gly Gly Met Ala Pro Glu Ser Pro Thr Gly Arg Asn Asp Gly
            340                 345                 350

Gly Lys Lys Lys Gln Thr His Arg Leu Pro Leu Pro Leu Ser Ile
        355                 360                 365

Ser Asn Ser Ser Phe Phe Pro Asn Lys Ser Thr Pro Ala Ser Pro Ile
    370                 375                 380

Ser Ala Pro Arg Ser Pro Gly Arg Thr Glu Asn Pro Pro Ser Pro Gly
385                 390                 395                 400

Ser Arg Trp Lys Lys Gly Lys Leu Ile Gly Arg Gly Thr Phe Gly His
                405                 410                 415

Val Tyr Val Gly Phe Asn Ser Asp Ser Gly Glu Met Cys Ala Met Lys
            420                 425                 430

Glu Val Thr Leu Phe Ser Asp Asp Pro Lys Ser Lys Glu Ser Ala Lys
        435                 440                 445

Gln Leu Gly Gln Glu Ile Ser Leu Leu Ser Arg Leu Gln His Pro Asn
    450                 455                 460

Ile Val Arg Tyr Tyr Gly Thr Glu Thr Val Asp Asp Lys Leu Tyr Ile
465                 470                 475                 480

Tyr Leu Glu Phe Val Ser Gly Gly Ser Ile His Lys Leu Leu Gln Glu
                485                 490                 495

Tyr Gly Gln Leu Gly Glu Pro Ala Ile Arg Ser Tyr Thr Gln Gln Ile
            500                 505                 510

Leu Ser Gly Leu Ala Tyr Leu His Ala Lys Asn Thr Val His Arg Asp
        515                 520                 525

Ile Lys Gly Ala Asn Ile Leu Val Asp Pro Ser Gly Arg Val Lys Leu
    530                 535                 540

Ala Asp Phe Gly Met Ala Lys His Ile Asn Gly Gln Gln Cys Pro Phe
545                 550                 555                 560

Ser Phe Lys Gly Ser Pro Tyr Trp Met Ala Pro Glu Val Ile Lys Ser
                565                 570                 575

Ser Asn Gly Gly Cys Asn Leu Ala Val Asp Ile Trp Ser Leu Gly Cys
            580                 585                 590

Thr Val Leu Glu Met Ala Thr Ala Lys Pro Pro Trp Ser Gln Tyr Glu
        595                 600                 605

Gly Ile Ala Ala Met Phe Lys Ile Gly Asn Ser Lys Glu Leu Pro Pro
    610                 615                 620

Ile Pro Asp His Leu Ser Glu Gln Cys Lys Asp Phe Ile Arg Lys Cys
625                 630                 635                 640

Leu Gln Arg Asp Pro Ser Gln Arg Pro Thr Ala Met Glu Leu Leu Gln
                645                 650                 655

His Ser Phe Ile Gln Tyr Lys Val Arg Leu Glu Lys Ser Val Met Ser
            660                 665                 670

Asp Pro Leu Glu His Leu Pro Val Ile Ser Cys Arg Pro Asn Ser Lys
        675                 680                 685

Val Ala Gly His Thr Thr Asn Ile Ser Ser Leu Gly Leu Glu Gly Gln
    690                 695                 700

Thr Ile Tyr Gln Arg Arg Gly Ala Lys Phe Ser Ser Lys His Ser Asp
705                 710                 715                 720

Ile His Ile Arg Ser Asn Ile Ser Cys Pro Val Ser Pro Cys Gly Ser
                725                 730                 735

Pro Leu Leu Arg Ser Arg Ser Pro Gln His Thr Asn Gly Arg Met Ser
            740                 745                 750

Pro Ser Pro Ile Ser Ser Pro Arg Thr Leu Ser Gly Ala Ser Thr Pro
        755                 760                 765

Leu Ser Gly Gly Asn Gly Ala Ile Pro Phe Asn His Ser Lys Gln Pro
    770                 775                 780

Thr Tyr Ser Asn Glu Gly Phe Ala Ile Ala Ser Arg Gly Pro Asp Asp
785                 790                 795                 800

His Phe Pro Asn Arg Pro Thr Asp Arg Asn Leu Gly Gln Phe Gly Arg
                805                 810                 815

Val His Gln Val Ser Gln Gly Ile Gln Glu Arg Ile Val Ser Glu Ala
            820                 825                 830

Asn Ile Leu Ser Pro Gln Phe Gly Lys Arg Leu Gly Asn Val Phe Asp
        835                 840                 845

Leu Arg Asp Arg Leu Ser Pro Ser Glu His Phe Thr Arg Pro Ala Leu
    850                 855                 860

Val Asp His Val Lys Pro Ser Pro Ser Leu Asp Leu Thr Thr Ser Ser
865                 870                 875                 880

Pro His His Gly Leu Lys Arg Asp Asn
                885

<210> SEQ ID NO 49
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="YODA10 FORWARD PRIMER (5' - 3')"
      /organism="Artificial Sequence"

<400> SEQUENCE: 49
ggtggatcct catggacgag                                          20

<210> SEQ ID NO 50
<211> LENGTH: 22

```
<212> TYPE: DNA
<213> ORGANISM: Artificial Sequence
<220> FEATURE:
<221> NAME/KEY: source
<222> LOCATION: 1..22
<223> OTHER INFORMATION: /mol_type="unassigned DNA"
      /note="YODA10 REVERSE PRIMER (3' - 5')"
      /organism="Artificial Sequence"

<400> SEQUENCE: 50
tcaggcaatc agaagcatag ag                                              22

<210> SEQ ID NO 51
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="YODA1 FORWARD PRIMER (5'- 3')"
      /organism="Artificial Sequence"

<400> SEQUENCE: 51
ggtggatcct catggacgag                                                 20

<210> SEQ ID NO 52
<211> LENGTH: 22
<212> TYPE: DNA
<213> ORGANISM: Artificial Sequence
<220> FEATURE:
<221> NAME/KEY: source
<222> LOCATION: 1..22
<223> OTHER INFORMATION: /mol_type="unassigned DNA"
      /note="YODA1 REVERSE PRIMER (5' - 3')"
      /organism="Artificial Sequence"

<400> SEQUENCE: 52
tcaggcaatc agaagcatag ag                                              22

<210> SEQ ID NO 53
<211> LENGTH: 28
<212> TYPE: DNA
<213> ORGANISM: Artificial Sequence
<220> FEATURE:
<221> NAME/KEY: source
<222> LOCATION: 1..28
<223> OTHER INFORMATION: /mol_type="unassigned DNA"
      /note="CA:YODA FORWARD PRIMER (5' - 3')"
      /organism="Artificial Sequence"

<400> SEQUENCE: 53
atgccttggt ggagtaaatc aaaagatg                                        28

<210> SEQ ID NO 54
<211> LENGTH: 28
<212> TYPE: DNA
<213> ORGANISM: Artificial Sequence
<220> FEATURE:
<221> NAME/KEY: source
<222> LOCATION: 1..28
<223> OTHER INFORMATION: /mol_type="unassigned DNA"
      /note="CA:YODA REVERSE PRIMER (5' - 3')"
      /organism="Artificial Sequence"

<400> SEQUENCE: 54
ctgaggaaga aaacataacc gatcaaaa                                        28

<210> SEQ ID NO 55
```

```
<211> LENGTH: 25
<212> TYPE: DNA
<213> ORGANISM: Artificial Sequence
<220> FEATURE:
<221> NAME/KEY: source
<222> LOCATION: 1..25
<223> OTHER INFORMATION: /mol_type="unassigned DNA"
      /note="Cer473845 FORWARD PRIMER (5' - 3')"
      /organism="Artificial Sequence"

<400> SEQUENCE: 55
gacttgagtt aatttagtta aagaa                                              25

<210> SEQ ID NO 56
<211> LENGTH: 22
<212> TYPE: DNA
<213> ORGANISM: Artificial Sequence
<220> FEATURE:
<221> NAME/KEY: source
<222> LOCATION: 1..22
<223> OTHER INFORMATION: /mol_type="unassigned DNA"
      /note="Cer473845"
      /organism="Artificial Sequence"

<400> SEQUENCE: 56
tcgcactgca aattgcttaa tc                                                 22

<210> SEQ ID NO 57
<211> LENGTH: 22
<212> TYPE: DNA
<213> ORGANISM: Artificial Sequence
<220> FEATURE:
<221> NAME/KEY: source
<222> LOCATION: 1..22
<223> OTHER INFORMATION: /mol_type="unassigned DNA"
      /note="F16P17-1 FORWARD PRIMER (5' - 3')"
      /organism="Artificial Sequence"

<400> SEQUENCE: 57
ccatttcagc ttcatcaacc ac                                                 22

<210> SEQ ID NO 58
<211> LENGTH: 21
<212> TYPE: DNA
<213> ORGANISM: Artificial Sequence
<220> FEATURE:
<221> NAME/KEY: source
<222> LOCATION: 1..21
<223> OTHER INFORMATION: /mol_type="unassigned DNA"
      /note="F16P17-1 REVERSE PRIMER (5' - 3')"
      /organism="Artificial Sequence"

<400> SEQUENCE: 58
tcgatggtgg ctgagacaat g                                                  21

<210> SEQ ID NO 59
<211> LENGTH: 22
<212> TYPE: DNA
<213> ORGANISM: Artificial Sequence
<220> FEATURE:
<221> NAME/KEY: source
<222> LOCATION: 1..22
<223> OTHER INFORMATION: /mol_type="unassigned DNA"
      /note="F16M19-1 FORWARD PRIMER (5' - 3')"
      /organism="Artificial Sequence"

<400> SEQUENCE: 59
atgttgcatg atgggagatt gg                                                 22
```

```
<210> SEQ ID NO 60
<211> LENGTH: 22
<212> TYPE: DNA
<213> ORGANISM: Artificial Sequence
<220> FEATURE:
<221> NAME/KEY: source
<222> LOCATION: 1..22
<223> OTHER INFORMATION: /mol_type="unassigned DNA"
      /note="F16M19-1 REVERSE PRIMER (5' - 3')"
      /organism="Artificial Sequence"

<400> SEQUENCE: 60
atgaagatag tatttgttat tg                                              22

<210> SEQ ID NO 61
<211> LENGTH: 22
<212> TYPE: DNA
<213> ORGANISM: Artificial Sequence
<220> FEATURE:
<221> NAME/KEY: source
<222> LOCATION: 1..22
<223> OTHER INFORMATION: /mol_type="unassigned DNA"
      /note="Cer469930 FORWARD PRIMER (5' - 3')"
      /organism="Artificial Sequence"

<400> SEQUENCE: 61
caagtttgca aaccctgaag at                                              22

<210> SEQ ID NO 62
<211> LENGTH: 22
<212> TYPE: DNA
<213> ORGANISM: Artificial Sequence
<220> FEATURE:
<221> NAME/KEY: source
<222> LOCATION: 1..22
<223> OTHER INFORMATION: /mol_type="unassigned DNA"
      /note="Cer469930 REVERSE PRIMER (5' - 3')"
      /organism="Artificial Sequence"

<400> SEQUENCE: 62
ttcctggtga ttctttacaa gc                                              22

<210> SEQ ID NO 63
<211> LENGTH: 23
<212> TYPE: DNA
<213> ORGANISM: Artificial Sequence
<220> FEATURE:
<221> NAME/KEY: source
<222> LOCATION: 1..23
<223> OTHER INFORMATION: /mol_type="unassigned DNA"
      /note="T12P18-1 FORWARD PRIMER (5' - 3')"
      /organism="Artificial Sequence"

<400> SEQUENCE: 63
tagttaatgc aaaccagagg agg                                             23

<210> SEQ ID NO 64
<211> LENGTH: 23
<212> TYPE: DNA
<213> ORGANISM: Artificial Sequence
<220> FEATURE:
<221> NAME/KEY: source
<222> LOCATION: 1..23
<223> OTHER INFORMATION: /mol_type="unassigned DNA"
      /note="T12P18-1 REVERSE PRIMER (5' - 3')"
      /organism="Artificial Sequence"

<400> SEQUENCE: 64
gcaaagtgga atatgtaaac tgg                                             23
```

<210> SEQ ID NO 65
<211> LENGTH: 23
<212> TYPE: DNA
<213> ORGANISM: Artificial Sequence
<220> FEATURE:
<221> NAME/KEY: source
<222> LOCATION: 1..23
<223> OTHER INFORMATION: /mol_type="unassigned DNA"
      /note="Cer450793 FORWARD PRIMER (5' - 3')"
      /organism="Artificial Sequence"

<400> SEQUENCE: 65
caaactgcaa acaaagcttt tgt                                               23

<210> SEQ ID NO 66
<211> LENGTH: 22
<212> TYPE: DNA
<213> ORGANISM: Artificial Sequence
<220> FEATURE:
<221> NAME/KEY: source
<222> LOCATION: 1..22
<223> OTHER INFORMATION: /mol_type="unassigned DNA"
      /note="Cer450793 REVERSE PRIMER (5' - 3')"
      /organism="Artificial Sequence"

<400> SEQUENCE: 66
ttttactccc aattctctcg tg                                                22

<210> SEQ ID NO 67
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="Cer464681 FORWARD PRIMER (5' - 3')"
      /organism="Artificial Sequence"

<400> SEQUENCE: 67
cgaatggcgt acccggaaat                                                   20

<210> SEQ ID NO 68
<211> LENGTH: 20
<212> TYPE: DNA
<213> ORGANISM: Artificial Sequence
<220> FEATURE:
<221> NAME/KEY: source
<222> LOCATION: 1..20
<223> OTHER INFORMATION: /mol_type="unassigned DNA"
      /note="Cer464681 REVERSE PRIMER (5' - 3')"
      /organism="Artificial Sequence"

<400> SEQUENCE: 68
ttcccgagaa atccaggctc                                                   20

<210> SEQ ID NO 69
<211> LENGTH: 645
<212> TYPE: PRT
<213> ORGANISM: Artificial Sequence
<220> FEATURE:
<223> OTHER INFORMATION: CONSENSUS SEQUENCE OF THE POLYPEPTIDE SEQ.ID.
      FROM 2 TO 48

<400> SEQUENCE: 69

Met Pro Ser Trp Trp Gly Lys Ser Ser Ser Lys Glu Lys Lys Lys
1               5                   10                  15

Glu Ser Phe Ile Asp Thr His Arg Lys Leu Glu Lys Lys Ser Gly Gly

```
                    20                  25                  30
Ser Arg Arg Asp Thr Ser Glu Lys Gly Ser Arg Ser Pro Ser Pro
                35                  40                  45
Ser Lys Val Ser Arg Cys Gln Ser Phe Ala Glu Arg Pro Ala Gln Pro
     50                  55                  60
Leu Pro Leu Pro Gly Pro Val Arg Thr Asp Ser Gly Ile Ser Ser Lys
 65                  70                  75                  80
Leu Glu Lys Lys Pro Ser Leu Leu Pro Leu Pro Pro Arg Pro Asp Gly
                 85                  90                  95
Thr Ala Ser Val Ser Ser Ser Ser Asp Ser Ser Pro Ala Asp
                100                 105                 110
Asn Gly Thr Arg Thr Ser Pro Ser Lys Gln Asn Ser Glu Lys Pro
                115                 120                 125
Ala Asn Asn His Ser Thr Ser Pro Lys Arg Pro Leu His Val Asn Leu
    130                 135                 140
Gln Pro Gly Ser Ala Pro Ser Ser Met Ser Ser Pro Ser Arg Ser Pro
145                 150                 155                 160
Arg Phe Gly Gln Val Asn Ser Ala Phe Trp Ala Gly Lys Pro Tyr Val
                165                 170                 175
Phe Leu Gly Ser Gly Cys Ser Ser Pro Gly Ser Gly Asn Ser Gly His
                180                 185                 190
Asn Ser Gly Gly Asp Ser Gly Gln Leu Phe Trp Gln Pro Ser Arg Gly
                195                 200                 205
Ser Pro Glu Cys Ser Pro Pro Ser Pro Arg Met Thr Ser Pro Gly Pro
    210                 215                 220
Ser Ser Arg His Ser Gly Ala Val Thr Pro Leu His Pro Arg Ala Gly
225                 230                 235                 240
Gly Ala Glu Ser Pro Thr Arg Asp Asp Gly Lys Gln His Arg Leu Pro
                245                 250                 255
Leu Pro Pro Leu Ser Asn Ser Pro Phe Ser Pro Asn Ser Thr Ser Pro
                260                 265                 270
Ser Pro Arg Ser Pro Gly Arg Ala Asn Pro Ser Pro Gly Ser Arg Trp
    275                 280                 285
Lys Lys Gly Lys Leu Leu Gly Arg Gly Thr Phe Gly His Val Tyr Val
    290                 295                 300
Gly Phe Asn Ser Ser Gly Glu Met Cys Ala Met Lys Glu Val Thr Leu
305                 310                 315                 320
Phe Ser Asp Asp Ala Lys Ser Lys Glu Ser Ala Lys Gln Leu Gly Gln
                325                 330                 335
Glu Ile Ser Leu Ser Arg Leu Arg His Pro Asn Ile Val Gln Tyr Tyr
                340                 345                 350
Gly Ser Glu Thr Val Asp Asp Lys Leu Tyr Ile Tyr Leu Glu Tyr Val
                355                 360                 365
Ser Gly Gly Ser Ile Tyr Lys Leu Leu Gln Glu Tyr Gly Gln Leu Gly
                370                 375                 380
Glu Ala Ile Arg Ser Tyr Thr Gln Gln Ile Leu Ser Gly Leu Ala Leu
385                 390                 395                 400
His Ala Lys Asn Thr Val His Arg Asp Ile Lys Gly Ala Asn Ile Leu
                405                 410                 415
Val Asp Pro Gly Arg Lys Leu Ala Asp Phe Gly Met Ala Lys His Ile
                420                 425                 430
Thr Gly Gln Ser Cys Pro Leu Ser Phe Lys Gly Ser Pro Tyr Trp Met
                435                 440                 445
```

Ala Pro Glu Val Ile Lys Asn Ser Asn Gly Cys Asn Leu Ala Val Asp
    450                 455                 460

Ile Trp Ser Leu Gly Cys Thr Val Leu Glu Met Ala Thr Thr Lys Pro
465                 470                 475                 480

Pro Trp Ser Gln Glu Gly Ala Ala Met Phe Lys Ile Gly Asn Ser Lys
                485                 490                 495

Leu Pro Ile Pro His Leu Ser Glu Gly Lys Asp Phe Arg Cys Leu Gln
            500                 505                 510

Arg Pro Arg Pro Thr Ala Leu Leu His Pro Phe Lys Asn Ala Ala Pro
        515                 520                 525

Glu Arg Pro Ser Ile Ser Ile Gly His Arg Asn Ser Leu Asp Ser His
    530                 535                 540

Arg Lys Ser Ser Ile His Ile Pro Arg Asn Ile Ser Cys Pro Val Ser
545                 550                 555                 560

Pro Gly Ser Pro Leu Leu Ser Arg Ser Pro Gln His Asn Gly Arg Ser
                565                 570                 575

Pro Ser Pro Ile Ser Ser Pro Arg Thr Ser Gly Ser Thr Pro Leu Thr
            580                 585                 590

Gly Gly Gly Ala Pro Phe Tyr Glu Gly Tyr Asn Gly Asp Asp Phe
        595                 600                 605

Ser Glu Ser Glu Asp Leu Gly Gln Phe Gly Leu Tyr Asp Gln Ser
    610                 615                 620

Val Leu Ala Arg Val Ser Gln Leu Leu His Val Lys Pro Ser Leu Asp
625                 630                 635                 640

Leu Pro Ser Arg Gly
                645

<210> SEQ ID NO 70
<211> LENGTH: 10283
<212> TYPE: DNA
<213> ORGANISM: Arabidopsis thaliana
<220> FEATURE:
<221> NAME/KEY: source
<222> LOCATION: 1..10283
<223> OTHER INFORMATION: /mol_type="unassigned DNA"
      /organism="Arabidopsis thaliana"

<400> SEQUENCE: 70

| | | | | |
|---|---|---|---|---|
| tgagattatt | gggactaatg | atggtaacta | tgatgaagtt | aaattggtca ccggtttggc | 60 |
| ataagcatta | atgtggacga | tggtaattta | gaaattgtgt | tgttgtaagc aaaataattt | 120 |
| taaaacatac | tttaaatttg | tgattcttgt | ttattatggt | ttatattccg aataatctta | 180 |
| catcctttt | cacttttaa | atattttgca | tctagaatta | ctaaatcaat ttcaaattac | 240 |
| actaaaata | aaataaaaaa | actaaacccg | gatagaactt | tacgatctta ctcccaacac | 300 |
| ttgaaaaaac | aaatgatttg | gagaaatgca | aaagaaataa | agggccacgg ttaggtatac | 360 |
| gtacttaagt | cggaaaattc | aacatttgtt | aattgcagag | tctctatgaa gctttatgtt | 420 |
| ataatatatg | tttacttata | attgtatggt | ttctacatac | tcaagagttg catgagttca | 480 |
| cacttgcttt | taaaagaaa | tacttctgct | aataaaacag | taatctaata catgagttca | 540 |
| tatattaata | tatacaccac | tataaatgag | tataggcctt | gtcattatca ttattattta | 600 |
| tcattgtcaa | tgtcattata | cttgttaatt | cttatagtat | aatattagtt atgtcccctg | 660 |
| gctcgaggtc | aaaatgaaag | aaaaggcaaa | ggtcaacggt | acgaagcaag gaaccaccga | 720 |
| attcaaaggc | tctctaattt | aacatgctcg | tctataaaca | cgtgaagatg acattgacat | 780 |

```
gcaagcaatg atattattat acattcaaat taacattacc ggaaacagaa ataaactaga    840
tgtcccaatt cgtatacatt gatcgtttta tgaatagatt atataaatta agggcaaaaa    900
catccaattt gaatgtcgtt gatgcgttac acatcttact cttaatcaaa atcgtactat    960
ttttttttta tgatctaact atttatttt ataatatcat attttaacag ctaatgattt   1020
acattaatta agtttgtgtg tgattattcc attacgcatt gtgcctacgg atacgctctt   1080
gaaacatcaa aaatctaaca ttaatttgat gcgacgtaaa aacacaaact aatcaatgtt   1140
tcgatattta aacgcttcat ttttctcata actaccaata aatagaatga cgaatacatg   1200
taatggttaa atacttaatt taggtctgga gcaaatattt ttgaaattat attattcgaa   1260
cagaatcata tctcacaaaa atatactttg atattgcatg ttcacctaat ataatcttca   1320
taaatctgtt ggttcataaa ctaatatgtg tataatacac gtaccttata tatgataata   1380
tgaaaaaatc atgggatgtt gatttatttt atacattatg gttttgtgc tttacactga    1440 taaaaatcat aacaacgcgt ttcacaaaag cctaacgtga catcattatc tccaatctga   1500
ccgttaagat caattagctg acgtgttata acacatcatt gtcctcttgt catatacttt   1560
tttttttcta ttttcacaag ccacccaatg atttggaagt gttttcatat tctaatcttc   1620
tgagaaaaaa atcattataa aagtcagcaa ctaaaactta gcataaatca agataacaat   1680
tctcaaatta caaaacaatt cataacttat cccataaatc aagattattt ttttcctcaa   1740
atttctcttc ttgatcaaat catgcaatta gaaagaagaa gaaacatgac actttgttt    1800 aggttcgaat caatcaaagt atggtatttt tttccactca aacacctaat gaattggaag   1860
tatttcatat tcttcccata tttgagaata ttactataaa gtaccaaaat tcaacaaaat   1920
tagcatagaa tagatcaagc aaattaatct caaaatgttt actaatcttt tatcgtttta   1980
gatcaatcat agacgacaac taagaaacaa aaaaaaaga tactactcat tagcttaatt   2040
agtccaatga tcaagactca aaatttcaaa acttttttca attatggtaa acaaaatata   2100
tacacaaaaa aaatcagaac aaaatcggag ttctgtcttt tcatttttt ttttacaag    2160 ttctgtcttt ttcaaggtaa taaaaaagtt ataaaaaatc gaaataatta attaaggatg   2220
atgttttaat tatcggttat aatcaaaatt agttactact agtacaaaga ttaacgcacc   2280
aaaggagaag aaatctgaag aagtgaatgc tttcttcaaa cgcgctctct ctttctctct   2340
ctctctctct atctccagtt cttattctct ctctctttct atctctacca aatttctgag   2400
aacctcttcg tcttcttcgt tatctcttcc cttcttctgt gtcactaact cacttcactg   2460
ttagtggaag aagctcttac catattcaca cttgtaagca acgattttag ggatctgaaa   2520
cgctttcact gtttctgttt tggattcttc gattgctttt gagctttcga tttgattcca   2580
tttcaagctg ctgaatctgg taattttcc aagaaattag gtttcgatta agctttccct    2640
cactatcaat tttctccatg aaattggaaa acttgcttcg ggtggtgttt tgttgtcttg   2700
tgttaatcct ccaattttgt gtgtgtagat ttgagcaatt ggttgttcta cttagggttt   2760
tcgttttgtt gttgtttctg gggtttctgg aattttctg tgtagatccg tttgtgaggt    2820
gggaattttg agttactgtt tggaaatgga tcttgtgtag cttaggttga agatgatcac   2880 attgatttt gaaactagct caaactaatc tgaagatgat acttttttat tatcatcact    2940
caagatgcta tttttttta tatctcttgg gtgttctatc atttagaat ttgctgaaaa     3000 aattgggctt ctgtgaattc tggtgaattt tgtatctgtc tgtatcttca atttcacacg   3060
gaatcatagt tgttgtaaac cctaacgctg ggttttgttg ttgtaatcag atctttcagg   3120
ttcttcttgg tattgtggtc aaaacaccaa tgggataata ataaaatggt gtttatattg   3180
```

```
ggacttttct tcgtttgttg acctatgttg ggtcaaccaa gtatgatctc tgaagtggtc    3240
aaaaggagag ttactttgta atgttgaaca agagctttta aaagagtgat agtgtgagtg    3300
agtgtgcctc ttggtttgtg ggaagaagat catgccttgg tggagtaaat caaaagatga    3360
aaaaaagaaa actaataagg agagtatcat tgatgcgttt aatcggaaac tgggattcgc    3420
atctgaggat aggtctagtg gaagatcaag aaaatcaaga cgacgacgtg atgagattgt    3480
gtctgaaaga ggagctatat ctcgattacc atcaagatct ccctctcctt ctactcgggt    3540
ttcacgctgt cagagttttg cagaaagatc tcctgctgta cctcttcctc gtcctattgt    3600
ccgtcctcat gtaaccagta ctgattcagg aatgaatgga tcacagagac caggtttaga    3660
tgcaaatttg aagccgtcat ggttgccact tccaaagccc catggtgcta caagcatacc    3720
tgataatacc ggtgctgagc ctgattttgc cactgcttct gtgtctagtg gaagttctgt    3780
gggtgacatt ccatctgatt ctcttctcag tccattggcg tctgattgtg aaaatgggaa    3840
ccgaacacca gtaaacatat cttcgaggtg agtttgaatt gtgattgtta ctattgtgta    3900
ttgtgctctc tctctctatt gctctctatt tctaaacatg ttatatccta ctctttatgt    3960
atagggatca gtcaatgcat agtaacaaaa actcagctga gatgtttaag ccagtcccta    4020
ataaaaatag gattctgtct gcatctccta ggcggagacc tctgggaact catgtgaaga    4080
atctacaaat cccccaacga gatttagtgc tatgcagtgc tccagatagt ttgttgtcta    4140
gtccttccag gagtccaatg agatccttta ttccagatca agtctcaaac catgggttgt    4200
tgattagtaa accatattca gatgtttcct tgcttggatc tggacagtgc tcaagccccg    4260
gttcaggtta caactcaggt aacaattcca ttggtggaga tatggctact cagctgtttt    4320
ggcctcaaag caggtgtagc cctgaatgtt cccctgtgcc tagtccaaga atgacaagcc    4380
ctggtcctag ctctagaata cagagtggtg ctgttacacc tcttcatcct cgagctggag    4440
ggtcaactac tgggtctcct actagaagac ttgatgataa cagacagcaa agccatcgtc    4500
tgcctctccc gccgttatta atctctaata cttgtccgtt ttcacccaca tattcagcag    4560
cgacatctcc gtctgtcccc cgaagtccgg caagggcaga ggctacggtt agccctggat    4620
cgcgatggaa aaagggaga ttgctgggga tgggaagttt tggacatgtg tatcttggct    4680
ttaacaggtt cgtaactaaa caagtctggt tttagtttca aagatgttct gattgctcat    4740
tgtatcgcat tttatactgg ctatggccta tgggaagaat atcactgctg aatccatccc    4800
atactggtag aaattattgt tccatatgtt ggttaagttt ctcaggggca aatctcagtt    4860
ttcatggtta caaattacaa taaactgatt tgttctcttc acaaaatatt gaataggaga    4920
actcaaatgt tatatttcta tgtcaccccct gttttgatcg ttatgttttt cttcctcagt    4980
gaaagtgggg agatgtgtgc catgaaagag gttactctat gctcagatga tcctaagtca    5040
agggagagtg cacaacaatt ggggcaagta agttacacat catcatctgt tcagaacaac    5100
ggaagctgct ctttggtgct tttgtttttg aattttctaa cctttctgct tctctttcaa    5160
tgattgactc tcgcaggaaa tttcagttct aagccgttta cgacaccaaa atatagtgca    5220
gtattatggc tctgaaaccg taagttttac agatatttct tggacatttc tgttctctga    5280
tactatcaac tgtttcagct caaccaagtc atgcacatga ctagattctt tacttttcccc    5340 tcccaattca ggtcgatgac aagctgtata tatctggga gtatgtctcc ggtggttcga    5400
tctataaact tcttcaagag tatggacaat tggtgagaa tgccattcgt aactacacac    5460
aacaaatttt atcagggctc gcatatttgc acgccaaaaa tactgttcat aggtgaggca    5520
```

```
gtgaattcta tccattcttc tgatacctcg ttttccttca tccttcatta gttggagaat    5580
tagatgaaca tggatttaa ttttattcag ggacatcaaa ggagcaaata tattggtgga     5640
tcctcatgga cgagtaaaag ttgctgattt tgggatggca aaacatgtat gtatatgttc    5700
tctgcattct ctgttttgtt tttgtcctgt ttgaatttt cctttacgca gaaacaactg     5760
atctgaataa actatgctaa gcctagttag aaactttcct aagtctaata caaattcata    5820
aacaaaatgc agattactgc tcaatctggt cctttatcat tcaaggggag cccatattgg    5880
atggcacctg aggtcagtat gctgctacaa cctgtctgtt tcaatgttga caggcgttat    5940
gctgatgctt tattatcttg cttggatttc aggtgataaa gaattcaaat ggcagtaacc    6000
ttgcggtcga catatggagt cttggatgta ctgttttaga aatggctaca acgaaacctc    6060
catggagcca gtatgaaggg gttagtaaat catataagta ctcaacaaac atgagattga    6120
atgatgcgac tcttccatcc ttatgtattc gagttcttta caggttcctg ctatgttcaa    6180
gattggaaac agcaaggagc ttccagatat ccctgatcat ttatctgaag aggggaagga    6240
ttttgtaaga aaatgcctac aaagaaaccc cgcaaatcgt cctacagctg ctcagctttt    6300
ggatcatgct tttgtaagaa atgtgatgcc gatggaaagg cctattgtga gtggcgagcc    6360
tgcagaagcc atgaatgtag cttcgagcac catgagatca ctggtatgaa agctcatatt    6420
cctcaattct aaattctcta tgcttctgat tgcctgacaa atctgtttgt ttcaggacat    6480
tggacatgca aggagtcttc cgtgcttaga ctcggaagat gcaaccaatt accagcagaa    6540
aggattaaaa catggctcgg gattcaggtc ttagccattt cgttctacc ttcattttcc     6600
aagcatcaaa gcttctttgt ggctaaactt tcctccttt ttggtcacag tatatcccaa     6660
tctcctagga acatgtcatg cccgatttca ccagtcggta gtccaatctt tcactcgcat    6720
tcaccacaca ttagcggaag aagatctcca tccccaatat ctagtcccca cgctctctct    6780
ggttcatcaa caccttttaac tgggtgtggt ggagccatcc cgttccatca ccaaagacaa    6840
actacagtta acttcttgca tgaaggcata ggatcaagca aagcccggg aagtggcgga     6900
aatttctaca ccaacagttt ctttcaggag cctagtaggc agcaagatcg gtcgcggagt    6960
agtccaagga ctcctcctca tgtatttggg gacaacaacg gatcgatcca gccaggctat    7020
aattggaaca aggacaacca gccagtccta tctgatcatg tgtcccaaca gctcttaagt    7080
gagcatctga aactgaagtc cctcgacctg agacccggtt tttcaactcc cggatcaaca    7140
aacagaggac cctaacccgt tcgagtcaaa tgattcgaca ccaatgacag aaccataaaa    7200
cccagtggaa aaaacatca aaacaagtag ctgcagaaac tcctccagga tctcggaatt    7260
gcaacacagc ctgaagggtc aggatcttga ggtttaggat cggggttagg gttactgagc    7320
cgcgtctcaa aaccctgaac cattggctaa tatcatgaat gaggattcgt ttttttcgtc    7380
tttggaaaat ctgaagagct ctttgtcttg tctctctctc ttttctctg aggatatatg     7440
ggagtgtgag atagagagat caacaaaaat tgattttgtg tataggaact tgtggtggta    7500
gaacagatca tcacctaatt tgtctatttc cctcttcttc cgtctctgtc tggtctggtt    7560
cgttgctgat gaagaagaag aaaaaaaaga gggcaaaagc ttaaatctct taaaacctaa    7620
actctttgat gtaatctatc tttattgtaa gagaatctca aattagatta ttaatccact    7680
ctcttctttg attaatactc gcttctattc actttggttc caaaattcaa actttactgc    7740
ttttggaatc aatatctttt ttaaaaaaaa ttaacgttaa attatactcc aaagaaaaaa    7800
tcactgtttg ttacatttga atgcaaaact tttcatataa aatacaagaa agaatgagc     7860
tatccttgat ttcttgtttc aaaccaaagt acgatgccac cttcgtactt cgataagcct    7920
```

```
ccattcttaa acatgctgaa ccggtttcga atatttgtgt caatcatctt gacaagcttt    7980
cccgcaggtg atggttgttc ccatgcatgt ctcatgttgt tcctttccgc catatggaat    8040
gaattgtgtt ttgaaacacg taccggagga taaacgcttt agtatagtcc tgagctttat    8100
cggtggtcaa cttaagaacc tctttccaag ctgccgagaa cttgtccaga agcactcatt    8160
tgacatttca tgagttcctc ccatatcttg aatgtgtaag gcataaaaac aaacaaatgt    8220
tctatgttcc ccttcgggta ctggcaaaac acgcaactca catttgcgtt tcttttccac    8280
ttttgcgttc gatctcctgt tgccaatcta ttctttgttg ctagccaagt gataaaagag    8340
tacttccggg tggagtgagg gaaccatatc cctttgtact cctctatagt tggtttagca    8400
acccgaacct gtgaagtctc ctttgtcccg aacttcttgt tgtatcgatc gttccttccc    8460
ttccacaaca taatacccga gtcttgactc ctgataagct tttgtttcct cacctcctcc    8520
tctacaagat ttatctatgt ttttccttc gatgtgtgtc catcacctca cctactgtgc    8580 tggttttga tattccaact aaataaaacc tctctcccca agcttctcgt ataggcatcc    8640
catagggctc cacatatcaa atcaaaagga agtagaccac ccatttttat gccaaatgca    8700
tgaaccacga gttgtgttgt ctttgacaga ccataaagaa ccaccacgaa tgagatattt    8760
tatcacccaa tctccccata aggaaccgtg tgccgacaga atacgccata ctaacttcag    8820
catgcttatt ttattagcct cttctaaagt tacaaaacgg tcatctaaag tatcaattac    8880
aacaaactaa aacaagtgtg tatgtatacc ttttcatgat caatactttc tagcatcaca    8940
gagtaaggcg ctcgagctga tcataaaagc aaacaaatca tagaattaat aattaaacat    9000
atcacagaag taaagaatat aagatatcaa atacaaaact caacagagac caaagtggct    9060
cgtatataaa accagttacc aacaaatagt aagactcaag tgttgagttt ttgcaactaa    9120
tttattatac catccatata taagagtaaa gtcggatcaa aatctgatga atgaaggaga    9180
ataaataata tatatataga tgttgaaagt cagatgttga gatttaacca atgtgctaca    9240
gcggattttt tattactata tgaatttaga atgtataaat tagatgtatg tgaatatttt    9300
atttcaaatt tatgattttg ttacatattt gtaggtttgg atacaaaatc ttctatattt    9360
ttattataac acagaaaaaa tgatagtttc tttgatataa ttttctttcc tttttctttt    9420
ctgaaatccg aaaaaaactg gaatttttaaa taattaatat ataggaaaaa gaaattaatg    9480
aagaagaaag atgttttgtt ttttattgat taaatttta aaatataaaa atcaagaagt    9540
agaaaagaaa ttaatgaaga agaaagatgg ttttgttttt ttattctatt tattaatgtt    9600
ttaaaattta taaaattaat aaaaagaaaa gaaattaatg aagaagaaag atgttttct    9660 tttttgagtt tttaaatttt aaacaaataa aattaagttt ttttctaagg gtaaaattga    9720
gatttgtttt tttcgtatga gatgtgtgaa tgaatctgtc aatactttat actttaaatt    9780
ttattagtca ccaataaagt agtttgagtt tttttttcctg gcaacagaaa aaattgaagc    9840
ttttttcaga caaattttga agaagatggt ttgttttgg gaattttccc attgtaaatt    9900
tcacatttaa gagtatatat tacagaggaa gatctaggtc gtggaaatcg agcaagtgag    9960
aacaacaatg aaaagaata tatattatta tttaaattac aaaatcgtcc acacaattaa    10020
ttatgagagc ttagaaagtt gtctacgttt tatacacatt taacactttc ttacaaagaa    10080
aacaaaccat atatagacaa agaacgacga tcatggattc ttcttcaata atgatgatgt    10140
aagtaagtaa cataaacaac ttaagattaa aaaaggatt tgaagagaaa attaatctta    10200
caacttacgt tacaacccc aaagcctttt tttttttct ctgtaaatat ctcagtgttg    10260
```
cattttttgg tcaggtcgtc tca                                         10283

<210> SEQ ID NO 71
<211> LENGTH: 2235
<212> TYPE: DNA
<213> ORGANISM: Artificial Sequence
<220> FEATURE:
<221> NAME/KEY: source
<222> LOCATION: 1..2235
<223> OTHER INFORMATION: /mol_type="unassigned DNA"
      /note="Arabidopsis thaliana CA:YODA mutant"
      /organism="Artificial Sequence"

<400> SEQUENCE: 71

```
atgccttggt ggagtaaatc aaaagatgaa aaaagaaaa ctaataagga gagtatcatt      60
gatgcgttta atcggaaact gggattcgca tctgaggata ggtctagtgg aagatcaaga    120
aaatcaagac gacgacgtga tgagattgtg tctgaaagag gagctatatc tcgattacca    180
tcaagatctc cctctccttc tactcgggtt tcacgctgtc agagttttgc agaaagatct    240
cctgctgtac ctcttcctcg tcctattgtc cgtcctcatg taaccagtac tgattcagga    300
atgaatggat cacagagacc aggtttagat gcaaatttga agccgtcatg gttgccactt    360
ccaaagcccc atggtgctac aagcatacct gataataccg gtgctgagcc tgattttgcc    420
actgcttctg tgtctagtgg aagttctgtg ggtgacattc catctgattc tcttctcagt    480
ccattggcgt ctgattgtga aaatgggaac cgaacaccag taaacatatc ttcgagggat    540
cagtcaatga aatacagag tggtgctgtt acacctcttc atcctcgagc tggagggtca    600
actactgggt ctcctactag aagacttgat gataacagac agcaaagcca tcgtctgcct    660
ctcccgccgt tattaatctc taatacttgt ccgttttcac ccacatattc agcagcgaca    720
tctccgtctg tcccccgaag tccggcaagg gcagaggcta cggttagccc tggatcgcga    780
tggaaaaaag ggagattgct ggggatggga agttttggac atgtgtatct ggctttaac     840
agtgaaagtg gggagatgtg tgccatgaaa gaggttactc tatgctcaga tgatcctaag    900
tcaagggaga gtgcacaaca attggggcaa gaaatttcag ttctaagccg tttacgacac    960
caaaatatag tgcagtatta tggctctgaa accgtcgatg acaagctgta tatatatctg   1020
gagtatgtct ccggtggttc gatctataaa cttcttcaag agtatggaca atttggtgag   1080
aatgccattc gtaactacac acaacaaatt ttatcagggc tcgcatattt gcacgccaaa   1140
aatactgttc atagggacat caaaggagca aatatattgg tggatcctca tggacgagta   1200
aaagttgctg attttgggat ggcaaaacat attactgctc aatctggtcc tttatcattc   1260
aaggggagcc catattggat ggcacctgag gtgataaaga attcaaatgg cagtaacctt   1320
gcggtcgaca tatggagtct tggatgtact gttttagaaa tggctacaac gaaacctcca   1380
tggagccagt atgaagggt cctgctatg ttcaagattg aaacagcaa ggagcttcca      1440
gatatccctg atcatttatc tgaagagggg aaggattttg taagaaaatg cctacaaaga   1500
aaccccgcaa atcgtcctac agctgctcag cttttggatc atgcttttgt aagaaatgtg   1560
atgccgatgg aaaggcctat tgtgagtggc gagcctgcag aagccatgaa tgtagcttcg   1620
agcaccatga gatcactgga cattggacat gcaaggagtc ttccgtgctt agactcggaa   1680
gatgcaacca attaccagca gaaaggatta aaacatggct cgggattcag tatatcccaa   1740
tctcctagga acatgtcatg cccgatttca ccagtcggta gtccaatctt tcactcgcat   1800
tcaccacaca ttagcggaag aagatctcca tccccaatat ctagtcccca cgctctctct   1860
ggttcatcaa caccttttaac tgggtgtggt ggagccatcc cgttccatca ccaaagacaa   1920
```

```
actacagtta acttcttgca tgaaggcata ggatcaagca gaagcccggg aagtggcgga    1980
aatttctaca ccaacagttt ctttcaggag cctagtaggc agcaagatcg gtcgcggagt    2040
agtccaagga ctcctcctca tgtattttgg gacaacaacg gatcgatcca gccaggctat    2100
aattggaaca aggacaacca gccagtccta tctgatcatg tgtcccaaca gctcttaagt    2160
gagcatctga aactgaagtc cctcgacctg agacccggtt tttcaactcc cggatcaaca    2220
aacagaggac cctaa                                                     2235

<210> SEQ ID NO 72
<211> LENGTH: 743
<212> TYPE: PRT
<213> ORGANISM: Artificial Sequence
<220> FEATURE:
<223> OTHER INFORMATION: Arabidopsis thaliana CA:YODA mutant

<400> SEQUENCE: 72
```

| | | | | | | | | | | | | | | |
|---|---|---|---|---|---|---|---|---|---|---|---|---|---|---|
| Met | Pro | Trp | Trp | Lys | Ser | Lys | Asp | Glu | Lys | Lys | Thr | Asn | Lys | Glu |
| 1 | | | | 5 | | | | | 10 | | | | | 15 |
| Ser | Ile | Ile | Asp | Ala | Phe | Asn | Arg | Lys | Leu | Gly | Phe | Ala | Ser | Glu | Asp |
| | | | 20 | | | | | 25 | | | | | 30 | | |
| Arg | Ser | Ser | Gly | Arg | Ser | Arg | Lys | Ser | Arg | Arg | Arg | Asp | Glu | Ile |
| | | 35 | | | | | 40 | | | | | 45 | | |
| Val | Ser | Glu | Arg | Gly | Ala | Ile | Ser | Arg | Leu | Pro | Ser | Arg | Ser | Pro | Ser |
| 50 | | | | | 55 | | | | | 60 | | | | | |
| Pro | Ser | Thr | Arg | Val | Ser | Arg | Cys | Gln | Ser | Phe | Ala | Glu | Arg | Ser | Pro |
| 65 | | | | 70 | | | | | 75 | | | | | 80 | |
| Ala | Val | Pro | Leu | Pro | Arg | Pro | Ile | Val | Arg | Pro | His | Val | Thr | Ser | Thr |
| | | | 85 | | | | | 90 | | | | | 95 | | |
| Asp | Ser | Gly | Met | Asn | Gly | Ser | Gln | Arg | Pro | Gly | Leu | Asp | Ala | Asn | Leu |
| | | | 100 | | | | | 105 | | | | | 110 | | |
| Lys | Pro | Ser | Trp | Leu | Pro | Leu | Pro | Lys | Pro | His | Gly | Ala | Thr | Ser | Ile |
| | | 115 | | | | | 120 | | | | | 125 | | | |
| Pro | Asp | Asn | Thr | Gly | Ala | Glu | Pro | Asp | Phe | Ala | Thr | Ala | Ser | Val | Ser |
| | 130 | | | | | 135 | | | | | 140 | | | | |
| Ser | Gly | Ser | Ser | Val | Gly | Asp | Ile | Pro | Ser | Asp | Ser | Leu | Leu | Ser | Pro |
| 145 | | | | | 150 | | | | | 155 | | | | | 160 |
| Leu | Ala | Ser | Asp | Cys | Glu | Asn | Gly | Asn | Arg | Thr | Pro | Val | Asn | Ile | Ser |
| | | | | 165 | | | | | 170 | | | | | 175 | |
| Ser | Arg | Asp | Gln | Ser | Met | Arg | Ile | Gln | Ser | Gly | Ala | Val | Thr | Pro | Leu |
| | | | 180 | | | | | 185 | | | | | 190 | | |
| His | Pro | Arg | Ala | Gly | Gly | Ser | Thr | Thr | Gly | Ser | Pro | Thr | Arg | Arg | Leu |
| | | 195 | | | | | 200 | | | | | 205 | | | |
| Asp | Asp | Asn | Arg | Gln | Gln | Ser | His | Arg | Leu | Pro | Leu | Pro | Pro | Leu | Leu |
| | 210 | | | | | 215 | | | | | 220 | | | | |
| Ile | Ser | Asn | Thr | Cys | Pro | Phe | Ser | Pro | Thr | Tyr | Ser | Ala | Ala | Thr | Ser |
| 225 | | | | | 230 | | | | | 235 | | | | | 240 |
| Pro | Ser | Val | Pro | Arg | Ser | Pro | Ala | Arg | Ala | Glu | Ala | Thr | Val | Ser | Pro |
| | | | | 245 | | | | | 250 | | | | | 255 | |
| Gly | Ser | Arg | Trp | Lys | Lys | Gly | Arg | Leu | Leu | Gly | Met | Gly | Ser | Phe | Gly |
| | | | 260 | | | | | 265 | | | | | 270 | | |
| His | Val | Tyr | Leu | Gly | Phe | Asn | Ser | Glu | Ser | Gly | Glu | Met | Cys | Ala | Met |
| | | 275 | | | | | 280 | | | | | 285 | | | |
| Lys | Glu | Val | Thr | Leu | Cys | Ser | Asp | Pro | Lys | Ser | Arg | Glu | Ser | Ala |
| | 290 | | | | | 295 | | | | | 300 | | | | |

```
Gln Gln Leu Gly Gln Glu Ile Ser Val Leu Ser Arg Leu Arg His Gln
305                 310                 315                 320

Asn Ile Val Gln Tyr Tyr Gly Ser Glu Thr Val Asp Asp Lys Leu Tyr
                325                 330                 335

Ile Tyr Leu Glu Tyr Val Ser Gly Gly Ser Ile Tyr Lys Leu Leu Gln
            340                 345                 350

Glu Tyr Gly Gln Phe Gly Glu Asn Ala Ile Arg Asn Tyr Thr Gln Gln
        355                 360                 365

Ile Leu Ser Gly Leu Ala Tyr Leu His Ala Lys Asn Thr Val His Arg
370                 375                 380

Asp Ile Lys Gly Ala Asn Ile Leu Val Asp Pro His Gly Arg Val Lys
385                 390                 395                 400

Val Ala Asp Phe Gly Met Ala Lys His Ile Thr Ala Gln Ser Gly Pro
                405                 410                 415

Leu Ser Phe Lys Gly Ser Pro Tyr Trp Met Ala Pro Glu Val Ile Lys
            420                 425                 430

Asn Ser Asn Gly Ser Asn Leu Ala Val Asp Ile Trp Ser Leu Gly Cys
        435                 440                 445

Thr Val Leu Glu Met Ala Thr Thr Lys Pro Pro Trp Ser Gln Tyr Glu
450                 455                 460

Gly Val Pro Ala Met Phe Lys Ile Gly Asn Ser Lys Glu Leu Pro Asp
465                 470                 475                 480

Ile Pro Asp His Leu Ser Glu Glu Gly Lys Asp Phe Val Arg Lys Cys
                485                 490                 495

Leu Gln Arg Asn Pro Ala Asn Arg Pro Thr Ala Ala Gln Leu Leu Asp
            500                 505                 510

His Ala Phe Val Arg Asn Val Met Pro Met Glu Arg Pro Ile Val Ser
        515                 520                 525

Gly Glu Pro Ala Glu Ala Met Asn Val Ala Ser Ser Thr Met Arg Ser
530                 535                 540

Leu Asp Ile Gly His Ala Arg Ser Leu Pro Cys Leu Asp Ser Glu Asp
545                 550                 555                 560

Ala Thr Asn Tyr Gln Gln Lys Gly Leu Lys His Gly Ser Gly Phe Ser
                565                 570                 575

Ile Ser Gln Ser Pro Arg Asn Met Ser Cys Pro Ile Ser Pro Val Gly
            580                 585                 590

Ser Pro Ile Phe His Ser His Ser Pro His Ile Ser Gly Arg Arg Ser
        595                 600                 605

Pro Ser Pro Ile Ser Ser Pro His Ala Leu Ser Gly Ser Ser Thr Pro
610                 615                 620

Leu Thr Gly Cys Gly Gly Ala Ile Pro Phe His His Gln Arg Gln Thr
625                 630                 635                 640

Thr Val Asn Phe Leu His Glu Gly Ile Gly Ser Ser Arg Ser Pro Gly
                645                 650                 655

Ser Gly Gly Asn Phe Tyr Thr Asn Ser Phe Phe Gln Glu Pro Ser Arg
            660                 665                 670

Gln Gln Asp Arg Ser Arg Ser Ser Pro Arg Thr Pro Pro His Val Phe
        675                 680                 685

Trp Asp Asn Asn Gly Ser Ile Gln Pro Gly Tyr Asn Trp Asn Lys Asp
690                 695                 700

Asn Gln Pro Val Leu Ser Asp His Val Ser Gln Gln Leu Leu Ser Glu
705                 710                 715                 720
```

His Leu Lys Leu Lys Ser Leu Asp Leu Arg Pro Gly Phe Ser Thr Pro
                725                 730                 735

Gly Ser Thr Asn Arg Gly Pro
        740

<210> SEQ ID NO 73
<211> LENGTH: 63
<212> TYPE: PRT
<213> ORGANISM: Arabidopsis thaliana

<400> SEQUENCE: 73

Val Pro Ala Met Phe Lys Ile Gly Asn Ser Lys Glu Leu Pro Asp Ile
1               5                   10                  15

Pro Asp His Leu Ser Glu Glu Gly Lys Asp Phe Val Arg Lys Cys Leu
            20                  25                  30

Gln Arg Asn Pro Ala Asn Arg Pro Thr Ala Ala Gln Leu Leu Asp His
        35                  40                  45

Ala Phe Val Arg Asn Val Met Pro Met Glu Arg Pro Ile Val Ser
    50                  55                  60

<210> SEQ ID NO 74
<211> LENGTH: 63
<212> TYPE: PRT
<213> ORGANISM: Arabidopsis thaliana
<220> FEATURE:
<223> OTHER INFORMATION: At5g66850 YODA kinase domain

<400> SEQUENCE: 74

Ala Ala Ala Met Phe Lys Val Met Arg Asp Ser Pro Pro Ile Pro Glu
1               5                   10                  15

Ser Met Ser Pro Glu Gly Lys Asp Phe Leu Arg Leu Cys Phe Gln Arg
            20                  25                  30

Asn Pro Ala Glu Arg Pro Thr Ala Ser Met Leu Leu Glu His Arg Phe
        35                  40                  45

Leu Lys Asn Ser Leu Gln Pro Thr Ser Pro Ser Asn Ser Asp Val
    50                  55                  60

<210> SEQ ID NO 75
<211> LENGTH: 53
<212> TYPE: PRT
<213> ORGANISM: Arabidopsis thaliana
<220> FEATURE:
<223> OTHER INFORMATION: At5g66850 YODA N-terminal domain

<400> SEQUENCE: 75

Met Arg Trp Leu Pro Gln Ile Ser Phe Ser Ser Pro Ser Ser Ser Pro
1               5                   10                  15

Ser Ser Ser Leu Lys Pro Val Ala Ser Tyr Ser Glu Ser Pro Asp Pro
            20                  25                  30

Asp Arg Asn Gln Asp Arg Asp Arg Phe His Arg Arg Leu Phe Arg Phe
        35                  40                  45

Asn Arg Gly Arg Leu
    50

<210> SEQ ID NO 76
<211> LENGTH: 71
<212> TYPE: PRT
<213> ORGANISM: Arabidopsis thaliana
<220> FEATURE:
<223> OTHER INFORMATION: At1g53570 YODA kinase domain

<400> SEQUENCE: 76

```
-continued

Val Ala Ala Ile Phe Lys Ile Gly Asn Ser Lys Asp Thr Pro Glu Ile
1               5                   10                  15

Pro Asp His Leu Ser Asn Asp Ala Lys Asn Phe Ile Arg Leu Cys Leu
            20                  25                  30

Gln Arg Asn Pro Thr Val Arg Pro Thr Ala Ser Gln Leu Leu Glu His
        35                  40                  45

Pro Phe Lys Arg Asx Thr Thr Arg Val Ala Ser Thr Ser Leu Pro Lys
        50              55                  60

Asp Phe Pro Pro Arg Ser Tyr
65                  70
```

METHOD FOR INCREASING PATHOGEN RESISTANCE IN PLANTS

CROSS REFERENCE TO RELATED APPLICATION

This Application is a 371 of PCT/EP2013/077076 filed on Dec. 18, 2013 which, in turn, claimed the priority of European Patent Application No. 12197751.6 filed on Dec. 18, 2012, both applications are incorporated herein by reference.

FIELD OF THE INVENTION

The present invention relates to a method for increasing fungal resistance in a plant, wherein said resistance is increased by the introduction of nucleic acid sequences coding for YODA polypeptides or by the modification of endogenous YODA nucleic acid sequences. The present invention is also related to nucleic acid constructs, recombinant vectors, cells, transgenic plants, crops, propagation material, compositions and harvestable part of a plant comprising said nucleic acid sequences.

BACKGROUND OF THE INVENTION

Plant diseases which are caused by various pathogens such as, for example viruses, bacteria, oomycetes and fungi, can lead to, considerable yield losses in crop plant cultivation, which firstly has economic consequences, but, secondly, also endangers the safety of human nutrition. Since the last century, chemical fungicides have been employed for controlling fungal diseases. While the use of these substances has succeeded in reducing the extent of plant diseases, it cannot be ruled out even now that these compounds have a harmful effect on humans, animals and the environment. If the consumption of conventional plant protection agents is to be reduced to a minimum in the long term, it is therefore important to study the natural pathogen defense of various plants against different causative organisms, and to exploit them in a targeted manner for the generation of pathogen-resistant plants by means of recombinant manipulation, for example by the introduction of external resistance genes or by the manipulation of the endogenous gene expression in the plants.

There are only few approaches, which confer a resistance to pathogens, mainly fungal and oomycete pathogens, to plants. This shortcoming can partly be attributed to the complexity of the biological systems in question. Another fact which stands in the way of obtaining resistances to pathogens is that little is known about the interactions between pathogen and plant. The large number of different pathogens, the infection mechanisms developed by these organisms and the defense mechanisms developed by the plant families, genera and species interact with one another in many different ways.

The infections caused by the fungal, oomycete and bacterial pathogens lead to the activation of the plant's defense mechanisms in the infected plants. Thus, the activation of plant and animal innate immunity systems involves a specific detection of microbe-associated molecular-patterns (MAMPs) by different sets of host pattern-recognition receptors (PRRs). Several members of the plant leucine-reach-repeat (LRR) receptor-like kinase (RLK) family have been found to function as PRRs. Thus, FLS2 and EFR RLKs are PRRs for the bacterial MAMPs flagellin and EF-Tu, respectively, whereas LysM/CERK have been suggested to be the receptor for the fungal MAMP, chitosan. The initiation of the immune responses mediated by these PRRs involves the formation of MAMPs-induced complex with additional RLKs, the endocytosis of RLKs proteins and the activation of MAPK-signaling cascades. Some LRR-RLKs, such as FERONIA, BAK1 and ER; have dual functions controlling plant immunity and different cell growth and developmental processes. The molecular and genetic bases of this double functionality remain elusive.

Thus the ER protein negatively regulates, through its genetic interaction with two closely related paralogs (ERL1 and ERL2) and the Too Many Mouths (TMM) LRR receptor-like protein, several developmental processes such as stomatal patterning, inflorescence architecture, lateral organ shape, ovule development and transpiration efficiency. A MAPK signaling cascade, which includes the YODA MAP3K, and the MKK4/5 and MPK3/6 kinase modules, has been placed downstream of the receptors in stomata pattering, but biochemical and genetic interactions among these components have not been proved due to lethality-associated phenotypes of some of corresponding mutants.

Zygote development also depends on the YODA (MAP kinase signalling pathway). Loss of the MAPKK kinase gene YODA or the two MAP kinase genes MPK3/MPK6 blocks zygote elongation, such that the first division results in an abnormally small basal cell that typically fails to form a recognizable suspensor (Lukowitz, W., et al., Cell 116: 109-19 (2004)). Hyperactive forms of YODA have the opposite effect, causing abnormally long suspensors and often completely inhibiting growth of the proembryo (Lukowitz, W., et al., Cell 116: 109-19 (2004)).

Until now, the strategy for generating fungus-resistant plants has frequently involved the crossing-in of quantitative resistance traits (resistance QTLs). However, the disadvantage of this procedure is that undesirable traits are frequently also crossed in. Moreover, the breeding methods required are very complicated and time-consuming.

DESCRIPTION OF THE INVENTION

The present invention is based on the object of providing a method for generating a resistance of plants to pathogens. The object is achieved by the embodiments characterized in the claims.

The invention therefore relates to a method of increasing the resistance to one or more pathogens in a monocotyledonous or dicotyledonous plant, or a part of a plant, for example in an organ, tissue, a cell or a part of a plant cell, for example in an organelle, which comprises introducing into, and expressing in, the plant or plant cell a YODA nucleic acid which codes for a YODA protein, and which mediates an increased pathogen resistance, preferably an increased resistance to fungal, oomycete, and/or bacterial pathogens.

In a further embodiment, the invention relates to a method of increasing the resistance to one or more pathogen(s) in a monocotyledonous or dicotyledonous plant, or a part of a plant, for example in an organ, a tissue, a cell or a part of a plant cell, for example in an organelle, in which method an endogenous DNA sequence which codes for YODA protein- and which mediates an increased pathogen resistance, preferably an increased resistance to fungal, oomycete and/or bacterial pathogens, is increased in the plant, plant part or plant cell in comparison with the original or wild-type plant, or a part thereof, or in which method the endogenous gene sequence or preferably the 5'-untranslated region (5'UTR) is modified in comparison with the original sequence.

Originally, it has been found that an hypomorphic, non-embryo lethal mutation (elk2/YODA10) in *Arabidopsis* YODAgene lead to an enhanced susceptibility of these YODA10 plants to necrotrophic and biotrophic fungi, and to bacteria and that the gene could therefore play a role in mediating the pathogen resistance of plants.

Furthermore, plants with a constitutive activation of YODA (CA:YODA) showed broad-spectrum resistance, indicating that YODA regulates MAPK-signaling cascades, which initiate innate immunity. This function is distinct from that regulated by YODA in the control of developmental cues.

Surprisingly, however, it has now been found that the constitutive activation of YODA (CA:YODA) gene, does not activate the salicylic acid, the jasmonate or the ethylene defense signalling, or the tryptophan-derived metabolites biosynthetic pathway required for resistance.

One embodiment is a method for increasing fungal resistance in a plant, a plant part, or a plant cell, characterised in that the method comprises the step of increasing the expression and/or activity of a YODA protein in the plant, plant part, or plant cell in comparison to a wild type plant, wild type plant part or wild type plant cell, herewith the method according to the invention.

Another embodiment is the method of the invention, wherein said YODA protein comprises an amino acid sequence having at least 80% identity with SEQ ID NO: 2, 4, 6, 8, 10, 12, 14, 16, 18, 20, 22, 24, 26, 28, 30, 32, 34, 36, 38, 40, 42, 44, 46, 48, 69 or 72.

A further embodiment is the method according to the invention, comprising introducing an exogenous nucleotide sequence which codes for an amino acid sequence having at least 80% identity with SEQ ID NO: 2, 4, 6, 8, 10, 12, 14, 16, 18, 20, 22, 24, 26, 28, 30, 32, 34, 36, 38, 40, 42, 44, 46, 48, 69 or 72 into a plant, a part of a plant, or a plant cell, and expressing said nucleotide sequence in the plant, the part of the plant, or the plant cell; wherein said nucleotide sequence is increased in the plant, the part of the plant, or the plant cell in comparison with the original, or wild-type plant, part of the plant, or plant cell.

In the method according to the invention, it is preferred to obtain a race-unspecific resistance. Thus, for example, it is possible to achieve, by the method according to the invention, a broad-range resistance to obligatory-biotrophic and/or hemibiotrophic and/or necrotrophic fungi, oomycete and/or bacteria of plants.

Genes with high identity to YODA probably mediate similar functions. Preferably, the genes or the used nucleic acids or the expressed proteins have 40% or more identity, preferably at least 50%, at least 60%, at least 70%, at least 80%, at least 85%, at least 90%, at least 95%, at least 97%, at least 98%, at least 99% or more identity, in comparison with the respective YODA sequence of *Arabidopsis* (AtYODA) (SEQ ID NO: 1 or SEQ ID NO: 70 [cDNA sequence with UTR] or the protein sequence SEQ ID No.: 2). The genes with the highest homologies to AtYODA from *Solanum lycopersicum* SlYODA1 (Solyc08g081210.1.1), SlYODA2 (Solyc03g025360.1.1), SlYODA3 (Solyc06g036080.1.1), *Vitis vinifera*VvYODA 1(XP003631415.1), VvYODA2 (XP003634098.1), VvYODA3 (CAN65619.1), *Populus trichocarpa* PtYODA1 (XP002304501.1), PtYODA2 (XP002322482.1), PtYODA3 (XP002318210.1), *Oryza sativa Japonica* OsYODA1 (NP001053542.1), *Oryza sativa Japonica* OsYODA2 (NP001047673.1), *Glycine max* GmYODA1 (XP003548172.1), GmYODA2 (XP003533990.1), *Glycine max* GmYODA3 (XP003556116.1), GmYODA4 (XP003536457.1), *Glycine max* GmYODA5 (XP003538696.1), GmYODA6 (XP003532415.1), *Cucumus melo* subsp. *melo* CmYODA1 (ADN34290.1), *Sorghum bicolor* SbYODA1 (XP002448319.1), *Sorghum bicolor* SbYODA2 (XP_002452783.1), *Zea mays* ZmYODA1 (CAW45396.1), *Triticum aestivum* TaYODA1 (AK335442.1), and *Hordeum vulgare* subsp. *vulgare* HvYODA1 (BAJ98424.1) probably exert similar functions in the plant as YODA polypeptide from *Arabidopsis* (AtYODA).

The nucleic acid sequence according to the invention, i.e. the nucleic acid sequence which codes for the YODA protein, or functional parts of it and which mediates an increased pathogen resistance, preferably an increased resistance to fungal or bacterial pathogens, and which is, in the methods according to the invention, introduced into, and expressed in, the plant or plant cell or a part thereof, or the endogenous DNA sequence according to the invention, which is increased in the plant or plant cell in comparison with the original or wild-type plant or its part, or where the endogenous gene sequence or preferably the 5'-untranslated region (5'UTR) is modified in comparison with this original sequence, is selected from the group consisting of (a) nucleic acid molecule which codes for at least one polypeptide comprising the sequence shown in SEQ ID No.: 2, 4, 6, 8, 10, 12, 14, 16, 18, 20, 22, 24, 26, 28, 30, 32, 34, 36, 38, 40, 42, 44, 46, 48, 69 or 72;

(b) nucleic acid molecule which comprises at least one polynucleotide of the sequence shown in SEQ ID No.: 1, 3, 5, 7, 9, 11, 13, 15, 17, 19, 21, 23, 25, 27, 29, 31, 33, 35, 37, 39, 41, 43, 45, 47, 70 or 71;

(c) nucleic acid molecule which codes for a polypeptide whose sequences has at least 50%, preferably at least 60%, at least 70%, at least 80%, at least 85%, at least 90%, at least 95%, at least 97%, at least 98% or at least 99%, identity with any one of the sequences shown in SEQ ID No.: 2, 4, 6, 8, 10, 12, 14, 16, 18, 20, 22, 24, 26, 28, 30, 32, 34, 36, 38, 40, 42, 44, 46, 48, 69 or 72; preferably the nucleic acid molecule has the same or a similar biological function as a nucleic acid molecule encoding a polypeptide as shown in SEQ ID No.: 2, 4, 6, 8, 10, 12, 14, 16, 18, 20, 22, 24, 26, 28, 30, 32, 34, 36, 38, 40, 42, 44, 46, 48, 69 or 72;

(d) nucleic acid molecule which comprises at least one polynucleotide whose sequences has at least 50%, preferably at least 60%, at least 70%, at least 80%, at least 85%, at least 90%, at least 95%, at least 97%, at least 98% or at least 99% identity with any one of the sequences shown in SEQ ID No.: 1, 3, 5, 7, 9, 11, 13, 15, 17, 19, 21, 23, 25, 27, 29, 31, 33, 35, 37, 39, 41, 43, 45, 47, 70 or 71; preferably the nucleic acid molecule has the same or a similar biological function as a nucleic acid molecule comprising a nucleic acid sequence as shown in SEQ ID No.: 1, 3, 5, 7, 9, 11, 13, 15, 17, 19, 21, 23, 25, 27, 29, 31, 33, 35, 37, 39, 41, 43, 45, 47, 70 or 71;

(e) nucleic acid molecule according to (a) to (d) which codes for a fragment or an epitope of the sequences as shown in SEQ. ID No.: 2, 4, 6, 8, 10, 12, 14, 16, 18, 20, 22, 24, 26, 28, 30, 32, 34, 36, 38, 40, 42, 44, 46, 48, 69 or 72; preferably wherein the fragment is a functional fragment; preferably the fragment confers fungal resistance; preferably the fragment has the same or a similar biological activity than a nucleic acid comprising a polynucleotide of the sequence shown in SEQ ID No.: 1, 3, 5, 7, 9, 11, 13, 15, 17, 19, 21, 23, 25, 27, 29, 31, 33, 35, 37, 39, 41, 43, 45, 47, 70 or 71;

(f) nucleic acid molecule which codes for a polypeptide which is recognized by a monoclonal antibody directed against a polypeptide which is encoded by the nucleic acid molecules as shown in (a) to (d);

(g) nucleic acid molecule which hybridizes under stringent conditions with the complement of a nucleic acid molecule as shown in (a) to (d); and (h) nucleic acid molecule which can be isolated from a DNA library using a nucleic acid molecule as shown in (a) to (d) or their part-fragments of at least 15 nt, preferably 20 nt, 30 nt, 50 nt, 100 nt, 200 nt or 500 nt, as probe under stringent hybridization conditions;

(i) a nucleic acid encoding the same YODA protein as the YODA nucleic acids of (a) to (d) above, but differing from the YODA nucleic acids of (a) to (d) above due to the degeneracy of the genetic code;

or a complementary sequence thereof.

In the description, the term of the "sequence(s) according to the invention" is used for simplification reasons, and refers, depending on the context, to the nucleic acid and/or amino acid sequences disclosed herein. The skilled worker will know from the context what they refer to.

One embodiment is the method according to the invention, wherein said nucleotide sequence comprises at least one nucleic acid molecule according to the invention.

In a further embodiment, the invention therefore relates to a method of generating a plant with an increased resistance to one or more plant pathogens, preferably with a broad-spectrum resistance, in particular to fungal pathogens and bacterial pathogens, for example from the classes Ascomycetes, Basidiomycetes, Deuteromycetes, Chytridiomycetes, Zygomycetes or Oomycetes, or bacteria, by introducing and expressing a sequence according to the invention, which codes for a protein comprising all or part of the YODA. Preferably, the protein with a deletion in the N-terminal domain, like CA-YODA, resulting in a constitutive activation of YODA.

One embodiment is the method according to the invention, comprising modifying an endogenous nucleotide sequence which codes for an amino acid sequence having at least 80% identity with SEQ ID NO: 2, 4, 6, 8, 10, 12, 14, 16, 18, 20, 22, 24, 26, 28, 30, 32, 34, 36, 38, 40, 42, 44, 46, 48, 69 or 72, and/or the 5'-untranslated region (5'UTR) in comparison with the original sequence.

One embodiment is the method according to the invention, wherein a fungal or a bacterial pathogen resistance is generated or increased.

One embodiment is the method according to the invention, wherein the fungal pathogen is a necrotroph, a biotroph or an Oomycete pathogen.

One embodiment is the method according to the invention, comprising a) introducing into a plant cell a recombinant expression cassette comprising the nucleic acid molecule according to the invention in an operable linkage with a promoter which is active in plants;

b) regenerating a plant from the plant cell, and c) expressing said nucleic acid molecule to generate or to increase a pathogen resistance in said plant.

One embodiment is the method according to the invention, wherein the promoter is a pathogen-inducible promoter or an epidermis, or mesophyll-specific promoter, or the promoter is a stress induced promoter; preferably when the promoter is selected from the group consisting of a promoter induced by: osmotic stress, drought stress, cold stress, heat stress, oxidative stress, nutrient deficiency, infection by a fungus, infection by an oomycete, infection by a virus, infection by a bacterium, nematode infestation, pest infestation, weed infestation, and herbivory.

One embodiment is the method according to the invention, wherein the plant is selected from the group consisting of: soybean, potato, cotton, rape, oilseed rape, canola, sunflower, alfalfa, clover, banana, blackberry, blueberry, strawberry, raspberry, cantaloupe, carrot, cauliflower, coffee, cucumber, eggplant, grape, honeydew, lettuce, mango, melon, onion, papaya, pepper, pineapple, pumpkin, spinach, squash, tobacco, *tomato*, tomatillo, watermelon, apple, peach, pear, cherry, plum, broccoli, cabbage, cauliflower, Brussels sprouts, kohlrabi, currant, avocado, orange, lemon, grapefruit, tangerine, artichoke, cherry, walnut, peanut, endive, leek, arrowroot, beet, cassava, turnip, radish, yam, sweet potato; pea, bean, sugarcane, turfgrass, *Miscanthus*, switchgrass, wheat, maize, sweet corn, rice, millet, sorghum, barley, and rye.

One embodiment is the method according to the invention, wherein said nucleotide sequence is in operable linkage with a pathogen-inducible promoter or an epidermis- and/or mesophyll-specific promoter.

In a further embodiment, the protein-encoding cDNA (or the mRNA including the UTR sequence(s)) sequence for expression in a cell of a plant that, upon expression of the DNA to RNA and transcription of the RNA to produce an encoded peptide or polypeptide, enhances the ability of the plant or plant cell to withstand an abiotic or biotic stress, or enhances the yield or value of the plant, or a crop or product produced from the plant.

In one embodiment, the resistance is obtained by introducing, and expressing, a nucleic acid sequence according to the invention, for example a YODA nucleic acid from *Arabidopsis* (Acc.-No. NM_105047.2), from *Solanum lycopersicum* SlYODA1 (Solyc08g081210.1.1), SlYODA2 (Solyc03g025360.1.1), SlYODA3 (Solyc06g036080.1.1), *Vitis vinifera* VvYODA1 (XP003631415.1), VvYODA2 (XP003634098.1), VvYODA3 (CAN65619.1), *Populus trichocarpa* PtYODA1 (XP002304501.1), PtYODA2 (XP002322482.1), PtYODA3 (XP002318210.1), *Oryza sativa Japonica* OsYODA1 (NP001053542.1), *Oryza sativa Japonica* OsYODA2 (NP001047673.1), *Glycine max* GmYODA1 (XP003548172.1), GmYODA2 (XP003533990.1), *Glycine max* GmYODA3 (XP003556116.1), GmYODA4 (XP003536457.1), *Glycine max* GmYODA5 (XP003538696.1), GmYODA6 (XP003532415.1), *Cucumus melo* subsp. *melo* CmYODA1 (ADN34290.1), *Sorghum bicolor* SbYODA1 (XP002448319.1), *Sorghum bicolor* SbYODA2 (XP_002452783.1), *Zea mays* ZmYODA1 (CAW45396.1), *Triticum aestivum* TaYODA1 (AK335442.1), and *Hordeum vulgare* subsp. *vulgare* HvYODA1 (BAJ98424.1).

On the other hand, it is also possible to increase the endogenous expression or activity of one of these sequences by methods known to the skilled worker, for example by mutating a UTR region, preferably the 5'-UTR, a promoter region, a genomically coding region for the active center, for binding sites, for localization signals, for domains, clusters and the like, such as, for example, of coding regions for the N-terminal, the Kinase or the C-terminal domains. The activity can be increased in accordance with the invention by mutations which affect the secondary, tertiary or quaternary structure of the protein.

Mutations can be inserted for example by an EMS mutagenesis. Domains can be identified by suitable computer programs such as, for example, SMART or InterPRO, for example as described in Andersen P., The Journal of Biol. Chemistry, 279, 38, 40053, (2004) or Mudgil, Y., Plant Physiology, 134, 59, (2004), and literature cited therein. The suitable mutants can then be identified for example by TILLING (for example as described by Henikoff, S., et al., Plant Physiol. 135: 630-6 (2004)).

In another embodiment, the introduction and expression of a sequence according to the invention into a plant, or increasing or modifying or mutating an endogenous sequence according to the invention, if appropriate of one or both untranslated regions, in a plant is combined with increasing the polypeptide quantity, activity or function of other resistance factors, preferably of a Bax inhibitor 1 protein (BI-1), preferably of the Bax inhibitor 1 protein from *Hordeum vulgare* (GenBank Acc.-No.: AJ290421), from, *Nicotiana tabacum* (GenBank Acc.-No.: AF390556), rice (GenBank Acc.-No.: AB025926), *Arabidopsis* (GenBank Acc.-No.: AB025927) or tobacco and oilseed rape (GenBank Acc.-No.: AF390555, Bolduc N et al. (2003) Planta 216, 377 (2003)) or of ROR2 (for example from barley (GenBank Acc.-No.: AY246906), SnAP34 (for example from barley (GenBank Acc.-No.: AY247208) and/or of the lumenal binding protein BiP for example from rice (GenBank Acc.-No. AF006825). An increase can be achieved for example by mutagenesis or overexpression of a transgene, inter alia.

"YODA protein" or "YODA polypeptide" means, for the purposes of the invention, a protein with the full or parts of the sequence, which confers enhanced pathogen resistance when expressed in plants. The terms "polypeptide" and "protein" are used herein interchangeably.

"YODA protein" is understood as meaning a sequence which comprises an N-terminal domain, a kinase domain and a C-terminal domain (Lukowitz, W., et al., Cell 116: 109-19 (2004)). For example, the polypeptide which is employed in the method according to the invention, or the polypeptide according to the invention, has an activity which is involved in the plant innate immunity or in the regulation of the gene expression in the context of the stomata developmental processes.

The kinase domain of the YODA protein as referred to herein preferably comprises a sequence having at least 60%, at least 70%, at least 80%, at least 90%, at least 95%, at least 97%, at least 98%, at least 99% or more identity with the kinase domain as shown in SEQ ID No: 73. SEQ ID NO: 73 corresponds to amino acid coordinates 606 to 668 of SEQ ID NO: 2 (AtYODA, see also FIG. 4B, upper panel). Also preferably, the kinase domain may have a sequence as show in SEQ ID NO: 73.

The "YODA protein" is encoded for example by a nucleic acid molecule comprising a nucleic acid molecule selected from the group consisting of
(a) nucleic acid molecule which codes for at least one polypeptide comprising the sequence shown in SEQ ID No.: 2, 4, 6, 8, 10, 12, 14, 16, 18, 20, 22, 24, 26, 28, 30, 32, 34, 36, 38, 40, 42, 44, 46, 48, 69 or 72;
(b) nucleic acid molecule which comprises at least one polynucleotide of the sequence shown in SEQ ID No: 1, 3, 5, 7, 9, 11, 13, 15, 17, 19, 21, 23, 25, 27, 29, 31, 33, 35, 37, 39, 41, 43, 45, 47, 70 or 71;
(c) nucleic acid molecule which codes for a polypeptide whose sequence has at least 40%, at least 50%, at least 60%, at least 70%, at least 80%, at least 90%, at least 95%, at least 97%, at least 98%, at least 99% or more identity with the sequences SEQ ID No: 2, 4, 6, 8, 10, 12, 14, 16, 18, 20, 22, 24, 26, 28, 30, 32, 34, 36, 38, 40, 42, 44, 46, 48, 69 or 72;
(d) nucleic acid molecule which comprises at least one polynucleotide whose sequences has at least 50%, preferably at least 60%, at least 70%, at least 80%, at least 85%, at least 90%, at least 95%, at least 97%, at least 98% or at least 99% identity with any one of the sequences shown in SEQ ID No.: 1, 3, 5, 7, 9, 11, 13, 15, 17, 19, 21, 23, 25, 27, 29, 31, 33, 35, 37, 39, 41, 43, 45, 47, 70 or 71; preferably the nucleic acid molecule has the same or a similar biological function as a nucleic acid molecule comprising a nucleic acid sequence as shown in SEQ ID No.: 1, 3, 5, 7, 9, 11, 13, 15, 17, 19, 21, 23, 25, 27, 29, 31, 33, 35, 37, 39, 41, 43, 45, 47, 70 or 71;
(e) nucleic acid molecule according to (a) to (d) which codes for a functional fragment or an epitope of the sequences as shown in SEQ. ID No.: 2, 4, 6, 8, 10, 12, 14, 16, 18, 20, 22, 24, 26, 28, 30, 32, 34, 36, 38, 42, 44, 46, 48, 69 or 72;
(f) nucleic acid molecule which codes for a polypeptide which is recognized by a monoclonal antibody directed against a polypeptide which is encoded by the nucleic acid molecules as shown in (a) to (d);
(g) nucleic acid molecule which hybridizes under stringent conditions with a nucleic acid molecule as shown in (a) to (d) or their part-fragments consisting of at least 15 nucleotides (nt), preferably 20 nt, 30 nt, 50 nt, 100 nt, 200 nt or 500 nt;
(h) nucleic acid molecule which can be isolated from a DNA library using a nucleic acid molecule as shown in (a) to (d) or their part-fragments of at least 15 nt, preferably 20 nt, 30 nt, 50 nt, 100 nt, 200 nt or 500 nt, as probe under stringent hybridization conditions; or comprises a complementary sequence thereof, or constitutes a functional equivalent thereof;
(i) nucleic acid molecule encoding the same YODA protein as the YODA nucleic acids of (a) to (d) above, but differing from the YODA nucleic acids of (a) to (d) above due to the degeneracy of the genetic code.

Preferably, the YODA protein encoded by the nucleic acid molecule of (a) to (i) comprises a kinase domain as set forth above.

The terms "to lessen", "to reduce" or "to repress" or their substantives are used synonymously in the present text.

An increase in the expression can be obtained as described herein. An increase in the expression or function is understood as meaning herein both the activation or enhancement of the expression or function of the endogenous protein, including a de novo expression, increase of protein activity, and an increase or enhancement by expression of a transgenic protein or factor.

For the purposes of the invention, "organism" means "nonhuman organisms" as long as the term relates to a viable multi-celled organism.

For the purposes of the invention, "plants" means all dicotyledonous or monocotyledonous plants. Preferred are plants which can be subsumed under the class of the Liliatae (Monocotyledoneae or monocotyledonous plants). The term includes the mature plants, seeds, shoots and seedlings, and parts, propagation material, plant organs, tissue, protoplasts, callus and other cultures, for example cell cultures derived from the above, and all other types of associations of plant cells which give functional or structural units. Mature plants means plants at any developmental stage beyond the seedling stage. Seedling means a young, immature plant in an early developmental stage.

Dicotyledonous plants are also preferred. The term includes the mature plants, seeds, shoots and seedlings, and parts, propagation material, plant organs, tissue, protoplasts, callus and other cultures, for example cell cultures derived from the above, and all other types of associations of plant cells which give functional or structural units. Mature plants means plants at any developmental stage beyond the seedling stage. Seedling means a young, immature plant in an early developmental stage.

"Plant" also comprises annual and perennial dicotyledonous or monocotyledonous plants and includes by way of example, but not by limitation, those of the genera *Glycine, Vitis, Asparagus, Populus, Pennisetum, Lolium, Oryza, Zea, Avena, Hordeum, Secale, Triticum, Sorghum, Saccharum* and *Lycopersicum*.

In a preferred embodiment, the method according to the invention is applied to monocotyledonous plants, for example from the family Poaceae, especially preferably to the genera *Oryza, Zea, Avena, Hordeum, Secale, Triticum, Sorghum* and *Saccharum*, very especially preferably to agriculturally important plants such as, for example, *Hordeum vulgare* (barley), *Triticum aestivum* (wheat), *Triticum aestivum* subsp. *spelta* (spelt), *Triticale, Avena sativa* (oats), *Secale cereale* (rye), *Sorghum bicolor* (sorghum), *Zea mays* (maize), *Saccharum officinarum* (sugarcane) or *Oryza sativa* (rice). Preferably, the plant is soy (*Glycine max*).

"Nucleic acids" means biopolymers of nucleotides which are linked with one another via phosphodiester bonds (polynucleotides, polynucleic acids). Depending on the type of sugar in the nucleotides (ribose or deoxyribose), one distinguishes the two classes of the ribonucleic acids (RNA) and the deoxyribonucleic acids (DNA).

The term "crop" means all plant parts obtained by growing plants agriculturally and collected within the harvesting process.

"Resistance" means the preventing, the repressing, the reducing or the weakening of disease symptoms of a plant as the result of infection by a pathogen. The symptoms can be manifold, but preferably comprise those which directly or indirectly lead to an adverse effect on the quality of the plant, on the quantity of the yield, on the suitability for use as feed or foodstuff, or else which make sowing, growing, harvesting or processing of the crop more difficult.

In a preferred embodiment, the following disease symptoms are weakened, reduced or prevented: formation of pustules and hymenia on the surfaces of the affected tissues, maceration of the tissues, spreading necrosis of the tissue, etc.

An "increased pathogen resistance" means that the defense mechanisms of a certain plant or in a part of a plant, for example in an organ, a tissue, a cell or an organelle, have an increased resistance to one or more pathogens as the result of using the method according to the invention in comparison with a suitable control, for example the wild type of the plant ("control plant", "original plant"), to which the method according to the invention has not been applied, under otherwise identical conditions (such as, for example, climatic conditions, growing conditions, type of pathogen and the like). Preferably, at least the epidermis and/or mesophyll tissue in a plant, or the organs which have an epidermis and/or mesophyll tissue, have an increased resistance to the pathogens. For example, the resistance in the leaves is increased.

The increased resistance preferably manifests itself in a reduced manifestation of the disease symptoms, where disease symptoms-in addition to the abovementioned adverse effects-also comprise for example the penetration efficiency of a pathogen into the plant or the plant cell, or the proliferation efficiency of the pathogen in or on the same. In this context, the disease symptoms are preferably reduced by at least 10% or at least 20%, especially preferably by at least 40% or 60%, very especially preferably by at least 70% or 80%, most preferably by at least 90% or 95% in comparison with the control plant.

In this context, the increased resistance preferably manifests itself in a reduced manifestation of the disease symptoms, where the term disease symptoms-in addition to the above mentioned adverse effects-also comprises for example the penetration efficiency of a pathogen into the plant or the plant cell, or the proliferation efficiency in or on the same. Modifications in the cell wall structure, for example, may constitute a principal mechanism of pathogen resistance, as demonstrated for example in Jacobs A. K. et al., Plant Cell 15 (11), 2503 (2003).

For the purposes of the invention, "pathogen" means organisms whose interactions with a plant lead to the above-described disease symptoms; in particular, pathogens mean organisms from the kingdom Fungi or the kingdom Bacteria. Preferably, pathogen is understood as meaning a organism which penetrates epidermis or mesophyll cells, especially preferably pathogens which penetrate plants via stomata and subsequently penetrate mesophyll cells. Preferably the pathogen is a fungal pathogen, preferably, a biotrophic, hemibiotrophic, necrotrophic, or heminecrotrophic fungus. Organisms which are preferably mentioned in this context are those from the phyla Ascomycota, Basidiomycota, Heterokontophyta and Proteobacteria. Especially preferred in this context are the families Pseudomonaceae, Peronosporaceae, Erysiphaceae and Pseudeurotiaceae. Preferably, the pathogen is a fungal pathogen, preferably a rust pathogen (i.e., a fungal pathogen of the order Pucciniales), preferably a fungal pathogen of the family Phacopsoraceae, more preferably a fungal pathogen of the genus *Phacopsora*, most preferably *Phakopsora pachyrhizi* and *Phakopsora meibomiae*, also known as soybean rust.

Especially preferred are organisms of these families which belong to the genera *Erysiphe, Monographella, Fusarium* or *Pseudomonas*. Very especially preferred are the species *Erysiphe cichoracearum, Monographella cucumerina,* and *Pseudomonas syringae*.

However, it is to be assumed that the methods according to the invention also bring about a resistance to further pathogens.

Especially preferred are Ascomycota such as, for example, *Fusarium oxysporum* (*fusarium* wilt on *tomato*), *Septoria nodorum* and *Septoria tritici* (glume blotch on wheat), *Botrytis cinerea* (noble rot on grapes, *tomato* and strawberries), Basidiomycetes such as, for example, *Puccinia graminis* (stem rust on wheat, barley, rye, oats), *Puccinia recondite* (leaf rust on wheat), *Puccinia disperse* (leaf rust on rye), *Puccinia hordei* (leaf rust on barley), *Puccinia coronata* (crown rust on oats).

Further preferred pathogens are pathogens causing stalk rot diseases, in particular *Fusarium* stalk rot, *Gibberella* stalk rot, *Diplodia* stalk rot, and Charcoal rot and pathogens causing anthracnose. Preferred pathogens causing *Fusarium* stalk rot are *Fusarium verticillioides, Fusarium* proliferatum or *Fusarium subglutinans*. A preferred pathogen causing *Gibberella* stalk rot is *Fusarium graminearum*. A preferred pathogen causing *Diplodia* stalk rot is *Diplodia maydis*. A preferred pathogen causing Charcoal rot is *Macrophomina phaseolina*. A preferred pathogen causing anthracnose is *Colletotrichum graminicola*.

In one embodiment, the method according to the invention leads to a resistance in *Arabidopsis thaliana* to the pathogens *Plectosphaerella cucumerina, Golovinomyces cichoracearum, Hyaloperonospora arabidopsidis* and *Pseudomonas syringae*. In another preferred embodiment of the invention method according to the invention leads to enhanced resistance in soybean plants to rust, preferably soybean rust.

In a preferred embodiment, a nucleic acid molecule according to the invention additionally comprises the untranslated sequence at the 3' and at the 5' terminus of the coding gene region: at least 500, preferably 200, especially preferably 100 nucleotides of the sequence upstream of the 5' terminus of the coding region and at least 100, preferably 50, especially preferably 20 nucleotides of the sequence downstream of the 3' terminus of the coding gene region.

Moreover, nucleic acid sequences which are especially preferred in the present invention are isolated nucleic acid sequences. An "isolated" nucleic acid molecule is separated from other nucleic acid molecules which are present in the natural origin of the nucleic acid. An "isolated" nucleic acid preferably contains no sequences which naturally flank the nucleic acid in the genomic DNA of the organism from which the nucleic acid originates (for example sequences which are located at the 5' and 3' termini of the nucleic acid; however, this does not affect the abovementioned embodiments comprising 5'- and 3'-UTR regions). In different embodiments, the isolated molecule may comprise for example less than approximately 5 kb, 4 kb, 3 kb, 2 kb, 1 kb, 0.5 kb or 0.1 kb of nucleotide sequences which naturally flank the nucleic acid molecule in the genomic DNA of the cell from which the nucleic acid originates. All the nucleic acid molecules mentioned here may be for example RNA, DNA or cDNA.

The nucleic acid molecules according to the invention can be isolated using standard techniques of molecular biology and the sequence information provided herein. Using comparative algorithms as they can be found for example on the NCBI homepage under http://www.ncbi.nlm.nih.gov, it is possible to identify for example a homologous sequence, or homologous, conserved sequence regions, at the DNA or amino acid level. Essential portions of this sequence or the entire homologous sequence can be used as hybridization probe using standard hybridization techniques (such as, for example, described in Sambrook et al. (1989), see above) for isolating further nucleic acid sequences which are useful in the method from other organisms by screening cDNA libraries and/or genomic libraries.

Moreover, a nucleic acid molecule according to the invention or a part thereof can be isolated by means of polymerase chain reaction, where oligonucleotide primers based on the sequences specified herein or parts thereof are used (for example, it is possible to isolate a nucleic acid molecule comprising the complete sequence or part thereof by means of polymerase chain reaction using oligonucleotide primers which have been generated on the basis of the very same sequence). For example, mRNA can be isolated from cells (for example by the guanidinium thiocyanate extraction method by Chirgwin et al., Biochemistry 18, 5294 (1979)) and cDNA prepared therefrom by means of reverse transcriptase (for example Moloney MLV reverse transcriptase, obtainable from Gibco/BRL, Bethesda, Md. or AMV reverse transcriptase, available from Seikagaku Amerika, Inc., St. Petersburg, Fla.). Synthetic oligonucleotide primers for the amplification by means of polymerase chain reaction can be generated on the basis of the sequences disclosed herein. A nucleic acid according to the invention can be amplified using cDNA or, alternatively, genomic DNA as template and suitable oligonucleotide primers by means of standard PCR amplification techniques. The nucleic acid amplified thus can be cloned into a suitable vector and characterized by means of DNA sequence analysis. Oligonucleotides which correspond to a nucleotide sequence coding for a protein according to the invention can be prepared by synthetic standard methods, for example using an automated DNA synthesizer.

The term "DNA fragment" as used in the present context is understood as meaning portions of the DNA which code for a protein according to the invention when this biological activity consists in mediating an increase in the pathogen resistance (preferably the resistance to fungal and/or bacterial pathogens).

The term "fragments of the protein" as used in the present context refers to portions of the protein whose biological activity comprises mediating an increase in the pathogen resistance (preferably the resistance to fungal and/or bacterial pathogens) in plants.

In an especially preferred embodiment, the invention relates to a YODA protein which has the activity shown in the examples. In one embodiment, a YODA protein is understood as meaning a protein with a homology to one of the amino acid sequences shown in SEQ ID No.: 2, 4, 6, 8, 10, 12, 14, 16, 18, 20, 22, 24, 26, 28, 30, 32, 34, 36, 38, 42, 44, 46, 48, 69 or 72 or in the figures, for example a YODA polypeptide from *Arabidopsis thaliana* (AtYODA) according to SEQ ID NO: 2, and/or from grapevine (*Vitis vinifera*) according to SEQ ID No.: 4, 6, and/or 8, and/or from Poplar (*Populus trichocarpa*) according to SEQ ID NO: 10, 12, and/or 14, and/or from rice (*Oryza sativa Japonica*) according to SEQ ID NO: 16, and/or 18 and/or from soybean (*Glycine max*) according to SEQ. ID NO: 20, 22, 24, 26, 28, and/or 30 and/or and/or from melon (*Cucumus melo* subsp. *melo*) according to SEQ ID NO: 32 and/or from *tomato* (*Solanum lycopersicum*) according to SEQ. ID NO: 34, 36, and/or 38, and/or from sorghum (*Sorghum bicolor*) according to SEQ ID NO: 40, and/or 42, and/or from corn (*Zea mays*) according to SEQ ID NO: 44 and/or from wheat (*Triticum aeastivum*) according to SEQ. ID NO: 46 and/or from barley (*Hordeum vulgare*) according to SEQ. ID NO: 48 or according to one of the consensus sequences according to SEQ ID NO: 69, or a functional fragment thereof. In one embodiment, the invention relates to functional equivalents of the abovementioned polypeptide sequences.

Preferably, the YODA protein has a sequence which has at least 50%, preferably at least 60%, at least 70%, at least 80%, at least 85%, at least 90%, at least 95%, at least 97%, at least 98% or at least 99%, identity with any of the sequence shown in SEQ ID No.: 2, 4, 6, 8, 10, 12, 14, 16, 18, 20, 22, 24, 26, 28, 30, 32, 34, 36, 38, 40, 42, 44, 46, 48, 69 or 72; preferably the polypeptide has the same or a similar biological function as a polypeptide as shown in SEQ ID NO: 2, 4, 6, 8, 10, 12, 14, 16, 18, 20, 22, 24, 26, 28, 30, 32, 34, 36, 38, 40, 42, 44, 46, 48, 69 or 72; preferably the expression of the YODA polypeptide confers enhanced fungal resistance.

"Polypeptide quantity" means for example the number of molecules, or moles, of YODA polypeptide molecules in an organism, a tissue, a cell or a cell compartment. "Increasing" the polypeptide quantity means the molar increase in the number of the respective polypeptides in an organism, a tissue, a cell or a cell compartment-for example by one of the methods described here in below-in comparison with a suitable control, for example the wild type (control plant) of the same genus and species to which this method has not been applied, under otherwise identical conditions (such as, for example, culture conditions, age of the plants and the like). The increase in this context amounts to at least 5%, preferably at least 10% or at least 20%, especially preferably at least 40% or 60%, very especially preferably at least 70% or 80%, most preferably at least 90%, 95% or 99%, in particular 100%, particularly preferably more than 100%, preferably more than 150%, 200% or 300%.

Identity between two nucleic acid sequences is understood as meaning the identity of the nucleic acid sequence over in each case the entire sequence length, which is calculated by comparison with the aid of the program algorithm GAP (Wisconsin Package Version 10.0, University of Wisconsin, Genetics Computer Group (GCG), Madison, USA; Altschul et al., Nucleic Acids Res. 25, 3389 (1997)), setting the following parameters:
Gap weight: 50 Length weight: 3
Average match: 10 Average mismatch: 0

For example, a sequence which has at least 80% identity with the sequence SEQ ID NO: 1 at the nucleic acid level is understood as meaning a sequence which, upon comparison with the sequence SEQ ID NO 1 by the above program algorithm with the above parameter set, has at least 80% identity.

Identity between two polypeptides is understood as meaning the identity of the amino acid sequence over in each case the entire sequence length which is calculated by comparison with the aid of the program algorithm GAP (Wisconsin Package Version 10.0, University of Wisconsin, Genetics Computer Group (GCG), Madison, USA), setting the following parameters:
Gap weight: 8 Length weight: 2
Average match: 2.912 Average mismatch: −2.003

For example, a sequence which has at least 80% identity at the polypeptide level with the sequence SEQ ID NO: 2 is understood as meaning a sequence which, upon comparison with the sequence SEQ ID NO 2 by the above program algorithm with the above parameter set, has at least 80% identity.

Removing part of the N-terminal negative regulatory domain of YODA (CA:YODA) was proposed to allow YODA to become constitutively active (Lukowitz, W., et al., Cell 116: 109-19 (2004)). This end terminal region characterizes the YODA M3PK clade and defines the putative orthologue sequences that are suitable for a functional deletion for constitutive activation as shown in FIGS. 1 and 2. In a preferred embodiment, the sequence which codes for the polypeptide according to the invention has a deletion in the N-terminal negative regulatory domain. Preferably, the N-terminus of the YODA protein is deleted as indicated in FIG. 1 (i.e., CA:YODA deletion). Preferably, the N-terminal amino acids 184-322 of the AtYODA protein are deleted. Preferably, the N-terminal amino acids of YODA proteins derived from plant species other than *Arabidopsis* corresponding to the amino acids 184-322 of the AtYODA protein are deleted. Preferably, 5, 10, 15, 20, 25, 30, 35, 40, 45, 50, 55, 60, 65, 70, 75, 80, 85, 90, 95, 100, 105, 110, 115, 120, 125, 130, 135, or 138 amino acids, preferably consecutive amino acids, preferably counted from the N-terminus (i.e., AtYODA amino acid residue 184) or the C-terminus (i.e., AtYODA amino acid residue 322)) corresponding to the amino acids 184-322 of the AtYODA protein are deleted. The invention is also directed to respective nucleic acid molecules encoding such N-terminal deleted proteins and the use of these nucleic acids for conferring enhanced fungal resistance, preferably, in a plant.

In accordance with the invention, the activity of the abovementioned polypeptides is introduced into, and expressed in, a plant or a part of a plant, preferably in/into the epidermal cells and/or mesophyll cells of a plant, as illustrated hereinabove, or the expression of the endogenous polypeptide is increased analogously.

In one embodiment, the activity of a YODA protein is increased in lemma, palea and/or glume.

Within the context of the invention, "introduction" or "to introduce" comprises all methods which are suitable for directly or indirectly introducing, into a plant or a cell, compartment, tissue, organ or seed, a nucleic acid sequence according to the invention, or generating it therein. The introduction may lead to a transient or to a stable presence of a nucleic acid sequence according to the invention.

"Introduction" or "to introduce" comprises, for example, methods such as transfection, transduction or transformation.

One embodiment is a recombinant DNA expression cassette, herewith the expression cassette according to the invention, comprising a nucleic acid molecule according to the invention.

One embodiment is the recombinant DNA expression cassette according to the invention, wherein said nucleic acid sequence is in operable linkage with a promoter which is functional in plants.

One embodiment is a recombinant vector comprising the expression cassette according to the invention.

One embodiment is a cell comprising the nucleic acid molecule according to the invention, a DNA expression cassette according to the invention, or a vector comprising said expression cassette.

One embodiment is a transgenic nonhuman organism or a plant, comprising a nucleic acid molecule according to the invention, a DNA expression cassette according to the invention, or a vector comprising said expression cassette, or comprising a cell comprising said nucleic acid molecule, said expression cassette, or said vector. Preferably, said organism or plant is selected from the group consisting of soybean, potato, cotton, rape, oilseed rape, canola, sunflower, alfalfa, clover, banana, blackberry, blueberry, strawberry, raspberry, cantaloupe, carrot, cauliflower, coffee, cucumber, eggplant, grape, honeydew, lettuce, mango, melon, onion, papaya, pepper, pineapple, pumpkin, spinach, squash, tobacco, *tomato*, tomatillo, watermelon, apple, peach, pear, cherry, plum, broccoli, cabbage, cauliflower, Brussels sprouts, kohlrabi, currant, avocado, orange, lemon, grapefruit, tangerine, artichoke, cherry, walnut, peanut, endive, leek, arrowroot, beet, cassava, turnip, radish, yam, sweet potato; pea, bean, sugarcane, turfgrass, *Miscanthus*, switchgrass, wheat, maize, sweet corn, rice, millet, sorghum, barley, and rye.

One embodiment is a method for generating a transgenic plant which is resistant to oomycetes and/or fungi and/or bacterial pathogens, comprising using the nucleic acid molecule according to the invention, a DNA expression cassette according to the invention, a vector comprising said expression cassette, or a cell comprising said nucleic acid molecule, said expression cassette, or said vector.

One embodiment is a crop, propagation material or composition comprising the nucleic acid molecule according to the invention, a DNA expression cassette according to the invention, or a vector comprising said expression cassette, or comprising a cell comprising said nucleic acid molecule, said expression cassette, or said vector.

One embodiment is the use of any of the nucleic acid molecule according to the invention, the DNA expression cassette according to the invention, or a vector comprising said expression cassette, a plant part, or plant cell to provide a fungal resistant plant, plant part, or plant cell.

The introduction of an expression cassette according to the invention into an organism or cells, tissue, organs, parts or seeds thereof (preferably into plants or plant cells, tissue, organs, parts or seeds) can advantageously be carried out using vectors which comprise the expression cassettes. The expression cassette can be introduced into the vector (for example a plasmid) via a suitable restriction cleavage site. The plasmid obtained is first introduced into E. coli cells. Correctly transformed E. coli cells are selected, cultured, and the recombinant plasmid is obtained using methods with which the skilled worker is familiar. Restriction analysis and sequencing may be used for verifying the cloning step.

The vectors may take the form of, for example, plasmids, cosmids, phages, viruses or else agrobacteria. In an advantageous embodiment, the expression cassette is introduced by means of plasmid vectors. Preferred vectors are those which make possible a stable integration of the expression cassette into the host genome.

One embodiment is the harvestable part of a transgenic nonhuman organism or plant, herewith harvestable part according to the invention, comprising a nucleic acid molecule according to the invention, a DNA expression cassette according to the invention, or a vector comprising said expression cassette, or comprising a cell comprising said nucleic acid molecule, said expression cassette, or said vector, wherein the harvestable part is preferably a transgenic seed of the transgenic plant.

One embodiment is the product derived from a nonhuman organism comprising a nucleic acid molecule according to the invention, a DNA expression cassette according to the invention, or a vector comprising said expression cassette, or comprising a cell comprising said nucleic acid molecule, said expression cassette, or said vector, or plant which is resistant to oomycetes and/or fungi and/or bacterial pathogens, obtained by the method comprising using the nucleic acid molecule according to the invention, a DNA expression cassette according to the invention, a vector comprising said expression cassette, or a cell comprising said nucleic acid molecule, said expression cassette, or said vector, from a plant producible by the method according to the invention or from the harvestable part according to the invention.

One embodiment is a method for the production of a product, herewith the method for the production of a product according to the invention, comprising
a) growing a plant comprising the nucleic acid molecule according to the invention, a DNA expression cassette according to the invention, or a vector comprising said expression cassette, or comprising a cell comprising said nucleic acid molecule, said expression cassette, or said vector or obtainable by the method of the invention.
b) producing said product from or by the plant and/or part, preferably seeds, of the plant.

A particular embodiment is the method for the production of a product according to the invention, which comprises:
a) growing a plant comprising the nucleic acid molecule according to the invention, a DNA expression cassette according to the invention, or a vector comprising said expression cassette, or comprising a cell comprising said nucleic acid molecule, said expression cassette, or said vector or obtainable by the method according to the invention and removing the harvestable parts according to the invention; and
b) producing said product from or by the harvestable parts of the plant.

One embodiment is the method for the production of a product according to the invention, wherein the product is meal or oil, preferably, soybean meal or soybean oil.

"Epitope" is understood as meaning the regions of an antigen which determine the specificity of the antibodies (the antigenic determinant). Accordingly, an epitope is the portion of an antigen which actually comes into contact with the antibody.

Such antigenic determinants are those regions of an antigen to which the T-cell receptors react and, as a consequence, produce antibodies which specifically bind the antigenic determinant/epitope of an antigen. Accordingly, antigens, or their epitopes, are capable of inducing the immune response of an organism with the consequence of the formation of specific antibodies which are directed against the epitope. Epitopes consist for example of linear sequences of amino acids in the primary structure of proteins, or of complex secondary or tertiary protein structures. A hapten is understood as meaning an epitope which is dissociated from the context of the antigen environment. Although haptens have by definition an antibody directed against them, haptens are, under certain circumstances, not capable of inducing an immune response in an organism, for example after an injection. To this end, haptens are coupled with carrier molecules. An example which may be mentioned is dinitrophenol (DNP), which, after coupling to BSA (bovine serum albumin), has been used for generating antibodies which are directed against DNP (Bohn, A., Konig, W., Immunology 47 (2), 297 (1982)).

Haptens are therefore in particular substances (frequently low-molecular weight substances or small substances) which, while they themselves do not trigger immune response, will indeed trigger such a response when coupled to a large molecular carrier.

The antibodies generated thus also include those which can bind to the hapten alone.

In one embodiment, the present invention relates to an antibody against a polypeptide characterized herein, in particular to a monoclonal antibody which binds a polypeptide which comprises an amino acid sequence or consists thereof, as shown in the sequences shown in SEQ ID No.: 2, 4, 6, 8, 10, 12, 14, 16, 18, 20, 22, 24, 26, 28, 30, 32, 34, 36, 38, 40, 42, 44, 46, 48, 69 or 72.

Antibodies within the scope of the present invention can be used for identifying and isolating polypeptides disclosed in accordance with the invention from organisms, preferably plants, especially preferably monocotyledonous plants, or further preferably dicotyledonous plants. The antibodies can either be monoclonal, polyclonal or synthetic in nature or else consist of antibody fragments such as Fab, Fv or scFv fragments, which are formed by proteolytic degradation. "Single chain" Fv (scFv) fragments are single-chain fragments which, linked via a flexible linker sequence, only comprise the variable regions of the heavy and light antibody chains. Such scFv fragments can also be produced as recombinant antibody derivatives. A presentation of such antibody fragments on the surface of filamentous phages makes possible the direct selection, from combinatory phage libraries, of scFv molecules which bind with high affinity.

Monoclonal antibodies can be obtained in accordance with the method described by Köhler and Milstein (Nature 256 (1975), 495).

Screening cDNA libraries or genomic libraries of other organisms, preferably of the plant species mentioned further below, which are suitable as transformation hosts, using the nucleic acid sequences described in SEQ ID No: 1, 3, 5, 7, 9, 11, 13, 15, 17, 19, 21, 23, 25, 27, 29, 31, 33, 35, 37, 39, 41, 43, 45, 47, 70 or 71 or parts of the same as probe is also a method known to the skilled worker for identifying homologs in other species. In this context, the probes derived from the nucleic acid sequence as shown in SEQ ID No: 1, 3, 5, 7, 9, 11, 13, 15, 17, 19, 21, 23, 25, 27, 29, 31, 33, 35, 37, 39, 41, 43, 45, 47, 70 or 71 have a length of at least 20 bp, preferably at least 50 bp, especially preferably at least 100 bp, very especially preferably at least 200 bp, most preferably at least 400 bp. The probe can also be one or more kilobases in length, for example 1 kb, 1.5 kb or 3 kb. A DNA strand which is complementary to the sequences described in SEQ ID No: 1, 3, 5, 7, 9, 11, 13, 15, 17, 19, 21, 23, 25, 27, 29, 31, 33, 35, 37, 39, 41, 43, 45, 47, 70 or 71 or a fragment of same strand with a length of between 20 bp and several kilobases may also be employed for screening the libraries.

In the method according to the invention, those DNA molecules which hybridize under standard conditions with the nucleic acid molecules described by SEQ ID No: 1, 3, 5, 7, 9, 11, 13, 15, 17, 19, 21, 23, 25, 27, 29, 31, 33, 35, 37, 39, 41, 43, 45, 47, 70 or 71 and which code for YODA proteins, with the nucleic acid molecules which are complementary to the above or with parts of the above and which, as complete sequences, code for polypeptides which essentially have identical properties, preferred functional properties, to the polypeptides described in SEQ ID No: 2, 4, 6, 8, 10, 12, 14, 16, 18, 20, 22, 24, 26, 28, 30, 32, 34, 36, 38, 40, 42, 44, 46, 48, 69 or 72 may also be used.

"Standard hybridization conditions" is to be understood in the broad sense and means, depending on the application, stringent or else less stringent hybridization conditions. Such hybridization conditions are described, inter alia, in Sambrook J, Fritsch E F, Maniatis T et al., in Molecular Cloning (A Laboratory Manual), 2nd edition, Cold Spring Harbor Laboratory Press, 1989, pages 9.31-9.57) or in Current Protocols in Molecular Biology, John Wiley & Sons, N.Y. (1989), 6.3.1-6.3.6.

The skilled worker, based on his technical knowledge, would choose hybridization conditions which allow him to differentiate between specific and unspecific hybridizations.

For example, the conditions during the wash step can be selected from among low-stringency conditions (with approximately 2*SSC at 50[deg.] C.) and high-stringency conditions (with approximately 0.2*SSC at 50[deg.] C., preferably at 65[deg.] C.) (20*SSC: 0.3M sodium citrate, 3M NaCl, pH 7.0). Moreover, the temperature during the wash step can be raised from low-stringency conditions at room temperature, approximately 22[deg.] C., to higher-stringency conditions at approximately 65[deg.] C. The two parameters, salt concentration and temperature, can be varied simultaneously or else singly, keeping in each case the other parameter constant. During the hybridization, it is also possible to employ denaturant agents such as, for example, formamide or SDS. In the presence of 50% formamide, the hybridization is preferably carried out at 42[deg.] C. Some examples of preferred conditions for hybridization and wash step are detailed hereinbelow:
(1) Hybridization conditions can be selected for example among the following conditions:
a) 4*SSC at 65[deg.] C.,
b) 6*SSC at 45[deg.] C.,
c) 6*SSC, 100 [mu]g/ml denatured fragmented fish sperm DNA at 68[deg.] C.,
d) 6*SSC, 0.5% SDS, 100 [mu]g/ml denatured salmon sperm DNA at 68[deg.] C.,
e) 6*SSC, 0.5% SDS, 100 [mu]g/ml denatured fragmented salmon sperm DNA, 50% formamide at 42[deg.] C.,
f) 50% formamide, 4*SSC at 42[deg.] C.,
g) 50% (vol/vol) formamide, 0.1% bovine serum albumin, 0.1% Ficoll, 0.1% polyvinylpyrrolidone, 50 mM sodium phosphate buffer pH 6.5, 750 mM NaCl, 75 mM sodium citrate at 42[deg.] C.,
h) 2* or 4*SSC at 50[deg.] C. (low-stringency condition),
i) 30 to 40% formamide, 2* or 4*SSC at 42[deg.] C. (low-stringency condition), or
j) 500 mN sodium phosphate buffer pH 7.2, 7% SDS (g/V), 1 mM EDTA, 10 [mu]g/ml single stranded DNA, 0.5% BSA (g/V) (Church and Gilbert, Proc. Natl. Acad. Sci. U.S.A. 81:1991 (1984))
(2) Wash steps can be selected for example among the following conditions:
a) 0.015 M NaCl/0.0015 M sodium citrate/0.1% SDS at 50[deg.] C.,
b) 0.1*SSC at 65[deg.] C.,
c) 0.1*SSC, 0.5% SDS at 68[deg.] C.,
d) 0.1*SSC, 0.5% SDS, 50% formamide at 42[deg.] C.,
e) 0.2*SSC, 0.1% SDS at 42[deg.] C., or
f) 2*SSC at 65[deg.] C. (low-stringency condition).

In one embodiment, the hybridization conditions are selected as follows:

A hybridization buffer comprising formamide, NaCl and PEG 6000 is chosen. The presence of formamide in the hybridization buffer destabilizes double-strand nucleic acid molecules, whereby the hybridization temperature can be lowered to 42[deg.] C. without thereby reducing the stringency. The use of salt in the hybridization buffer increases the renaturation rate of a duplex DNA, in other words the hybridization efficiency. Although PEG increases the viscosity of the solution, which has a negative effect on the renaturation rates, the presence of the polymer in the solution increases the concentration of the probe in the remaining medium, which increases the hybridization rate. The composition of the buffer is Hybridization Buffer
250 mM sodium phosphate buffer pH 7.2
1 mM EDTA
7% SDS (g/v)
250 mM NaCl
10 [mu]g/ml ssDNA
5% polyethylene glycol (PEG) 6000
40% formamide The hybridizations are carried out for approximately 12 hours at 42[deg.] C., for example overnight. The filters are then washed 3* with 2*SSC+0.1% SDS for in each case approximately 10 minutes.

"Gene expression" and "expression" are to be understood as being synonymous and mean the realization of the information which is stored in a nucleic acid molecule.

The "modification" according to the invention of nucleotide sequences or amino acid sequences preferably comprises mutating them, or mutations. For the purposes of the present invention, "mutations" means the modification of the nucleic acid sequence of a gene variant in a plasmid or in the genome of an organism. Mutations can be generated for example as the consequence of errors during replication, or by mutagens. The spontaneous mutation rate in the cell genome of organisms is very low; however, the skilled person in the art knows a multiplicity of biological, chemical or physical mutagens and methods of mutating nucleotide sequences in a random or targeted manner, and therefore ultimately potentially also for modifying the amino acid sequences which they encode.

Mutations comprise substitutions, additions, deletions of one or more nucleic acid residues. Substitutions are understood as meaning the exchange of individual nucleic acid bases, where one distinguishes between transitions (substitution of a purine base for a purine base, and of a pyrimidine base for a pyrimidine base) and transversions (substitution of a purine base for a pyrimidine base, or vice versa).

Addition or insertion is understood as meaning the incorporation of additional nucleic acid residues in the DNA, which may result in reading-frame shifts. In the case of such reading frame shifts, one distinguishes between in-frame insertions/additions and out-of-frame insertions. In the case of the in-frame insertions/additions, the reading frame is retained, and a polypeptide which is lengthened by the number of the amino acids encoded by the inserted nucleic acids is formed. In the case of out-of-frame insertions/additions, the original reading frame is lost, and the formation of a complete and functional polypeptide is in many cases no longer possible, which of course depends on the site of the mutation.

Deletions describe the loss of one or more base pairs, which likewise leads to in-frame or out-of-frame reading-frame shifts and the consequences which this entails with regard to the formation of an intact protein.

The skilled worker is familiar with the mutagenic agents (mutagens) which can be used for generating random or targeted mutations and both the methods and techniques which may be employed. Such methods and mutagens are described for example in van Harten A. M. ("Mutation breeding: theory and practical applications", Cambridge University Press, Cambridge, UK (1998)), Friedberg E., Walker G., Siede W. ("DNA Repair and Mutagenesis", Blackwell Publishing (1995)), or Sankaranarayanan K., Gentile J. M., Ferguson L. R. ("Protocols in Mutagenesis", Elsevier Health Sciences (2000)).

Customary methods and processes of molecular biology such as, for example, the in-vitro mutagenesis kit, "LA PCR in vitro Mutagenesis Kit" (Takara Shuzo, Kyoto), or PCR mutagenesis using suitable primers, may be employed for introducing targeted mutations.

As already mentioned above, a multiplicity of chemical, physical and biological mutagens exists.

Those mentioned herein below are given by way of example, but not by limitation.

Chemical mutagens may be divided according to their mechanism of action. Thus, there are base analogs (for example 5-bromouracil, 2-aminopurine), mono- and bifunctional alkylating agents (for example monofunctional agents such as ethyl methyl sulfonate, dimethyl sulfate, or bifunctional agents such as dichloroethyl sulfite, mitomycin, nitrosoguanidine-dialkyl nitrosamine, N-nitrosoguanidine derivatives) or intercalating substances (for example acridine, ethidium bromide).

Examples of physical mutagens are ionizing radiations. Ionizing radiations are electromagnetic waves or corpuscular radiations which are capable of ionizing molecules, i.e. of removing electrons from them. The ions which remain are in most cases highly reactive so that they, in the event that they are formed in live tissue, are capable of inflicting great damage for example to the DNA and thereby inducing mutations (at low intensity). Examples of ionizing radiations are gamma radiation (photon energy of approximately one mega electron volt MeV), X-ray radiation (photon energy of several or many kilo electron volt keV) or else ultraviolet light (UV light, photon energy of over 3.1 eV). UV light causes the formation of dimers between bases, thymidine dimers are most common, and these give rise to mutations.

To the traditional generation of mutants by treating the seeds with mutagenizing agents such as, for example, ethyl methyl sulfonate (EMS) (Birchler, J. A. and Schwartz, D., Biochem. Genet. 17 (11-12), 1173 (1979); Hoffmann, G. R., Mutat. Res. 75 (1), 63 (1980)) or ionizing radiation there has now been added the use of biological mutagens, for example transposons (for example Tn5, Tn903, Tn916, Tn1000, May B. P. et al., Proc. Natl. Acad. Sci USA. 100 (20), 11541 (2003)) or molecular-biological methods such as the mutagenesis by T-DNA insertion (Feldman, K. A., Plant Journal 1, 71 (1991), Koncz, C., et al., Plant Mol. Biol. 20: 963-76 (1992))

To generate mutated gene variants, it is preferred to use chemical or biological mutagens. Among the chemical agents, it is especially preferred to generate mutants by using EMS (ethyl methyl sulfonate) mutagenesis. Among the generation of mutants using biological mutagens, the T-DNA mutagenesis or the transposon mutagenesis may be mentioned by preference.

Thus, for example, it is also possible to employ those polypeptides in the method according to the invention which are obtained as the result of a mutation of a nucleotide sequence coding for a polypeptide according to the invention, for example according to SEQ ID No: 2, 4, 6, 8, 10, 12, 14, 16, 18, 20, 22, 24, 26, 28, 30, 32, 34, 36, 38, 42, 44, 46, 48, 69 or 72.

The term "recombinant" means for example with regard to a nucleic acid sequence, an expression cassette or a vector comprising said nucleic acid sequence or an organism transformed with said nucleic acid sequence, expression cassette or vector, all those constructs or organisms which are the result of recombinant methods and in which either (a) the YODA protein nucleic acid sequence or
(b) a genetic control sequence, for example a promoter, which is operably linked with the YODA protein nucleic acid sequence, or
(c) (a) and (b) are not located in their natural genetic environment or have been modified by recombinant methods, it being possible for the modification to be, for example, a substitution, addition, deletion, or insertion of one or more nucleotide residue(s).

Natural genetic environment means the natural chromosomal locus in the organism of origin, or the presence in a genomic library. In the case of a genomic library, the natural genetic environment of the nucleic acid sequence is preferably retained at least in part. The environment flanks the nucleic acid sequence at least on one side and has a sequence length of at least 50 bp, preferably at least 500 bp, especially preferably at least 1000 bp, very especially preferably at least 5000 bp. A naturally occurring expression cassette-for example the naturally occurring combination of the YODA protein promoter with the corresponding YODA protein gene-becomes a recombinant expression cassette when the latter is modified by means of non-natural, synthetic ("artificial") methods such as, for example, mutagenization. Suitable methods have been described (U.S. Pat. No. 5,565,350; WO 00/15815).

As used herein, the term "transgenic" refers to an organism, e.g., a plant, plant cell, callus, plant tissue, or plant part that exogenously contains the nucleic acid, recombinant construct, vector or expression cassette described herein or a part thereof which is preferably introduced by non-essentially biological processes, preferably by Agrobacteria transformation. The recombinant construct or a part thereof is stably integrated into a chromosome, so that it is passed on to successive generations by clonal propagation, vegetative propagation or sexual propagation.

Preferred successive generations are transgenic too. Essentially biological processes may be crossing of plants and/or natural recombination.

A transgenic plant, plant cell or tissue for the purposes of the invention is thus understood as meaning that an exogenous YODA nucleic acid, recombinant construct, vector or expression cassette including one or more YODA nucleic acids is integrated into the genome by means of gene technology.

The term "exogenous" nucleic acid refers to a nucleic acid that has been introduced in a plant by means of gene technology. An "exogenous" nucleic acid can either not occur in a plant in its natural form, be different from the nucleic acid in question as found in a plant in its natural form, or can be identical to a nucleic acid found in a plant in its natural form, but integrated not within its natural genetic environment. The corresponding meaning of "exogenous" is applied in the context of protein expression. For example, a transgenic plant containing a transgene, i.e., an exogenous nucleic acid, may, when compared to the expression of the endogenous gene, encounter a substantial increase of the expression of the respective gene or protein in total. A transgenic plant according to the present invention includes an exogenous YODA nucleic acid integrated at any genetic loci and optionally the plant may also include the endogenous gene within the natural genetic background.

Thus, method for increasing fungal resistance, preferably resistance to Phacopsoracea, for example soy bean rust, in a plant, plant part, or plant cell, by increasing the expression of a YODA protein or a functional fragment thereof, or a splice variant thereof, wherein the YODA protein is encoded by (i) an exogenous nucleic acid having at least 50% identity, at least 60% identity, preferably at least 70% sequence identity, at least 80%, at least 90%, at least 95%, at least 98%, at least 99% sequence identity, or even 100% sequence identity with SEQ ID NO: 1, 3, 5, 7, 9, 11, 13, 15, 17, 19, 21, 23, 25, 27, 29, 31, 33, 35, 37, 39, 41, 43, 45, 47, 70 or 71, or a splice variant thereof;

(ii) an exogenous nucleic acid encoding a protein having at least 50% identity, at least 60%, preferably at least 70% sequence identity, at least 80%, at least 90%, at least 95%, at least 98%, at least 99% sequence identity, or even 100% sequence identity with SEQ ID NO: 2, 4, 6, 8, 10, 12, 14, 16, 18, 20, 22, 24, 26, 28, 30, 32, 34, 36, 38, 40, 42, 44, 46, 48, 69 or 72, a functional fragment thereof; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a YODA protein; preferably wherein the nucleic acid molecule codes for a polypeptide which has essentially identical properties to the polypeptide described in SEQ ID NO: 2, 4, 6, 8, 10, 12, 14, 16, 18, 20, 22, 24, 26, 28, 30, 32, 34, 36, 38, 40, 42, 44, 46, 48, 69 or 72; preferably the encoded protein confers enhanced fungal resistance relative to control plants; and/or by (iv) an exogenous nucleic acid encoding the same YODA protein as any of the nucleic acids of (i) to (iii) above, but differing from the nucleic acids of (i) to (iii) above due to the degeneracy of the genetic code is a further embodiment of the invention.

The increase according to the invention of the pathogen resistance can also be obtained by manipulating the expression of the plant's own protein, i.e. the endogenous protein, which corresponds to the protein according to the invention, or of an endogenous nucleotide sequence, which constitutes a sequence according to the invention, and which may also comprise the 5'- and/or 3'-UTR region. It is, then, an endogenous nucleotide or peptide sequence which mediates an increase of the pathogen resistance or it is an amino acid sequence according to the invention which codes for such a protein. This manipulation can be achieved by any modification of the sequence, preferably a mutation, but also for example by a modification of the promoter DNA sequence of the protein-encoding gene. Such a modification, which results in a modified, preferably increased, expression rate of the endogenous gene according to the invention, can be effected by means of deletion or insertion of DNA sequences. As a rule, a modification of the 5'-UTR region in total and/or of the promoter sequence of endogenous genes according to the invention will lead to a modification of the expressed amount of the gene and/or the function of the expressed gene or gene product, and therefore preferably also to a modification of the activity which can be detected in the cell or in the plants. The modification of the 5'-UTR region in total and/or of the promoter sequence of the endogenous gene according to the invention may also lead to a modification of the amount of, and/or the function of, a protein according to the invention in the cell.

Another possibility of increasing the activity and the content of the endogenous protein according to the invention is to up-regulate transcription factors which are involved in the transcription of the corresponding endogenous gene, for example by means of overexpression. The means for overexpressing transcription factors are known to the skilled worker and are also disclosed for proteins according to the invention within the context of the present invention.

Moreover, an increased expression of the endogenous gene according to the invention can be achieved by a regulator protein, which is not present in the untransformed organism, interacting with the promoter of these genes. Such a regulator may take the form of a chimeric protein which consists of a DNA binding domain and a transcription activator domain, as described for example in WO 96/06166.

The generation of a transformed organism (or of a transformed cell) requires the introduction of the relevant DNA molecules into the relevant host cell, and subsequently the formation of the corresponding RNAs and proteins as the result of gene expression.

A multiplicity of methods (Keown et al., Methods in Enzymology 185, 527(1990)) is available for this procedure, which is referred to as transformation (or transduction or transfection). Thus, the DNA or RNA can be introduced for example directly by means of microinjection or by bombardment with DNA-coated microparticles. Also, it is possible to chemically permeabilize the cell, for example using polyethylene glycol, so that the DNA can reach the cell by diffusion. The DNA can also be introduced into the cell by means of protoplast fusion with other DNA-comprising units such as minicells, cells, lysosomes or liposomes. A further suitable method of introducing DNA is electroporation, where the cells are reversibly permeabilized by means of an electrical pulse. Such methods have been described (for example in Bilang et al., Gene 100, 247 (1991); Scheid et al., Mol. Gen. Genet. 228, 104 (1991); Guerche et al., Plant Science 52, 111 (1987); Neuhause et al., Theor. Appl. Genet. 75, 30 (1987); Klein et al., Nature 327, 70(1987); Howell et al., Science 208, 1265 (1980); Horsch et al., Science 227, 1229 (1985); DeBlock et al., Plant Physiology 91, 694 (1989); "Methods for Plant Molecular Biology" (Weissbach and Weissbach, eds.) Academic Press Inc. (1988); and "Methods in Plant Molecular Biology" (Schuler and Zielinski, eds.) Academic Press Inc. (1989)).

In plants, the above-described methods for the transformation and regeneration of plants from plant tissue or plant cells are exploited for the purposes of transient or stable transformation. Suitable methods are mainly protoplast transformation by means of polyethylene-glycol-induced DNA uptake, the biolistic method with the gene gun, known as the particle bombardment method, electroporation, the incubation of dry embryos in DNA-comprising solution, and microinjection.

Besides these "direct" transformation techniques, transformation can also be effected by bacterial infection by means of *Agrobacterium tumefaciens* or *Agrobacterium rhizogenes*. The methods are described for example in Horsch et al. Science 225, 1229 (1985).

If agrobacteria are used, the expression cassette is to be integrated into specific plasmids, which may either be a shuttle or intermediate vector or a binary vector. If a Ti or Ri plasmid is used for the transformation, at least the right border, but in most cases both the right and the left border, of the Ti or Ri plasmid T-DNA as flanking region is linked with the expression cassette to be introduced.

It is preferred to use binary vectors. Binary vectors are capable of replicating both in *E. coli* and in *agrobacterium*. As a rule, they comprise a selection marker gene and a linker or polylinker flanked by the right and left T-DNA border sequence. They can be transformed directly into *agrobacterium* (Holsters et al., Mol. Gen. Genet. 163, 181 (1978)). The selection marker gene, for example the nptII gene, which mediates resistance to kanamycin, permits transformed agrobacteria to be selected. The *agrobacterium* which, in the present case, acts as the host organism should already comprise a helper Ti plasmid with the vir region, which is required for transferring the T-DNA to the plant cell. An *agrobacterium* thus transformed can be used for transforming plant cells. The use of T-DNA for the transformation of plant cells has been studied and described in great detail (EP 120 516; Hoekema, in "The Binary Plant Vector System", Offsetdrukkerij Kanters B. V., Alblasserdam, Chapter V; An et al. EMBO J. 4, 277 (1985)). Various binary vectors are known and in some cases commercially available, such as, for example, pB1101.2 or pBIN19 (Clontech Laboratories, Inc. USA).

In the event that DNA or RNA is injected or electroporated into plant cells, the plasmid used need not meet particular requirements. Simple plasmids such as those from the pUC series may be used. If intact plants are to be regenerated from the transformed cells, it is necessary for an additional selection marker gene to be located on the plasmid.

Stably transformed cells, i.e. those which comprise the introduced DNA integrated into the DNA of the host cell, can be distinguished from untransformed cells when a selection marker is constituent of the introduced DNA (McCormick et al, Plant Cell Reports 5, 81 (1986)). For example, any gene which is capable of mediating a resistance to antibiotics or herbicides (such as kanamycin, G 418, bleomycin, hygromycin or phosphinothricin) may act as a marker. Transformed cells which express such a marker gene are capable of surviving in the presence of concentrations of a suitable antibiotic or herbicide which destroy an untransformed wildtype. Examples include the bar gene, which mediates resistance to the herbicide phosphinothricin (Rathore et al., Plant Mol. Biol. 21 (5), 871 (1993)), the nptII gene, which mediates resistance to kanamycin, the hpt gene, which mediates resistance to hygromycin, or the EPSP gene, which mediates resistance to the herbicide glyphosate. The resulting plants can be bred and hybridized in the customary manner. Two or more generations should be cultivated in order to ensure that the genomic integration is stable and hereditary.

The above mentioned methods are described for example in Jones et al. ("Techniques for Gene Transfer", in "Transgenic Plants", Vol. 1, Engineering and Utilization, edited by Kung S. D. and Wu R., Academic Press, p. 128-143 (1993), and in Potrykus, Annu. Rev. Plant Physiol. Plant Molec. Biol. 42, 205 (1991)). It is preferred to clone the construct to be expressed into a vector which is suitable for transforming *Agrobacterium tumefaciens*, for example into pBin 19 (Bevan et al., Nucl. Acids Res. 12, 8711 (1984)).

When a transformed plant cell has been generated, an intact plant can be obtained using methods known to the skilled worker. An example of a starting material used here are callus cultures. The formation of shoot and root from this as yet undifferentiated cell biomass can be induced in a known manner. The plantlets obtained can be planted out and bred.

A person skilled in the art also knows methods for regenerating plant parts and intact plants from plant cells. For example, methods described by Fennell et al., Plant Cell Rep, 11, 567 (1992); Stoeger et al., Plant Cell Rep. 14, 273 (1995); Jahne et al., Theor. Appl. Genet. 89, 525 (1994), are used for this purpose.

The present invention furthermore relates to a recombinant nucleic acid molecule comprising the following elements in 5'-3' orientation: regulatory sequences of a promoter which is active in plant cells, a DNA sequence according to the invention in operative linkage therewith, if appropriate, regulatory sequences which, in the plant cell, may act as transcription, termination and/or polyadenylation signals in operable linkage therewith.

In said recombinant expression constructs/expression cassettes, a nucleic acid molecule whose expression (transcription and, if appropriate, translation) generates a YODA protein is preferably in operable linkage with at least one genetic control element (for example a promoter) which ensures expression in plants. If the expression construct is to be introduced directly into the plant and the YODA protein generated therein in plants, then plant-specific genetic control elements (for example promoters) are preferred. However, the YODA protein can also be generated in other organisms or in vitro and then introduced into the plant. In this context, preference is given to all prokaryotic or eukaryotic genetic control elements (for example promoters) which permit the expression in the plant selected in each case for the production.

Preferably, the invention comprises a recombinant vector construct or expression construct/cassettte comprising:

(i) a nucleic acid having at least 50% identity, at least 60% identity, preferably at least 70% sequence identity, at least 80%, at least 90%, at least 95%, at least 98%, at least 99% sequence identity, or even 100% sequence identity with SEQ ID NO: 1, 3, 5, 7, 9, 11, 13, 15, 17, 19, 21, 23, 25, 27, 29, 31, 33, 35, 37, 39, 41, 43, 45, 47, 70 or 71 or a splice variant thereof;

(ii) a nucleic acid coding for a protein having at least 50% identity, at least 60% identity, preferably at least 70% sequence identity, at least 80%, at least 90%, at least 95%, at least 98%, at least 99% sequence identity, or even 100% sequence identity with SEQ ID NO: 2, 4, 6, 8, 10, 12, 14, 16, 18, 20, 22, 24, 26, 28, 30, 32, 34, 36, 38, 40, 42, 44, 46, 48, 69 or 72; preferably the encoded protein confers enhanced fungal resistance relative to control plants;

(iii) a nucleic acid capable of hybridizing under stringent conditions with a complementary sequence of any of the nucleic acids according to (i) or (ii); preferably encoding a YODA protein; preferably wherein the nucleic acid molecule codes for a polypeptide which has essentially identical properties to the polypeptide described in SEQ ID NO: 2, 4, 6, 8, 10, 12, 14, 16, 18, 20, 22, 24, 26, 28, 30, 32, 34, 36, 38, 40, 42, 44, 46, 48, 69 or 72; preferably the encoded protein confers enhanced fungal resistance relative to control plants; and/or (iv) a nucleic acid encoding the same YODA protein as any of the nucleic acids of (i) to (iii) above, but differing from the nucleic acids of (i) to (iii) above due to the degeneracy of the genetic code, operably linked with (b) a promoter and (c) a transcription termination sequence.

The terms "operatively linked (therewith)" or "functionally linked (therewith)" are understood as meaning for example the sequential arrangements of a promoter with the nucleic acid sequence to be expressed and, if appropriate, further regulatory elements such as, for example, a terminator in such a way that each of the regulatory (or regulation) elements is capable of fulfilling its function upon the transgenic expression of the nucleic acid sequence, depending on the arrangement of the nucleic acid sequences to give sense or antisense RNA. A direct linkage in the chemical meaning of the word is not required here. Genetic control sequences such as, for example, enhancer sequences, may also exert their function, on the target sequence from positions at a certain distance, or even from other DNA molecules.

Preferred arrangements are those in which the nucleic acid sequence to be expressed recombinantly is positioned after the sequence which acts as the promoter, so that the two sequences are bonded covalently with one another. In this context, it is preferred that the distance between the promoter sequence and the nucleic acid sequence to be expressed recombinantly is less than 200 base pairs, especially preferably less than 100 base pairs, very especially preferably less than 50 base pairs.

The generation of a functional linkage and the generation of an expression cassette can be carried out by means of customary recombination and cloning techniques as described for example in Maniatis T., Fritsch E. F. and Sambrook J., "Molecular Cloning: A Laboratory Manual", Cold Spring Harbor Laboratory, Cold Spring Harbor (N.Y.) (1989), in Silhavy T. J., Berman M. L. and Enquist L. W. "Experiments with Gene Fusions", Cold Spring Harbor Laboratory, Cold Spring Harbor (N.Y.) (1984), in Ausubel F. M. et al., "Current Protocols in Molecular Biology", Greene Publishing Assoc. and Wiley Interscience (1987) and in Gelvin et al., in "Plant Molecular Biology Manual" (1990). However, it is also possible to position, between the two sequences, further sequences which exert for example the function of a linker with specific restriction enzyme cleavage sites, or of a signal peptide. The insertion of sequences may also lead to the expression of fusion proteins. It is preferred that the expression cassette, consisting of a linkage of promoter and nucleic acid sequence to be expressed, can be present in vector-integrated form and inserted into a plant genome by, for example, transformation.

The method according to the invention can advantageously be combined with other methods which bring about a pathogen resistance (for example against insects, fungi, bacteria, nematodes and the like), stress resistance or another improvement of the plant characteristics. Examples are mentioned inter alia in Dunwell J. M., J. Exp. Bot. 51, (Spec No) 487 (2000).

The invention furthermore relates to nucleic acid molecules which comprise nucleic acid molecules coding for YODA proteins from *Arabidopsis* according to the polynucleotides SEQ. ID NO: 1, and the nucleic acid sequences which are complementary thereto, and the sequences which are derived due to the degeneracy of the genetic code, where the nucleic acid molecules do not consist of SEQ ID NO: 3, 5, 7, 9, 11, 13, 15, 17, 19, 21, 23, 25, 27, 29, 31, 33, 35, 37, 39, 41, 43, 45, 47, 70 or 71. The invention furthermore relates to nucleic acid molecules which comprise nucleic acid molecules coding for YODA proteins from soybean plants according to the polynucleotides SEQ. ID No.: 19, 21, 23, 25, 27, 29, and the nucleic acid sequences which are complementary thereto, and the sequences which are derived due to the degeneracy of the genetic code, where the nucleic acid molecules do not consist of SEQ ID No: 3, 5, 7, 9, 11, 13, 15, 17, 31, 33, 35, 37, 39, 41, 43, 45, 47, 70 or 71.

The invention furthermore relates to the YODA protein from *Arabidopsis* according to SEQ. ID NO: 2 or one which comprises these sequences, which do not correspond to one of the sequences of SEQ ID No.: 4, 6, 8, 10, 12, 14, 16, 18, 20, 22, 24, 26, 28, 30, 32, 34, 36, 38, 40, 42, 44, 46 or 48. The invention furthermore relates to the YODA protein from soybean plants according to SEQ. ID No.: 20, 22, 24, 26, 28 or 30 or one which comprises these sequences, do not correspond to one of the sequences of SEQ ID No.: 2, 4, 6, 8, 10, 12, 14, 16, 18, 32, 34, 36, 38, 42, 44, 46 or 48.

The invention furthermore relates to transgenic expression cassettes comprising one of the nucleic acid sequences according to the invention. In the transgenic expression cassettes according to the invention, the nucleic acid sequence coding for the YODA proteins from *Arabidopsis* is linked with at least one genetic control element as defined above in such a manner that the expression (transcription and, if appropriate, translation) can be effected in any organism, preferably in dicotyledonous plants. Genetic control elements which are suitable for this purpose are described above. The transgenic expression cassettes may also comprise further functional elements as defined above.

Such expression cassettes comprise for example a nucleic acid sequence according to the invention, for example a nucleic acid sequence which is essentially identical to a nucleic acid molecule as shown in SEQ ID No.: 1, 3, 5, 7, 9, 11, 13, 15, 17, 19, 21, 23, 25, 27, 29, 31, 33, 35, 37, 39, 41, 43, 45, 47, 70 or 71 or a fragment thereof according to the invention, where said nucleic acid sequence is preferably in sense orientation or in antisense orientation relative to a promoter and can therefore lead to the expression of sense or antisense RNA, said promoter being a promoter which is active in plants, preferably a promoter which can be induced by pathogen attack. Also comprised according to the invention are transgenic vectors which encompass said transgenic expression cassettes.

Plant-specific promoters mean in principle any promoter which is capable of controlling the expression of genes, in particular foreign genes, in plants or plant parts, plant cells, plant tissues, plant cultures. Here, the expression can be for example constitutional, inducible or development-dependent The following are preferred:

a) Constitutive Promoters

"Constitutive" promoter means those promoters which ensure expression in numerous, preferably all, tissues over a relatively large period of plant development, preferably at all times during plant development. In particular, a plant promoter or a promoter derived from a plant virus is preferably used. The promoter of the 35S transcript of the CaMV cauliflower mosaic virus (Franck et al. Cell 21, 285 (1980); Odell et al. Nature 313, 810 (1985); Shewmaker et al. Virology 140, 281 (1985); Gardner et al. Plant Mol Biol 6, 221 (1986)) or the 19S CaMV Promoter (U.S. Pat. No. 5,352,606; WO 84/02913; Benfey et al. EMBO J. 8, 2195-2202 (1989)) is particularly preferred. A further suitable constitutive promoter is the rubisco small subunit (SSU) promoter (U.S. Pat. No. 4,962,028), the promoter of *agrobacterium* nopaline synthase, the TR double promoter, the *agrobacterium* OCS (octopine synthase) promoter, the ubiquitin promoter (Holtoff S et al. Plant Mol Biol 29, 637 (1995)), the ubiquitin 1 promoter (Christensen et al. Plant Mol Biol 18, 675 (1992); Bruce et al. Proc Natl Acad Sci USA 86, 9692 (1989)), the Parsley ubiquitin promoter (see e.g. US 2007/0006347), the maize ubiquitin promoter, the Smas promoter, the cinnamyl-alcohol dehydrogenase promoter (U.S. Pat. No. 5,683,439), the promoters of vacuolar ATPase subunits or the promoter of a proline-rich protein from wheat (WO 91/13991), and further promoters of genes whose constitutive expression in plants is known to the skilled worker. Especially preferred as constitutive promoter is the promoter of nitrilase-1 (nit1) gene from *A. thaliana* (GenBank Acc.-No.: Y07648.2, Nucleotide 2456-4340, Hillebrand et al. Gene 170, 197 (1996)).

b) Tissue-Specific Promoters

One embodiment employs promoters with specificities for the anthers, ovaries, flowers, leaves, stems, roots and seeds.

Seed-specific promoters are, for example, the promoter of phaseolin (U.S. Pat. No. 5,504,200; Bustos et al. Plant Cell 1(9), 839 (1989)), of the 2S albumin gene (Joseffson et al. J Biol Chem 262, 12196 (1987)), of legumin (Shirsat et al. Mol Gen Genet 215(2), 326 (1989)), of the USP (unknown seed protein; Bäumlein et al. Mol Gen Genet 225(3), 459 (1991)), of the napin gene (U.S. Pat. No. 5,608,152; Stalberg et al. L Planta 199, 515 (1996)), of the gene coding for the sucrose binding protein (WO 00/26388) or the legumin B4 promoter (LeB4; Bäumlein et al. Mol Gen Genet 225, 121 (1991); Bäumlein et al. Plant Journal 2(2), 233 (1992); Fiedler et al. Biotechnology (NY) 13(10), 1090 (1995)), the oleosin promoter from *arabidopsis* (WO 98/45461), the Bce4 promoter from *Brassica* (WO 91/13980). Further suitable seed-specific promoters are those of the genes coding for the high molecular weight glutenin (HMWG), gliadin, branching enzyme, ADP glucose pyrophosphatase (AGPase) or starch synthase. Further preferred promoters are those allowing seed-specific expression in monocotyledons such as maize, barley, wheat, rye, rice etc. It is possible and advantageous to employ the promoter of the lpt2 or lpt1 gene (WO 95/15389, WO 95/23230) or the promoters described in WO 99/16890 (promoters of the hordein gene, of the glutelin gene, of the oryzin gene, of the prolamin gene, of the gliadin gene, of the zein gene, of the kasirin gene or of the secalin gene).

Tuber-, storage root- or root-specific promoters are, for example, the patatin class I promoter (833) or the promoter of the potato cathepsin D inhibitor.

Leaf-specific promoters are, for example, the promoter of the cytosolic FBPase from potato (WO 97/05900), the SSU promoter (small subunit) of the rubisco (ribulose-1,5-bisphosphate carboxylase) or the ST-LSI promoter from potato (Stockhaus et al. EMBO J. 8, 2445 (1989)). Epidermis-specific promoters are, for example the promoter of the OXLP gene ("oxalate oxidase like protein"; Wei et al. Plant Mol. Biol. 36, 101 (1998)) and a promoter consisting of the GSTA1 promoter and the WIR1a intron (WO 2005/035766) and the GLP4 promoter (WO 2006/1288832 PCT/EP 2006/062747).

Examples of other tissue-specific promoters are: flower-specific promoters, for example the phytoene synthase promoter (WO 92/16635) or the promoter of the Prr gene (WO 98/22593) and anther-specific promoters, for example the 5126 promoter (U.S. Pat. Nos. 5,689,049, 5,689,051), the glob-I promoter and the [gamma]-zein promoter.

c) Chemically Inducible Promoters

The expression cassettes may also comprise a chemically inducible promoter (review article: Gatz et al. Annu. Rev. Plant Physiol Plant Mol Biol 48, 89 (1997)) through which expression of the exogenous gene in the plant can be controlled at a particular point in time. Promoters of this type, such as, for example, the PRP1 promoter (Ward et al. Plant Mol Biol 22, 361 (1993)), a salicylic acid-inducible promoter (WO 95/19443), a benzenesulfonamide-inducible promoter (EP 0 388 186), a tetracycline-inducible promoter (Gatz et al. Plant J 2, 397 (1992)), an abscisic acid-inducible promoter (EP 0 335 528) and an ethanol- or cyclohexanone-inducible promoter (WO 93/21334) can likewise be used.

d) Stress- or Pathogen-Inducible Promoters

Very especially advantageous is the use of pathogen-inducible promoters which make possible an expression only when required (i.e. in the case of attack by pathogens).

In one embodiment, the method according to the invention therefore uses promoters which are active in plants which are pathogen-inducible promoters.

Pathogen-inducible promoters comprise the promoters of genes which are induced as a result of pathogen attack, such as, for example, genes of PR proteins, SAR proteins, [beta]-1,3-glucanase, chitinase etc. (for example Redolfi et al. Neth J Plant Pathol 89, 245 (1983); Uknes, et al. Plant Cell 4, 645 (1992); Van Loon Plant Mol Viral 4, 111 (1985); Marineau et al. Plant Mol Bid 9, 335 (1987); Matton et al. Molecular Plant-Microbe Interactions 2, 325 (1987); Somssich et al. Proc Natl Acad Sci USA 83, 2427 (1986); Somssich et al. Mol Gen Genetics 2, 93 (1988); Chen et al. Plant J 10, 955 (1996); Zhang and Sing Proc Natl Acad Sci USA 91, 2507 (1994); Warner, et al. Plant J 3, 191 (1993); Siebertz et al. Plant Cell 1, 961 (1989))

Also comprised are wounding-inducible promoters such as that of the pinII gene (Ryan Ann Rev Phytopath 28, 425 (1990); Duan et al. Nat Biotech 14, 494 (1996)), of the wun1 and wun2 gene (U.S. Pat. No. 5,428,148), of the win1 and win2 gene (Stanford et al. Mol Gen Genet 215, 200 (1989)), of the systemin gene (McGurl et al. Science 225, 1570 (1992)), of the WIP1 gene (Rohmeier et al. Plant Mol Biol 22, 783 (1993); Eckelkamp et al. FEBS Letters 323, 73 (1993)), of the MPI gene (Corderok et al. Plant J 6(2), 141 (1994)) and the like.

A source of further pathogen-inducible promoters is the PR gene family. A series of elements in these promoters have proved advantageous. Thus, the nucleotide region of nucleotide −364 to nucleotide −288 in the promoter of PR-2d mediates salicylate specificity (Buchel et al. (1996) Plant Mol Biol 30, 493). The sequence 5'-TCATCTTCTT-3' occurs repeatedly in the promoter of the barley [beta]-1,3-glucanase and in more than 30 other stress-induced genes. In tobacco, this region binds a nuclear protein whose abundance is increased by salicylate. The PR-1 promoters from tobacco and *Arabidopsis* (EP-A 0 332 104, WO 98/03536) are also suitable as pathogen-inducible promoters. Preferred, since particularly specifically induced by pathogens, are the "acidic PR-5"-(aPR5) promoters from barley (Schweizer et al. Plant Physiol 114, 79 (1997)) and wheat (Rebmann et al. Plant Mol Biol 16, 329 (1991)). aPR5 proteins accumulate within approximately 4 to 6 hours after attack by pathogens and only show very little background expression (WO 99/66057). One approach for obtaining an increased pathogen-induced specificity is the generation of synthetic promoters from combinations of known pathogen-responsive elements (Rushton et al. Plant Cell 14, 749 (2002); WO 00/01830; WO 99/66057). Other pathogen-inducible promoters from different species are known to the skilled worker (EP-A 1 165 794; EP-A 1 062 356; EP-A 1 041 148; EP-A 1 032 684).

Further pathogen-inducible promoters comprise the Flachs Fis1 promoter (WO 96/34949), the Vst1 promoter (Schubert et al. Plant Mol Biol 34, 417 (1997)) and the tobacco EAS4 sesquiterpene cyclase promoter (U.S. Pat. No. 6,100,451).

Other preferred promoters are those which are induced by biotic or abiotic stress, such as, for example, the pathogen-inducible promoter of the PRP1 gene (or gst1 promoter), for example from potato (WO 96128561; Ward et al. Plant Mol Biol 22, 361 (1993)), the heat-inducible hsp70 or hsp80 promoter from tomato (U.S. Pat. No. 5,187,267), the chill-inducible alpha-amylase promoter from potato (WO 96/12814), the light-inducible PPDK promoter or the wounding-inducible pinII promoter (EP-A 0 375 091).

e) Mesophyll-Tissue-Specific Promoters

Mesophyll tissue means the leaf tissue, between the epidermis layers, consisting of the palisade mesophyll, the spongy mesophyll and the vascular bundles.

In one embodiment, the method according to the invention employs mesophyll-tissue-specific promoters such as, for example, the promoter of the wheat germin 9f-3.8 gene (GenBank Acc.-No.: M63224) or the barley GerA promoter (WO 02/057412). Said promoters are particularly advantageous since they are both mesophyll-tissue-specific and pathogen-inducible. Also suitable is the mesophyll-tissue-specific *Arabidopsis* CAB-2 promoter (GenBank Acc.-No.: X15222), and the *Zea mays* PPCZm1 promoter (GenBank Acc.-No.: X63869) or homologs thereof. Mesophyll-tissue-specific means that the transcription of a gene is limited to as few as possible plant tissues which comprise the mesophyll tissue as the result of the specific interaction of cis elements present in the promoter sequence and transcription factors binding to these elements; preferably, it means a transcription which is limited to the mesophyll tissue.

Further mesophyll-specific promoters are PPCZm1 (=PEPC; Kausch, Plant Mol. Biol. 45, 1 (2001)); OsrbcS (Kyozuka et al., Plant Phys. 102, 991-(1993)); OsPPDK, acc. AC099041; TaGF-2.8, acc. M63223 (Schweizer, Plant J. 20, 541 (1999)); TaFBPase, acc. X53957; TaWIS1, acc. AF467542 (US 20021115849); HvBIS1, acc. AF467539 (US 2002/115849); ZmMIS1, acc. AF467514 (US 2002/115849); HvPR1a, acc. X74939 (Bryngelsson et al., Molecular Plant-Microbe Interactions 7 (2), 267 (1994); HvPR1b, acc. X74940 (Bryngelsson et al., Molecular Plant-Microbe Interactions 7 (2), 267 (1994)); HvB1,3gluc; acc. AF479647; HvPrx8, acc. AJ276227 (Kristensen et al., Molecular Plant Pathology 2 (6), 311(2001)); and HvPAL, acc. X97313 (Wei, Plant Molecular Biology 36, 101 (1998)).

f) Epidermis-Specific Promoters

"Epidermal tissue" or epidermis means the outer tissue layers of the plants. The epidermis can be monolayer to multilayer; there is an epidermis-"enriched" gene expression, such as, for example, of Cer3, which may act as marker (Hannoufa, Plant J. 10 (3), 459 (1996)).

By "epidermis", the skilled worker preferably understands the prevailing epiderm of primary aerial plant parts, for example of the shoots, the leaves, the flowers, the fruits and the seeds.

Epidermis-specific promoters are, for example, WIR5 (=GstA1), acc. X56012 (Dudler & Schweizer, unpublished); GLP4, acc. AJ310534 (Wei, Plant Molecular Biology 36, 101 (1998)); GLP2a, acc. AJ237942 (Schweizer, Plant J. 20, 541 (1999).); Prx7, acc. AJ003141 (Kristensen, Molecular Plant Pathology 2 (6), 311(2001)); GerA, acc. AF250933 (Wu, Plant Phys. Biochem. 38, 685 (2000)); OsROC1, acc. AP004656; RTBV, acc. AAV62708, AAV62707 (Klöti, PMB 40, 249 (1999)) and Cer3 (Hannoufa, Plant J. 10 (3), 459 (1996)).

g) Development-Dependent Promoters

Examples of further suitable promoters are fruit ripening-specific promoters such as, for example, the fruit ripening-specific promoter from *tomato* (WO 94/21794, EP 409 625). Development-dependent promoters include some of the tissue-specific promoters because the development of individual tissues naturally takes place in a development-dependent manner.

Constitutive, and leaf- and/or stem-specific, pathogen-inducible, root-specific, mesophyll-tissue-specific promoters are particularly preferred, with constitutive, pathogen-inducible, mesophyll-tissue-specific and root-specific promoters being most preferred.

A further possibility is for further promoters which make expression possible in further plant tissues or in other organisms such as, for example, *E. coli* bacteria to be operably linked to the nucleic acid sequence to be expressed. All the promoters described above are in principle suitable as plant promoters.

Other promoters which are suitable for expression in plants are described (Rogers et al. Meth in Enzymol 153, 253 (1987); Schardl et al. Gene 61, 1 (1987); Berger et al. Proc Natl Acad Sci USA 86, 8402 (1989)).

Moreover, the average person skilled in the art is capable of isolating further suitable promoters by means of routine methods. Thus, the person skilled in the art can identify for example further epidermis-specific regulatory nucleic acid elements, with the aid of customary methods of molecular biology, for example with hybridization experiments or with DNA-protein binding studies. Here, a first step involves, for example, the isolation of the desired tissue from the desired organism from which the regulatory sequences are to be isolated, wherefrom the total poly(A)+RNA is isolated and a cDNA library is established. In a second step, those clones from the first library whose corresponding poly(A)+RNA molecules only accumulate in the desired tissue are identified by means of hybridization with the aid of cDNA clones which are based on poly(A)+RNA molecules from another tissue. Then, promoters with tissue-specific regulatory elements are isolated with the aid of these cDNAs thus identified. Moreover, a person skilled in the art has available further PCR-based methods for the isolation of suitable tissue-specific promoters.

The nucleic acid sequences present in the expression cassettes or vectors of the invention may be operably linked to further genetic control sequences besides a promoter. The term genetic control sequences has a wide meaning and means all sequences which have an influence on the coming into existence or the function of the recombinant nucleic acid molecule of the invention. For example, genetic control sequences modify transcription and translation in prokaryotic or eukaryotic organisms. The expression cassettes of the invention preferably comprise a promoter with an above-mentioned specificity 5'-upstream from the particular nucleic acid sequence which is to be expressed transgenically, and a terminator sequence as additional genetic control sequence 3'-downstream, and if appropriate further conventional regulatory elements, in each case operably linked to the nucleic acid sequence to be expressed transgenically.

Genetic control sequences also comprise further promoters, promoter elements or minimal promoters capable of modifying the expression-controlling properties. It is thus possible for example through genetic control sequences for tissue-specific expression to take place additionally dependent on particular stress factors. Corresponding elements are described for example for water stress, abscisic acid (Lam E and Chua N H, J Biol Chem 1991; 266(26): 17131) and heat stress (Schoffl F et al., Molecular & General Genetics 217(2-3): 246, 1989).

It is possible in principle for all natural promoters with their regulatory sequences like those mentioned above to be used for the method of the invention. It is additionally possible also for synthetic promoters to be used advantageously.

Genetic control sequences further comprise also the 5'-untranslated regions (5'-UTR), introns or noncoding 3' region of genes such as, for example, the actin-1 intron, or the Adh1-S introns 1, 2 and 6 (generally: The Maize Handbook, Chapter 116, Freeling and Walbot, Eds., Springer, New York (1994)). It has been shown that these may play a significant function in the regulation of gene expression. It has thus been shown that 5'-untranslated sequences are capable of enhancing transient expression of heterologous genes. An example of a translation enhancer which may be mentioned is the 5' leader sequence from the tobacco mosaic virus (Gallie et al. Nucl Acids Res 15, 8693 (1987)) and the like. They may in addition promote tissue specificity (Rouster J et al. Plant J 15, 435 (1998)). Especially preferred is the natural 5'-UTR of the AtYODA or GmYODA gene, in particular that with the sequence of SEQ ID NO: 1, 19, 21, 23, 25, 27, or 29 or a sequence with at least 50%, 60%, 70%, 80%, 90%, 95%, 97% or in particular 99% or more identity thereto.

The recombinant nucleic acid molecule according to the invention may advantageously comprise one or more so-called enhancer sequences in operable linkage with the promoter, which make increased transgenic expression of the nucleic acid sequence possible. Additional advantageous sequences such as further regulatory elements or terminators can also be inserted at the 3' end of the nucleic acid sequences to be expressed recombinantly. The nucleic acid sequences to be expressed recombinantly may be present in one or more copies in the gene construct.

Polyadenylation signals suitable as control sequences are plant polyadenylation signals, preferably those which correspond essentially to T-DNA polyadenylation signals from *Agrobacterium tumefaciens*, in particular to gene 3 of the T-DNA (octopine synthase) of the Ti plasmid pTiACHS (Gielen et al. (1984) EMBO J 3:835) or functional equivalents thereof. Examples of particularly suitable terminator sequences are the OCS (octopine synthase) terminator and the NOS (nopaline synthase) terminator.

Control sequences additionally mean those which make homologous recombination or insertion into the genome of a host organism possible or allow deletion from the genome. In homologous recombination, for example, the natural promoter of a particular gene can be specifically replaced by a promoter with specificity for the embryonal epidermis and/or the flower.

A recombinant nucleic acid molecule and a vector derived from it may comprise further functional elements. The term functional element has a wide meaning and means all elements which have an influence on the production, replication or function of the nucleic acid molecules, the vectors or the transgenic organisms of the invention. Non-restrictive examples which may be mentioned are:

a) Selection markers which confer a resistance to a metabolism inhibitor such as 2-deoxyglucose 6-phosphate (WO 98/45456), antibiotics or biocides, preferably herbicides, for example kanamycin, G 418, bleomycin, hygromycin or phosphinotricin and the like. Especially preferred selection markers are those which confer a resistance to herbicides. Examples which may be mentioned are: DNA sequences which code for phosphinothricin acetyltransferases (PAT), which inactivate glutamine synthase inhibitors (bar and pat gene), 5-enolpyruvylshikimate-3-phosphate synthase (EPSP synthase genes) which confer resistance to Glyphosat(R) (N-(phosphonomethyl)glycine), the gox gene, which codes for the Glyphosat(R)-degrading enzyme (glyphosate oxidoreductase), the deh gene (coding for a dehalogenase which inactivates dalapon), and bxn genes which code for bromoxynil-degrading nitrilase enzymes, the aasa gene, which confers a resistance to the antibiotic spectinomycin, the streptomycin phosphotransferase (SPT) gene, which makes possible a resistance to streptomycin, the neomycin phosphotransferase (NPTII) gene, which confers a resistance to kanamycin or geneticidin, the hygromycin phosphotransferase (HPT) gene, which mediates a resistance to hygromycin, the acetolactate synthase gene (ALS), which mediates a resistance to sulfonylurea herbicides (for example mutated ALS variants with, for example, the S4 and/or Hra mutation), and the acetolactate synthase gene (ALS), which mediates a resistance to imidazolinone herbicides.

b) Reporter genes which code for easily quantifiable proteins and ensure via an intrinsic color or enzymic activity an assessment of the transformation efficiency or of the location or timing of expression. Very particular preference is given in this connection to reporter proteins (Schenborn E. and Groskreutz D. Mol Biotechnol. 1999; 13(1):29) such as the green fluorescence protein (GFP) (Sheen et al. (1995) Plant Journal 8(5):777; Haselhoff et al. (1997) Proc Natl Acad Sci USA 94(6):2122; Reichel et al. (1996) Proc Natl Acad Sci USA 93(12):5888; Tian et al. (1997) Plant Cell Rep 16:267; WO 97/41228; Chui et al. (1996) Curr Biol 6:325; Leffel et al. (1997) Biotechniques. 23(5):912-8), the chloramphenicoltransferase, a luciferase (Ow et al. (1986) Science 234:856; Millar et al. (1992) Plant Mol Biol Rep 10:324), the aequorin gene (Prasher et al. (1985) Biochem Biophys Res Commun 126(3):1259), the [beta]-galactosidase, R-locus gene (codes for a protein which regulates the production of anthocyanin pigments (red coloration) in plant tissue and thus makes possible the direct analysis of the promoter activity without the addition of additional adjuvants or chromogenic substrates; Dellaporta et al., In: Chromosome Structure and Function: Impact of New Concepts, 18th Stadler Genetics Symposium, 11:263, (1988), with [beta]-glucuronidase being very especially preferred (Jefferson et al., EMBO J. 1987, 6, 3901).

c) Origins of replication which ensure replication of the expression cassettes or vectors of the invention in, for example, *E. coli*. Examples which may be mentioned are ORI (origin of DNA replication), the pBR322 on or the P15A on (Sambrook et al.: Molecular Cloning. A Laboratory Manual, 2nd ed. Cold Spring Harbor Laboratory Press, Cold Spring Harbor, N. Y., 1989).

d) Elements which are necessary for *agrobacterium*-mediated plant transformation, such as, for example, the right or left border of the T-DNA or the vir region.

To select successfully transformed cells, it is generally required additionally to introduce a selection marker which confers to the successfully transformed cells a resistance to a biocide (for example a herbicide), a metabolism inhibitor such as 2-deoxyglucose 6-phosphate (WO 98/45456) or an antibiotic. The selection marker permits the selection of the transformed cells from untransformed cells (McCormick et al. (1969) Plant Cell Reports 5:81).

The present invention furthermore relates to transgenic plant cells and to transgenic plants which comprise a nucleic acid sequence according to the invention or a recombinant nucleic acid molecule according to the invention, and to parts of the plants, transgenic crops and transgenic propagation material of these plants, such as protoplasts, plant cells, calli, seeds, tubers, cuttings, and to the transgenic progeny of this plant.

The invention furthermore relates to plants which, as the result of natural processes or artificial induction, comprise one or more mutations in a nucleic acid molecule which comprises the nucleic acid sequence as shown in SEQ ID NO: 1, 3, 5, 7, 9, 11, 13, 15, 17, 19, 21, 23, 25, 27, 29, 31, 33, 35, 37, 39, 41, 43, 45, 47, 70 or 71, where said mutation brings about an increase of the activity, function or polypeptide quantity of one of the polypeptide encoded by the nucleic acid molecules as shown in SEQ ID NO: 1, 3, 5, 7, 9, 11, 13, 15, 17, 19, 21, 23, 25, 27, 29, 31, 33, 35, 37, 39, 41, 43, 45, 47, 70 or 71. For example a mutation generated, and identified, by TILLING.

Preferred in this context are dicotyledonous plants, in particular those which belong to the families Solanaceae and Cucurbitaceae, very especially preferred plants are selected from the plant genera *Calibrachoa, Capsicum, Nicotiana, Nierembergia, Petunia, Solanum, Cucurbita, Cucumis*, and *Citrullus*very especially preferred are plants selected among the genera *Glycine*, preferably, *Glycine max* (Soy), *Calibrachoa×hybrida, Capsicum annuum* (pepper), *Nicotiana tabacum* (tobacco), *Nierenbergia scoparia* (cupflower), *Petunia×hybrida, Solanumlycopersicum* (tomato), *Solanumtuberosum* (potato), *Solanummelongena* (eggplant), *Cucurbitamaxima* (squash), *Cucurbita pepo* (pumpkin, zucchini), *Cucumis metuliferus* (Horned melon) *Cucumis melo* (Musk melon), *Cucumis sativus* (cucumber) and *Citrullus lanatus* (watermelon).

Also preferred in this context are monocotyledonous plants, in particular those which belong to the family Poaceae, very especially preferred plants are selected from the plant genera *Hordeum, Avena, Secale, Triticum, Sorghum, Zea, Saccharum* and *Oryza*, very especially preferred are plants selected among the genera *Hordeum vulgare* (barley), *Triticum aestivum* (wheat), *Triticum aestivum* subsp. *spelta* (spelt), *Triticale, Avena sativa* (oats), *Secale cereale* (rye), *Sorghum bicolor* (sorghum), *Zea mays* (maize), *Saccharum officinarum* (sugarcane) and *Oryza sativa* (rice).

As a consequence, one embodiment of the invention relates to a plant, comprising a nucleic acid sequence according to the invention which comprises a mutation which brings about, in the plants or parts thereof, an increase of the activity of one of the proteins encoded by the nucleic acid molecules of the invention. For example, the mutation concerns one or more amino acid residues which are identified in the consensus sequence in the figures as being conserved or highly conserved.

Consequently, a preferred embodiment is a transgenic plant, transgenic plant part, or transgenic plant cell overexpressing an exogenous YODA protein. Preferably, the YODA protein overexpressed in the plant, plant part or plant cell is encoded by
(i) an exogenous nucleic acid having at least 50% identity with SEQ ID NO: 1, 3, 5, 7, 9, 11, 13, 15, 17, 19, 21, 23, 25, 27, 29, 31, 33, 35, 37, 39, 41, 43, 45, 47, 70 or 71, or a splice variant thereof; or by (ii) an exogenous nucleic acid encoding a protein having at least 50% identity with SEQ ID NO: 2, 4, 6, 8, 10, 12, 14, 16, 18, 20, 22, 24, 26, 28, 30, 32, 34, 36, 38, 40, 42, 44, 46, 48, 69 or 72, preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a YODA protein; preferably wherein the nucleic acid molecule codes for a polypeptide which has essentially identical properties to the polypeptide described in SEQ ID NO: 2, 4, 6, 8, 10, 12, 14, 16, 18, 20, 22, 24, 26, 28, 30, 32, 34, 36, 38, 40, 42, 44, 46, 48, 69 or 72; preferably the encoded protein confers enhanced fungal resistance relative to control plants; and/or by (iv) an exogenous nucleic acid encoding the same YODA protein as any of the nucleic acids of (i) to (iii) above, but differing from the nucleic acids of (i) to (iii) above due to the degeneracy of the genetic code.

In a preferred embodiment, the invention also relates to transgenic plants transformed with at least a) a nucleic acid sequence which comprises the nucleic acid molecules as shown in SEQ ID NO: 1, 3, 5, 7, 9, 11, 13, 15, 17, 19, 21, 23, 25, 27, 29, 31, 33, 35, 37, 39, 41, 43, 45, 47, 70 or 71; the nucleic acid sequences which are complementary thereto, or the nucleic acid molecules which code for the polypeptides as shown in SEQ ID NO: 2, 4, 6, 8, 10, 12, 14, 16, 18, 20, 22, 24, 26, 28, 30, 32, 34, 36, 38, 40, 42, 44, 46, 48, 69 or 72;

b) a transgenic expression cassette which comprises one of the nucleic acid sequences according to the invention, or a vector according to the invention, and cells, cell cultures, tissue, parts-such as for example leaves, roots and the like or propagation material in the case of plant organisms-derived from such organisms.

In one embodiment, the plant according to the invention, or the plant used according to the invention, is other than *Arabidopsis thaliana*.

Host organisms or starting organisms which are preferred as "transgenic organisms" are especially plants as defined above. In one embodiment, the transgenic organism is a mature plant, seed, shoot and seedling, and parts, propagation material and cultures derived therefrom, for example cell cultures. "Mature plant" means plants at any developmental stage beyond the seedling stage. "Seedling" means a young immature plant in an early developmental stage. Plants which are particularly preferred as host organisms are plants to which the method according to the invention for obtaining a pathogen resistance in accordance with the abovementioned criteria can be applied. In one embodiment, the plant is a dicotyledonous plant such as, for example, soy, calibrachoa, peppers, tobacco, cupflower, petunia, *tomato*, potato, eggplant, squash, pumpkin, zucchini, melon, cucumber or watermelon, in particular selected among the genera *Calibrachoa×hybrida, Capsicumannuum* (pepper), *Nicotianatabacum*(tobacco), *Nierenbergiascoparia* (cupflower), *Petunia×hybrida, Solanumlycopersicum* (tomato), *Solanumtuberosum* (potato), *Solanummelongena* (eggplant), *Cucurbitamaxima* (squash), *Cucurbitapepo* (pumpkin, zucchini), *Cucumis metuliferus* (Horned melon) *Cucumismelo* (Musk melon), *Cucumissativus* (cucumber) and *Citrullus lanatus* (watermelon). In another embodiment, the plant is a monocotyledonous plant such as, for example, wheat, oats, sorghum/millet, barley, rye, maize, rice, buckwheat, sorghum, triticale, spelt or sugarcane, in particular selected among the genera *Hordeumvulgare* (barley), *Triticumaestivum* (wheat), *Triticumaestivum* subsp *spelta* (spelt), *Triticale, Avenasativa*

(oats), *Secalecereale* (rye), *Sorghumbicolor* (sorghum), *Zeamays* (maize), *Saccharumofficinarum* (sugarcane) and *Oryzasativa* (rice).

The transgenic organisms can be generated with the above-described methods for the transformation or transfection of organisms.

The invention furthermore relates to the use of the transgenic organisms according to the invention and of the cells, cell cultures, parts-such as, for example, roots, leaves and the like in the case of transgenic plant organisms-, and transgenic propagation material such as seeds or fruits for the preparation of foodstuffs or feeding stuffs, pharmaceuticals or fine chemicals.

Harvestable parts of the transgenic plant according to the present invention are part of the invention. Preferably, the harvestable parts comprise the YODA nucleic acid or YODA protein. The harvestable parts may be seeds, roots, leaves and/or flowers comprising the YODA nucleic acid or YODA protein or parts thereof. Preferred parts of soy plants are soy beans comprising the YODA nucleic acid or YODA protein.

Products derived from a transgenic plant according to the present invention, parts thereof or harvestable parts thereof are part of the invention. A preferred product is meal or oil, preferably, soybean meal or soybean oil. Preferably, the soybean meal and/or oil comprises the YODA nucleic acid or YODA protein.

In one embodiment the method for the production of a product comprises
a) growing the plants of the invention or obtainable by the methods of invention and
b) producing said product from or by the plants of the invention and/or parts, e.g. seeds, of these plants.

In a further embodiment the method comprises the steps a) growing the plants of the invention, b) removing the harvestable parts as defined above from the plants and c) producing said product from or by the harvestable parts of the invention.

The product may be produced at the site where the plant has been grown, the plants and/or parts thereof may be removed from the site where the plants have been grown to produce the product. Typically, the plant is grown, the desired harvestable parts are removed from the plant, if feasible in repeated cycles, and the product made from the harvestable parts of the plant. The step of growing the plant may be performed only once each time the methods of the invention is performed, while allowing repeated times the steps of product production e.g. by repeated removal of harvestable parts of the plants of the invention and if necessary further processing of these parts to arrive at the product. It is also possible that the step of growing the plants of the invention is repeated and plants or harvestable parts are stored until the production of the product is then performed once for the accumulated plants or plant parts. Also, the steps of growing the plants and producing the product may be performed with an overlap in time, even simultaneously to a large extend or sequentially. Generally the plants are grown for some time before the product is produced.

In one embodiment the products produced by said methods of the invention are plant products such as, but not limited to, a foodstuff, feedstuff, a food supplement, feed supplement, fiber, cosmetic and/or pharmaceutical. Foodstuffs are regarded as compositions used for nutrition and/or for supplementing nutrition. Animal feedstuffs and animal feed supplements, in particular, are regarded as foodstuffs.

In another embodiment the inventive methods for the production are used to make agricultural products such as, but not limited to, plant extracts, proteins, amino acids, carbohydrates, fats, oils, polymers, vitamins, and the like.

It is possible that a plant product consists of one or more agricultural products to a large extent.

The transgenic plants of the invention may be crossed with similar transgenic plants or with transgenic plants lacking the nucleic acids of the invention or with non-transgenic plants, using known methods of plant breeding, to prepare seeds. Further, the transgenic plant cells or plants of the present invention may comprise, and/or be crossed to another transgenic plant that comprises one or more exogenous nucleic acids, thus creating a "stack" of transgenes in the plant and/or its progeny. The seed is then planted to obtain a crossed fertile transgenic plant comprising the YODA nucleic acid. The crossed fertile transgenic plant may have the particular expression cassette inherited through a female parent or through a male parent. The second plant may be an inbred plant. The crossed fertile transgenic may be a hybrid. Also included within the present invention are seeds of any of these crossed fertile transgenic plants. The seeds of this invention can be harvested from fertile transgenic plants and be used to grow progeny generations of transformed plants of this invention including hybrid plant lines comprising the exogenous nucleic acid.

Thus, one embodiment of the present invention is a method for breeding a fungal resistant plant comprising the steps of
(a) crossing a transgenic plant described herein or a plant obtainable by a method described herein with a second plant;
(b) obtaining a seed or seeds resulting from the crossing step described in (a);
(c) planting said seed or seeds and growing the seed or seeds to plants; and
(d) selecting from said plants the plants expressing a YODA protein, preferably encoded by
(i) an exogenous nucleic acid having at least 60% identity with SEQ ID NO: 1, 3, 5, 7, 9, 11, 13, 15, 17, 19, 21, 23, 25, 27, 29, 31, 33, 35, 37, 39, 41, 43, 45, 47, 70 or 71, or a splice variant thereof;
(ii) an exogenous nucleic acid encoding a protein having at least 60% identity with SEQ ID NO: 2, 4, 6, 8, 10, 12, 14, 16, 18, 20, 22, 24, 26, 28, 30, 32, 34, 36, 38, 40, 42, 44, 46, 48, 69 or 72; preferably the encoded protein confers enhanced fungal resistance relative to control plants;
(iii) an exogenous nucleic acid capable of hybridizing under stringent conditions with a complementary sequence of any of the nucleic acids according to (i) or (ii); preferably encoding a YODA protein; preferably wherein the nucleic acid molecule codes for a polypeptide which has essentially identical properties to the polypeptide described in SEQ ID NO: 2, 4, 6, 8, 10, 12, 14, 16, 18, 20, 22, 24, 26, 28, 30, 32, 34, 36, 38, 40, 42, 44, 46, 48, 69 or 72; preferably the encoded protein confers enhanced fungal resistance relative to control plants; and/or by
(iv) an exogenous nucleic acid encoding the same YODA protein as any of the nucleic acids of (i) to (iii) above, but differing from the nucleic acids of (i) to (iii) above due to the degeneracy of the genetic code.

Another preferred embodiment is a method for plant improvement comprising
(a) obtaining a transgenic plant by any of the methods of the present invention;
(b) combining within one plant cell the genetic material of at least one plant cell of the plant of (a) with the genetic material of at least one cell differing in one or more gene from the plant cells of the plants of (a) or crossing the transgenic plant of (a) with a second plant;

(c) obtaining seed from at least one plant generated from the one plant cell of (b) or the plant of the cross of step (b);

(d) planting said seeds and growing the seeds to plants; and (e) selecting from said plants, plants expressing the nucleic acid encoding the YODA protein; and optionally (f) producing propagation material from the plants expressing the nucleic acid encoding the YODA protein.

The transgenic plants may be selected by known methods as described above (e.g., by screening for the presence of one or more markers which are encoded by plant-expressible genes co-transferred with the YODA gene or screening for the YODA nucleic acid itself).

According to the invention, the expression of a structural gene can, of course, also be effected, or influenced, independently of the embodiment of the method according to the invention or the use of the subject matter according to the invention.

The examples which follow are embodiments of the invention, and they are not intended to limit the scope of the invention as contained in the remainder of the description, the figures and the claims.

Sequences:
SEQ ID NO: 1 and 2: AtYODA1 NM_105047.2 (AT1G63700)
SEQ ID NO: 3 and 4 VvYODA1 (XP003631415.1) (LOC100263296)
SEQ ID NO: 5 and 6 VvYODA2 (XP003634098.1) (LOC100242348)
SEQ ID NO: 7 and 8 VvYODA3 (CAN65619.1)
SEQ ID NO: 9 and 10 PtYODA1 (XP002304501.1)
SEQ ID NO: 11 and 12 PtYODA2 (XP002322482.1)
SEQ ID NO: 13 and 14 PtYODA3 (XP002318210.1)
SEQ ID NO: 15 and 16 OsYODA1 (NP001053542.1) (Os04g0559800)
SEQ ID NO: 17 and 18 OsYODA2 (NP001047673.1) (Os02g0666300)
SEQ ID NO: 19 and 20 GmYODA1 (XP003548172.1) (LOC100792783)
SEQ ID NO: 21 and 22 GmYODA2 (XP003533990.1) (LOC100819762)
SEQ ID NO: 23 and 24 GmYODA3 (XP003556116.1)
SEQ ID NO: 25 and 26 GmYODA4 (XP003536457.1)
SEQ ID NO: 27 and 28 GmYODA5 (XP003538696.1)
SEQ ID NO: 29 and 30 GmYODA6 (XP003532415.1)
SEQ ID NO: 31 and 32 CmYODA1 (ADN34290.1)
SEQ ID NO: 33 and 34 SlYODA1 (Solyc08g081210.1.1)
SEQ ID NO: 35 and 36 SlYODA2 (Solyc03g025360.1.1)
SEQ ID NO: 37 and 38 SlYODA3 (Solyc06g036080.1.1)
SEQ ID NO: 39 and 40 SbYODA1 (XP002448319.1)
SEQ ID NO: 41 and 42 SbYODA2 (XP002452783.1)
SEQ ID NO: 43 and 44 ZmYODA1 (CAW45396.1)
SEQ ID NO: 45 and 46 TaYODA1 (AK335442.1)
SEQ ID NO: 47 and 48 HvYODA1 (BAJ98424.1)
SEQ ID NO: 49 to 54: primers
SEQ ID NO: 55 to 68: markers
SEQ ID NO: 69: consensus sequence of the polypeptide SEQ ID No. from 2 to 48.
SEQ ID NO: 70: 5'UTR in combination with the sequence of AtYODA
SEQ ID NO: 71 and 72: CA:YODA mutant
SEQ ID NO: 73: kinase domain of AtYODA1

Figure 1:
FIG. 1. Alignment and consensus sequence of the polypeptide sequences of YODA (herein also referred to as YDA) from *Arabidopsis thaliana*, grapevine, *Populus trichocarpa*, rice, soybean, melon, tomato, sorghum, corn, wheat and barley CA:YDA deletion is indicated with white arrows. The kinase domain is included in a box. The proline (P) mutated in the yda10 allele is showed with a black arrow.! is anyone of IV, $ is anyone of LM, % is anyone of FY and # is anyone of NDQEBZ.
Figure 2:
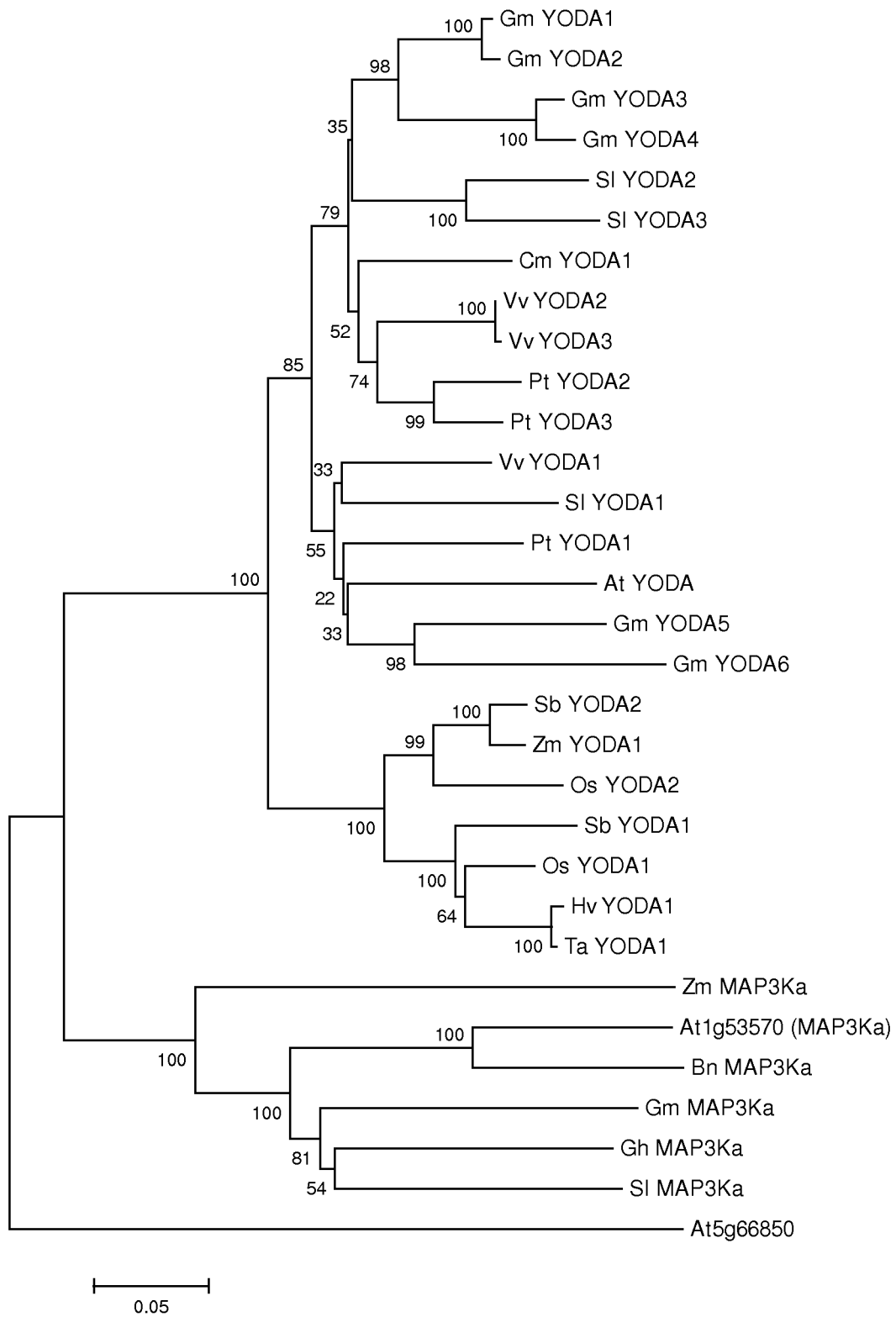
FIG. 2. Phylogenetic tree of putative YODA orthologs. Evolutionary relationship inferred using the Neighbor-Joining method (see material and methods) based on the full length protein sequence of *Arabidopsis thaliana* AtYODA1 protein (At1 g63700) and putative orthologs from *Solanum lycopersicum* SlYODA1 (Solyc08g081210.1.1), SlYODA2 (Solyc03g025360.1.1), SlYODA3 (Solyc06g036080.1.1), *Vitis vinifera* VvYODA1 (XP003631415.1), VvYODA2 (XP003634098.1), VvYODA3 (CAN65619.1), *Populus trichocarpa* PtYODA1 (XP002304501.1), PtYODA2 (XP002322482.1), PtYODA3 (XP002318210.1), *Oryza sativa Japonica* OsYODA1 (NP001053542.1), OsYODA2 (NP001047673.1), *Glycine max* GmYODA1 (XP003548172.1), GmYODA2 (XP003533990.1), GmYODA3 (XP003556116.1), GmYODA4 (XP003536457.1), GmYODA5 (XP003538696.1), GmYODA6 (XP003532415.1), *Cucumus melo* subsp. *melo* CmYODA1 (ADN34290.1), *Sorghum bicolor* SbYODA1 (XP002448319.1), *Sorghum bicolor* SbYODA2 (XP002452783.1), *Zea mays* ZmYODA1 (CAW45396.1), *Triticum aestivum* TaYODA1 (AK335442.1), and *Hordeum vulgare* subsp. *vulgare*HvYODA1 (BAJ98424.1). The tree also included the six members of the A2 Glade of MAPKKK proteins in *Arabidopsis* (At1g53570 and At5g66850), in *Zea mays* ZmMAP3Ka (NP001130629), in *Glycine max* GmMAP3Ka (XP003531452.1), in *Brassica napus* BnMAP3Ka (CAA08995.1), in *Solanum lycopersicum* SlMAP3Ka (NP001234485.1), and in *Gossypium hirsutum* GhMAP3Ka (AD152619.1) to which YODA1 belongs (Peterson et al., 2010). Sequences were obtained from the NCBI and Solgenomics databases. The tree is drawn to scale, with branch lengths in the same units as those of the evolutionary distances used to infer the phylogenetic tree. The evolutionary distances were computed using the Poisson correction method and are in the units of the number of amino acid substitutions per site. The analysis involved 15 amino acid sequences. All positions containing gaps and missing data were eliminated. Evolutionary analyses were conducted in MEGA5 (Tamura et al., 2011).

(A) Developmental phenotype of 6 weeks-old *Arabidopsis* transgenic plants overexpressing YDA1 gene under 35S promoter.
(B) Disease rating (DR) scores (average±SE) 11 days after inoculation of plants with $4 \times 10^6$ spores/ml of PcBMM. DR varies between 0 (no symptoms) and 5 (dead plant). The agb1-2 and ern1/irx1-6 mutants (in Col-0 background), that are hypersusceptible and resistant to PcBMM, respectively, were included for comparison.
(C) PcBMM biomass quantification in the indicated genotypes 3 days post inoculation. Specific primers of PcBMM β-TUBULIN and *Arabidopsis* UBIQUITIN21 genes were used for qRT-PCR. Values are represented as fold-increase in expression compared to the wild type plants. Error bars indicate SE (n=2).
(D) Transcriptional profiling of YDA1 gene in the detailed genotypes. Gene expression was normalized to the levels of AtUBQ21. Error bars indicate SE (n=2).

Letters indicate that data are significantly different from the wild type plants (ANOVA 0.05; Bonferroni test).

EXAMPLES OF THE INVENTION

General Methods
Biological Material and Growth Conditions
*Arabidopsis thaliana* plants were grown in sterilized soil as described previously (Hernández-Blanco et al., Plant Cell 19: 890-903 (2007)). The following lines in Col-0 background were used: elk2/YODA10 (Lease et al., Plant Cell 13: 2631-41 (2001)), er-105 (Torii et al., Plant Cell 8: 735-46

(1996)), mpk3-1(Lee and Ellis., J. Biol. Chem. 282:25020-9 (2007)),cerk1-2 (Miya et al., Proc. Natl. Acad. Sci. USA 104: 19613-8 (2007)), fls2 (Zipfel et al., Nature 428: 764-7 (2004)), ap2c1 and AP2C1-overexpressing lines #640.1 and #640.2 (OE:AP2C1; Schweighofer et al., Plant Cell 19: 2213-24 (2007)), coil-1 (Feys et al., Plant Cell 6:751-59 (1994), ein2 (Guzmán and Ecker, Plant Cell 2: 513-23 (1990)), sid2-1 (Nawrath and Métraux, Plant Cell 11: 1393-404 (1999)), agb1-1 (Lease et al., Plant Cell 13: 2631-41 (2001)), agb1-2 (Ullah et al., Plant Cell 15: 393-409 (2003)), irx1-6 (Hernández-Blanco et al., Plant Cell 19: 890-903 (2007)), mlo2-6-12 (Consonni et al., Plant Physiol. 152: 1544-61 (2010)), eds1-2 (Garcia et al., PLoS Pathog. 6: e1000970 (2010)) and cpr5 (Bowling et al., Plant Cell 9: 1573-84 (1997)). The yoda1 and CA:YODA plants used in some experiments were in La-0 background. (Lukowitz et al., Cell 116: 109-19 (2004)). Double mutant lines were generated by crossing the yoda10/elk2 allele with yoda1, er-105, mpk3, cerk1-2, fls2, ap2c1, coil-1, ein2, sid2-1 and agb1-1 mutants and selecting homozygous combinations in F2 progeny using allele-specific PCR amplifications for genotyping. The CA:YODA plants in Col-0 background were obtained by crossing CA:YODA in La-0 with Col-0 and yoda10 plants followed by four backcrossed with these genotypes. Genotyping of the yoda10 mutation in all of the double mutants was confirmed by PCR amplification followed by XbaI digestion, and the yodel mutation was confirmed by PCR amplification and MseI digestion. The er-1 mutation was confirmed by PCR amplification followed by HindIII digestion. The coil-1 and ein2 mutants were confirmed by growing seeds in 50 µM JA and 10 µM ACPC plates respectively. The oligonucleotides used for detecting the different mutant lines are showed in Table 1.

Mapping and cloning ELK2/YODA gene. ELK2 gene was mapped using 288 plants from an elk2 (Col-0)×Ws-2 F2, that were selected based on the elk2 development-associated phenotype, which was confirmed in the F3 populations from the selected F2 plants. The mapping performed by Servicio de Cartografia Genética (Proyecto GEFA; Universidad Miguel Hernández, Elche, Spain) localized ELK2 between Cer473845 and Cer450793 markers (1 and 1 recombination, respectively, in 576 meiotic events). Shotgun sequencing allowed the identification of new SNPs (single nucleotide polymorphism) between Col-0 and Ws-2 (See Table 1). These new markers were used for fine-mapping of ELK2 between BACS F9N112, F2K11/F24D7.

Figure 3:
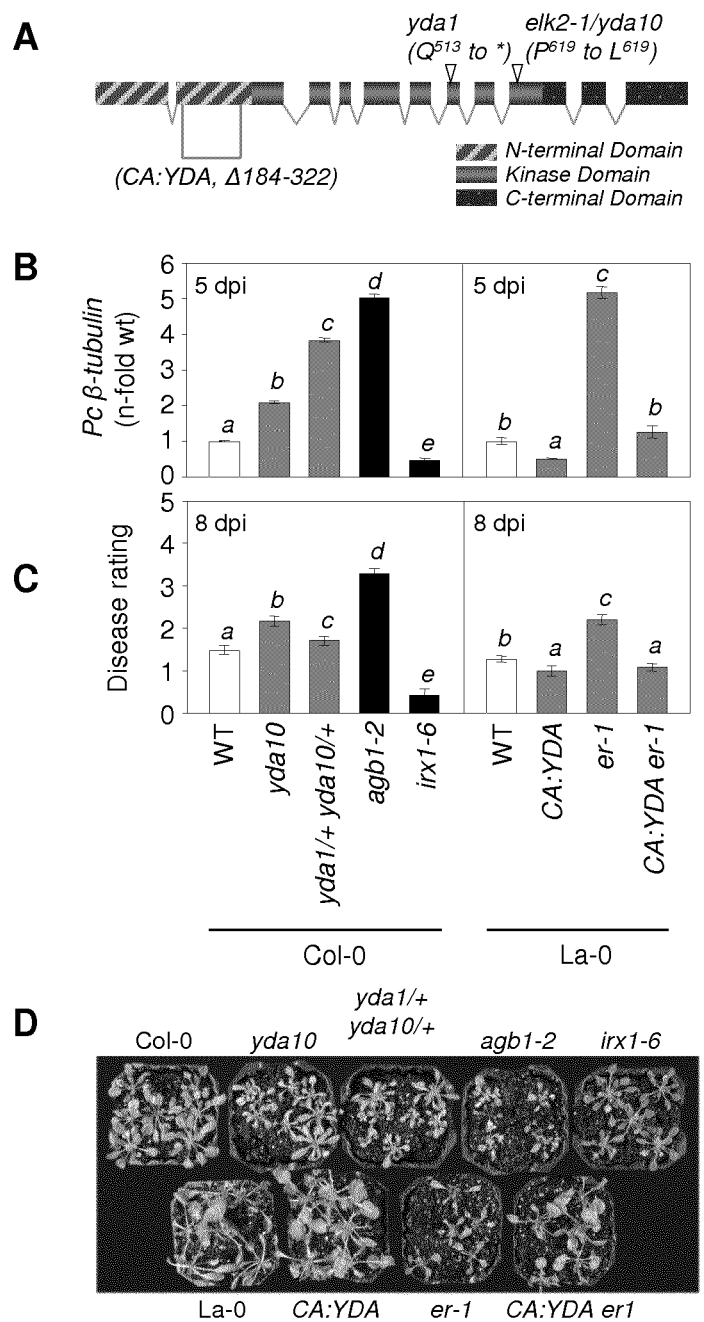
FIG. 3. YODA regulates *Arabidopsis* resistance to the necrotrophic fungus *Plectosphaerella cucumerina*. (A) Structure of the YODAgene. The boxes correspond to the exons, and the gaps to the introns. YODA regulatory N-terminal, kinase and C-terminal domains are indicated. The amino acids mutated in the YODA10 and YODA1 alleles, or deleted in the N-domain of CA-YODA plants, showing a constitutive activation of YODA (Bergamann et al., 2004), are indicated. (B) Resistance of the YODA10 and YODA10/+YODA1/+ mutants and of CA-YODA plants to *P. cucumerina* BMM (PcBMM). Determination, by quantitative real-time PCR (qRT-PCR), of fungal DNA (Pcβ-TUBULIN) in the inoculated plants at 5 days post-inoculation (dpi) with a spore suspension ($4 \times 10^6$ spores/ml) of PcBMM. Values (±standard error, SE) were normalized to *Arabidopsis* UBIQUITIN21 and are represented as the average of the n-fold-increased expression compared with the corresponding wild-type plants (Col-0 and La-0 respectively). The hypersusceptible and resistant mutants agb1-1 and irx1-6, respectively, were included for comparison. (C) Average disease rating (DR±SE) of the indicated genotypes at 8 dpi. DR varies between 0 (no symptoms) and 5 (dead plant). Letters indicate values statistically different from those of wild-type plants (ANOVA P<0.05, Bonferroni's test). (D) Disease symptoms of the indicated genotypes at 8 dpi. Data are from one out of three independent experiments performed, which gave similar results.

The putative genes from all these BACS were completely sequenced in elk2 and Col-0 plants resulting in the identification of a single-based change (C to T) on YODA gene, which that resulted in a change of $P^{619}$ to L (FIGS. 1 and 3 A2).

Inoculation of Arabidopsis thaliana with Pathogens

Three-week-old Arabidopsis plants were inoculated with a spore suspension ($4 \times 10^6$ spores/ml) of Plectosphaerella cucumerina BMM. Disease progression was estimated by determining the average Disease Rating (DR, 0-5; 0, no infection; 5, dead plant), trypan blue staining and relative quantification of fungal DNA by qPCR as previously described (Sánchez-Vallet et al., Plant J. 63: 115-27 (2010)). At least three independent experiments were performed, and statistically significant differences among the inoculated Arabidopsis genotypes were determined by one-way analysis of variance and Bonferroni post hoc test, as previously reported (Sánchez-Rodriguez et al., Mol. Plant Microbe Interact 22: 953-63 (2009) Inoculation with Pseudomonas syringae pv. Tomato DC3000 was done as reported (Zipfel et al. Nature 428: 764-7 (2004)). Quantification of bacterial growth in the inoculated plants was determined at 2 and 4 dpi as previouslypreviosuly described (Zipfel et al. Nature 428: 764-7 (2004)). Plant inoculations with Hyaloperonopora arabidopsidis Noco and Emwa isolates were done as reported (Llorente et al., Plant J. 43: 165-80 (2005)). Inoculation of Arabidopsis genotypes with powdery mildew fungus (Golovinomyces cichoracearum isolate CBGP) was done by Consonni et al., 2010.

Fusarium and Colletotrichum Resistance Screening in Corn

Transgenic maize plants are grown in greenhouse or phyto-chamber under standard growing conditions in a controlled environment (20-25° C., 60-90% humidity).

Shortly after plants enter the reproductive phase the transgenic plants are inoculated near the base of the stalk using a fungal suspension of spores ($10^5$ spores in PBS solution) of Fusarium ssp. or Colletotrichum graminicola. Plants are incubated for 2-4 weeks at 20-25° C. and 60-90% humidity.

For scoring the disease, stalks are split and the progression of the disease are scored by observation of the characteristic brown to black color of the fungus as it grows up the stalk. Disease ratings are conducted by assigning a visual score.

Per experiment the diseased leaf area of more than 10 transgenic plants (and wild-type plants as control) is scored. For analysis the average of the diseased leaf area of the non-transgenic mother plant is set to 100% to calculate the relative diseased leaf area of the transgenic lines.

Inoculation of Soybean Plants with Pathogens

10 $T_1$ plants per event are potted and grown for 3-4 weeks in the phytochamber (16 h-day- und 8 h-night-Rhythm at a temperature of 16 and 22° C. und a humidity of 75%) till the first 2 trifoliate leaves are fully expanded. The plants are-inoculated with spores of P. pachyrhizi.

In order to obtain appropriate spore material for the inoculation, soybean leaves which had been infected with rust 15-20 days ago, are taken 2-3 days before the inoculation and transferred to agar plates (1% agar in $H_2O$). The leaves are placed with their upper side onto the agar, which allows the fungus to grow through the tissue and to produce very young spores. For the inoculation solution, the spores are knocked off the leaves and were added to a Tween-$H_2O$ solution. The counting of spores is performed under a light microscope by means of a Thoma counting chamber. For the inoculation of the plants, the spore suspension is added into a compressed-air operated spray flask and applied uniformly onto the plants or the leaves until the leaf surface is well moisturized. For macroscopic assays a spore density of $1-5 \times 10^5$ spores/ml is used. For the microscopy, a density of $>5 \times 10^5$ spores/ml is used. The inoculated plants are placed for 24 hours in a greenhouse chamber with an average of 22° C. and >90% of air humidity. The following cultivation is performed in a chamber with an average of 25° C. and 70% of air humidity. For the evaluation of the pathogen development, the inoculated leaves of plants are stained with aniline blue 48 hours after infection. The progression of the soybean rust disease is scored by the estimation of the diseased area (area which is covered by sporulating uredinia) on the backside (abaxial side) of the leaf. Additionally the yellowing of the leaf is taken into account Gene Expression Analyses RNA extractions of Arabidopsis thaliana were done as described (Llorente et al., Plant J. 43: 165-80 (2005)). Real-time qPCR analyses were performed as previously reported (Sánchez-Vallet et al., Plant J. 63: 115-27 (2010)). The oligonucleotide sequences, designed using PRIMER EXPRESS v2.0 (Applied Biosystems), used for qPCR have been described previously (Sanchez-Vallet et al., 2010)), except those of and LOX2 genes (5'-ATCAACAAGC-CCCAATGGAA-3' and 5'-CGGCGTCATGAGAGATAG-CAT-3'). qPCR results are mean values (±SDs) from two technical replicates. Differences in expression ratios (ΔCt) among the samples were analysed by ANOVA (LSD test) using StatGraphics (StatPoint Technologies, Inc.). Experiments for qPCR were performed at least three times.

Example 1

YODA1 Mutant Identification

Figure 4:
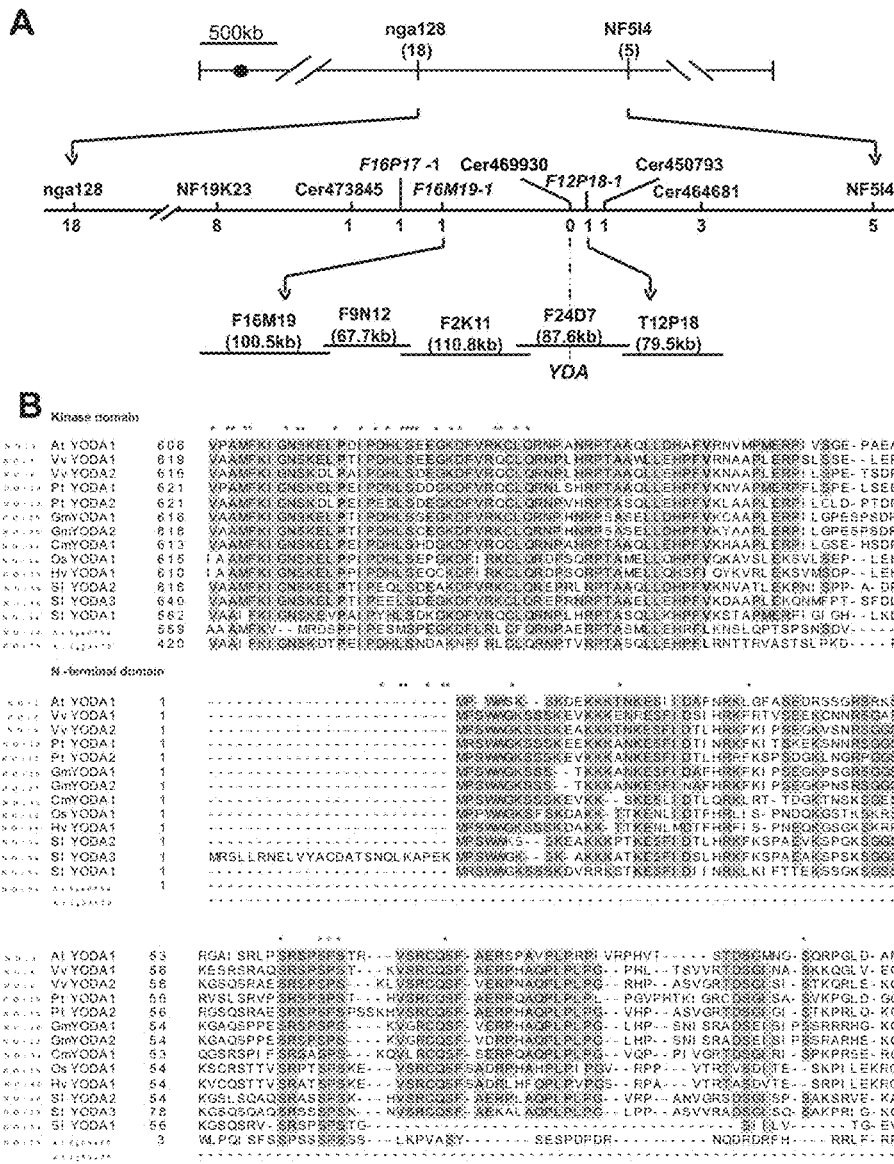
FIG. 4. Mapping of elk2/YODA10 mutation. (A) The elk2/YODA10 mutation was mapped to the bottom of chromosome 1 between markers nga128 (BAC F7A10) and SNP10490 (BAC T27F4). Fine mapping using additional markers delimit the elk2 mutation between markers Cer473845 and Cer450793 (1 and 1 recombinations in 576 meiotic events). Shotgun sequencing allowed the identification of new SNPs (single nucleotide polymorphism) between Col-0 and Ws-2 ecotypes that were used for the development of additional SNPs markers, that allowed to map the mutation between F16M19-1 and F12P18-1 markers (in F18M19 and P12P18 BACS, respectively). The number of heterozygous plants found for each genetic marker of the indicated BAC is detailed in brackets. (B) Alignment of the Kinase domain of *Arabidopsis* YODA protein and YODA orthologs. The proline (P) residue mutated in the YODA10 allele, which is highly conserved in all the YODA orthologs, is showed. Alignment of part of the N-terminal regulatory domain of the YODA clade of MAP3K.

In a screening performed to identify mutants defective in Arabidopsis immune responses against fungal pathogens, we found out that the elk2 mutant line (Lease et al., Plant Cell 13: 2631-41 (2000) was impaired in resistance to fungi with different lifestyles, including the necrotrophs Plectosphaerella cucumerina and Botrytis cinerea, the biotroph Golovinomyces cichoracearum and the vascular pathogen Fusarium oxysporum (Llorente et al., Plant J. 43: 165-80 (2005); FIG. 3). These data suggested that ELK2 played a relevant function in the regulation of Arabidopsis immune response to fungal pathogens and therefore we performed a map-based cloning of ELK2 gene that was found to correspond to YODA MAP3K (FIG. 4). The mutation in elk2 (YODA10yda10) mutant allele caused amino acid transition to Leu$^{619}$ of a highly conserved Pro$^{619}$ from the C-terminal Kinase domain of the MAP3K Glade defined by YODA protein (FIG. 1, FIG. 3 A, FIG. 4B). Interestingly, this Pro$^{619}$ to Leu transition resulted in a hypomorphic, viable mutation of YODA protein in contrast to the embryo-lethal YODA alleles previously isolated and characterized (e.g. YODA1). To probe that elk2 (YODA10) was a new mutant allele of YODA we generated the hemizygous YODA10/YODA1 plants harboring one chromosome from each parental mutant, and we found out that these plants, like YODA10, supported higher fungal biomass of P. cucumerina BMM and have stronger disease ratings than those observed in wild-type Col-0 plants, but these susceptibility parameters were lower than those observed in the hypersusceptible agb1-1 mutant (FIG. 3 B-D). These data corroborated that elk2 (YODA10) was a hypomorphic mutation of YODA gene.

Example 2

Figure 5:
FIG. 5. Macroscopic phenotypes of CA:YODA lines in Col-0, La-0 and er-1 backgrounds. (A) Rosette of 4-week-old plants, flower inflorescence, 6-week-old plants and siliques attached to pedicels from wild-type plants (Col-0 and La-0), YODA10 and er-1 mutants and CA:YODAplants (in Col-0, La-0 and er) are showed. Plants were grown for 3 weeks under short day conditions (14h dark/10 h light) and then transferred to long day conditions (for 8h dark/16 h light) 3 weeks. (B) Average disease rating (DR±SE) of the indicated genotypes at 8 dpi. DR varies between 0 (no symptoms) and 5 (dead plant). Letters indicate values statistically different from those of wild-type plants (ANOVA P<0.05, Bonferroni's test). Data are from one out of three independent experiments performed, which gave similar results. Resistance of the CA-YODA plants (in Col-0 background) to *P. cucumerina* BMM (PcBMM). Determination, by quantitative real-time PCR (qRT-PCR), of fungal DNA (Pcf3-TUBULIN) in the inoculated plants at 5 days post-inoculation (dpi) with a spore suspension ($4 \times 10^6$ spores/ml) of PcBMM. Values (±standard error, SE) were normalized to *Arabidopsis* UBIQUITIN21 and are represented as the average of the n-fold-increased expression compared with the corresponding wild-type plants (Col-0). The hypersusceptible and resistant mutants agb1-1 and ern1, respectively, were included for comparison.
Figure 5:
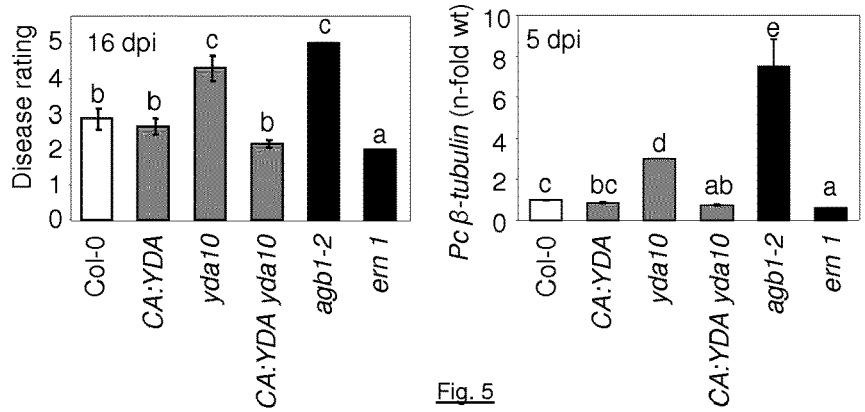
Figure 6:
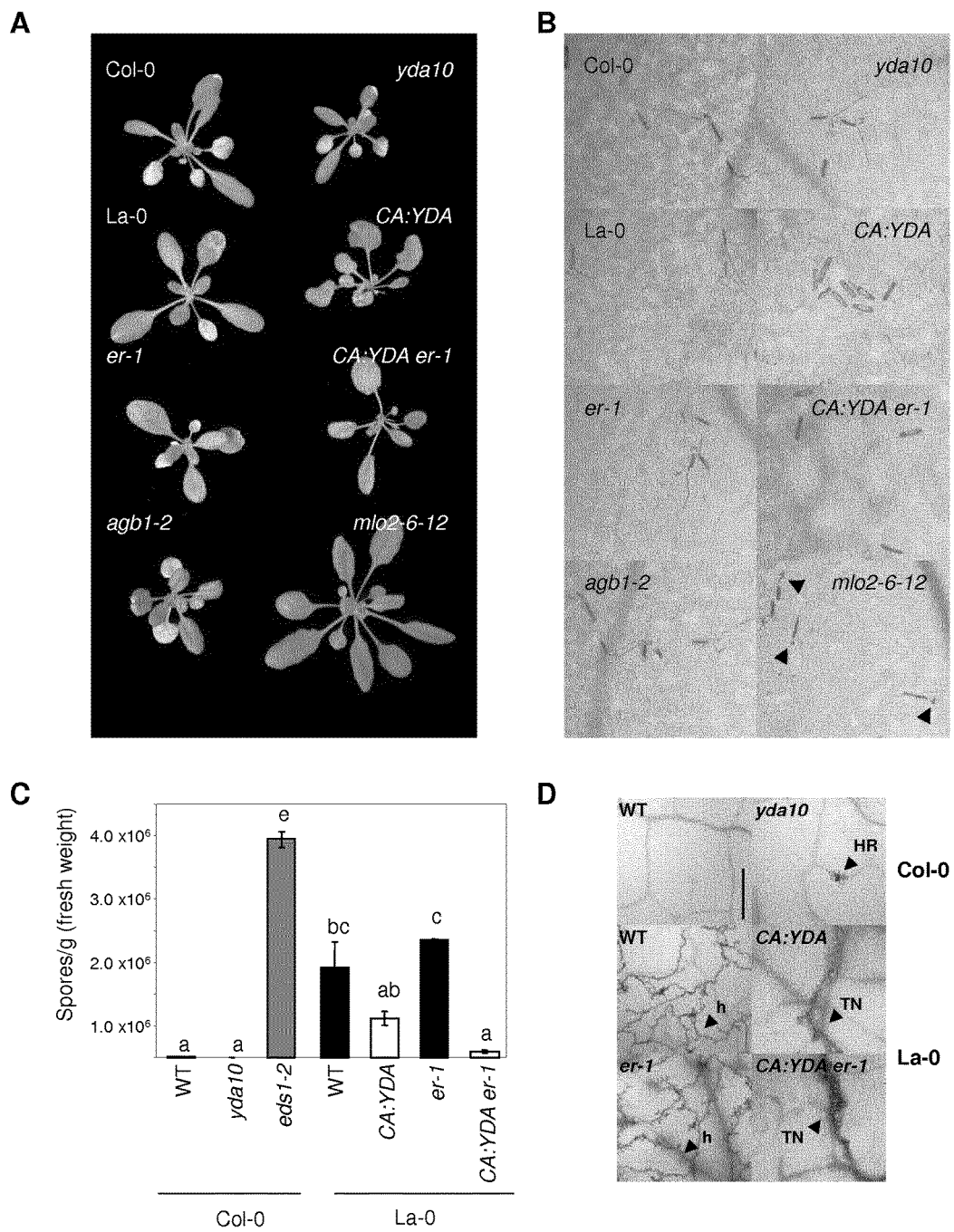
FIG. 6. Constitutive activation of YODA (CA-YODA) confers broad spectrum resistance to biotrophic pathogens. (A) Resistance of CA:YODA plants to powdery mildew fungus. Representative photographs depicting macroscopic infection phenotypes of wild-type plants (WT, Col-0 and La-0), YODA10 mutant(in Col-0 background), and CA:YODA, er-1 and CA:YODA er-1 plants (in La-0 background) upon inoculation with the powdery mildew causal agent *G. orontii*. Images were taken at 11 dpi. (B) Trypan blue staining of I *G. orontii* Inoculated leaves at 24 hours post inoculation. (C) Resistance of CA:YODA plants to the oomycete *Hyaloperonospora arabidopsidis*. Two-week-old plants were infected with *H. arabidopsidis* isolate Cala2, and inoculated leaves and conidiospore counting was performed at 7 dpi. (D) Inoculated leaves were stained with trypan blue at 7 dpi and examined under a light microscope. HR, hypersensitive response; h, hyphae; TN, trailing necrosis. Bar=0.5 mm. Accession Col-0 that contains the RPP2 gene conferring resistance to Cala2, and the gene-for gene deficient mutant eds1-2 were included as controls. Standard errors of the average values are shown. Significantly different classes are indicated by lower-case letters (one-way ANOVA, Bonferroni's post-hoc test, P<0.05 each). These assays were performed at least three times and gave similar results. (E) Wild type plants (Col-0 and La-0), YODA10, er-1 and the corresponding CA:YODA line (in were La-0 and er-1 backgrounds) were spray inoculated with a suspension of *Pseudomonas syringae* pv. *tomato* DC3000 ($OD_{\lambda 600}$=0,2 in 10 mM $MgCl_2$, 0,035% silwet). The resistance and susceptible mutants cpr5-1 and agb1-2, respectively, (in Col-0 background) were included for comparison. Growth of the bacterial pathogen was assessed at 2 dpi. (white bars) and 4 dpi (black bars). Means and standard errors are shown (n=10 plants per treatment). Letters indicate values statistically different from those of wild-type plants (ANOVA P<0.05, Bonferroni's test).
Figure 6:
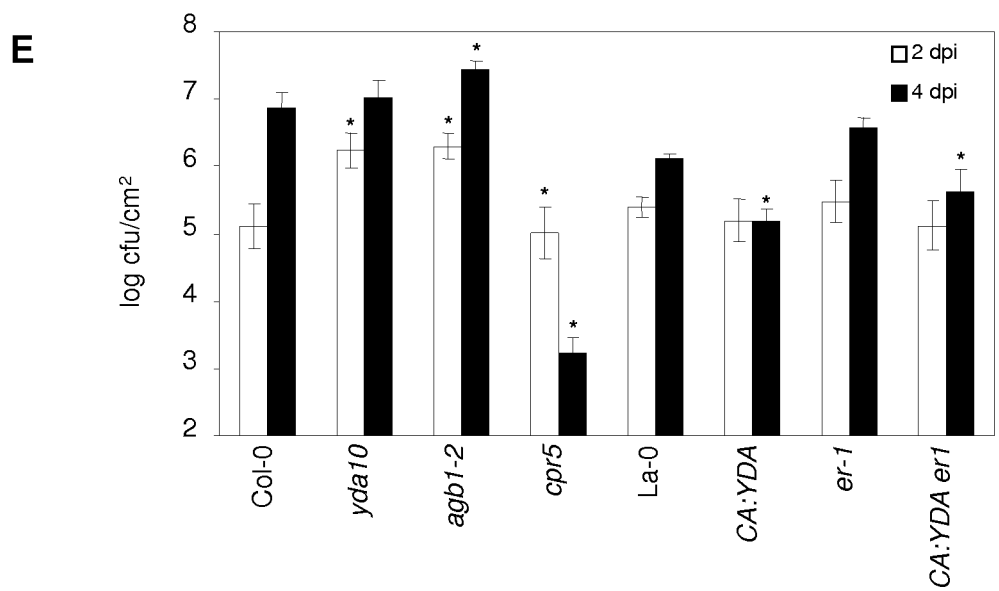

Constitutive Activation of the YODA Activity Leads to an Enhanced Immune Response Deletion of a portion of the N-terminal domain of YODA (amino acids 184-322) has been shown to result in a constitutive activation of the YODA activity (FIG. 3 B-D; Lukowitz, W., et al., Cell 116: 109-19 (2004)). Moreover, expression of CA-YODA protein version in YODA1 mutant (YODA1CA-YODA) was shown to suppress the YODA1 developmental-associated phenotypes (Lukowitz, W., et al., Cell 116: 109-19 (2004)). We generated CA-YODA and CA-YODA/YODA10 lines by crossing the previously described CA-YODA plants (in La-0 background) with YODA10 and Col-0 wild-type plants, and we observed the described CA-YODA developmental associated phenotypes (e.g. silique curvature) in the CA-YODA (Col-0) and CA-YODA/YODA10 plants obtained (FIG. 5 A). Moreover the YODA10-developmental associated phenotypes were suppressed in the CA-YODA/YODA10 lines (FIG. 5 A).

Remarkably, CA-YODA lines were found to be more resistant than the corresponding wild-type plants (Col-0 or La-0) to different type of pathogens including the necrotrophic fungus P. cucumerinaBMM, the biotrophic powdery mildew fungus, the oomycete H. arabidopsidis and the bacterium Pseudomonas syringae pv. tomato DC3000, further indicating that the constitutive activation of YODA protein resulted in broad-spectrum resistance to pathogens (FIGS. 3B-D and FIGS. 5B and 6). Moreover, expression of CA-YODA in yodel 0 allele suppressed its susceptibility phenotype to P. cucumerina BMM (FIG. 5B). These data indicate that YODA regulates Arabidopsis immune response to different pathogens and that its constitutive activation leads to an enhanced immune response.

Example 3

Figure 7:
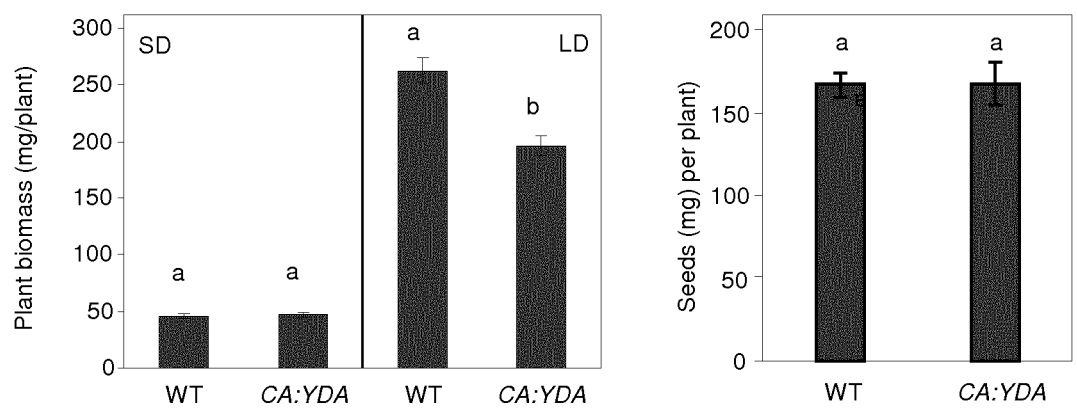
FIG. 7. Constitutive activation of YODA (CA:YODA) has no detrimental effect on fitness. In order to determine the plant biomass analysis, plants were grown for 3 weeks either under long day (16 hours light, 8 hours dark, 21° C. day, 20° C. night, 65% humidity) or under short day (10 hours light, 14 hours dark, 21° C. light and 20° C. night, 65% humidity) conditions. Fresh weight from individual rosettes was obtained, La-0 (n=25) and CA:YODA (n=30). Bars represent average values ±SD.Seeds yield of fully grown plants that were grown for 3 weeks under short day conditions and then transferred for 3 additional weeks to long day conditions was recorded. Seeds were harvested 4 weeks later from individual plants (n=20). Bars represent average values±SD.

Constitutive Activation of the YODA Activity does not have Trade-offs Under Short Days Growth Plant biomass and seed yield was determined in the CA:YODA lines and in La-0 wild-type plants in order to evaluate the trade-off costs of the observed enhanced resistance (FIG. 7). The CA:YODA plants had less biomass when grown exclusively under long days. However, no significant difference was observed in the plant biomass or seed yield when plants were grown initially under short days.

Example 4

Cloning of YODA Overexpression Constructs for Transformation in Corn, Soybean and Arabidopsis thaliana For soybean transformation, the AtYODA full-length cDNA (as shown in SEQ ID NO: 1) was synthesized in a way that allows directed cloning into a soybean transformation vector, in a way that the YODA full-length gene is located in sense direction between the parsley ubiquitin promoter (PcUbi) and an Agrobacterium tumefaciens derived octopine synthase terminator (OCS) terminator. The final binary soybean transformation vector is composed of: (1) a Spectinomycin/Streptomycin resistance cassette for bacterial selection (2) a pVS1 origin for replication in Agrobacteria (3) a pBR322 origin of replication for stable maintenance in E. coli and (4) between the right and left border: an AHAS selection under control of a Arabidopsis Acetohydroxyacid synthase large-subunit promoter (including the 5"UTR intron of the Arabidopsis actin gene) and the above described YODA expression cassette. The cloning reaction was transformed into E. coli (DH5alpha), miniprepped and screened by specific restriction digestions. A positive clone from each vector construct was sequenced and submitted soy transformation.

For corn transformation, the AtYODA full-length cDNA (as shown in SEQ ID 1) was synthesized in a way that allows directed cloning into a corn transformation vector, in a way that the YODA full-length gene is located in sense direction between the maize ubiquitin promoter (ZmUbi) and an Agrobacterium tumefaciens derived nopaline synthase terminator (NOS) terminator.

The final binary corn plant transformation vector is composed of: (1) a Spectinomycin/Streptomycin resistance cassette for bacterial selection (2) a pVS1 origin for replication in Agrobacteria (3) a pBR322 origin of replication for stable maintenance in E. coli and (4) between the right and left border: an AHAS selection under control of a Zea mays acetohydroxyacid synthase gene promoter and the above described YODA expression cassette.

The cloning reaction was transformed into *E. coli* (DH5alpha), mini-prepped and screened by specific restriction digestions. A positive clone from each vector construct was sequenced and submitted soy transformation.

For transformation of *Arabidopsis thaliana*, the AtYODA full-length cDNA was synthesized in a way that allows directed cloning into an *Arabidopsis* transformation vector (pGWB2), in a way that the YODA full-length gene is located in sense direction between the CaMV 35S promoter (35SCaMV) and an *Agrobacterium tumefaciens* derived nopaline synthase terminator (NOS). The final binary *Arabidopsis* transformation vector is composed of: (1) a Kanamycin/Hygromycin resistance cassette for bacterial selection (2) a trfA loci origin for replication in Agrobacteria (3) a Col E1 origin of replication for stable maintenance in *E. coli* and (4) between the right and left border: an NPT II selection gene (Kanamycin plant resistance) under control of NOS promoter, an HPT selection gene (Hygromycin plant resistance) under control of 35S promoter, and the above described YODA expression cassette under the control of CaMV 35S promoter. The cloning reaction was transformed into *E. coli* (DH5alpha), mini-prepped and screened by specific restriction digestions. A positive clone from each vector construct was sequenced and submitted *Arabidopsis* transformation.

Example 5

Transformation of Corn, Soybean and *Arabidopsis thaliana*

5.1 Maize Transformation

The corn expression vector construct (see example 4) was transformed into corn.

*Agrobacterium* cells harboring a plasmid containing the gene of interest and the mutated maize AHAS gene were grown in YP medium supplemented with appropriate antibiotics for 1-2 days. One loop of *Agrobacterium* cells was collected and suspended in 1.8 ml M-LS-002 medium (LS-inf). The cultures were incubated while shaking at 1,200 rpm for 5 min-3 hrs. Corn cobs were harvested at 8-11 days after pollination. The cobs were sterilized in 20% Clorox solution for 5 min, followed by spraying with 70% Ethanol and then thoroughly rinsed with sterile water. Immature embryos 0.8-2.0 mm in size were dissected into the tube containing *Agrobacterium* cells in LS-inf solution.

The constructs were transformed into immature embryos by a protocol modified from Japan Tobacco *Agrobacterium* mediated plant transformation method (U.S. Pat. Nos. 5,591,616; 5,731,179; 6,653,529; and U.S. Patent Application Publication No. 2009/0249514). Two types of plasmid vectors were used for transformation. One type had only one T-DNA border on each of left and right side of the border, and selectable marker gene and gene of interest were between the left and right T-DNA borders. The other type was so called "two T-DNA constructs" as described in Japan Tobacco U.S. Pat. No. 5,731,179. In the two DNA constructs, the selectable marker gene was located between one set of T-DNA borders and the gene of interest was included in between the second set of T-DNA borders. Either plasmid vector can be used. The plasmid vector was electroporated into *Agrobacterium*.

*Agrobacterium* infection of the embryos was carried out by inverting the tube several times. The mixture was poured onto a filter paper disk on the surface of a plate containing co-cultivation medium (M-LS-011). The liquid agro-solution was removed and the embryos were checked under a microscope and placed scutellum side up. Embryos were cultured in the dark at 22° C. for 2-4 days, and transferred to M-MS-101 medium without selection and incubated for four to seven days. Embryos were then transferred to M-LS-202 medium containing 0.75 µM imazethapyr and grown for three weeks at 27° C. to select for transformed callus cells.

Plant regeneration was initiated by transferring resistant calli to M-LS-504 medium supplemented with 0.75 µM imazethapyr and growing under light at 26° C. for two to three weeks. Regenerated shoots were then transferred to a rooting box with M-MS-618 medium (0.5 µM imazethapyr). Plantlets with roots were transferred to soil-less potting mixture and grown in a growth chamber for a week, then transplanted to larger pots and maintained in a greenhouse until maturity.

Transgenic maize plant production is also described, for example, in U.S. Pat. Nos. 5,591,616 and 6,653,529; U.S. Patent Application Publication No. 2009/0249514; and WO/2006136596, each of which are hereby incorporated by reference in their entirety. Transformation of maize may be made using *Agrobacterium* transformation, as described in U.S. Pat. Nos. 5,591,616; 5,731,179; U.S. Patent Application Publication No. 2002/0104132, and the like. Transformation of maize (*Zea mays* L.) can also be performed with a modification of the method described by Ishida et al. (Nature Biotech., 1996, 14:745-750). The inbred line A188 (University of Minnesota) or hybrids with A188 as a parent are good sources of donor material for transformation (Fromm et al., Biotech, 1990, 8:833), but other genotypes can be used successfully as well. Ears are harvested from corn plants at approximately 11 days after pollination (DAP) when the length of immature embryos is about 1 to 1.2 mm. Immature embryos are co-cultivated with *Agrobacterium tumefaciens* that carry "super binary" vectors and transgenic plants are recovered through organogenesis. The super binary vector system is described in WO 94/00977 and WO 95/06722. Vectors are constructed as described. Various selection marker genes are used including the maize gene encoding a mutated acetohydroxy acid synthase (AHAS) enzyme (U.S. Pat. No. 6,025,541). Similarly, various promoters are used to regulate the trait gene to provide constitutive, developmental, inducible, tissue or environmental regulation of gene transcription.

Excised embryos can be used and can be grown on callus induction medium, then maize regeneration medium, containing imidazolinone as a selection agent. The Petri dishes are incubated in the light at 25° C. for 2-3 weeks, or until shoots develop. The green shoots are transferred from each embryo to maize rooting medium and incubated at 25° C. for 2-3 weeks, until roots develop. The rooted shoots are transplanted to soil in the greenhouse. T1 seeds are produced from plants that exhibit tolerance to the imidazolinone herbicides and which are PCR positive for the transgenes.

5.2 Soybean Transformation

The soybean expression vector construct (see example 4) was transformed into soy.

5.2.1 Sterilization and Germination of Soy Seeds

Virtually any seed of any soy variety can be employed in the method of the invention. A variety of soybean cultivar (including Jack, Williams 82, Jake, Stoddard and Resnik) is appropriate for soy transformation. Soy seeds were sterilized in a chamber with a chlorine gas produced by adding 3.5 ml 12N HCl drop wise into 100 ml bleach (5.25% sodium hypochlorite) in a desiccator with a tightly fitting lid. After 24 to 48 hours in the chamber, seeds were removed and approximately 18 to 20 seeds were plated on solid GM medium with or without 5 µM 6-benzyl-aminopurine (BAP) in 100 mm Petri dishes. Seedlings without BAP are more elongated and roots develop, especially secondary and lateral root formation. BAP strengthens the seedling by forming a shorter and stockier seedling.

Seven-day-old seedlings grown in the light (>100 pEinstein/m$^2$s) at 25° C. were used for explant material for the three-explant types. At this time, the seed coat was split, and the epicotyl with the unifoliate leaves have grown to, at minimum, the length of the cotyledons. The epicotyl should be at least 0.5 cm to avoid the cotyledonary-node tissue (since soycultivars and seed lots may vary in the developmental time a description of the germination stage is more accurate than a specific germination time).

For inoculation of entire seedlings, see Method A (example 5.2.3.1 and 5.2.3.2) or leaf explants, see Method B (example 5.2.3.3).

For Method C (see example 5.2.3.4), the hypocotyl and one and a half or part of both cotyledons are removed from each seedling. The seedlings are then placed on propagation media for 2 to 4 weeks. The seedlings produce several branched shoots to obtain explants from. The majority of the explants originates from the plantlet growing from the apical bud. These explants are preferably used as target tissue.

5.2.2—Growth and Preparation of *Agrobacterium* Culture

*Agrobacterium* cultures were prepared by streaking *Agrobacterium* (e.g., *A. tumefaciens* or *A. rhizogenes*) carrying the desired binary vector (e.g. H. Klee. R. Horsch and S. Rogers 1987 *Agrobacterium*-Mediated Plant Transformation and its further Applications to Plant Biology; Annual Review of Plant Physiology Vol. 38: 467-486) onto solid YEP growth medium (YEP media: 10 g yeast extract, 10 g Bacto Peptone, 5 g NaCl, Adjust pH to 7.0, and bring final volume to 1 liter with H2O, for YEP agar plates add 20 g Agar, autoclave) and incubating at 25° C. until colonies appeared (about 2 days). Depending on the selectable marker genes present on the Ti or Ri plasmid, the binary vector, and the bacterial chromosomes, different selection compounds were be used for *A. tumefaciens* and *A. rhizogenes* selection in the YEP solid and liquid media. Various *Agrobacterium* strains can be used for the transformation method.

After approximately two days, a single colony (with a sterile toothpick) was picked and 50 ml of liquid YEP was inoculated with antibiotics and shaken at 175 rpm (25° C.) until an OD600 between 0.8-1.0 is reached (approximately 2 d). Working glycerol stocks (15%) for transformation are prepared and one-ml of *Agrobacterium* stock aliquoted into 1.5 ml Eppendorf tubes then stored at −80° C.

The day before explant inoculation, 200 ml of YEP were inoculated with 5 µl to 3 ml of working *Agrobacterium* stock in a 500 ml Erlenmeyer flask. The flask was shaken overnight at 25° C. until the $OD_{600}$ was between 0.8 and 1.0. Before preparing the soy explants, the Agrobacteria were pelleted by centrifugation for 10 min at 5,500×g at 20° C. The pellet was resuspended in liquid CCM to the desired density ($OD_{600}$ 0.5-0.8) and placed at room temperature at least 30 min before use.

5.2.3—Explant Preparation and Co-Cultivation (Inoculation)

Several methods for soybean transformation are known in the art. In the context of the present invention, Method A described herein below has been used for generating transgenic soybean plants. However, other methods such as Method B or Method C (see 5.2.3.3 and 5.2.3.3) can be applied as well.

5.2.3.1 Method A: Explant Preparation on the Day of Transformation.

Seedlings at this time had elongated epicotyls from at least 0.5 cm but generally between 0.5 and 2 cm. Elongated epicotyls up to 4 cm in length had been successfully employed. Explants were then prepared with: i) with or without some roots, ii) with a partial, one or both cotyledons, all preformed leaves were removed including apical meristem, and the node located at the first set of leaves was injured with several cuts using a sharp scalpel.

This cutting at the node not only induced *Agrobacterium* infection but also distributed the axillary meristem cells and damaged pre-formed shoots. After wounding and preparation, the explants were set aside in a Petri dish and subsequently co-cultivated with the liquid CCM/*Agrobacterium* mixture for 30 minutes. The explants were then removed from the liquid medium and plated on top of a sterile filter paper on 15×100 mm Petri plates with solid co-cultivation medium. The wounded target tissues were placed such that they are in direct contact with the medium.

5.2.3.2 Modified Method A: Epicotyl Explant Preparation

Soyepicotyl segments prepared from 4 to 8 d old seedlings were used as explants for regeneration and transformation. Seeds of soya cv. L00106CN, 93-41131 and Jack were germinated in 1/10 MS salts or a similar composition medium with or without cytokinins for 4 to 8 d. Epicotyl explants were prepared by removing the cotyledonary node and stem node from the stem section. The epicotyl was cut into 2 to 5 segments. Especially preferred are segments attached to the primary or higher node comprising axillary meristematic tissue.

The explants were used for *Agrobacterium* infection. *Agrobacterium* AGL1 harboring a plasmid with the gene of interest (GOI) and the AHAS, bar or dsdA selectable marker gene was cultured in LB medium with appropriate antibiotics overnight, harvested and resuspended in a inoculation medium with acetosyringone. Freshly prepared epicotyl segments were soaked in the *Agrobacterium* suspension for 30 to 60 min and then the explants were blotted dry on sterile filter papers. The inoculated explants were then cultured on a co-culture medium with L-cysteine and TTD and other chemicals such as acetosyringone for increasing T-DNA delivery for 2 to 4 d. The infected epicotyl explants were then placed on a shoot induction medium with selection agents such as imazapyr (for AHAS gene), glufosinate (for bar gene), or D-serine (for dsdA gene). The regenerated shoots were subcultured on elongation medium with the selective agent.

For regeneration of transgenic plants the segments were then cultured on a medium with cytokinins such as BAP, TDZ and/or Kinetin for shoot induction. After 4 to 8 weeks, the cultured tissues were transferred to a medium with lower concentration of cytokinin for shoot elongation. Elongated shoots were transferred to a medium with auxin for rooting and plant development. Multiple shoots were regenerated.

Many stable transformed sectors showing strong cDNA expression were recovered. Soyplants were regenerated from epicotyl explants. Efficient T-DNA delivery and stable transformed sectors were demonstrated.

5.2.3.3 Method B: Leaf Explants

For the preparation of the leaf explant the cotyledon is removed from the hypocotyl. The cotyledons are separated from one another and the epicotyl is removed. The primary leaves, which consist of the lamina, the petiole, and the stipules, are removed from the epicotyl by carefully cutting at the base of the stipules such that the axillary meristems were included on the explant. To wound the explant as well as to stimulate de novo shoot formation, any pre-formed shoots are removed and the area between the stipules is cut with a sharp scalpel 3 to 5 times.

The explants are either completely immersed or the wounded petiole end dipped into the *Agrobacterium* suspension immediately after explant preparation. After inoculation, the explants are blotted onto sterile filter paper to remove excess *Agrobacterium* culture and place explants with the wounded side in contact with a round 7 cm Whatman paper overlaying the solid CCM medium (see above). This filter paper prevents *A. tumefaciens* overgrowth on the soy-explants. Wrap five plates with Parafilm™ "M" (American National Can, Chicago, Ill., USA) and incubate for three to five days in the dark or light at 25° C.

5.2.3.4 Method C: Propagated Axillary Meristem

For the preparation of the propagated axillary meristem explant propagated 3-4 week-old plantlets are used. Axillary meristem explants can be pre-pared from the first to the fourth node. An average of three to four explants could be obtained from each seedling. The explants are prepared from plantlets by cutting 0.5 to 1.0 cm below the axillary node on the internode and removing the petiole and leaf from the explant. The tip where the axillary meristems lie is cut with a scalpel to induce de novo shoot growth and allow access of target cells to the *Agrobacterium*. Therefore, a 0.5 cm explant included the stem and a bud.

Once cut, the explants are immediately placed in the *Agrobacterium* suspension for 20 to 30 minutes. After inoculation, the explants are blotted onto sterile filter paper to remove excess *Agrobacterium* culture then placed almost completely immersed in solid CCM or on top of a round 7 cm filter paper overlaying the solid CCM, depending on the *Agrobacterium* strain. This filter paper prevents *Agrobacterium* overgrowth on the soy-explants. Plates are wrapped with Parafilm™ "M" (American National Can, Chicago, Ill., USA) and are incubated for two to three days in the dark at 25° C.

5.2.4—Shoot Induction

After 3 to 5 days co-cultivation in the dark at 25° C., the explants were rinsed in liquid SIM medium (to remove excess *Agrobacterium*) (SIM, see Olhoft et al 2007 A novel *Agrobacterium rhizogenes*-mediated transformation method of soy using primary-node explants from seedlings In Vitro Cell. Dev. Biol. Plant (2007) 43:536-549; to remove excess *Agrobacterium*) or Modwash medium (1×B5 major salts, 1×B5 minor salts, 1×MSIII iron, 3% Sucrose, 1×B5 vitamins, 30 mM MES, 350 mg/L Timentin™ pH 5.6, WO 2005/121345) and blotted dry on sterile filter paper (to prevent damage especially on the lamina) before placing on the solid SIM medium. The approximately 5 explants (Method A) or 10 to 20 (Methods B and C) explants were placed such that the target tissue was in direct contact with the medium. During the first 2 weeks, the explants could be cultured with or without selective medium. Preferably, explants were transferred onto SIM without selection for one week.

For leaf explants (Method B), the explant should be placed into the medium such that it is perpendicular to the surface of the medium with the petiole imbedded into the medium and the lamina out of the medium.

For propagated axillary meristem (Method C), the explant was placed into the medium such that it was parallel to the surface of the medium (basipetal) with the explant partially embedded into the medium.

Wrap plates with Scotch 394 venting tape (3M, St. Paul, Minn., USA) were placed in a growth chamber for two weeks with a temperature averaging 25° C. under 18 h light/6 h dark cycle at 70-100 μE/m²s. The explants remained on the SIM medium with or without selection until de novo shoot growth occurred at the target area (e.g., axillary meristems at the first node above the epicotyl). Transfers to fresh medium can occur during this time. Explants were transferred from the SIM with or without selection to SIM with selection after about one week. At this time, there was considerable de novo shoot development at the base of the petiole of the leaf explants in a variety of SIM (Method B), at the primary node for seedling explants (Method A), and at the axillary nodes of propagated explants (Method C).

Preferably, all shoots formed before transformation were removed up to 2 weeks after co-cultivation to stimulate new growth from the meristems. This helped to reduce chimerism in the primary transformant and increase amplification of transgenic meristematic cells. During this time the explant may or may not be cut into smaller pieces (i.e. detaching the node from the explant by cutting the epicotyl).

5.2.5—Shoot Elongation

After 2 to 4 weeks (or until a mass of shoots was formed) on SIM medium (preferably with selection), the explants were transferred to SEM medium (shoot elongation medium, see Olhoft et al 2007 A novel *Agrobacterium rhizogenes*-mediated transformation method of soy using primary-node explants from seedlings. In Vitro Cell. Dev. Biol. Plant (2007) 43:536-549) that stimulates shoot elongation of the shoot primordia. This medium may or may not contain a selection compound.

After every 2 to 3 weeks, the explants were transferred to fresh SEM medium (preferably containing selection) after carefully removing dead tissue. The explants should hold together and not fragment into pieces and retain somewhat healthy. The explants were continued to be transferred until the explant dies or shoots elongate. Elongated shoots >3 cm were removed and placed into RM medium for about 1 week (Method A and B), or about 2 to 4 weeks depending on the cultivar (Method C) at which time roots began to form. In the case of explants with roots, they were transferred directly into soil. Rooted shoots were transferred to soil and hardened in a growth chamber for 2 to 3 weeks before transferring to the greenhouse. Regenerated plants obtained using this method were fertile and produced on average 500 seeds per plant.

After 5 days of co-cultivation with *Agrobacterium tumefaciens* transient expression of the gene of interest (GOI) was widespread on the seedling axillary meristem explants especially in the regions wounding during explant preparation (Method A). Explants were placed into shoot induction medium without selection to see how the primary-node responds to shoot induction and regeneration. Thus far, greater than 70% of the explants were formed new shoots at this region. Expression of the GOI was stable after 14 days on SIM, implying integration of the T-DNA into the soy genome. In addition, preliminary experiments resulted in the formation of cDNA expressing shoots forming after 3 weeks on SIM.

For Method C, the average regeneration time of a soy plantlet using the propagated axillary meristem protocol was 14 weeks from explant inoculation. Therefore, this method has a quick regeneration time that leads to fertile, healthy soy plants.

5.3 Transformation of *Arabidopsis thaliana*

*Arabidopsis thaliana* plants were transformed by Floral Dip as described by Clough and Bent (Floral dip: a simplified method for *Agrobacterium*-mediated transformation of *Arabidopsis thaliana*. Plant J, 1998, 16:735-43).

Example 6

Figure 8:
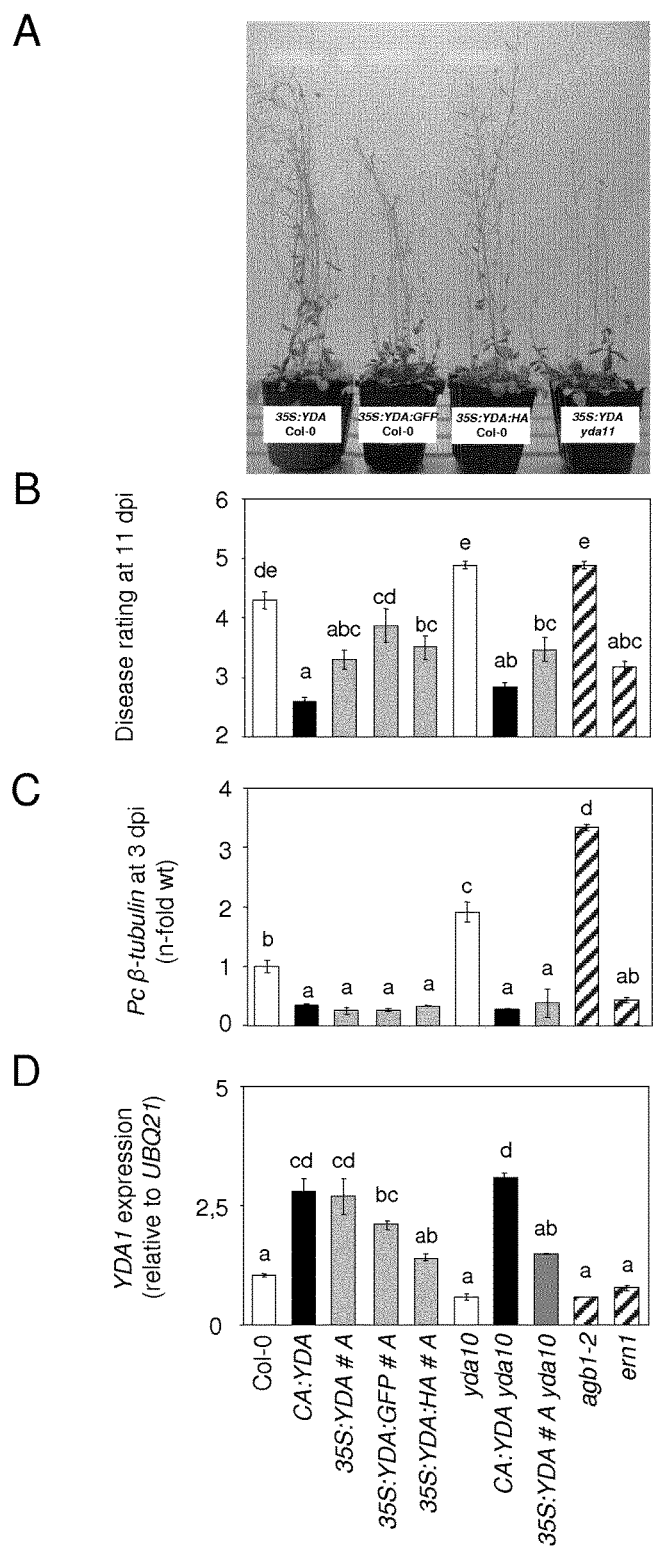
FIG. 8. Defence response of transgenic *Arabidopsis* lines overexpressing YDA1 under control of the CaMV 35S promoter to the necrotrophic fungus *Plectosphaerella cucumerina* PcBMM.

Defence Response of Transgenic Lines Overexpressing AtYODA1 to the Necrotrophic Fungus *Plectosphaerella cucumerina* PcBMM Transgenic *Arabidopsis thaliana* plants overexpressing the full-length AtYODA1 gene under control of the CaMV 35S promoter, as well as, suitable control plants were inoculated with the necrotrophic fungus *Plectosphaerella cucumerina* PcBMM as described herein above (see Plant Inoculation with pathogens). The results are shown in FIG. 8. As can be seen in FIG. 8, the generated transgenic plants show increased pathogen resistance. Interestingly, the pleiotropic symptoms as observed for CA-YODA plants were not present in the YODA overexpressing lines. Under unstressed conditions, no phenotypical differences between wild-type plants and CaMV 35S:YODA plants were observed.

The invention claimed is:

1. A method for increasing fungal and/or bacterial resistance in a plant, a plant part, or a plant cell, comprising introducing into a plant, plant part or plant cell an exogenous nucleic acid encoding a YODA protein; wherein the expression level and/or activity of the YODA protein is increased in the plant, plant part or plant cell comprising the exogenous nucleic acid in comparison to a control plant, control plant part or control plant cell that does not comprise the exogenous nucleic acid; and wherein the exogenous nucleic acid is selected from the group consisting of:
   a) an exogenous nucleic acid encoding a polypeptide comprising the amino acid sequence of SEQ ID NO: 72;
   b) an exogenous nucleic acid encoding a polypeptide having at least 90% identity to the amino acid sequence of SEQ ID NO: 69;
   c) an exogenous nucleic acid comprising the nucleotide sequence of SEQ ID NO: 71; and
   d) an exogenous nucleic acid having at least 90% identity to a polynucleotide encoding the amino acid sequence of SEQ ID NO: 69.

2. A method for increasing fungal and/or bacterial resistance in a plant, a plant part, or a plant cell, comprising modifying the expression level of an endogenous nucleic acid encoding a YODA protein in the plant, plant part or plant cell by transforming the plant, plant part or plant cell with an exogenous nucleic acid selected from the group consisting of:
   a) a nucleic acid encoding an amino acid sequence having at least 90% identity to SEQ ID NO: 69;
   b) a nucleic acid encoding a polypeptide comprising the amino acid sequence of SEQ ID NO:69; and
   c) a nucleic acid that is at least 90% identical to a polynucleotide encoding the amino acid sequence of SEQ ID NO:69.

3. The method according to claim 1, wherein the fungal resistance is to a pathogen that is a necrotroph, a biotroph or an Oomycete pathogen.

4. The method according to claim 1, further comprising regenerating a plant from the plant cell or plant part, wherein the exogenous nucleic acid is operably linked to a promoter that is active in a plant.

5. The method according to claim 4, wherein the promoter is a pathogen-inducible promoter, an epidermis or mesophyll-specific promoter, or a stress inducible promoter.

6. The method according to claim 1, wherein the plant is selected from the group consisting of: soybean, potato, cotton, rape, oilseed rape, canola, sunflower, alfalfa, clover, banana, blackberry, blueberry, strawberry, raspberry, cantaloupe, carrot, cauliflower, coffee, cucumber, eggplant, grape, honeydew, lettuce, mango, melon, onion, papaya, pepper, pineapple, pumpkin, spinach, squash, tobacco, tomato, tomatillo, watermelon, apple, peach, pear, cherry, plum, broccoli, cabbage, cauliflower, Brussels sprouts, kohlrabi, currant, avocado, orange, lemon, grapefruit, tangerine, artichoke, cherry, walnut, peanut, endive, leek, arrowroot, beet, cassava, turnip, radish, yarn, sweet potato; pea, bean, sugarcane, turfgrass, *Miscanthus*, switchgrass, wheat, maize, sweet corn, rice, millet, sorghum, barley, and rye.

7. The method according to claim 1, wherein the exogenous nucleic acid is in operable linkage with a pathogen-inducible promoter or an epidermis- and/or mesophyll-specific promoter.

8. A recombinant DNA expression cassette comprising at least one exogenous nucleic acid molecule selected from the group consisting of:
   a) an exogenous nucleic acid encoding a polypeptide comprising the amino acid sequence of SEQ ID NO: 72;
   b) an exogenous nucleic acid encoding a polypeptide having at least 90% identity to the amino acid sequence of SEQ ID NO: 69;
   c) an exogenous nucleic acid comprising the nucleotide sequence of SEQ ID NO: 71; and
   d) an exogenous nucleic acid having at least 90% identity to a polynucleotide encoding the amino acid sequence of SEQ ID NO: 69.

9. The recombinant DNA expression cassette according to claim 8, wherein said exogenous nucleic acid is in operable linkage with a promoter which is functional in plants.

10. A recombinant vector, comprising the expression cassette of claim 8.

11. A cell comprising at least one exogenous nucleic acid molecule selected from the group consisting of:
   a) an exogenous nucleic acid encoding a polypeptide comprising the amino acid sequence of SEQ ID NO: 72;
   b) an exogenous nucleic acid encoding a polypeptide having at least 90% identity to the amino acid sequence of SEQ ID NO: 69;
   c) an exogenous nucleic acid comprising the nucleotide sequence of SEQ ID NO: 71; and
   d) an exogenous nucleic acid having at least 90% identity to a polynucleotide encoding the amino acid sequence of SEQ ID NO: 69.

12. A transgenic plant, comprising at least one exogenous nucleic acid molecule selected from the group consisting of:
   a) an exogenous nucleic acid molecule encoding a polypeptide comprising the amino acid sequence of SEQ ID NO: 72;

b) an exogenous nucleic acid molecule encoding a polypeptide having at least 90% identity to the amino acid sequence of SEQ ID NO: 69;

c) an exogenous nucleic acid molecule comprising the nucleotide sequence of SEQ ID NO: 71; and d) an exogenous nucleic acid molecule having at least 90% identity to a polynucleotide encoding the amino acid sequence of SEQ ID NO: 69.

13. The transgenic plant according to claim 12, wherein plant is selected from the group consisting of soybean, potato, cotton, rape, oilseed rape, canola, sunflower, alfalfa, clover, banana, blackberry, blueberry, strawberry, raspberry, cantaloupe, carrot, cauliflower, coffee, cucumber, eggplant, grape, honeydew, lettuce, mango, melon, onion, papaya, pepper, pineapple, pumpkin, spinach, squash, tobacco, *tomato*, tomatillo, watermelon, apple, peach, pear, cherry, plum, broccoli, cabbage, cauliflower, Brussels sprouts, kohlrabi, currant, avocado, orange, lemon, grapefruit, tangerine, artichoke, cherry, walnut, peanut, endive, leek, arrowroot, beet, cassava, turnip, radish, yam, Sweet potato; pea, bean, sugarcane, turfgrass, Misconthus, switchgrass, wheat, maize, sweet corn, rice, millet, sorghum, barley, and rye.

14. A method for generating a transgenic plant which is resistant to oomycetes, fungi, and/or bacterial pathogens, comprising introducing into a plant, a plant part or a plant cell at least one exogenous nucleic acid molecule selected from the group consisting of:

a) an exogenous nucleic acid molecule encoding a polypeptide comprising the amino acid sequence of SEQ ID NO: 72;

b) an exogenous nucleic acid molecule encoding a polypeptide having at least 90% identity to the amino acid sequence of SEQ ID NO: 69;

c) an exogenous nucleic acid molecule comprising the nucleotide sequence of SEQ ID NO: 71; and d) an exogenous nucleic acid molecule having at least 90% identity to a polynucleotide encoding the amino acid sequence of SEQ ID NO: 69.

15. A crop, propagation material or composition comprising at least one exogenous nucleic acid molecule selected from the group consisting of:

a) an exogenous nucleic acid molecule encoding a polypeptide comprising the amino acid sequence of SEQ ID NO: 72;

b) an exogenous nucleic acid molecule encoding a polypeptide having at least 90% identity to the amino acid sequence of SEQ ID NO: 69;

c) an exogenous nucleic acid molecule comprising the nucleotide sequence of SEQ ID NO: 71; and d) an exogenous nucleic acid molecule having at least 90% identity to a polynucleotide encoding the amino acid sequence of SEQ ID NO: 69.

16. A harvestable part of the plant according to claim 12, wherein the harvestable part comprises the exogenous nucleic acid molecule, and wherein the harvestable part is a transgenic seed.

17. A method for the production of a product, comprising:
a) growing the transgenic plant according to claim 12; and
b) producing said product from the transgenic plant or a part thereof.

18. The method according to claim 2, wherein the modification results in constitutive activation of the YODA protein in the transformed plant, the transformed plant part, or the transformed plant cell in comparison with a control plant, control plant part, or control plant cell.

19. A method for generating a transgenic plant which is resistant to an oomycete pathogen, a fungal pathogen and/or a bacterial pathogen, the method comprising introducing into a plant cell a vector comprising an exogenous nucleic acid molecule selected from the group consisting of:

a) an exogenous nucleic acid molecule encoding a polypeptide comprising the amino acid sequence of SEQ ID NO: 72;

b) an exogenous nucleic acid molecule encoding a polypeptide having at least 90% identity to the amino acid sequence of SEQ ID NO: 69;

c) an exogenous nucleic acid molecule comprising the nucleotide sequence of SEQ ID NO: 71; and d) an exogenous nucleic acid molecule having at least 90% identity to a polynucleotide encoding the amino acid sequence of SEQ ID NO: 69, and regenerating a transgenic plant from the transformed plant cell.

20. A transgenic plant produced by the method according to claim 19, wherein the transgenic plant has resistance to an Oomycete, a fungal and/or bacterial pathogen.

21. The method according to claim 14 further comprising regenerating a transgenic plant from the plant cell or plant part.

22. The method according to claim 14, wherein the exogenous nucleic acid is in a DNA expression cassette or in a vector.

23. The method according to claim 17 further comprising removing the harvestable part from the transgenic plant.

* * * * *

UNITED STATES PATENT AND TRADEMARK OFFICE
CERTIFICATE OF CORRECTION

PATENT NO. : 10,196,649 B2
APPLICATION NO. : 14/652285
DATED : February 5, 2019
INVENTOR(S) : Molina Fernandez et al.

Page 1 of 1

It is certified that error appears in the above-identified patent and that said Letters Patent is hereby corrected as shown below:

On the Title Page

Item (30) Foreign Application Priority Data: Please correct "12197751" to read -- 12197751.6 --

In the Specification

Column 27, Line 52: Please correct "(833)" to read -- (B33) --

Column 38, Line 30: Please correct "A2 Glade" to read -- A2 clade --

Column 39, Line 44: Please correct "(Pcf3-TUBULIN)" to read -- (Pcβ-TUBULIN) --

Column 44, Line 10: Please correct "yodel 0" to read -- yoda10 --

Column 44, Line 49: Please correct "5"UTR" to read -- 5'UTR --

Column 47, Line 8: Please correct "ρEinstein/m²s" to read -- μEinstein/m²s --

Column 47, Line 47: Please correct "OD600" to read -- $OD_{600}$ --

In the Claims

Column 258, Line 48, Claim 10: Please correct "vector," to read -- vector --

Signed and Sealed this
Fourth Day of June, 2019

Andrei Iancu
*Director of the United States Patent and Trademark Office*